United States Patent [19]
Habib et al.

[11] Patent Number: 5,780,055
[45] Date of Patent: Jul. 14, 1998

[54] CUSHIONING BEADS AND TABLET COMPRISING THE SAME CAPABLE OF FORMING A SUSPENSION

[75] Inventors: Yacoub S. Habib; Ralph Shangraw, both of Baltimore; Larry L. Augsburger, Ellicott City, all of Md.

[73] Assignee: University of Maryland, Baltimore, Baltimore, Md.

[21] Appl. No.: 709,415

[22] Filed: Sep. 6, 1996

[51] Int. Cl.$^6$ ............................................. A61K 9/20
[52] U.S. Cl. .................. 424/464; 424/489; 424/480
[58] Field of Search .......................... 424/464, 489, 424/469, 465, 494, 480

[56] References Cited

U.S. PATENT DOCUMENTS

| | | |
|---|---|---|
| 4,886,669 | 12/1989 | Ventquras et al. |
| 5,147,655 | 9/1992 | Ibsen |
| 5,283,065 | 2/1994 | Doyon et al. |
| 5,643,591 | 7/1997 | Mehra et al. ............... 424/465 |

FOREIGN PATENT DOCUMENTS 0273005  6/1988  European Pat. Off.

OTHER PUBLICATIONS

Aulton et al. *Drug Development and Industrial Pharmacy,* 20(20):3069–3104 (1994).

Habib et al, "Synthesis and Evaluation of Carbopol Beads Produced by Dry Powder Layering", *American Association of Pharmaceutical Scientists,* Abstract and Poster (Nov. 1995).

Habib et al, "Synthesis and Evaluation of Beads Containing Partially Neutralized Carbopol Produced by Extrusion Spheronization", *American Association of Pharmaceutical Scientists,* Abstract and Poster (Nov. 1995).

*Primary Examiner*—Thurman K. Page
*Assistant Examiner*—William E. Benston, Jr.
*Attorney, Agent, or Firm*—Sughrue, Mion, Zinn, Macpeak & Seas, PLLC

[57] ABSTRACT

Cushioning beads comprising microcrystalline cellulose and a disintegrant (preferably croscarmellose sodium) are disclosed. The cushioning beads are prepared by extrusion-spheronization, followed by freeze-drying. Also disclosed, are water-dispersible tablets having high tensile strength, comprising the cushioning beads and biologically active ingredient-loaded beads, wherein optionally, the tablets can contain a viscosity enhancer in the form of separate beads, or as a component of the biologically active ingredient-loaded beads such that viscosity is rapidly generated when the tablets come in contact with water, and a homogenous suspension is formed, which can be easily swallowed by children and the elderly, with minimal effect of the biologically active ingredient release properties. The tablets are useful for sustained delivery of large doses of biologically active ingredients where swallowing of a large tablet or capsule poses a problem.

53 Claims, 55 Drawing Sheets

$\ln(1/1-D)$

P $\ln(1/1-D)$

P 5,780,055

1

CUSHIONING BEADS AND TABLET COMPRISING THE SAME CAPABLE OF FORMING A SUSPENSION

FIELD OF THE INVENTION

The present invention relates to cushioning beads, and tablets comprising the same, capable of forming a suspension, and useful for delivering biologically active ingredients, such as pharmaceuticals.

BACKGROUND OF THE INVENTION

I. Introduction

Tablets and capsules are generally unsuitable for administering high doses of biologically active ingredients since individual large dosage forms are difficult to swallow, or necessitate the administration of several tablets or capsules at a time, leading to impaired patient compliance. Further, chewable tablets are not ideal in all situations, especially with older and younger people, due to the need for chewing, the failure to mask unpleasant taste, and their unsuitability for the incorporation of controlled-release coated pellets which can get crushed upon chewing.

Oral liquid suspensions of pharmaceutical materials are designed primarily for those who experience difficulty in swallowing solid medication. However, they are not suitable for the incorporation of controlled-release particles into aqueous vehicles, since this often results in premature release of the biologically active ingredient into the suspending media during storage. This presents a significant challenge, and accounts for the fact that very few sustained-release liquid products are on the market. Different strategies have been investigated to formulate sustained-release suspensions, the most successful utilize ion-exchange resins to bind charged molecules. Limitations of this system include low drug-loading capability and its applicability to only ionic drugs.

The formulation of a solid oral dosage form, whether tablet or capsule, which disintegrates rapidly in water to form an instantaneous homogenous suspension of adequate viscosity to be swallowed could circumvent the problems of administering large dosages without premature release from controlled-release particles. Moreover, it could provide improved packaging and transportation properties, and a ready measured dose.

The key to the development of such a dosage form is a rapidly disintegrating tablet which disperses to form a viscous suspension. A delay in the development of a viscous gel is essential if disintegration of the tablet is to be achieved. On the other hand, a rapidly developing viscosity is necessary to provide adequate suspension properties.

Conceptually, the system should contain a swellable material which is able to generate viscosity on contact with water, at least one biologically active ingredient for immediate or sustained release delivery of the biologically active ingredient, and a filler system which confers properties, such as compactibility and the capability to disintegrate quickly.

The inclusion of a viscosity increasing agent, as a fine powder, in the tablet matrix without any processing would interfere with disintegration and result in the formation of a voluminous hydrophilic mass which is impossible to disperse. Thus, it is necessary to incorporate such an agent into the tablet as granules or spheres so that the disintegration process occurs before the viscosity build-up.

Beads and coated beads are often incorporated into hard gelatin capsules to provide conventional or controlled

2 release dosage forms, respectively. Compaction of beads into tablets has always been of interest, but during the compaction process there is a possibility that the beads will crack due to the applied force. If the beads have been coated by a rate controlling membrane to sustain or delay the delivery of the biologically active ingredient, cracking of the membrane will cause the delivery system to fail. Matrix fillers involving soft granules or microcrystalline cellulose (MCC) have been used with varying degrees of success.

II. Sustained Release Liquid Oral Drug Delivery Systems

Considerable research effort has been spent on oral, solid sustained- or controlled- release drug delivery systems (Ghebre-Sellasie, *Multiparticulate Oral Drug Delivery*, Marcel Dekker, Inc. (1994)). Multi-particulates can be filled into hard gelatin capsules or be compressed into tablets. An alternative approach for the oral administration of multi-particulates is to suspend them in a liquid vehicle to form a suspension or into a dry powder system or a tablet, which is reconstituted with water by the patient prior to administration. These types of dosage forms overcome the above-mentioned problems, and are often preferred for infants, children, and the elderly because of the ease in swallowing and the flexibility in administration.

A. Approaches Used to Formulate Sustained-Release Oral Suspensions

The formulation of oral suspensions that exhibit sustained-release activity presents many challenges due to the substantial loss of the biologically active ingredient to the surrounding suspending medium during storage. Different approaches have been undertaken in the past to overcome this problem (Chang, *Pharm. Technol.*, 16 (March) :134 and 136 (1992)). The following is a brief discussion of each of the different strategies utilized:

1. Sustained-Release Suspensions Of Poorly Water-Soluble Biologically Active Ingredients Different microencapsulation techniques, such as spray congealing, spray drying, solvent evaporation, etc., can be used to prepare slow-release microencapsulated particles for incorporation in a suspension dosage form. The amount of biologically active ingredient leaching out during the shelf-life is minimized because of the low solubility of the biologically active ingredient in the aqueous suspending vehicle. However, there is always a concern that the biologically active ingredient could continue to leach out of the sustained release coating, resulting in significant physical instability which might be accompanied by chemical instability if the biologically active ingredient is susceptible to hydrolysis in the suspending medium. Moreover, this technique can only be utilized for poorly water-soluble biologically active ingredients.

The preparation of a slow-release, fine monolithic matrix containing the biologically active ingredient for incorporation into suspending vehicles has been described (Robinson et al. *J. Am. Pharm. Assoc., Sci. Ed.*, 47:874–878 (1958); and Smith et al. *J. Pharm. Sci.*, 59:776–779 (1970)). Poorly water-soluble biologically active ingredients, such as sulfonamide and dextromethorphan, were dispersed in a molten wax, and the mixture was congealed by spraying under controlled conditions. Sulfamethylthiadiazole (Robinson et al, supra) mixed with hydrogenated caster oil heated to 140° C. was spray congealed to yield powder with an average surface diameter of 34 μm. A second sustained release powder of sulfamethylthiadiazole was prepared by mixing it with glyceryl distearate melted at 80° C., followed by cooling and milling. A poorly water-soluble salt of dextromethorphan (Smith et al. supra) was crystallized from different solvent systems and was coated with a triglyceride fatty acid mixture. The coated crystals were dispersed in an aqueous suspension to yield a stable suspension having prolonged in vitro release.

2. Saturated Drug Suspension as a Suspending Medium

A method of preparing sustained-action liquid dosage forms for various compounds by microencapsulating the biologically active ingredient and subsequently suspending the microencapsulated form in a vehicle saturated with the biologically active ingredient has been described (Carrais, U.S. Pat. No. 4,902,513 (1990)).

Saturation of the vehicle with the biologically active ingredient prevents undesirable leaching from sustained-release microcapsules during storage. The biologically active ingredient in the saturated solution provides the immediately available portion for absorption. The medication in the microencapsulated reservoir is designed to be released at a relatively slow rate. However, for such a system, fluctuations in the storage temperature may result in appreciable nucleation, crystal growth, and alteration in dissolution profiles.

3. Non-aqueous Vehicles

The use of oleaginous vehicles, such as almond oil, sesame oil, sunflower oil, etc., for the preparation of oral liquid suspensions has been described (Mulligan, European Patent 295,941). The enhanced bioavailability, improved absorption characteristics, and reduced intersubject variability have been demonstrated for various biologically active ingredients including amoxicillin trihydrate, dextromethorphan, erythromycin ethyl succinate, guaifenesin, potassium chloride, prednisolone, and roxithromycin.

Thus, the biologically active ingredient loss into the suspending vehicle can be eliminated by minimizing the solubility of the biologically active ingredient in the suspending vehicle, or by choosing a vehicle which does not cause the biologically active ingredient to leach during storage. However, oily suspending vehicles or non-aqueous solvents could potentially act as plasticizers for the polymeric membrane coating responsible for sustaining or delaying the biologically active ingredient action, and thus could cause an unwanted change in its permeability characteristics.

4. Protective Coatings

Enteric coatings are usually intended to release the biologically active ingredient after some time delay, or after the tablet has passed through one part of the gastrointestinal (GI) tract into another. Enteric protective coatings can be utilized to extend the shelf-life when a product is stored in an aqueous acidic medium (Ghebre-Sellasie, supra). However, upon ingestion, the coatings are designed to break down, and the drug is released from particles over a period of time.

Controlled-release liquid suspensions of dual-coated dosage forms have been developed (Benton et al, U.S. Pat. No. 4,876,094). Biologically active ingredient-loaded microparticles or matrix beads with a particle size of less than 1400 μm were coated with two layers prior to suspending them in a sugar-based acidic vehicle. The first coating consisted of an ingestible hydrophobic fat having a melting point of 101° F. or lower. Low melting fats were selected such that the materials would become softened at body temperature, thus rendering the coating permeable after ingestion. Various fatty materials and glycerides, such as cocoa butter and partially hydrogenated vegetable oils and their blends could be applied as the first coat. The second layer consisted of zein or the enteric polymer cellulose acetate phthalate. The overcoat materials were insoluble in the suspending medium, but became readily permeable in the GI tract. This dual coating technique has been used successfully in the formulation of a controlled-release suspension of vitamin C, a highly water-soluble unstable compound, as well as antihistamines and analgesics. However, long-term studies on the stability of the suspensions are not available.

5. Reconstitution

Ready-made suspensions might be associated with chemical instability of the biologically active ingredient or with some physical instability, such as cacking tendencies and dissolution profile changes. In such instances, a reconstitutible suspension can be always considered. This approach has been widely implemented in antibiotics intended for immediate release delivery of biologically active ingredients, but has never been used for sustained release delivery of biologically active ingredients. However, the increased cost and packaging problems of such units can be a limiting factor (Katare et al, Indian J. Pharm. Sci., 50:19 (1988)).

6. Optimizing Vehicle Composition

The use of syrups of varying water concentration for liquid pharmaceuticals is widespread. Previous studies have shown that the solubility of a given compound in syrup may be significantly different from water (Shihab et al, J. Pharm. Sci., 77:455–457 (1988); Valdez et al, J. Pharm. Sci., 57:2093–2096 (1968); Paruta, J. Pharm. Sci., 53:1252–1254 (1964); and Paruta et al, J. Pharm. Sci., 55:1208–1211 (1966)). It has been found that increasing the concentration of sucrose, glucose, or sorbitol tends to decrease the solubility of sorbic acid in aqueous vehicles by decreasing the activity of water (Shihab et al, supra). Calculation of the free energy and enthalpy changes indicated that the dissolution process for sorbic acid became progressively unfavorable upon increasing the sugar concentration. The effect of polarity and dielectric constants of the dissolution media on the solvency characteristics of syrup vehicles on some relatively nonpolar biologically active ingredients, such as quinine alkaloids, phenobarbital, PABA, and sulphanilamide was investigated (Paruta, supra (1964)). Solubility increased upon increasing the sugar concentration. This can be explained on the basis of decreasing polarity of the syrup vehicles upon increasing the sugar concentration. A syrup may be selected to exhibit lower biologically active ingredient solubility in the vehicle.

7. In Situ Gelling Mechanisms

Novel oral liquid theophylline formulations that were transformed from the liquid state to a matrix gel in the environment of the stomach and produced prolonged release of the biologically active ingredient have been developed (Zatz et al, U.S. Pat. No. 4,717,713). The utilization of some macromolecular excipients is known to influence biologically active ingredient dissolution and biological availability. This may result from complexation with the biologically active ingredient, increasing bulk viscosity in the digestive tract or delaying the breakup of granules into smaller particles. Gelling agents used in the study included xanthan gum, sodium alginate, gelatin, carrageenan, methyl cellulose, and mixtures thereof, in amounts varying from approximately 0.3 to 5.0% by weight of the vehicle. Useful vehicles include aqueous, mixed and non-aqueous solutions or suspensions of the gelling agents. After gel formation, biologically active ingredient release from the preparation was controlled by diffusion of the biologically active ingredient through the gelatinous matrix. Gas-producing salts, such as calcium carbonate and other carbonates could be incorporated in the formulation to produce a "floating" gelatinous matrix, which could potentially prolong the retention of the dosage form in the stomach.

8. Ion-Exchange Resins

Ion-exchangers are solid high-molecular weight polyelectrolytes that can exchange their mobile ions of equal charge with the surrounding medium. The resulting ion-exchange is reversible and stoichiometric, with the displacement of one ionic species by another. Ion-exchange resin-biologically active ingredient complexes have been used to formulate sustained release products of acidic or basic biologically active ingredients (Keating, U.S. Pat. No. 2,990,332; Raghunathan, U.S. Pat. No. 4,221,778; Raghunathan et al. *J. Pharm. Sci.,* 70:379–384 (1981); and Amsel et al. *Pharm. Technol.,* 8(4):28–48 (1984)). The ion-exchange resin consists of two principal parts: a structural portion consisting of a polymer matrix, usually styrene cross-linked with divinyl benzene, and a functional portion which is the ion-active group to which the biologically active ingredient is bound. The functional group may be acidic (sulfonic or carboxylic) or basic (usually amine). When the polymer-biologically active ingredient complex is swallowed, the reverse reaction takes place, and the biologically active ingredient is liberated. The ion-exchange resins system, also known as Pennkinetic® system, was considered as a technical breakthrough that has made it to the market. However, this technique has its own limitations, such as the possibility of low biologically active ingredient-loading capacity, and the applicability only to ionic biologically active ingredient species. Delsym® is a commercial example of a dextromethorphan Pennkinetic® suspension currently available in the market.

9. Rapidly Disintegrating Tablets for the Formation of Instantaneous Immediate or Sustained Release Suspensions Although oral formulations comprising particles of an biologically active ingredient suspended in a viscous aqueous vehicle have been previously described, these compositions are formulated as ready-to-use suspensions from the outset and are handled, transported and stored as such. Formulations have been patented (Benzon, U.S. Pat. No. 5,147,655; Ventouras, European Patent 0-273-055; and Ventouras et al, U.S. Pat. No. 4,886,669) in which the product is stored in a ready-to-use dry form, and converted to a suspension by adding an aqueous carrier or pre-mixed gel. This presents the important advantage of increased storage stability over a premanufactured suspension, and permits a wider range of active substances to be incorporated. Moreover, it provides improved packaging, handling and transportation properties due to the fact that the ready-to-use suspension is prepared in situ by the end user. Furthermore, it is easy to measure out the exact dosages of the biologically active ingredient because the particles comprising the biologically active ingredient are present as dry powders, tablets or capsules in a unit dosage form. Such formulations make it possible to administer large individual dosages of a biologically active ingredient in that they do not impose size limitations, as do conventional tablets or capsules.

A description of the composition and manufacture of powders for suspension is found in Benzon, supra. This patent primarily deals with powders and presents only one example of a tabletted product involving coated potassium chloride crystals which deform plastically to produce strong tablets. Moreover, most of the examples given in this patent involve the admixture of the biologically active ingredient-loaded particles with a premixed viscous gel medium. The use of powders either in bulk or as premeasured doses are much less convenient than tablets or capsules.

A water-dispersible tablet containing biologically active ingredient-loaded microparticles, a disintegrant, and a swellable material capable of generating a high viscosity when coming in contact with water was described previously (Ventouras, supra; and Ventouras et al, supra). On contact with water, the tablet disintegrates "rapidly" to surpass the opposite swelling effect caused by the viscosity enhancer. After the tablet has disintegrated in water, the viscosity enhancer swells, resulting in a homogenous suspension consisting of biologically active ingredient-loaded beads. The disintegration time of the tablets produced by these patents was between one and two minutes, which can result in viscosity build-up within the tablet matrix before disintegration, whereby incomplete dispersion occurs. These patents used dry granules of MCC and lactose prepared by slugging as the filler binder. Dry granulation of MCC tends to decrease its compactibility. Moreover, the presence of lactose, a water-soluble excipient, prolongs the disintegration time. These patents did not claim sustained release as a possible application but, rather, used coated micropellets of methylxanthines.

In order to formulate a self-disintegrating tablet to be dispersed extemporaneously in an aqueous carrier to deliver sustained-release biologically active ingredient-loaded pellets, it is essential that such tablets exhibit the following properties:

(1) Possess a quickly hydrating swellable material incorporated in aggregates, such as granules or spheres, that allow the tablet to disintegrate first followed by viscosity build-up; and (2) Possess a filler system to be mixed with the sustained-release biologically active ingredient-loaded pellets and the viscosity enhancer needed to form a tablet. This filler should have minimal segregation propensity (similar size, density, and shape), and should cushion the sustained-release biologically active ingredient-loaded pellets to prevent dose dumping.

B. Formulation of Suspensions

General considerations to be addressed during the development of conventional biologically active ingredient suspensions also apply to the development of sustained-release suspensions (Bodemeier et al, *Multiparticular Oral Delivery Drug* (Ghebre-Sellassie) Mercel Dekker, New York, N.Y., pages 143–157 (1994)). These considerations include the selection of proper suspending vehicles, suspending agents, surfactants, flavoring agents, preservatives, and other ingredients to formulate a stable, elegant, and pharmaceutically acceptable dosage form.

The principle or theory of suspensions has been described extensively in numerous articles and reviews (Kennon et al, *The Theory of Practice of Industrial Pharmacy*, (Lachman et al, Eds.), Lea & Febiger, Philadelphia, Pa., pages 162–183 (1976); Falkiewics, *Pharmaceutical Dosage Forms: Disperse Systems*, (Lieberman et al, Eds.), Mercel Dekker, New York, N.Y., Volume 1, pages 13–48 (1988); Nash, *Pharmaceutical Dosage Forms: Disperse Systems*, (Lieberman et al, Eds.), Mercel Dekker, New York, N.Y., Volume 1, pages 151–198 (1988); and Offner III et al, *Pharmaceutical Dosage Forms: Disperse Systems*, (Lieberman et al, Eds.), Mercel Dekker, New York, N.Y., Volume 2, pages 231–264 and 317–334 (1989)). Important characteristics for sustained-release suspensions containing biologically active ingredient-loaded spheres or microparticles are listed below:

(1) Excipient selection: A typical suspension contains a wetting agent, suspending agent, flocculating agent or protective colloid, sweetener, preservative, buffer system, flavoring agent and coloring agent.

(2) Reduced sedimentation rate: Modification of the particle size and/or the viscosity of the liquid medium have been the most popular approaches employed to improve suspension stability. The particle size of the spheres or microparticles can be controlled by using a smaller-size extrusion screen for pellets produced by extrusion-spheronization, or by varying the agitation rate with microparticles formed by emulsification processes (e.g., solvent evaporation, melt dispersion, and interfacial polymerization methods), or by the atomization conditions with microparticles formed by spray drying or spray congealing. With respect to the dispersion medium, an inverse relationship exists between the rate of particle settling and the viscosity of the external medium.

C. Gelling Agents

Gelling agents are usually substances which form colloidal dispersions in an aqueous environment, the colloidal particles forming a three-dimensional network or grid-like structure throughout the liquid phase. The viscous gel medium may be one which becomes less viscous or dissolves in response to pH changes or enzymes degradation, such that diffusion through the gel does not influence the release of active substance from the particles.

Examples of useful gelling or swelling agents are hydrophilic polymers, such as pectin agar, carrageenan, acacia gum, guar gum, xanthan gum, alginic acid and acrylic acid polymers, such as carbomers.

1. Carbomers

Carbomer resins (B.F. Goodrich literature, Cleveland, Ohio) are crosslinked acrylic acid polymers. The molecular structure of carbomer resins in the partially and fully solvated states are depicted in FIGS. 1A and 1B, respectively. A high percentage of carboxylic acid groups allow the resins to be water-swellable. In the presolvated dry state, a molecule of carbomer is tightly coiled. When dispersed in water, carbomer begins to hydrate and uncoil, resulting in partial build-up of viscosity. The molecule must completely uncoil to achieve the highest and most consistent viscosity. This is accomplished by neutralizing the polymer with a base. Neutralization with a water-soluble base ionizes the resin, generating negative charges along the polymer backbone. Repulsion of these negative charges causes expansion of the molecule, thereby causing the molecule to rapidly thicken. Overneutralization by strong bases can collapse the resin structure, resulting in a permanent loss of viscosity. The dissociated individual resins vary by molecular weight, degree of crosslinking and molecular architecture. These differences are responsible for the specific rheological characteristics and thickening efficiency of each carbomer resin.

Carbomers 934P (60 ppm benzene), 971P and 974P are the pharmaceutical grades used in oral, topical and novel biologically active ingredient delivery applications. They are unneutralized molecules which require the addition of a base to achieve maximum viscosity. Two neutralized versions of carbomers have been recently introduced into the market. EX161 and EX214 are salts of the 934P and 974P grades which do not require the addition of a base.

In solid dose formulation, carbomer has been used as dry tablet binder (Vila-Jato et al, *Int. J. Pharm.*, 30:229–236 (1986)), and as controlled release agent via a hydrophilic matrix mechanism. Several papers dealing with these products have been published demonstrating their utility in achieving sustained release with diverse active principles (Vila-Jato et al, supra; Choulis et al, *J. Pharm. Sci.*, 64(6):1033–1035 (1975); Choulis et al, *Pharmazie*, 31(July):466–470 (1976); Salib et al, *Pharm. Ind.*, 45(9):902–906 (1983); Agabeyoglu, *Drug. Dev. Ind. Pharm.*, 12(4):569–576 (1986); Graf et al, *Pharm. Ind.*, 48(6):661–665 (1986); Malley et al, *Drug Dev. Ind. Pharm.*, 13(1):67–79 (1987); Bulut-Öner et al, *Farmaco*, 44:739–742 (1989); Capan et al, *Pharm. Ind.*, 51:443–448 (1989); Baun et al, *Pharm. Acta Helv.*, 46:94–113 (1971); Ciftci et al, *Pharm. Res.*, 7(4):359–363 (1990); Pérez-Marcos et al, *Int. J. Pharm.*, 67:113–121 (1991); and Durrani et al, *Drug Dev. Ind. Pharm.*, 20(15):2439–2447 (1994)). These papers deal exclusively with the 934 type of resin. Some research papers have focused on the possibilities that are offered by controlling the release of hydrosoluble substances when used in conjunction with hydroxypropyl cellulose (Satoh et al, *Chem. Pharm. Bull.*, 37(6):1642–1644 (1989)). Their practical value is evident from various patents (Decrosta et al, U.S. Pat. No. 4,666,705; Ueda et al, Japanese Patent 6,277,335; and Hirofumi et al, Japanese Patent 63,101,332). Moreover, carbomer has been used in the preparation of microcapsules intended for sustained release delivery of biologically active ingredients (Salib et al, supra; and El-Egakey et al, *Drug Dev. Ind. Pharm.*, 9(5):895–908 (1983)).

In liquid oral dose formulations and topical applications, carbomer has been utilized for its rheological modification properties to thicken a wide range of aqueous and alcoholic solutions, to suspend insoluble ingredients and to stabilize emulsions (Plazier-Vercammen et al, *Pharmazie*, 46:646–650 (1991); Banga et al, *Drug Dev. Ind. Pharm.*, 15(5):691–704 (1989); El-Assasy et al, *Drug Dev. Ind. Pharm.*, 11(1):65–81 (1985); Soci et al, *J. Pharm. Sci.*, 69(4):403–406 (1980); Ruiz et al, *Farmaco*, 49(February):147–152 (1994); Touitou et al, *J. Pharm. Sci.*, 81(February):131–134 (1992); Chawdry et al, *Indian Drugs*, 31(January):36–40 (1994); Demou et al, *Pharm. Acta. Helv.*, 68(May):215–219 (1994); Banga et al, *Pharm. Res.*, 10(May):697–702 (1993); Taylor, *Cosmet-Toiletries*, 93(April):71–73 (1978); Mercado et al, *Drug Dev. Ind. Pharm.*, 19(8):887–902 (1993); González et al, *Int. J. Pharm.*, 104:107–113 (1994); Amin et al, *Drug Dev. Ind. Pharm.*, 20(7):1309–1316 (1994); Dal-Zotto et al, *Farmaco*, 46(December):1459–1474 (1991); Baichwal et al, *Indian J. Pharm. Sci.*, 51(5):178–181 (1989); and Morimoto et al, *Drug Dev. Ind. Pharm.*, 13(7):1293–1305 (1987)). In novel biologically active ingredient delivery systems, carbomer has been used successfully in bioadhesives intended for the buccal, nasal, vaginal and rectal cavities (Harris et al, *J. Controlled Release*, 12(March):45–53 (1990); Anlar et al, *Pharm. Res.*, 11(February):231–236 (1994); Vidgren et al, *Drug Dev. Ind. Pharm.*, 18(5):581–597 (1992); Smart, *Drug Dev. Ind. Pharm.*, 18(2):223–232 (1992); Chu et al, *Pharm. Res.*, 8(November):1408–1412 (1991); Nagai et al, *Pharm. Int.*, 6(August):196–200 (1985); and Morimoto et al, *J. Pharm. Pharmacol.*, 37(February):134–136 (1985)). Carbomers are compatible with most of the ingredients used in personal care and pharmaceutical formulations. Soluble salts, such as sodium chloride, decrease the efficiency of carbomer resin mucilage. All monovalent cations affect carbomer resins similarly. Divalent and trivalent cations cause a more drastic loss in the ability of carbomers to build-up viscosity (Charman et al, *Drug Dev. Ind. Pharm.*, 17(2):271–280 (1991)).

Carbomer resins not only thicken solutions, but also provide a wide range of flow properties. Like numerous polysaccharide thickeners, such as modified cellulosics and natural gums, carbomer resins are shear thinning (the viscosity decreases with increasing shear rate). However, unlike most linear polysaccharides, carbomer resins display plastic rheological profiles. Carbomer solutions will not flow until a minimum force, called the yield value is reached. Carbomer resins provide excellent stability to oil-in-water (o/w) emulsions and suspensions. When used in conjunction with appropriate emulsifying agents and coemulsifiers, carbomer resins provide long term stability at ambient and elevated temperatures, as well as under freeze-thaw conditions. The yield value created by carbomer resins prevents "creaming" or separation of o/w emulsions by suspending and separating the oil droplets. It also allows particles to be permanently suspended throughout the medium, creating stable non-settling products, even when used at very low concentrations.

One of the major difficulties encountered with carbomer, as well as with other hygroscopic powders, is its poor dispersibility. These dry powder resins are highly hygroscopic and hydrate rapidly when added to water or polar solvents. Thus, carbomer resins will clump or incompletely hydrate when haphazardly introduced to polar media. The surfaces of these wet agglomerates quickly solvate and form a layer which prevent rapid wetting of the dry interior. This, together with the fluffy nature of carbomer, results in dispersion defects, such as grainy texture, reduced viscosity or the presence of partially wet agglomerates. Therefore, to avoid lengthy mixing times and to prepare high quality, reproducible carbomer resin dispersions, either proper dispersion techniques should be utilized or carbomer should be formulated in a readily dispersible less fluffy form, such as granules or spheres, or powder-layered on the surface of carrier seeds.

D. Powder-layering

Powder-layering can be traced to the 1956 patent by Blythe (U.S. Pat. No. 2,738,303). This process involved layering a drug powder onto nonpareils using syrup as the adhesive solution. There have been 40 years of research and development experience in the powder-layering technology, and a wide variety of products have been successfully developed and introduced into the market.

The term "layering" (Parikh, "Layering in Rotary Fluid Bed: A Unique Process for the Production of Spherical Pellets for Controlled Release", Presented in Interphex-USA (May 18, 1991)) involves the deposition of successive layers of a compound from solution/suspension or dry powder on core particles, which may be crystals or granules of the same material or an inert starter core, such as nonpareil seeds. In solution/suspension systems, the biologically active ingredient particles are dissolved or suspended in the binder solution. As the liquid evaporates, the dissolved substances crystallize out. On further evaporation, these crystals, or the particles that are initially suspended in the binder solution, are drawn toward each other and towards the starter core by capillary forces. The limitations of this process are that there is a limit to the amount of the biologically active ingredient which can be mixed with the binder solution, a problem with the removal of large quantities of liquid from the layered beads, and the possibility of recrystallization from the solution while drying.

In powder-layering, the biologically active ingredient does not come in contact with the binder solution until it is sprayed onto the inert seed material, as the binder and biologically active ingredient are sprayed from different ports. As the amount of binder solution needed is much less when compared to other layering techniques, drying will be very fast and the total process is much faster than the other processes.

The Aeromatic® rotoprocessor (see FIG. 2) is the latest development used in the powder-layering process. It is a modified fluid bed equipped with a spheronizer-like wheel. It utilizes frictional, centrifugal and gravitational forces, which are all induced by the rotary disc. The fluidized air affords efficient evaporating capacity. It consists of an inner and outer process chamber, called forming and drying zones, respectively, separated by a straight wall. The lower part of the forming zone is a rotary disc similar to the one in the spheronizer with a cone in the middle. The surface of the disc can be either smooth or textured. Beneath the rotary disc there is flushing air whose function is to prevent the product from depositing between the disc and the wall, and from penetrating the lower part. The straight wall can be pneumatically lifted allowing the product to pass into the outer drying zone. The drying zone is annular, and has a stationary perforated bottom through which preheated air flows upwards, drying the product as it is transferred from the forming zone to the drying zone by the centrifugal forces created by the rotary disc.

E. Extrusion-Spheronization

Extrusion and spheronization, as a process for the manufacture of multi-particulates, has gained increased usage during the past decade because of the increased popularity of multi-particulate controlled release oral dosage forms (Nesbitt, *Drug Dev. Ind. Pharm.*, 20(20):3207–3236 (1994)). Although proposed originally as a novel process, the mechanical mechanisms that produce a spherical multiparticulate using the extrusion-spheronization process are similar to those once used by the traditional pill making process (Rowe, *Pharm. Int.*, 6:119–123 (1985)).

Spheronization was invented in 1964 by Nakahara (U.S. Pat. No. 3,277,520). The process was not widely known until two review articles were published in 1970 by the Eli Lilly organization (Conine et al, *Drug Cosmet. Ind.*, pages 38–41 (April, 1970); and Reynolds, *Manuf. Che. Aerosol News*, 41:40–43 (1970)). Equipment design change has been minimal since the original patents. The spheronizer consists basically of a grooved horizontal plate rotating at high speed within a stationary vertical cylinder fitted with a door to allow release of the pellets. Although extrusion is usually regarded as a continuous process, spheronization equipment design limits the extrusion-spheronization process to a batch process or a multiple batch process.

There are five unit operations involved in the extrusion-spheronization process. These are: blending, granulation, extrusion, spheronization and drying. The moistened precompacted mass is extruded into strands, which are then rounded into pellets in a spheronizing machine, dried and subjected to further processing. The moisture content and composition of the mixture must be carefully selected in order that the desired plastic deformability (extrudability) is obtained. The particle size distribution of the pellets obtained is primarily determined by the extrudate density and water content (Dietrich, *Manuf. Chem.*, 60:29–33 (1989)).

Early workers in the extrusion-spheronization field always included MCC in their example formulas for use with this technique (Conine et al. supra; and Reynolds, supra). Miyake et al (*Yakazaigaku*, 33:161–166 (1973)) reported in 1973 that MCC exhibited the elasticity required for extrusion-spheronization, whereas corn starch and lactose could not be extruded and spheronized when mixed with various quantities of water. Additional work done by Harrison and coworkers (Harrison et al. *J. Pharm. Pharmacol.*, 37:686–691 (1985)) demonstrated that MCC has the ability to take up water into its intraparticulate voidage and become readily deformable. It was also shown that this excipient is insensitive to moisture concentration changes when compared to water-soluble crystalline material, such as lactose.

1. Effect of the Amount and Composition of Granulation Liquid on the Characteristics of Spheres Produced by Extrusion-Spheronization The amount and type of granulating fluid used to prepare extrudable masses has a major influence on the different properties of the spheres produced. Beart et al (*Int. J. Pharm.*, 95:135–141 (1993)) found that the amount of granulating fluid used had an influence on biologically active ingredient release from the pellets. A slower release was observed with increasing amounts of granulation fluid. These differences in release profiles were correlated with differences in hardness, density and structure of the pellets. Otsuka et al (*Drug. Dev. Ind. Pharm.*, 20(19):2977–2992 (1994)) attributed the change of the mechanical strength of the spherical granules produced using different quantities of water to difference in the internal porosity of the fluid-bed dried granules. Friability decreased with increasing the amount of granulating water added. On the other hand, the hardness of the tablets prepared from such granules seem to be inversely related to the strength of the intact granules. Thus, tablets prepared from harder granules showed a capping tendency.

The effect of changing the granulating liquid composition on the mechanical properties of granules was studied by Millili et al (*Drug Dev. Ind. Pharm.*, 16(8):1411–1426 (1990)). It was found that a difference in the release rate exists for pellets prepared with MCC and theophylline and granulated with different proportions of ethanol/water, but where the same amount of granulating fluid was used. Pellets prepared with higher percentage of water showed slower release, lower porosity, greater hardness and less compactibility.

The amount of granulating liquid is usually affected by the composition of the formulation. More granulating liquid is required as the level of MCC is increased (Elber et al, *Drug Dev. Ind. Pharm.*, 18(5):501–517 (1992)). Pinto et al (*Int. J. Pharm.*, 83:187–196 (1992)) studied the effect of different formulation and processing variables on the shape and size distribution of the spheroids, the drug release profile and the force required for steady-state extrusion, and found that the most important factor was the water content, in particular the water content at the die wall during extrusion. Factors which may be expected to decreased the water availability at the die wall (i.e., decreased water and decrease MCC content) were found to have a detrimental effect on the product in terms of size and size distribution. Formulations with higher water content were found to have the most significant variation in size, i.e., as the water content increases, the median sphere size and size distribution increase. Thus, changing the moisture content of the wet granulated mass prior to extrusion-spheronization (Hasznos et al, *Drug Dev. Ind. Pharm.*, 18(4):409–437 (1992)) has a major impact on the size and size distribution, as well as on other physico-mechanical and release properties of the spheres. Therefore, choosing the optimum granulating fluid level is of great importance to the production of spheres by extrusion-spheronization.

2. Characterization of the Optimal Liquid Level Suitable for Extrusion-Spheronization Wet powder masses intended for extrusion and spheronization must have specific rheological requirements which are largely affected by the type and amount of both of the solid ingredients, as well as the granulating fluid.

Optimum conditions for the extrusion-spheronization process can be determined by measuring the plasticity of the biologically active ingredient-excipient mixture as a function of the amount of granulation liquid added. A technique developed by Alleva et al (*Drug Dev. Ind. Pharm.*, 12(4):471–478 (1986)), directed towards the characterization of the granulation step prior to extrusion, was based on the principle of measuring the force granulation exerts on a load cell when the wetted material is stressed. This technique was utilized by Elber et al, supra, to study the extrudability of MCC containing sodium carboxymethyl cellulose as a binder (Avicel® RC 581).

Most commercial extruders do not allow for rheological measurements. The ram extruder provides a suitable alternative and lends itself to application of theory derived from capillary rheometry. Harrison et al (*J. Pharm. Pharmacol.*, 37:686–691 (1985)) used that system to characterize the rheological behavior of wet powder mixtures used in the extrusion-spheronization process. Force/displacement (flow rate/shear stress) curves were obtained for materials forced through dies in order to determine the quantity of water needed to form an extrudable mixture. It was found that the force/displacement curves exhibit three stages, namely: compression, steady-state flow and forced flow. The steady-state stage provided the highest quality extrudate. The usefulness of this technique for evaluating the suitability of preparations for processing has been established by many workers (Fielden et al, *J. Pharm. Pharmacol.*, 41:217–221 (1989); Fielden et al, *Int. J. Pharm.*, 81:205–224 (1992); and Bains et al, *Int. J. Pharm.*, 69:223–237 (1991)).

Shah et al (*Pharm. Research*, 11(3):355–360 (1994)) proposed an objective measure of extrudability of materials by monitoring the extrusion screen pressure and temperature induced by the stress used to force the wet mass through the small orifice, and frictional heat build up, respectively.

If a more critical evaluation of the product is required, it is necessary to consider size and range of sizes produced by the process. A preparation that is too dry is difficult to extrude and results in anisomeric particles, whereas that which is too wet results in gross agglomeration on the spheronizer plate, leading to grossly enlarged agglomerates. At an optimum water level, nearly spherical particles are usually obtained. Thus, image analysis of the freshly produced pellets can be used to determine the optimum water level (Kleinebudde, *Int. J. Pharm.*, 96:119–128 (1993); Kleinebudde, *Int. J. Pharm.*, 109:209–219 (1994a); and Kleinebudde, *Int. J. Pharm.*, 109:221–227 (1994b)).

F. Effect of Drying Conditions on on Physico-Mechanical Properties of Spheres

There is a remarkable difference in the physico-mechanical properties of pellets as a result of the drying technique. Kleinebudde (1994a), supra, compared freeze-drying, fluid-bed drying and oven drying. It was found that only a minor shrinking tendency can be seen during freeze-drying. Removing the water leaves a skeleton of solid materials with resultant freeze-dried pellets having similar size to the wet pellets, as well as high porosities. Evaporation of water in an oven or in a fluid bed is accompanied by a shrinking process. The resultant pellets are smaller than the wet ones, and are more dense.

Betaille et al (*Drug Dev. Ind. Pharm.*, 19(6):653–671 (1993)) compared two drying processes namely: oven and microwave drying. Microwave drying led to higher porosities compared to oven drying. Oven drying is considered to be a slow and less traumatic process, while microwave drying will lead to a quicker loss of water. During the microwave drying, shrinking of the matrix may be incomplete due to the rapidity of the process.

Dyer et al (*Drug Dev. Ind. Pharm.*, 20(20):3045–3068 (1994)) compared tray-drying and fluidized bed-drying of pellets containing MCC and lactose produced by extrusion-spheronization. The differentiating factor between the two processes is the rate of water removal from the spheres. The pellets dried by the fluidized-bed technique achieve the desired moisture content much more quickly due to the rapid evaporation of water, as a result of the turbulent motion of the air and the fluidized particles. In tray-drying, the water removal from dried material is slow due to the static nature of the technique. The free movement of individual fluidized particles lead to rapid migration of solute particles (lactose dissolved in the granulating water) within the spheres; those tray-dried entities are more likely to exhibit solute migration during the lengthy drying process. Thus, it was concluded that the drying method employed has a significant effect on the mechanical strength of the product prepared by extrusion-spheronization. The solubility of the excipients from which the pellets are composed affects the degree of solute migration occurring during drying. For beads containing water, and soluble materials such as lactose, it is not unreasonable to anticipate the presence of solute molecules of this component which have dissolved in the aqueous granulating fluid during the wet massing stage. Water removal from those beads during drying following spheronization would thus, lead to the formation of solid bridges within the spheres by fusion at the points of contact of the primary powder particles. This will result in a greater degree of bonding and hence, the formation of beads of greater strength than if the amount of lactose was replaced by a biologically active ingredient with poor water solubility, such as ibuprofen (Aulton et al. *Drug Dev. Ind. Pharm.*, 20(20):3069–3104 (1994)).

1. Freeze-Drying Freeze-drying or lyophilization (FTS Systems, Inc., Instruction Manual, Stone Ridge, N.Y., pages 1–20 (1991)), is in simple terms a dehydration technique. The aspect of the freeze-drying process that makes it different is that dehydration takes place while the product is in a frozen state and under vacuum. There are four basic steps in freeze-drying: Pretreatment (usually confined to biologicals), freezing, primary drying, and secondary drying, all of which are important to the success of the freeze-drying run.

In order to freeze a product properly, thermal analysis of the product must be conducted. Water has a freezing point of 0° C. Almost any product that has a constituent other than water will experience a heat of fusion/crystallization not only around 0° C., but also at a reduced temperature. In the sphere matrix there is essentially "unbound or free" solvent. This is the solvent that is not closely associated with the product itself. The solvent that is more closely associated with the product will freeze at some reduced temperature. The reduction in freezing point of the solvent may be due to weak solvent/solute bond formation. Thus, in order to freeze-dry a product, in the perfect sense of the word, the product temperature must be maintained below its lowest freezing point during all of the primary drying step.

The rate of freezing plays an important role in determining the crystalline size, among other things. Since the solvent crystal will eventually be subliming out of the product, a larger crystalline structure will produce a more porous, and consequently more quickly dried, product.

The driving force of sublimation during the primary drying is the pressure differential between the product and the condenser of the freeze-drier created by a temperature differential. A law of nature is that as the temperature of water is decreased, the pressure over that water also decreases. A specific temperature of water is always associated with a specific pressure. Thus, in order for a freeze-dryer to be effective, the temperature of the condenser must be lower than the temperature of the product. This temperature differential creates a pressure differential and the net migration of water vapor is towards the condenser, resulting in an increase in the condenser temperature. Therefore, primary drying is often a delicate balance between the energy input to the product and the pressure differential created between the product and the condenser due to the temperature differential.

When the product reaches a temperature above 0° C., secondary drying has begun. During secondary drying, the vacuum pump of the freeze-dryer creates the low pressure condition necessary for the removal of solvents. The solvent being removed in this phase is referred to as "bound" solvent. The amount of residual water in the product is dependent on the length of time the product remains in secondary drying.

G. Coating Formulations for Modified Release Multiparticulates

Aqueous solutions of water-soluble polymers (methyl cellulose and hydroxypropyl methylcellulose) are suitable only for isolating layers or fast-disintegrating coatings, with limited use in controlled-release multi-particulate systems. Water-based systems have been developed for pharmaceutical dosage forms instead of organic-based polymeric solutions because of their environmental and economic advantages. Because water has a high heat of vaporization, aqueous systems that might require lengthy processing times seemed initially to have a serious economic disadvantages despite their environmental advantages. However, in addition to the progress of fluidized bed technology, which reduced the lengthy processing times of aqueous based systems, the aqueous polymeric latexes and pseudolatexes that have been developed since the 1970's have overcome the disadvantages by their low-viscosities and high polymeric contents.

As with any film coating, the polymer has a key role in the properties and characteristics of a film intended to convey a modified release aspect on a multi-particulate system (Hogan, "Coating Formulations for Modified Release Multiparticulates", Fourth Symposium of the Pharmaceutical Compaction Research Laboratory and Information Center, Piscaraway, N.J. (Mar. 14, 1994)). Plasticizers are added to provide a desired modification in the mechanical properties of the polymer film.

1. Controlled Release Polymers a. Ethylcellulose

Ethylcellulose is used extensively in modified release coatings from organic solvent based system alone or in combination with other cellulosic polymers, notably hydroxypropyl methylcellulose.

In many ways, ethylcellulose is an ideal polymer for modified release coatings. It is odorless, tasteless and exhibits a high degree of stability, not only under physiological conditions, but also under normal storage conditions being stable to light and heat. Commercially, ethylcellulose is available in a wide range of viscosity and substitution types, giving a good range of possibilities to be employed. It also possesses good solubility in common solvents used for film coating, but this feature is nowadays of lesser importance with the advent of water dispersible pseudolatex presentations of ethylcellulose which have been especially designed for modified release coatings. The polymer is not usually used on its own, but normally in combination with secondary polymers, such as hydroxypropylmethyl cellulose or polyethylene glycols, which convey a more hydrophilic nature to the film by altering its structure by virtue of pores and channels through which biologically active ingredient solution can more easily diffuse. The films formed from ethylcellulose in organic solvents are very effective in controlling the biologically active ingredient release, and are still widely used in many commercial products.

b. Methacrylate Ester Copolymers

Structurally methacrylate ester copolymers bear a resemblance to the methacrylic acid polymers, but are totally esterified with no free carboxylic acid groups (Manufacture's Literature, Rohm Tech Inc., Malden, MA). Thus, these materials are neutral in character, and are insoluble over the entire pH range. However, they do possess the ability to swell and become permeable to water and dissolved substances. Thus, they find application in the coating of modified release dosage forms. Eudragit® RL is a poly(ethylacrylate, methylmethacrylate, triethylammonioethyl-methacrylate chloride) 1:2:0.2, and has slight sustained release activity. Eudragit® RS is a poly(ethylacrylate, methylmethacrylate, triethylammonioethyl-methacrylate chloride) 1:2:0.1, and has more sustained release activity. The two polymers Eudragit® RL and RS can be mixed and blended to achieve a desired release profile. The addition of hydrophilic materials, such as the soluble cellulose ethers, polyethylene glycols etc., will also enable modifications to be achieved with the final formulation. The polymer Eudragit® RL is strongly permeable, and thus only slightly retardant. For aqueous spraying, a pseudolatex form of the RL and RS polymers is available.

c. True Latexes

True latexes are very fine liquid dispersions of polymer in an aqueous phase produced by emulsion polymerization. The process starts with a monomer which, after purification, is emulsified as the internal phase with a suitable surfactant. Polymerization is activated by the addition of an initiator. Using this process Eudragit® L30D (poly(ethylmethacrylate methacrylic acid) 1:1, 30% aqueous dispersion) and NE30D (poly(ethylacrylate, methylmethacrylate) 2:1, 30% aqueous dispersion) are produced. Eudragit® L30D and NE30D are commonly used in combination for enteric coating.

d. Pseudolatexes

Commercially there are three main products which fall into the category of pseudolatexes, two of which utilize ethylcellulose as the polymer, while the third utilizes polymethacrylate copolymers. Characteristically, pseudolatexes are manufactured starting with the polymer itself and not the monomer. By a physical process, the polymer particle size is reduced, thereby producing a dispersion in water, the characteristics of which need not differ significantly from a true latex, including particle size considerations. The pseudolatex is also free of monomer residue and traces of initiator.

The earliest of the two ethylcellulose products (Aquacoat®), is manufactured by dissolving ethylcellulose in an organic solvent and emulsifying the solution in an aqueous continuous phase. The organic solvent is eventually removed by vacuum distillation, leaving a fine dispersion of polymer particles in water. Aquacoat® is composed of 30% (w/w) solids content of which 87% is ethylcellulose, 9.0% cetyl alcohol and 4.0% sodium lauryl sulfate. The cetyl alcohol and sodium lauryl sulfate act as a stabilizer and surfactant, respectively, and are added during later stages of production (Manufacture's Literature, FMC Corp., Malden, Mass.).

The newer of the ethylcellulose products is Surelease®, which is manufactured by a process based on phase inversion technology. The ethylcellulose is heated in the presence of dibutyl sebacate and oleic acid, and this mixture is introduced into a quantity of ammoniated water. The resulting phase inversion produces a fine dispersion of ethylcellulose particles in an aqueous continuous phase. The dibutyl sebacate is to be found in the ethylcellulose fraction, whilst the oleic acid and the ammonia together effectively stabilize the dispersed phase in water. Surelease®, unlike Aquacoat®, does not require the further addition of plasticizer. Surelease® also contains a quantity of fumed silica which acts as an antitack agent during the coating process. Its total nominal solid content is 25% (w/w) (Manufacture's Literature, Colorcon, West Point, Pa.).

Polymethacrylate copolymers, such as Eudragit® RL30D and RS30D, are composed of a 30% aqueous dispersion of polymethacrylate. These polymers are freely miscible in each other, and can be mixed and blended to achieve a desired release profile (Manufactures' Literature, Rohm Tech Inc., supra).

e. Plasticizers

Plasticizers are relatively low molecular weight materials which have the capacity to alter the physical properties of a polymer so as to render the polymer more useful in performing its function as a film coating material. Plasticizers make the film softer and more pliable. The mechanism of action of plasticizers is that the plasticizer molecules interpose themselves between the individual polymer strands, thus breaking down, to a large extent, the polymer-polymer interactions. This action is facilitated as the polymer-plasticizer interaction is considered to be stronger than the polymer-polymer interaction.

One fundamental property of a polymer is the glass transition temperature (Tg). This is the temperature at which a polymer changes from a hard glassy material to a softer rubbery material. The action of the plasticizer is to lower the glass transition temperature.

The commonly used plasticizers can be categorized into three groups: the polyols (glycerol, propylene glycol and polyethylene glycol), organic esters (phthalate esters, dibutyl sebacate, citrate ester and triacetin) and oils/glycerides (caster oil, acetylated monoglycerides and fractionated coconut oil).

2. Assessment of the Mechanical Properties of Polymeric Films Used to Coat Multi-particulates The assessment of the mechanical properties of the polymer films used for coating of multi-particulate spheres provides information which will help to understand the ability of these films to contribute to the deformation resistance of the millispheres, and thus their ability to withstand the stresses associated with their compaction into a tablet matrix. Among the different approaches utilized to assess the mechanical properties of the polymeric films are indentation testing, and the percentage of elongation of the free film before breakage.

Indentation testing provides a valuable means of assessing the mechanical properties of the polymer and the effect of the presence of other excipients within the film. This is fundamental to the further understanding of the manner in which polymer films will perform during tablet compression. Among the parameters which are particularly useful in this respect is the elastic modulus of the polymeric film. Those materials exhibiting a relatively low elastic modulus will therefore, undergo a relatively high instantaneous elastic strain at low loads during and following compression. This will confer a high resilience to the millisphere, and reduce its brittleness. Increasing the plasticizer content in a given polymeric film formulation will increase the permanent non-recoverable plastic deformation associated with the applied stress. Moreover, in addition to the polymer and plasticizer, the presence of other excipients within a polymer film (e.g., opacifiers, and pigments) may also exert a considerable influence on the mechanical properties of a given polymer film formulation.

Aulton et al, supra, studied the effect of plasticizers on the mechanical properties of polymethacrylate films, and found that increasing the plasticizer level would decrease the elastic modulus (and therefore the rigidity) of the film. Films with low elastic moduli are unlikely to satisfy the requirements for favorable tablet preparation due to the associated elastic recovery which will occur immediately on the removal of the applied stress. Thus, it was concluded that films exhibiting a relatively high elastic modulus provide greatest protection to the millisphere core and coat on compression.

Elongation at break can be used as a measure of the mechanical properties of films. Lehmann et al (*Drug Made in Germany*, 37(2):53–60 (1994)) used this approach to measure the elongation at break of films formed from polymethacrylate dispersions. Films 8×10 cm, 150–200 μm thick were formed by layering 15 ml of the 30% aqueous dispersions or mixtures thereof on teflon coated glass plates, and drying 15 hrs at 40° C. The films were equilibrated at 50% relative humidity for 24 hrs at room temperature. Eudragit® NE 30 D, the aqueous dispersion of methylmethacrylate-ethylacrylate copolymer, did not need addition of plasticizer, and the film showed high elongation at break of approximately 600%. Eudragit® RL 30 D and RS 30 D, copolymers of methylmethacrylate, ethylacrylate and triethyl ammonioethyl methacrylate, used in sustained release, exhibit graded permeability and give films of sufficient flexibility after the addition of approximately 20% triethyl citrate plasticizer, when the elongation of break was above 75%. An elongation at break of 75% or more is sufficient for the compression of coated particles with or without very small damage of the release controlling membrane.

The study of the elongation at break of ethylcellulose has not been reported in the literature because of the difficulty encountered in preparing the free films. This is due to the excessive adhesiveness to the casting surface, together with the brittleness of ethylcellulose.

H. Compaction of Tablets

The compaction of dry powders has been described in numerous articles (Leuenberger et al, *Pharm. Res.*, 3:12–22 (1986); Hersey et al, *Nature*, 228:96 (1971); Cole et al, *Pharm. Acta Helv.*, 50:28–32 (1975); Hersey et al, *J. Pharm. sci.*, 62:2060 (1981); David et al, *J. Pharm. Sci.*, 66:155–159 (1977); McKenna et al, *J. Pharm. Pharmacol.*, 34:347–351 (1981); Rees et al, *J. Pharm. Pharmacol.*, 30:601–607 (1978); Armstrong, *Int. J. Pharm.*, 49:1–13 (1989); Turba et al, *Chem.-Ing.-tech.*, 36:230–240 (1964); Rumpf, *Chem.-Ing.-tech.*, 46:1–11 (1974); and Shubert, *Chem.-Ing.-tech.*, 51:266–277 (1979)). It consists of two stages: compression of the particulate solid and bonding of the particles.

1. Tablet Strength - Compression Pressure Profiles

The simplest, and perhaps most universally used means to study the compaction process involves the relationship between punch force and tablet "hardness". The term "hardness" has been used for many years to describe the force required to break a tablet when subjected to a diametral load. Since the term "hardness" has a definite meaning in material science, it is probably best to use terms, such as "crushing strength" or "breaking strength" to describe this parameter. Crushing strength, however, is not a fundamental property of the compact. Tablet tensile strength measured by diametral compression is more appropriate. If the tablet fails under tension by splitting cleanly into diametral halves, then its tensile strength (σ) can be calculated using the Equation (1) below (Fell et al, *J. Pharm. Sci.*, 59:688–691 (1970))

$$\sigma = \frac{2P}{\Pi Dt}$$ Equation (1)

where P is the applied load, D is the tablet diameter, t is the tablet thickness. This equation applies only to cylindrical tablets and includes the following assumptions:

(1) The tablet is isotropic body;
(2) The tablet obeys Hooke's law; and
(3) The modules of elasticity in compression and tension are the same.

Despite the fact that none of the above-mentioned assumptions are currently met in pharmaceutical compacts, the use of this equation improves the reproducibility of the data, because the data is normalized with respect to tablet dimensions, since both diameter and thickness are included in the equation. Variations in the consolidation time (to maximum force), dwell time (at maximum force), contact time (time for compression and decompression excluding ejection), die resistance and ejection may give rise to changes in compaction mechanism and lamination, resulting in compacts with different strength characteristics (David et al, supra; Heistand et al, *J. Pharm. Sci.*, 66:510–519 (1977); and Schlanta et al, *J. Pharm. Sci.*, 53:562–564 (1970)).

2. Changes in Bed Density During Compaction

One of the effects of powder compaction is an increase in the bulk density of the starting material. Quite often, the relationship between the applied pressure and density or porosity appears linear over the normal tabletting range of the applied pressure. Various empirical equations have been proposed to characterize this relationship. Perhaps the best known and widely used the Heckel equation, i.e., Equation (2) below (*Trans. Metall. Soc. A.I.M.E.*, 221:671–675 (1961); and *Trans. Metall. Soc. A.I.M.E.*, 221:1001–1008 (1961)), which is based on the void spaces decreasing as a first order process.

$$\ln \frac{1}{1-D} = KP + A$$ Equation (2)

where D is the relative density of the compact at pressure P, K is a material constant and is the slope of the straight line portion of the plot. The reciprocal of K is the mean yield pressure of the material ($P_y$). The term A is a function of the original compact volume, and can be related to the densification that occurs during die filling plus that which occurs by particle rearrangement before any appreciable interparticle bonding starts.

Sheik-Salem et al (*J. Pharm. Pharmacol.*, 33:491–494 (1981)) noted that the Heckel equation is not derived from theoretical considerations of the compaction process, but is essentially a curve-fitting equation that provides reasonable correlation with the observed facts over a wide range of pressures, especially in the regions of interest where a compact is being formed. Several authors have used the Heckel equation to study the deformation mechanism of materials (Hersey et al (1971), supra; Hersey et al (1981), supra; McKenna et al, supra; Rees et al, supra; Sheik-Salem et al, supra; Fell et al, *J. Pharm. Sci.*, 60:1866–1869 (1971); York et al, *J. Pharm. Pharmacol.*, 25:1P-11P (1973); de Boer et al, *Powder Technol.*, 20:75–82 (1978); Rue et al, *J. Pharm. Pharmacol.*, 30:642–642 (1978); York, *J. Pharm. Pharmacol.*, 31:244–246 (1979); Chowhan et al, *Int. J. Pharm.*, 5:139–148 (1980); Paronen et al, *J. Pharm. Pharmacol.*, 35:627–635 (1983); Duberg et al, *Powder Technol.*, 46:67–75 (1986); Marchall et al, *Int. J. Pharm.*, 67:59–68 (1991); and Hussain et al, *Int. J. Pharm.*, 70:103–109 (1991)). Hersey et al (1971), supra, used Heckel's plots to differentiate between plastic deformation and fragmentation. These authors classified Heckel plots into two types (FIGS. 3A and 3B). In type 1 behavior (FIG. 3A), densification under pressure is due initially to particle rearrangement, and then subsequently to plastic deformation without any fragmentation; Heckel plots of different particle size fractions of a material are parallel. However, in type 2 behavior (FIG. 3B), consolidation occurs largely by fragmentation. Thus, the initial structure of the material is progressively destroyed so that above a certain pressure, coincident linear relations are obtained for all size fractions.

Caution should be observed in interpreting the results of Heckel analysis since the numerical value for the yield pressure has been shown to be dependent on experimental conditions, such as punch diameter, compaction rate and method of measuring relative density (York (1979), supra). Rees et al, supra, examined the effect of different contact times under compression on the relative density of tablets utilizing the Heckel equation. They noticed that for plastically deforming materials, such as MCC, tablet density increased with an increase in contact time. However, dicalcium phosphate, a brittle material, showed no changes in density with contact time. Roberts et al (*J. Pharm. Pharmacol.*, 37:377–384 (1985)) examined the effect of punch speed on the compaction of a variety of materials using the Heckel equation. For materials known to deform plastically, there was an increase in yield pressure with punch speed. This was attributed to either a change from plastic to brittle behavior, or a reduction in the amount of plastic deformation due to the time dependent nature of plastic flow. For materials known to consolidate by fragmentation, there was no change in yield pressure with punch speed. Roberts et al supra, also presented an equation, Equation (3) below, to determine the strain rate sensitivity (SRS) of the various materials tested.

$$SRS = \frac{P_{y2} - P_{y1}}{P_{y2}} \times 100 \quad \text{Equation (3)}$$

where $P_{y1}$ and $P_{y2}$ are yield pressures at fast and slow punch velocities, respectively. The materials which were more strain rate sensitive were those which deform plastically. Thus, Roberts et al, supra provided a quantitative measure of the strain rate sensitivity of materials.

3. Critical Aspects in the Compaction of Beads

Compaction of sustained release tablets containing coated pellets is becoming increasingly important. When such a dosage form is developed, the coated pellets must withstand the process of compaction without being damaged in order to prevent any undesirable effects on the biologically active ingredient release properties. The type and amount of coating agent, the size of the subunit, the selection of external additives having a cushioning effect, and the rate and magnitude of the applied pressure must be carefully considered (Chelik et al, *Drug Dev. Ind. Pharm.*, 20(20):3151–3173 (1994)).

The process of millisphere compaction involves the application of stress to polymer-coated spherical cores. In order to fully understand the interrelationships between the mechanical properties of the film, the millispheres and the resulting compacts, it is necessary not only to evaluate and quantify the mechanical properties of the polymers as free-films, but also to study the properties of the polymeric membrane in situ on the millisphere core. The desirable mechanical properties of coated millispheres to be compacted into a tablet together with excipients or placebo cushioning beads should be such that they are strong, not brittle and have low elastic resilience. It is important in this dosage form that the millispheres and their coatings remain undamaged and intact so that the release profile of the biologically active ingredient is not changed.

The mechanical properties of both uncoated and coated ibuprofen containing millispheres was investigated by Aulton et al, supra, using a single particle crushing assembly in which the force required to cause single millisphere fracture and particle displacement under an applied load is recorded. The generation of this information facilitated estimation of the tensile stress and elastic modulus for each millisphere formulation studied. These properties were related to the fundamental bonding forces arising from the pelletization process, which determine the strength of the millisphere, and to the contribution made to the overall mechanical properties of the millispheres by the presence of the film coating (and thus, in turn, its mechanical properties). The presence of a film coat applied by means of an aqueous polymeric dispersion of polymethacrylates also influenced the crushing strength and the elastic properties of ibuprofen millispheres. Increasing the polymer loading has the effect of increasing the crushing strength of millispheres, whilst simultaneously enhancing millisphere resilience (characterized by a reduction in the elastic modulus).

Maganti et al (*Int. J. Pharm.*, 95:29–42 (1993)) observed significant changes between the compaction properties of the powder and pellet forms of the same formulations. In their study, the powder formulations deformed plastically and produced stronger compacts, whereas their pellet forms exhibited elastic deformation and brittle fragmentation, which resulted in compacts of lower tensile strength. They reported that the addition of Surelease® as a coating material altered the deformation characteristics of uncoated pellets by introducing plasto-elastic properties into their previously brittle and elastic nature.

Juslin et al (*Pharm. Ind.*, 42:829–832 (1980)), in their study of the feasibility of achieving controlled release of a biologically active ingredient from compacts of coated spheres, observed that the biologically active ingredient release rate from phenazone spheres, coated with acrylates polymers mixed with different additives, increased with an initial increase in the applied pressure. This was attributed to the cracks in the coat that formed during compaction. However, the authors claimed that further increases in pressure again retarded the release profile, possibly due to closer interparticulate contacts within the tablet, which partly compensated for the leaks of the pellet coats.

Badwan et al (*Drug Dev. Ind. Pharm.*, 11:239–256 (1985)) reported an increase in the drug release profile of sulphamethamethoxazole beads when compacted into a tablet.

Bobmeier et al (*J. Pharm. Sci.*, 78:819–822 (1989)) compacted biodegradable spheres prepared from polylactides. They observed that the energy imparted during compaction caused fusion of the low molecular weight polylactide particles, resulting in transparent pellets with no visible particle boundaries.

Bechard et al (*Drug Dev. Ind. Pharm.*, 18:1927–1944 (1992)), in their investigations of the effect of compaction on biologically active ingredient release from compacts of varying mesh cuts of Aquacoat® coated microspheres containing chlorpheneramine maleate, reported massive film fracture occurring at high pressures, regardless of the microsphere particle size and external additives used.

Lehmann et al, supra, coated small particles such as crystals, granules and pellets of particle size in the range of 0.3–1.2 mm with aqueous dispersions of methacrylic acid and methacrylic ester copolymers for taste masking, resistance to gastric fluid and diffusion controlled sustained release properties, and compressed them into fast disintegrating tablets. An admixture of 25–50% of tabletting excipients as fillers and disintegrants was necessary. Some damage of the coatings were observed with some brittle coating polymers of polymethacrylates. More flexible films (having an elongation at break of more than 75%) were able to withstand the mechanical stress of compression so that the release pattern of the disintegrating tablet was very similar or nearly the same as the uncompressed particles. Examples were given for taste masking of paracetamol, sustained release preparation of potassium chloride and theophylline, and also enteric coated acetylsalicylic acid and indomethacin.

Haubitz et al (*Drugs in Germany*, 38(4) (1995)) produced theophylline-containing multiple units tablets with a pellet amount of 70% in MCC as a filler binder, crosslinked polyvinylpyrrolidone as a disintegrant and Aerosil® as a glidant. The pellets were produced by powder-layering theophylline in a Eudragit® NE 30 D matrix onto sugar spheres, followed by coating with an additional release controlling barrier. A decrease in the release of theophylline from compacted beads, was observed relative to uncompacted beads, and was attributed to delayed tablet disintegration and the reduction in the number of pores of the pressed pellets caused by local melting processes of the affected coat area with subsequent closing of the pores.

The selection of external additives is also of importance in the design of multiunit tablets since these additives are expected to prevent the occurrence of film cracking in the coated subunits. Their compactibility with the pellets, in terms of particle size, is also very critical, since a non-uniform size distribution can cause segregation, resulting in tabletting problems, such as, weight variation, poor content uniformity, etc. In order to minimize the occurrence of problems due to a non-uniform size distribution, placebo microspheres, with good "compaction" and "cushioning" properties, can also be used as diluents if the size of the active beads is much larger than that of the external powder additives. Another alternative would be to produce pellets of smaller sizes. Small-size biologically active ingredient-loaded pellets also improve the content uniformity of low dose biologically active ingredients. However, the surface area to be coated will increase as the size of the pellets decreases.

4. Use of Inert "Cushioning" Beads as Diluents

Good blending and minimal segregation is essential in order to achieve satisfactory uniformity of weight and content of the tablet dosage form. The potential problem of segregation in any particulate system must be addressed. It is influenced by factors, such as markedly differing particle size, density or shape. In order that the occurrence of segregation between the biologically active ingredient-loaded pellets and excipient particle is minimized, it is deemed necessary to choose large particle size excipients. This could be achieved by the preparation of inert beads of the same size and approximately the same density. The inert cushioning beads should be mechanically weaker than the coated biologically active ingredient-loaded ones.

Millili et al, supra, reported that the strength and physical properties of beads containing MCC were affected by the granulating solvent. In their work, water granulated MCC beads were found to be stronger, hard, and uniform in shape, whereas the 95/5 ethanol/water granulating solvent resulted in beads with lower strength and less uniform shape. On the other hand, the former beads exhibited poorer compressibility than the latter ones. This was attributed to the weak bonding of the 95% ethanol granulated pellets which ruptured upon compaction, exposing more smooth surface to surface contacts for bonding. The water granulated beads resisted rupturing due to their high bond strength, and allowed less surface-to-surface contacts for bonding to occur, thus producing weaker tablets.

Aulton et al. supra, tried to use different approaches to produce inert "cushioning" beads for cushioning of coated biologically active ingredient-loaded sustained action millispheres in order to prevent segregation due to size or density. Inert beads containing high MCC levels, by virtue of the inherent bonding capacity of this material, were exceedingly hard. In addition, inert beads containing high lactose levels were also very hard. This results from the partial dissolution of lactose during wet massing and extrusion, and the formation of solid bridges during drying. It was thought that the replacement of all or part of the granulating water with isopropyl alcohol (in which lactose was insoluble) might enable the preparation of softer inert cushioning beads which would readily fragment at low pressure during tabletting. This was not the case: the resulting beads were still too strong and required three times greater applied force than that of the biologically active ingredient-loaded beads before they crush. Thus, it was concluded that the admixture of biologically active ingredient-loaded beads and inert beads was not a viable proposition.

An attempt was made to mix the biologically active ingredient-loaded beads with large particle size excipients. Avicel® PH200 (200 μm average size) and Meggle Lactose EP grade D10 (coarse-crystalline) with a mean size equal to 800 μm at an optimized diluent blend of lactose 19.5%, MCC 20% (PH200) and magnesium stearate 0.5%, were chosen. The rest of the tablet contained biologically active ingredient-loaded beads. The uniformity of content of the biologically active ingredient was 4.22% (relative standard deviation) under the pilot-scale conditions utilized. It is accepted however, that this might not be the case on scaling-up the process.

In summary, the formulation of ready-made suspensions containing controlled release beads have been associated with premature leaching of the biologically active ingredient. The use of a dispersible tablet to form an instantaneous suspension can circumvent this problem together with the possibility of administering large doses of biologically active ingredients. The ideal tablet to form an instantaneous sustained release suspension should disintegrate quickly in water (less than 5 sec) followed by the formation of a viscous suspension (within 1–2 min) to delay the settling of the biologically active ingredient-loaded membrane-coated beads until the dose is swallowed by the patient. In order to formulate this tablet three components are needed:

(1) Biologically active ingredient-loaded membrane-coated beads intended to deliver the dose over a long period of time;

(2) A viscosity enhancer capable of delaying the sedimentation of the biologically active ingredient-loaded beads; and (3) A filler system capable of producing mechanically strong compacts while protecting the biologically active ingredient-loaded beads from fracturing.

FIG. 4 is a flow chart depicting the systematic approach used in the formulation of this dosage form.

III. Statement of the Problem

When large doses of biologically active ingredients are required, large tablets and capsules are not a viable option, since they are difficult to swallow, resulting in impaired patient compliance, especially among pediatric and geriatric patient populations. Liquid oral suspensions can be used to deliver large doses of biologically active ingredients. However, the incorporation of controlled-release particles into aqueous vehicles often results in premature loss of the biologically active ingredient during storage. The formulation of a special solid oral dosage form which can disintegrate rapidly in water to form an instantaneous homogenous suspension can be used to administer large dosages of biologically active ingredients. It eliminates the physical problems of biologically active ingredient leaching from sustained-release coated beads, as well as providing improved packaging and transportation properties, and a ready measured dose. To formulate such a dosage form, a rapidly disintegrating tablet capable of forming a viscous suspension is needed. The development of a viscous gel should follow the disintegration of the tablet otherwise, tablet disintegration would be prevented.

A swellable material capable of generating viscosity when coming in contact with water is needed together with a biologically active ingredient for immediate or sustained release delivery, and a filler system which possesses certain properties, among which are compactibility and the capability to disintegrate quickly.

Biologically active ingredient-loaded membrane-coated beads, when compacted to form a tablet, will fracture due to the applied force resulting in cracking of the membrane and subsequent failure of the delivery system. Mixing and compressing the biologically active ingredient-loaded beads with highly compressible fillers can minimize this damage. However, size differences between the fillers and the biologically active ingredient-loaded beads might result in segregation with consequent content uniformity and weight variation problems. The production of cushioning beads which deform at lower pressures during tabletting to prevent the fracture of the membrane-coated biologically active ingredient-loaded beads is needed to minimize the segregation propensity. The viscosity enhancer, biologically active ingredient-loaded membrane-coated beads and cushioning filler beads need to be mixed and compacted to form a tablet which can disintegrate quickly in water to form a homogenous suspension.

IV. Hypotheses

It was hypothesized in the present invention that the incorporation of the viscosity enhancer in separate entities, such as layering onto placebo or biologically active ingredient-loaded beads, or extrusion-spheronization to form beads might circumvent the problem of prolonged tablet disintegration. The incorporation of the viscosity enhancer as fine powder in a tablet matrix could prevent the rapid disintegration and subsequent dispersion of the contents of the tablet. It is believed that fine powder of the viscosity enhancer tend to network with each other, so that on contact with water, the networked polymer particles at the surface would hydrate, preventing the further penetration of water to the interior of the tablet, and the disintegration process would be inhibited.

It was also hypothesized in the present invention that freeze-drying of MCC pellets produced by extrusion-spheronization would improve compactibility over other drying techniques. The incorporation of materials which can increase the water uptake by the extrudate is also hypothesized in the present invention to improve the porosity and compactibility of the freeze-dried beads. MCC can be processed so that the size of the filler particles is equal to the size of the biologically active ingredient-loaded beads to minimize the segregation propensity.

It was also hypothesized in the present invention that a difference in the particle size of the filler would result in weight variation and content uniformity problems. A difference in the particle size between filler-binder and biologically active ingredient-loaded beads tend to cause segregation as manifested in weight variation and content uniformity.

It was also hypothesized in the present invention that unlike ethylcellulose films, which are very brittle, polymethacrylate films can withstand the stresses of compaction with minimal fracturing and slight change in the biologically active ingredient release kinetics. The type of membrane-coating applied to the biologically active ingredient-loaded beads is important in determining the ability of the coated beads to handle the mechanical stresses of the compaction.

It was also hypothesized in the present invention that a tablet composed of biologically active ingredient-loaded membrane-coated beads, processed viscosity enhancer and a filler system which disintegrate quickly in water to form an extemporaneous uniform suspension can be produced to provide a new delivery system to deliver sustained-released biologically active ingredients in the form of suspension to pediatric and geriatric patients.

SUMMARY OF THE INVENTION

An object of the present invention is to provide highly porous and compactible cushioning beads, and which are useful for tabletting with biologically active ingredient-loaded beads.

Another object of the present invention is to provide water-dispersible tablets having high tensile strength.

Still another object of the present invention is to provide tablets containing beads which give rise to sustained delivery of a biologically active ingredient.

Yet another object of the present invention is to provide tablets containing a swellable material able to rapidly generate viscosity when coming in contact with water.

An additional object of the present invention is to provide tablets which disintegrate rapidly in water, and form a homogenous suspension which can be easily swallowed by children and the elderly, with minimal effect on the biologically active ingredient release properties.

A further object of the present invention is to provide tablets which disintegrate rapidly in water, and form a homogenous suspension when large doses of biologically active ingredient are needed, but where swallowing of a large tablet or capsule poses a problem.

These and other objects of the present invention, which will be apparent from the detailed description of the invention provided hereinafter, have been met, in one embodiment, by a cushioning bead comprising microcrystalline cellulose, wherein said cushioning bead is prepared by extrusion-spheronization, followed by freeze-drying.

In another embodiment, the above-described objects of the present invention have been met by a tablet comprising:
(i) biologically active ingredient-loaded beads; and
(ii) cushioning beads comprising microcrystalline cellulose, wherein said cushioning beads are prepared by extrusion-spheronization, followed by freeze-drying.

DETAILED DESCRIPTION OF THE INVENTION

Figure 1A:
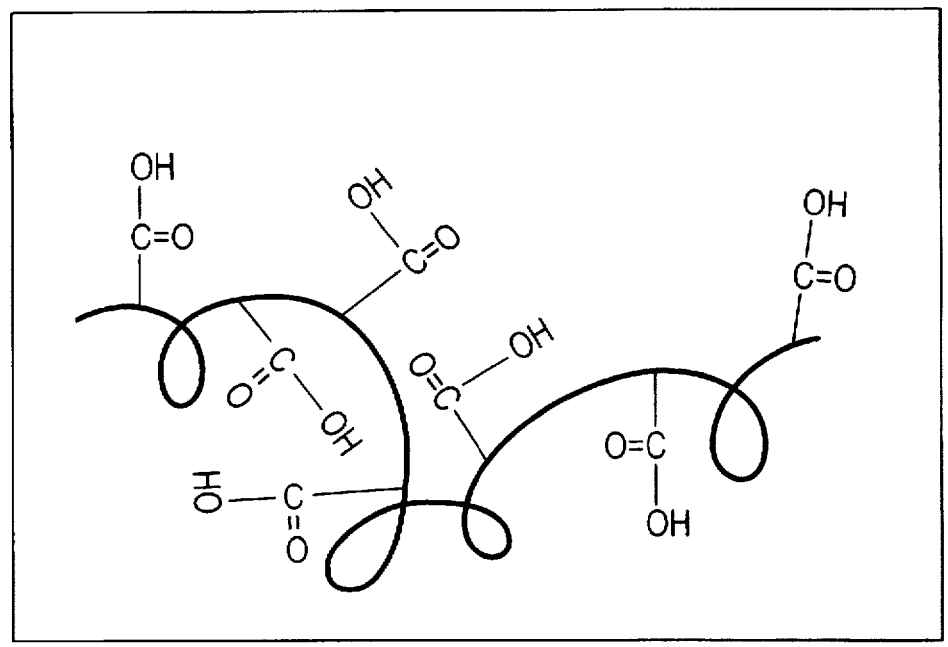
FIGS. 1A and 1B depict the molecular structure of carbomer resin in the partially solvated state (FIG. 1A), and the fully solvated state (FIG. 1B).
Figure 1B:
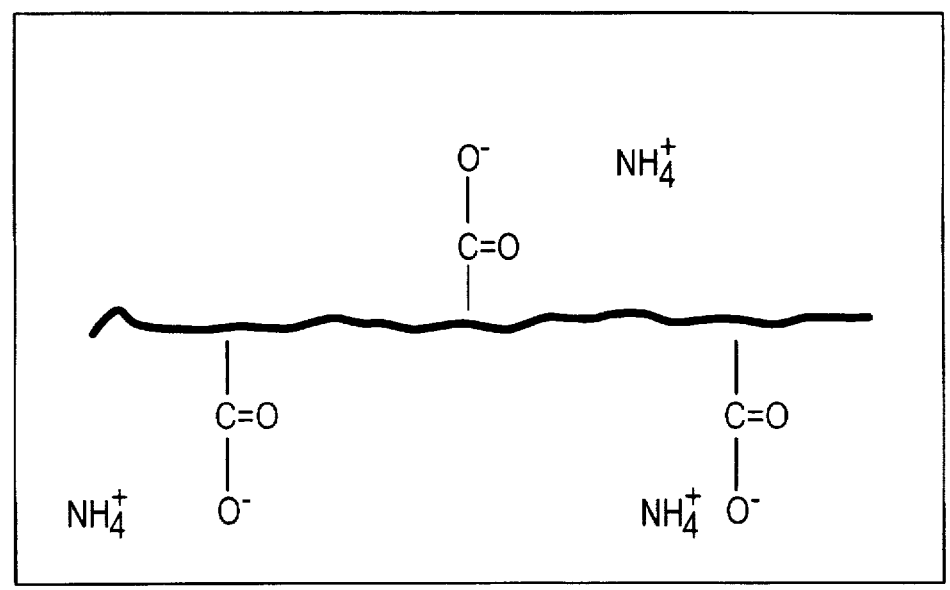

As discussed above, in one embodiment, the above-described objects of the present invention have been met by a cushioning bead comprising microcrystalline cellulose, wherein said cushioning bead is prepared by extrusion-spheronization, followed by freeze-drying.

Extrusion-spheronization is a well-known process (U.S. Pat. No. 3,277,520; Conine et al, *Drug Cosmet. Ind.*, April:38–41 (1970); and Reynolds et al, *Che. Aerosol News*, 41:40–43 (1970)).

Spheronizers are well-known in the art, and are commercially available from Niro-Aeromatic, Inc. Caleva, LUWA (Fuji Paudal), Machine Collete, Glatt Air Techniques and Patterson Kelley. A spheronizers is a device consisting of a vertical hollow cylinder (bowl) with a horizontal rotating disc (friction plate) located inside. Extrudate is charged onto the rotating plate and broken into short segments by contact with the friction plate, by collision between particles, and by collisions with the wall. Mechanical energy introduced by the spinning friction plate is transmitted into kinetic energy in the form of a "mechanically fluidized bed", a more-or-less random mixture of air-borne particles moving at high velocities. Further processing will cause the extrudate to deform gradually into a spherical shape.

Beads (or pellets) are distinguishable from granules. Pelletization is an agglomeration process that converts fine powders or granules of, e.g., bulk biologically active ingredient and/or excipient into small, free-flowing, spherical or semi-spherical units. As opposed to the process of granulation, the production of beads results in a narrow size-range distribution. The more spherical nature of the beads compared to granules provides better flow, and reduces segregation due to shape differences. Also, the good surface morphology of beads provides an optimal surface for applying a functional coating, when desired.

In the present invention, extrusion-spheronization is carried out by the method comprising the steps of:

(a) granulating the microcrystalline cellulose; and (b) extruding the resulting granulation obtained in step (a) onto a spheronizer.

Microcrystalline cellulose is well-known in the art, and is available from a variety of commercial sources, e.g., Avicel® (FMC), Emococel® (Mendell) and Vivocel® (JRS).

The amount of microcrystalline cellulose employed is not critical to the present invention, and depends upon the desired density, porosity, and compactibility of the final freeze-dried cushioning beads. Generally, the amount of microcrystalline cellulose employed is about 20–100%, preferably about 60–95%.

In a preferred embodiment, the cushioning beads also comprise a disintegrant. The particular disintegrant employed is not critical to the present invention. Examples of such disintegrants include croscarmellose sodium, sodium starch glycolate, crospovidone, starch, and pregelatinized starch. Croscarmellose sodium is the preferred disintegrant employed in the present invention.

Croscarmellose sodium is also well-known in the art, and is available from a variety of commercial sources, e.g., Ac-Di-Sol® (FMC) and Primellose® (AVEBE).

The amount of disintegrant employed is also not critical to the present invention, and depends upon the desired density, porosity, and compactibility of the freeze-dried cushioning beads. Generally, the amount of disintegrant employed is about 0–50%, preferably about 5.0–40%.

The weight ratio of microcrystalline cellulose to disintegrant employed is also not critical to the present invention, and depends upon the desired density, porosity, and compactibility of the final freeze-dried cushioning beads. Generally, the weight ratio of microcrystalline cellulose to disintegrant employed is about 1:0–0.2:0.8, preferably about 0.95:0.05–0.6:0.4.

The desired density (granular density) is generally in the range of 0.5–1.5 g/ml, and is preferably identical to that of the biologically active ingredient-loaded beads.

The desired porosity is generally in the range of 30–80%, preferably 50–70%.

The desired compactibility is that which upon compaction of the cushioning beads produces a tablet with a friability of not more than about 1.0%.

Microcrystalline cellulose (as well as the disintegrant) are powdery components, and are granulated in step (a) with water as the granulating agent. The water may be a hydroalcoholic solution containing an alcohol, such as ethyl alcohol or propyl alcohol. The amount of water (hydroalcoholic solution) used will affect the mechanical properties of the freeze-dried beads, including the porosity, density, and compactibility. The amount of water (hydroalcoholic solution) employed depends on the composition of the powder mixture used in step (a). Generally, the amount of water (hydroalcoholic solution) used is such to give a final concentration, for solids in the granulation extruded in step (b), of about 20–80% (w/v).

The cushioning beads can, in addition, contain water-soluble fillers, such as lactose and sorbitol, or other water-insoluble fillers, e.g., dibasic calcium phosphate. These components can be co-granulated with the microcrystalline cellulose and disintegrant in step (a).

The amount of filler (either water-soluble or water-insoluble) present in the cushioning beads is not critical to the present invention and depends upon the desired density, porosity and compactibility. Generally, the amount of filler (either water-soluble or water-insoluble) employed in the range of about 0–80%, preferably about 0–50%.

It was found in the present invention that there is a statistically significant interaction between croscarmellose sodium and MCC/lactose ratio on the tensile strength of the compacts. Increasing the percentage of croscarmellose sodium in the formulation predominantly containing MCC produces compacts with higher tensile strength than if such an increase occurred in a lactose-predominant formulation. As the concentration of croscarmellose sodium is increased to 8.0%, an increase in the MCC/lactose ratio produces tablets with higher tensile strengths. In the presence of 8.0% croscarmellose sodium in MCC, the high porosity associated with the high granulation fluid requirement results in softer beads, which readily deform upon the application of pressure to give hard tablets. In formulations dominated by lactose, the presence of 8.0% croscarmellose sodium increases the water requirement and porosity to a lesser extent, but these beads were still hard due to solid bridge formation.

The cushioning beads can also contain other additives, such as colorants (e.g., FD&C and D&C, and their lake forms); sweeteners (e.g., various sugars, such as sucrose, mannitol, saccharin and its salts, and aspartame); flavoring agents (e.g., Anathenole N.F., Benzaldehyde N.F., Vanillin N.F., Ethyl vanillin N.F., Ethyl acetate N.F., and Methyl salicylate N.F.); and buffering agents, as is conventionally employed in the art.

The pressure at which the granulation in step (b) is extruded is not critical to the present invention, and depends upon the composition of the granulation to be extruded, its initial moisture content, the rotation speed of the spheronizer, the configuration of the extrusion blade and shaft, and the aperture size and shape of the extrusion screen of the spheronizer.

The rotation speed of the spheronizer is not critical to the present invention, and depends upon the water content of the extrudate, the composition and characteristics of the extrudate, the size and texture of the friction plate, and the spheronizer residence time. Generally, the friction plate is rotated at a speed of about 200–1500 RPM, preferably about 400–700 RPM.

The shaft and blade design varies in accordance with how much compression is needed. A low pressure extruder may have regularly spaced screw flights which will give some compression, but the main function of the flights is to transport the material down the barrel of the extruder. Another design utilizes progressively closer screw flights, a decreasing helix angle, to develop very high compressive forces.

The aperture size of the extruder screen of the spheronizer is not critical to the present invention, and depends upon the desired size of the beads to be produced. Generally, the aperture size of the extruder screen ranges from about 0.2–2.0 mm, preferably about 0.5–1.5 mm.

The shape of the aperture is generally cylindrical, although it can have a tapered inlet or outlet, or have a conical shape.

The friction plate of the spheronizer may have variety of sizes and textures. The size of the friction plate is not critical to the present invention. Generally, the size of the friction plate ranges from about 230–1000 mm, and affects the working capacity of the spheronizer (0.25–1.5 to 25–60 liters, respectively). The friction plate generally will have a cross-hatch pattern where the grooves intersect each other at 90° angles. A possible more efficient pattern is a radial design plate, where grooves emanate from the center like spokes of a bicycle wheel. In this case, more cutting edges are perpendicular to the direction of rotation so the resulting transfer of energy is greater. The grid pattern is usually matched with the desired particle size. For example, a 1.0 mm granule would be processed on a friction plate with an opening (groove) that is 50–100% larger. The wider groove allows the extrudate to fall into the openings so that the leading edge of the peak will fracture with extrudate into uniform lengths.

The spheronizer residence time is not critical to the present invention, and depends upon the amount and composition of the material added, the desired shape and the degree of spheronization accomplished. Generally, the spheronizer residence time is about 2.0–20 min, preferably about 4.0–8.0 min.

The temperature at which extrusion is carried out is not critical to the present invention, and depends upon the extrusion pressure. Generally, extrusion is carried out at about 10°–30° C., preferably about 20°–25° C.

Freeze-drying in step (b) is generally carried out at temperatures below the freezing point or collapse temperature. This is accomplished by keeping the pressure in the system at a pressure that is below the freezing point of the product. Freeze-drying produces highly porous and compactible cushioning beads, since the removal of water in the frozen state leaves a skeleton of solid material. Evaporation of water by other drying techniques, such as tray-drying or fluid-bed drying is accompanied by disadvantageous shrinking, which results in highly dense, and less compactible beads.

As discussed above, in another embodiment, the above-described objects of the present invention have been met by a tablet comprising:
  (i) biologically active ingredient-loaded beads; and
  (ii) cushioning beads comprising microcrystalline cellulose (and optionally a disintegrant), wherein said cushioning beads are prepared by extrusion-spheronization, followed by freeze-drying.

The means for preparing the biologically active ingredient-loaded beads is not critical to the present invention. For example, the biologically active ingredient-loaded beads can be prepared by techniques well-known in the art such as, extrusion-spheronization, solution/suspension layering, powder layering, balling (a pelletization process in which finely divided particles are converted, upon the addition of appropriate quantities of liquid, to spherical particles by continuous rolling or tumbling action), or fluidized bed roto-granulation.

The particular biologically active ingredient employed is not critical to the present invention, and may be any substance which is suitable for peroral administration, although the present invention is not limited to the use of substances which are only suitable for peroral administration.

Examples of such biologically active ingredients include pharmaceuticals, pesticides and herbicides.

The particular pharmaceutical employed is not critical to the present invention. Examples of such pharmaceuticals include potassium chloride (administered in hypokalemia); lithium salts (administered in psychotherapy); nonsteroidal anti-inflammatory drugs, such as ibuprofen; calcium salts (administered in the therapy of hypocalcemic states or for calcium supplementation); sodium fluoride (administered in the treatment of osteoporosis); pridinol or a salt thereof (administered as a muscle relaxant); dimethindine or a salt thereof (administered as an antihistaminicum); methylxanthines, such as propoxyphylline, dipropylline and/or theophylline (administered as bronchodilators); O-β- hydroxymethyl-rutoside (administered in the treatment of venous diseases); butamirate or a salt thereof, codeine or a derivative thereof, or noscapine (administered as antitussive drugs); acetaminophen (administered as an antipyretic); vitamins or multivitamin preparations; β-blockers (administered as cardiovascular and vascular drugs); pyrisuccideanol, ticlopidine, dipyridamole or diazepam (administered against elderly or pediatric diseases); drugs used to balance hydroelectrolytes, such as for the treatment of diarrhoea; and erythromycin or a salt thereof or doxycycline or a salt thereof (administered as antibiotics).

The particular pesticide employed is not critical to the present invention. Examples of such pesticides include clomazone (Command®), sulfentrazone (Authority®) and clomazone/trifluralin (Commence®).

The particular herbicide employed is not critical to the present invention. Examples of such herbicides include zeta cypermephrin (Fury®), cadusafos (Rigby®) and bifenthrin (Brigade®).

Optionally, a coating material may be applied to the biologically active ingredient-loaded beads for controlling or sustaining the release properties of the biologically active ingredient, for taste masking, or for imparting resistance to gastric fluid.

The particular coating material employed is not critical to the present invention, and depends upon the purpose of the coating material, e.g., the desired release profile, the ability of the coating layer to stay intact, and the ability of the coating layer to withstand the mechanical stress of compaction without cracking.

Examples of coating materials useful for controlling or sustaining the release properties of the biologically active ingredient include methylcellulose, hydroxypropyl cellulose, ethylcellulose or latex derivatives thereof, such as Surelease® and Aquacoat®, and methylacrylate ester copolymers, such as Eudragit® RL 30D, RS 30D, L30 D-55, and NE30D.

Examples of coating materials useful for taste masking include the above-listed materials useful for controlling or sustaining the release properties of the biologically active ingredient.

Examples of coating materials useful for imparting resistance to gastric fluid include shellac, cellulose acetate phthalate (Aquateric®), cellulose acetate trimelliate, hydroxypropyl methylcellulose phthalate, polyvinyl acetate phthalate (Coateric®), hydroxypropyl methylcellulose acetate succinate (AQOAT®), and methacrylic acid copolymers, such as Eudragit® L30D and L100-55.

The thickness of the coating layer employed is not critical to the present invention, and depends upon the desired release profile of the biologically active ingredient. Generally, the thickness of the coating layer will be in the nano to micro ranges.

Alternatively, the above-listed materials (or polymers) can be incorporated in a matrix system together with the biologically active ingredient-loaded beads to, e.g., sustain its action. Such incorporation can be carried out during dry powder mixing prior to granulation, or in the granulation solution prior to extrusion-spheronization, or in the other techniques conventionally used to produce pellets or beads.

When incorporated into the matrix system, the amount of such materials (or polymers) employed is not critical to the present invention, and depends upon the purpose of the material, e.g., the desired release profile of the biologically active ingredient.

The tablets can also contain a viscosity enhancer. The particular viscosity enhancer employed is not critical to the present invention. Examples of such viscosity enhancers include carbomers, xanthan gum, guar gum, alginates, dextran, pectins, pregelatinized starches, polysaccharides, cellulose derivatives, such as sodium or calcium carboxymethylcellulose, hydroxypropyl cellulose or hydroxypropylmethyl cellulose. Carboxymethylene (carbomer) is the preferred viscosity enhancer because such is effective at very low concentrations (0.1–0.3% (w/w), and has a quick hydration rate.

The viscosity enhancer may be present as individual beads, or may be a component of the biologically active ingredient loaded-beads, if those beads are intended for immediate delivery of the biologically active ingredient, i.e., where no sustained action or coating material (or polymer) is employed. In this case, the amount of viscosity enhancer employed in the biologically active ingredient-loaded beads is not critical to the present invention.

The viscosity enhancer beads may be produced by extrusion-spheronization using a hydroalcoholic solution, or by powder-layering alone, or together with the biologically active ingredient. This approach avoids the detrimental effects of ionic salts or pH modifiers on the ability of the viscosity enhancer to build-up viscosity when hydrated. Also, extrusion-spheronization of the viscosity enhancer using a hydroalcoholic granulating liquid reduces the tackiness thereof.

The particular hydroalcoholic solution employed is not critical to the present invention. Examples of such hydroalcoholic solutions employed include ethyl alcohol, propyl alcohol, or a mixture thereof. The alcohols may be mixed with water to provide the hydroalcoholic solution.

The amount of alcohol in the hydroalcoholic solution employed is not critical to the present invention, and depends upon the viscosity enhancer employed, and the processability (in terms of tackiness) of the granulation and its extrudate. Generally, the amount of alcohol will be about 0–100%, preferably about 40–60%.

The size of the beads, whether they are the cushioning beads, biologically active ingredient loaded-beads or the viscosity enhancer beads, is not critical to the present invention, but a similar size and size distribution is required to minimize segregation. Larger beads tend to float at or near the top of the pellet mass prior to mixing in a hopper, or the feeding frame during tabletting, thereby severely altering the uniformity of the pellet blend, and causing variability in the biologically active ingredient content or potency of the tablet. Generally, the beads have an average diameter of about 0.2–2.0 mm, preferably about 0.5–1.5 mm. The biologically active ingredient-loaded beads generally should be smaller than approximately 2.0 mm, so that such can be transported continuously, together with the food content, through the digestive tract. In this manner, the quality, amount of timing of food uptake, as well as the movement and relaxation time of the body, is of minor influence on the release of the biologically active ingredient.

The weight ratio of cushioning beads to biologically active ingredient-loaded beads is not critical to the present invention, and depends upon the acceptable amount of dose dumping which can be tolerated. Increasing the percentage of the cushioning beads decreases the amount of dose dumping. Dose dumping can be attributed to the failure of the sustained-release properties of the biologically active ingredient, which is the result of cracks occurring in the membrane of the beads that are induced by the mechanical stresses of compaction. Generally, the weight ratio of cushioning beads to biologically active ingredient-loaded beads is about 20:80–90:10, preferably about 50:50–75:25.

When viscosity enhancer beads are present in the tablet, the weight ratio of cushioning beads to biologically active ingredient loaded-beads to viscosity enhancer beads is not critical to the present invention, and depends upon the desired viscosity required to keep the biologically active ingredient-loaded beads suspended until the suspension is swallowed by the patient. Generally, the viscosity enhancer, either as individual beads or as a component of the biologically active ingredient-loaded beads, is present in an amount to achieve an apparent viscosity, at 20° C., of 30–3000 mPa.s, preferably of 500–1000 mPa.s. This viscosity is required to form a homogenous suspension, depending on the size and density of the biologically active ingredient-loaded beads.

The tablets can also contain components traditionally employed in the formulation of tablets, e.g., a flavoring agent, a sweetener, a colorant agent, and a buffering agent, such as those listed above, as well as a lubricant, e.g., magnesium stearate, hydogenated vegetable oil, or stearic acid.

Tabletting of the beads is effected by the type and ratio of the cushioning beads surrounding the biologically active ingredient-loaded beads, the physical characteristics of the biologically active ingredient-loaded beads and other components present in the system, the type and characteristic of the coating material, if any, employed with the biologically active ingredient-loaded beads, and the compression pressure used in the production of tablet compacts.

The compression pressure used in the production of tablet compacts is not critical to the present invention, and depends upon the nature and percentage of the cushioning beads, the biologically active ingredient-loaded beads, and other excipients included in the tablet, such as a viscosity enhancer or lubricant, which is added to facilitate the ejection of the tablet from the die following compression. Typical lubricants employed, e.g., magnesium stearate, tend to produce tablets with lower tensile strengths. Generally, the compression pressure will be about 5–50 MPa, preferably about 10–30 MPa.

When using a viscosity enhancer, the tablets of the present invention are useful for preparing an immediate release suspension (when no coating material is used on the biologically active ingredient-loaded beads or when no polymer is incorporated in the matrix system of the biologically active ingredient-loaded beads) or a sustained release suspension (when a coating material is used on the biologically active ingredient-loaded beads or when a polymer is incorporated in the matrix system of the biologically active ingredient-loaded beads), and rapid disintegration when the tablet is immersed in an aqueous solution. The tablets of the present invention disintegrate in a couple of seconds, which has heretofore, not been achieved in the art, and give rise to a formation of a suspension in situ over a period of less than 1.0 min, which also heretofore, has not been achieved in the art.

The in situ suspension is useful for preparation of sustained release liquid products for either elderly or pediatric patients who cannot swallow tablets or capsules, or for patients who require large doses of biologically active ingredients, where swallowing large dosage forms is difficult.

The following examples are provided for illustrative purposes only and are in no way intended to limit the scope of the present invention.

In the Example below, all percentages are weight percentages, unless otherwise indicated.

EXAMPLE 1

Selection and Processing of the Viscosity Enhancer

I. Introduction

Many factors play a role in the selection of a viscosity enhancer to be incorporated in tablet systems intended to be dispersed instantaneously to form suspensions. Most important of which is the concentration needed in the dispersed phase to impart sufficient structure and/or viscosity to reduce the sedimentation or floating of the particles. Despite the fact that such tablet systems are not intended to be swallowed as such by the patient, it is desirable from a practical point of view to choose a polymer which requires the least possible concentration so that least bulky tablets can be produced. Apart from the viscosity produced by the polymers, the ideal polymer should preferably exhibit a minimum yield value (plastic flow) irrespective of the viscosity, so that sedimentation would not occur (Meyers et al, *J. Soc. Cosmet. Chem.*, 10:143–154 (1959)). The second factor to be considered is the rate of build-up of viscosity which should be fast enough to provide adequate suspension properties, yet should not interfere with the disintegration of the tablet.

In studying the rheology of different polymers, it is essential to simulate the rate of shear which will be encountered in administering the dosage form. Since most of the polymers exhibit plastic or pseudoplastic flow properties, viscosity cannot be determined without referring to the shear rate. This is because in Non-Newtonian systems, the shear rate is not proportional to shear stress. The shear rate exerted on the suspending vehicle by the sedimentation of the suspended particles is in the range of 0.001–0.1 sec$^{-1}$ (*Rheological Properties of Cosmetics and Toiletries*, Marcel Dekker, Inc. (1993)). For larger-size particles, such as that encountered with spheres, the shear rate is expected to be higher, especially when considering the fact that the dispersed particles exhibit an additional momentum imposed by the stirring action which occurs when the extemporaneous self-suspending tablet is stirred in water. Thus, the viscosities of the various polymers were studied over a shear rate range up to 1.0 sec$^{-1}$ using a couette attachment.

The couette (cup and bob) attachment offers the advantage of its ability to test low viscosity fluids so that valid measurements over the entire shear range can be measured. However, when plastic flow is encountered, the cup and bob attachments are more likely to produce variable shear stress across the distance between the shearing head and the container walls, resulting in a "plug effect". This "plug effect" can be partially eliminated by using the largest diameter bob possible, or by using the appropriate cone and plate attachments. In the current work the "plug effect" was minimized by the use of the largest diameter bob possible.

II. Experiments

A. Materials

Eight rapidly hydrating viscosity enhancers were evaluated for their Theological properties. Carbopol® EX214 grade (a previously neutralized salt of carbomer), Visquick® 21 and 11 (a combination of 2:1 and 1:1 guar gum/xanthan, respectively), Insta*Thick Xanthans, Insta*Thick Sodium Alginate®, Insta*Thick Carrageenan®, Insta*Thick Pectin® and Insta*Thick Gum Arabic®. The Insta*Thick® product line is a specially formulated line of viscosity enhancers produced by Zumbro Inc. to provide an instantaneous-dispersing quick-hydrating viscosity enhancers. These polymers, and all other materials used in the powder-layering and extrusion spheronization experiments are listed in Table 1 below.

TABLE 1

| Material | Trade Name | Supplier | Lot # |
|---|---|---|---|
| Carbomer, N.F. (salt) | Carbopol® EX214 | The B. F. Goodrich Company, Cleveland, OH | YJ002D3 |
| Guar gum/Xanthan (2:1) | Visquick® 21 | Zumbro, Inc. Hayfield, MN | G336-4 |
| Guar gum/Xanthan (1:1) | Visquick® 11 | Zumbro, Inc. Hayfield, MN | G173-4 |
| Xanthan Gum, N.F. | Insta*Thick Xanthan® | Zumbro, Inc. Hayfield, MN | G143-4 |
| Sodium Alginate, N.F. | Insta*Thick Sodium Alginate® | Zumbro, Inc. Hayfield, MN | G044-4 |
| Carrageenan, N.F. | Insta*Thick Carrageenan® | Zumbro, Inc. Hayfield, MN | G073-0 |
| Pectin, USP | Insta*Thick Pectin® | Zumbro, Inc. Hayfield, MN | G097-4 |
| Acacia, N.F. | Insta*Thick Gum Arabic® | Zumbro, Inc. Hayfield, MN | G234-4 |
| Microcrystalline Cellulose, N.F. | Avicel® PH101 | FMC Corp., Philadelphia., PA | 1173 |
| Mannitol, USP | Mannitol Powder | SPI-Polyols, Inc. New Castle, DE | 31631-6 |
| Croscarmellose Sodium, N.F. | Ac-Di-Sol® | FMC Corp., Philadelphia. PA | T 314 |
| Crospovidone, N.F. | Polyplasdone-XL® | ISP Technologies, Inc., Wayne, NJ | S50427 |
| Povidone, USP | Plasdone® K29-32 | ISP Technologies, Inc., Wayne, NJ | TX40430C |
| Povidone, USP | Plasdone® K90 | ISP Technologies, Inc., Wayne, NJ | A40903 |
| Sugar spheres, N.F. | Nu-Pareil® (18–20 Mesh) | Crompton Knowles Mahwah, NJ | |

Solutions of different concentrations of each polymer (Table 2 below) were prepared 24 hrs in advance to ensure complete hydration. Dispersions were prepared by slowly sprinkling a known quantity of each polymer into the vortex of a rapidly stirred premeasured quantity of distilled water using a Nuova II Stir Plate (Model SP18425, Thermolyne Corp., Dubuque, Iowa). The dispersions were stirred for an additional 10 mins, and saved in bottles until they were evaluated.

TABLE 2

| Viscosity Enhancer | Solution Concentration (% weight/volume) |
|---|---|
| Carbomer EX214 | 0.2%, 0.175%, 0.15% and 0.1% |
| Visquick® 21 | 1.0%, 0.75%, 0.5%, 0.25% and 0.125% |
| Visquick® 11 | 1.0%, 0.75%, 0.5%, 0.25% and 0.125% |
| Insta*Thick Xanthan® | 1.0%, 0.5%, 0.35%, 0.25% and 0.15% |
| Insta*Thick Sodium Alginate® | 2.0%, 1.5%, 1.0% and 0.5% |
| Insta*Thick Carrageenan® | 2.0%, 1.5%, 1.0% and 0.5% |
| Insta*Thick Pectin® | 4.0%, 2.0%, and 1.0% |
| Insta*Thick Gum Arabic® | 8.0% |

A Dynamic Stress Rheometer SR-200 (Rhiometrics, Piscataway, N.J.) with a couette (cup and bob) attachment was used to evaluate the viscosity of the different solutions of each polymer over a range of shear rate. A couette provides a large surface area to obtain low stress measurements for low viscosity fluids. Viscosity measurements using controlled stress were taken during the application of a stress that was linearly ramped.

Attempts to measure the hydration rate of some of the polymers listed in Table 1 above were made by sprinkling a known quantity of the polymer into the vortex of 20 ml of distilled water placed directly in the cup of the couette. Stirring of the dispersion was made via a tiny magnetic bar placed in the couette cup which in turn was placed over a magnetic stirrer. Stirring time was restricted to 30 sec, afterwhich the magnetic bar was removed from the cup and the viscosity of the dispersion in the couette was monitored as a function of time at a fixed shear rate of $0.1 \text{ sec}^{-1}$.

B. Powder-Layering of Carbomer EX214 on Sugar Beads

Figure 2:
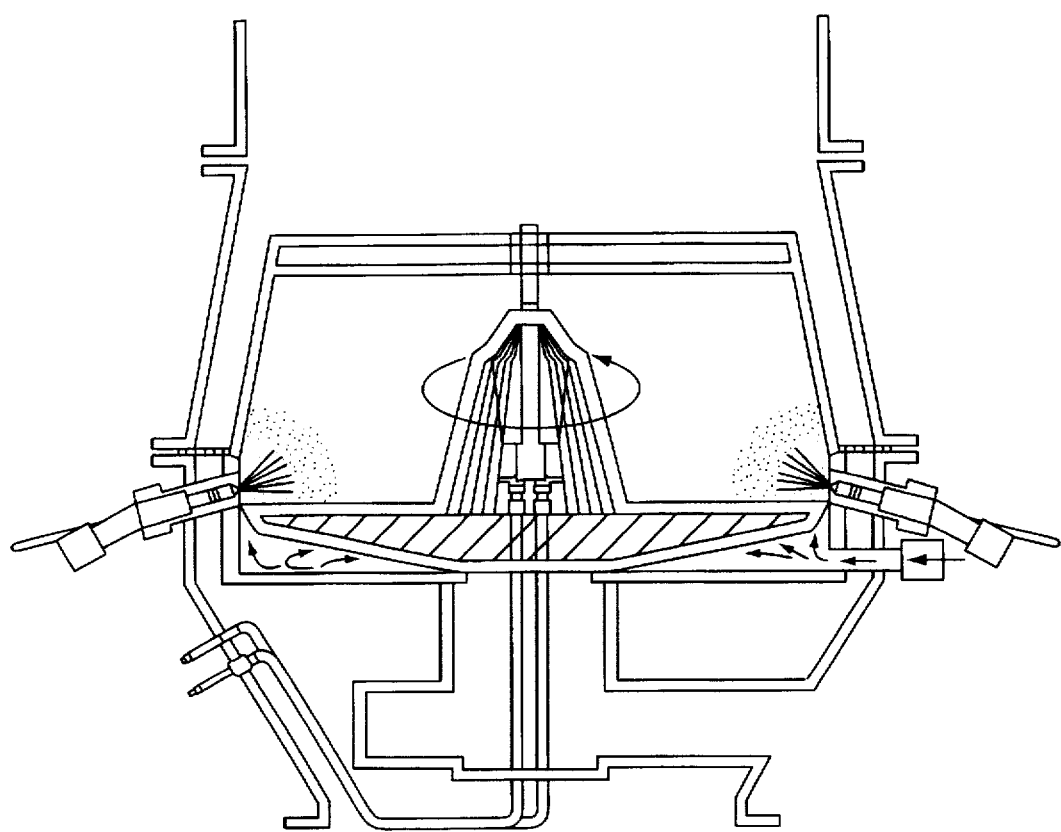
FIG. 2 shows a schematic diagram of an aeromatic rotoprocesser.

An Aeromatic® MP-1 with rotoprocessor module (FIG. 2) (Niro-Aeromatic, Columbia, Md.) was used to layer carbomer EX214 onto 18–20 mesh size cut of sugar spheres. Polyvinyl pyrollidone (PVP) dissolved in ethanol (USP) was used as the binder solution. The carbomer EX214 powder was fed through a screw feeder into the rolling bed of the sugar spheres after a 1.0 min lag period was allowed for the binder solution to wet the beads. Three different batches of powder-layered beads were produced by using three different alcoholic binder solutions: 2.0% PVP K29-32, 2.0% PVP K90, and 5.0% PVP K90. The layered beads were air-dried at room temperature overnight to allow the alcohol to evaporate. Table 3 below summarizes the process used to produce the layered beads.

TABLE 3

| Materials: | |
|---|---|
| Carbomer EX214 powder | |
| Binder solution | 2.0% or 5.0% alcoholic PVP K90 (Povidone, ISP) 2.0% alcoholic PVP K29-32 (Povidone, ISP) |
| Sugar spheres (18–20 mesh) | 1000 g |
| Equipment: | |
| Aeromatic MP-1 with rotoprocessor module | |
| Processing Conditions: | |
| Initial charge | 1000 g |
| Number of nozzles | 1 |
| Nozzle tip opening | 1.0 mm |
| Atomization air pressure | 1.75 bar |
| Gap pressure | 1.0 bar |
| Spray rate of binder solution | 8.9–9.8 g/min |
| Powder feed rate | 3.9–4.4 g/min |
| Rotary disc speed | 194 RPM |
| Total spraying time of the binder | 45–55 min |

The yield was calculated as the amount of carbomer EX214 sticking to the surface of sugar spheres relative to the amount added. The percentage load by weight was determined from the net weight of the dried product minus the initial weight of sugar spheres relative to the net weight of the dried product. The yield and percentage load by weight for the three different binder solutions are listed in Table 4 below. Magnified photographs of two selected batches of carbomer EX214 layered-beads were taken at a magnification of 23× using a Wild Leipz microscope (Wild Leipz USA Inc., Rockleigh, N.J.) connected to a Sony Video Printer (Model UP5000, Sony Corp., Tokyo, Japan).

TABLE 4

| Binder Solution | Rate of Addition of Solution (ml/min) | Rate of Addition of Powder (g/min) | Yield | % Load by Weight |
|---|---|---|---|---|
| 5.0% PVP K90 | 9.8 | 4.4 | 96.3% | 15.4% |
| 2.0% PVP K90 | 8.9 | 3.9 | 71.53% | 12.2% |
| 2.0% PVP K29-23 | 8.9 | 4.2 | 73.0% | 13.9% |

C. Release of Carbomer EX214 from Layered Beads

Each formulation was tested for the release of carbomer EX214 as a function of time by dispersing a precalculated amount of the beads sufficient to produce a concentration of approximately 0.175% carbomer in 2000 ml of distilled water placed in a 4.0 liter beaker stirred at a fixed speed (level 8) via a Nuova II Stir Plate (Model SP18425, Thermolyne Corp., Dubuque, Iowa). Samples of the supernatant were withdrawn via a syringe fitted with a stainless steel filter (200 μm opening) at 0.5, 1.0, 1.5, 3.0, 5.0, and 30 min. The amount of carbomer EX214 released was measured by titrating the carboxylic acid residues of carbomer EX214 in those samples against 0.01N NaOH to a pH end-point of 9.5. At pH 9.5, all of the COOH groups are neutralized since the pKa of carbomer EX214 is between 7 to 8. A Multi-Dosimat E145 automatic titrator (Brinkmann Instruments, Westbury, N.Y.) was used. The percentage of carbomer EX214 released at each time point was calculated as the ratio of the volume of the 0.01N NaOH required to neutralize the COOH groups of the carbomer EX214 present in the supernatant at that time point relative to that released at 30 min, at which time all of the carbomer EX214 is assumed to be released, multiplied by 100. The release profiles for the three different batches using the three different binder solutions were determined in triplicate.

D. Extrusion-Spheronization of Carbomer EX214

Different formulations containing 30% carbomer EX214 together with other excipients (Table 5 below) were prepared.

TABLE 5

| Code | MCC:Mannitol | % Ethanol/ H2O | Volume (ml) | Disintegrant Level & Type |
|---|---|---|---|---|
| Y3 | 100:0 | 50% | 1400 | No Disintegrant |
| Y4 | 100:0 | 50% | 1400 | 8.0% Croscarmellose Sodium |
| Y5A | 100:0 | 50% | 1600 | 8.0% Crospovidone |
| Y6A | 100:0 | 50% | 1400 | 16% Croscarmellose Sodium |
| Y7A* | 100:0 | 50% | 1800 | 16% Crospovidone |
| Y8A | 50:50 | 50% | 1200 | No Disintegrant |
| Y10 | 50:50 | 50% | 1300 | 8.0% Croscarmellose Sodium |
| Y9A | 50:50 | 50% | 1500 | 8.0% Crospovidone |
| Y11 | 50:50 | 50% | 1300 | 16% Croscarmellose Sodium |
| Y12 | 50:50 | 50% | 1700 | 16% Crospovidone |
| X4A | 100:0 | 25% | 1400 | No Disintegrant |

*This batch was generated in duplicate to check reproducibility.

The effect of certain formulation variables involved in the production of carbomer EX214 spheres by extrusion-spheronization was investigated to help in elucidating the significant factors affecting the release of carbomer EX214. The following factors were studied:

Effect of water-soluble excipients (as exemplified by mannitol) on the release of carbomer EX214 from spheres.

Effect of intra-sphere disintegrant type (croscarmellose sodium and crospovidone) and level (0%, 8.0%, and 16.0%) on the release of carbomer from spheres.

Effect of the granulating vehicle composition on the release of carbomer from spheres.

The powder mass of each formulation (1.0 Kg) was dry blended in a planetary mixer (Hobart Kitchen Aid Model K 45 SS, Hobart Corp., Troy, Ohio) for 5 min. This was followed by the addition of the granulating solution. A 50% alcohol-water system was used as the granulating agent. One additional formulation containing 30% carbomer EX214 in MCC was produced using 25% alcohol/water to study the effect of a lower alcohol level on the release of carbomer EX214. The required volume of the granulating liquid was added slowly over a period of 1.0 min. Wet granulation was continued for an additional 9.0 min until a cohesive, plastic mass was achieved. The wet mass was extruded through a 1.0 mm screen using the Nica® E-140 extruder (Niro-Aeromatic, Columbia, Md.). The extrudate was spheronized at 500 RPM for 5.0 min using the Nica® S-450 spheronizer (Niro-Aeromatic). Spheres produced were tray-dried at room temperature for 48 hrs, and the dried product was stored in double plastic bags for later evaluation.

E. Release of Carbomer EX214 from Beads Produced by Extrusion-Spheronization Each formulation was tested for the release of carbomer EX214 as a function of time by dispersing a precalculated amount (11.66 g) of the beads (20–30 mesh cut) sufficient to produce a concentration of 0.175% carbomer EX214 in 2000 ml of distilled water placed in a 4.0 liter beaker stirred at a fixed speed (level 8) via a Nuova II Stir Plate. Samples of the supernatant liquid were withdrawn via a syringe fitted with a stainless steel filter (200 μm opening) at 0.5, 1.0, 1.5, 3.0, 5.0, and 30 min. The amount of carbomer EX214 released was measured by titrating the carboxylic acid residues of carbomer EX214 against 0.01N NaOH solution to a pH end-point of 9.5, at which point all of the COOH groups were neutralized (the pKa of carbomer is between 7 to 8). A Multi-Dosimat E145 automatic titrator (Brinkmann Instruments, Westbury, N.Y.) was used.

The percentage of carbomer released at each time point was calculated as the ratio of the volume of the 0.01N NaOH required to neutralize the COOH groups of the carbomer EX214 present in the supernatant at that time point relative to that released at 30 min, at which time all the carbomer EX214 is assumed to be released, multiplied by 100. The release profile for each formulation was determined in triplicate.

III. Results and Discussion

A. Selection of Polymers to be Used as Viscosity Enhancers

The viscosity of different concentrations of carbomer EX214, Visquick® 11, Visquick® 21, and Insta*Thick Xanthan® as a function of the shear rate studied can be found in FIGS. 5–8, respectively. Insta*Thick Sodium Alginate®, Insta*Thick Carrageenan®, Insta*Thick Pectin® and Insta*Thick Gum Arabic® produced very low viscosities, even when used at high concentrations. Thus, these polymers were eliminated as potential candidate to be incorporated in the extemporaneous self-disintegrating tablet system.

When examining FIGS. 5–8, it is quite clear that these polymers exhibit shear thinning properties (viscosity decreasing with increasing shear rate). The initial increase in the viscosity at shear rates less than 0.1 sec$^{-1}$ can be attributed to the "plug effect".

Ellis et al (*Diabetic Medicine*, 8:378–381 (1991)) developed a method for monitoring the hydration rate of guar gum which involved the measuring of the change of viscosity at discrete time intervals over a period of 5 hrs using a Brookfield RVT rotoviscometer. Their initial hydration experiments encountered difficulties due to the aggregation and clump formation after the addition of water. This led to large differences in viscosity between replicates. To overcome this problem the guar samples were hydrated in screw-top glass jars which were rotated end-over-end for a minimum period of time needed to prevent aggregation.

A determination of the hydration rates of the polymers listed in Table 1 above by monitoring the change of viscosity as a function of time was attempted. Aggregation and clumping defects were observed. In some cases, the clumping was so marked that viscosity could not be measured, and in other cases, this led to large differences in the viscosity between replicates. Attempts of initially hydrating the polymers by mixing them in bottles to prevent aggregation resulted in almost complete hydration, thus further increases in viscosity could not be monitored.

Moreover, since the polymers to be used in the tablet system were further processed so as not to interfere with the disintegration process, measurement of the hydration rate of the polymer in the powder form is expected to be different from that in the processed state (powder-layering or extrusion-spheronization). Thus, the selection of the best polymer candidate to be incorporated in the tablet system was solely confined to its ability to increase the viscosity at the lowest possible concentration, rather than its hydration rate.

Figure 9:
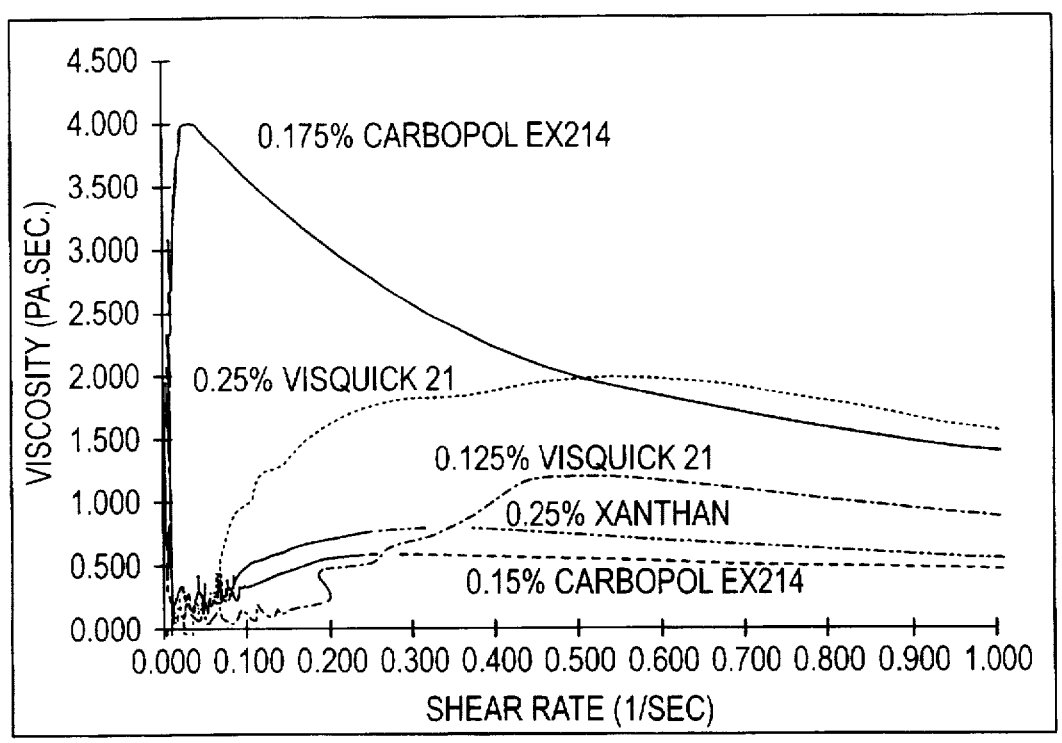
FIG. 9 shows viscosity of various polymers at concentrations suitable to be incorporated in self-disintegrating tablets as a function of shear rate.

An apparent viscosity range of 30–3000 mPa.sec was determined by Kimon (European Patent 0 273 005; and U.S. Pat. No. 4,886,669) to be appropriate to keep methyl xanthines-loaded beads (0.2–1.0 mm in size) suspended. FIG. 9 represents a plot of the viscosity produced by different polymer candidates at different concentrations as a function of the shear rate range believed to be exerted by the suspended particles. It is clear that carbomer EX214 achieved the required viscosity range at a relatively low concentration (0.175%).

B. Powder-Layering of Carbomer EX214 on Sugar Beads

Initial attempts of layering carbomer 971P using water as the binder solution failed. The idea behind using water as the binder solution was that it was expected that once the carbomer 971P powder comes in contact with the water-wetted surfaces of the beads, part of the carbomer would hydrate and would act as in situ binder for the remainder of the carbomer 971P powder. However, this was not the case, and the carbomer 971P grade was instead hydrating and causing agglomeration of the beads, preventing the free-rolling essential for successful powder-layering. The water, as a binder solution, was later replaced with a 5.0% aqueous solution of hydroxypropylmethyl cellulose. This did not provide any improvement as the beads continued to agglomerate.

These initial attempts suggested that there was a need to incorporate the binder in a non-aqueous solution which would not cause the carbomer 971P to hydrate rapidly. Polyvinyl pyrollidone (PVP) dissolved in ethanol was considered as a possible candidate. However, carbomer 971P has considerable solubility in ethanol, and hydration of the polymer could not be avoided, resulting in bead agglomeration. The partially-neutralized grade of carbomer (the EX214 grade) has minimal solubility in alcohol. Thus, further work was confined to layering carbomer EX214 using alcoholic PVP K29-32 or K90 as the binder solutions.

In the layering of carbomer EX214 on the surface of sugar spheres to enhance its dispersibility, two processing variables were studied. The first was the effect of similar alcoholic solutions of two different grades of PVP (K29-32 and K90) on the yield, percentage loading, and release profile as a function of time. The second was the effect of different concentrations of the PVP K90 binder solutions on the yield, percentage loading, and release profile of carbomer EX214 as a function of time.

Spray rate and powder application rate are considered to be the most critical variables in the powder layering process. Adding the powder too slowly leads to a wet bed and agglomeration of pellets. Adding the powder too quickly results in a dry bed with excessive loss of powder through the exhaust system and powder caking on the walls of the pan. Equally important is that the surface of the pellets will vary depending on the conditions of the bed. Pellets layered in a "dry" bed often have a rough surface. Pellets layered in a "wet" bed will have smoother surfaces, but the batch will have an increased number of twins and triplets. The slight roughness on the surfaces of the final product seen in magnified photographs can be attributed to the poor flowability observed when the carbomer EX214 was flowing through the screw feeder, rather than sub-optimal balance between spray rate and powder feed rate. This poor flowability introduced some powder lumps into the rolling bed thus causing a degree of surface roughness in the end product. Similar concentrations of PVP K29-32 and K90 produced a similar degree in surface roughness.

C. Effect of Binder Concentration and Type on the Yield and Percentage Loading

In order to study the effect of the binder concentration and type on the yield and percentage loading, the spray rate and powder application rate were fixed to approximately 9.0 ml/min and 4.0 g/min, respectively. The two binders studied at the 2.0% level showed similar yields and percentage loadings as seen in Table 4 above, indicating that the binder types studied had no effect on the yield and percentage loading. The 5.0% K90 formulation produced higher yield and higher percentage loading than the 2.0% K90 formulation, which can be attributed to the stronger adhesive power of the more viscous solution of 5.0% K90 when compared to that at the 2.0% level. Thus, more carbomer EX214 was sticking to the sugar spheres.

Figure 10:
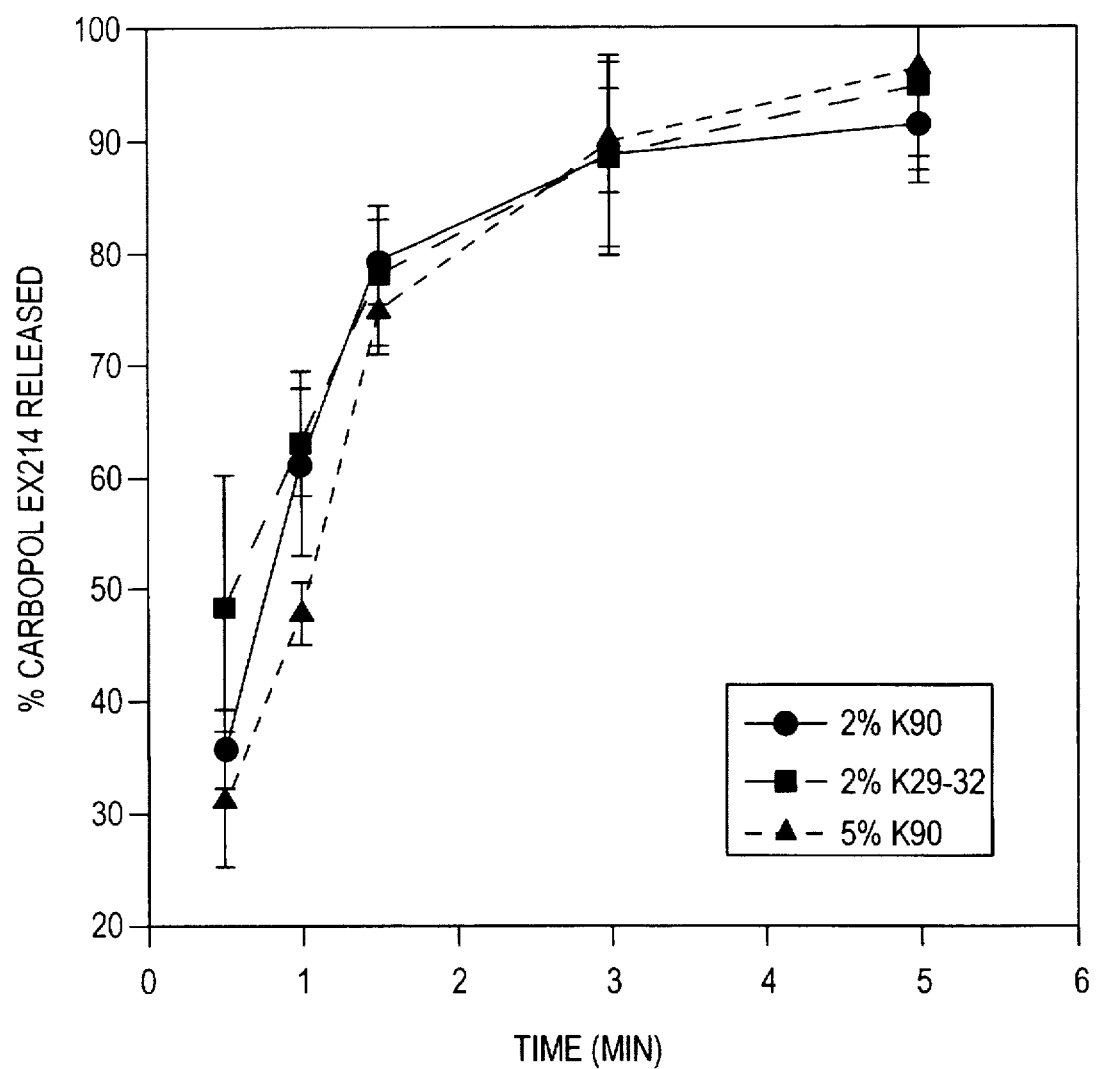
FIG. 10 shows release of carbomer EX214 as a function of time from powder-layered beads using different alcoholic PVP solutions.

D. Effect of Binder Type on the Release of Carbomer EX214 from Powder-Layered Beads When the carbomer EX214 layered beads were dispersed in water, the outermost layer of the polymer became hydrated, thereby impeding further penetration of water into deeper layers. The different release profiles were obtained based on the addition of a precalculated amount of the beads (calculated from the percentage load by weight—Table 4 above) sufficient to produce a final concentration of approximately 0.175% carbomer EX214 in water. Thus, beads with higher percentage loading (5.0% K90) required lower amount to achieve the desired concentration. The lower the amount of layered beads with higher percentage loading provided lower surface area available for the release of carbomer EX214, and thus resulting in slower release. This can be seen clearly with the 5.0% K90 batch which exhibits a high yield and a high percentage loading (Table 4 above), thereby giving a statistically significantly ($p<0.05$) slower release of Carbopol EX214 in the early time points, as can be seen in Table 6 below and FIG. 10.

In order to check the effect of different binders studied (K29-32 and K90) on the release profiles of carbomer EX214 from the different layered beads, batches having similar loading were compared. The 2.0% K90 and 2.0% K29-32 formulations with corresponding loading of 12.2% and 13.9%, respectively, produced similar release profiles as depicted in Table 6 below and FIG. 10, indicating a negligible effect of the binder type on the release of carbomer EX214.

TABLE 6

| Time (min) | 2.0% K29-32 | 2.0% K90 | 5.0% K90 |
|---|---|---|---|
| 0.5* | 35.63 | 48.19 | 31.25 |
| | (3.35)+ | (12.05) | (5.92) |
| 1.0** | 61.16 | 63.08 | 47.62 |
| | (8.20) | (4.75) | (2.84) |
| 1.5 | 79.22 | 78.01 | 89.90 |
| | (3.89) | (6.30) | (4.56) |
| 3.0 | 88.63 | 88.51 | 89.90 |
| | (8.18) | (8.88) | (4.56) |
| 5.0 | 91.27 | 94.73 | 96.34 |
| | (5.08) | (7.40) | (7.82) |

*Significant difference exists among the formulations $p < 0.1$, no difference between 2.0% K29 and 2.0% K90
**Significant difference exists among the formulations $p < 0.05$, no difference between 2.0% K29 and 2.0% K90
+Relative standard deviation Layering of carbomer EX214 on sugar spheres or on beads containing a biologically active ingredient exposes the polymer at the surface, rather than internally in a matrix system commonly encountered in beads produced by extrusion-spheronization. Thus, it would be expected that faster viscosity build-up is associated with powder-layered beads. The presence of polymer at the surface of the beads might result in quick hydration, which might impede the tablet disintegration. Moreover, layering carbomer EX214 on the surface of beads containing biologically active ingredient makes it more system-specific, and less robust to be used in other systems. Whereas, carbomer EX214 beads produced by extrusion-spheronization can be mixed with any beads containing biologically active ingredient, and compressed into a tablet, making them more diverse in application.

E. Extrusion-Spheronization of Carbomer EX214

A major problem encountered with processing any grade of carbomer is that it becomes very tacky when wetted, which introduces handling problems, such as those encountered with wet granulation techniques prior to extrusion-spheronization. Previous workers (Chow et al, "Fabrication and Characterization of Extruded and Spheronized Beads Containing Carbopol EX214) tried to circumvent this problem by modifying the pH or the ionic strength of the granulation fluid. However, high alkalinity (B.F. Goodrich literature, Cleveland, Ohio) can collapse the resin structure, resulting in a permanent loss in viscosity. Moreover, soluble salts decrease the efficacy of the carbomer resin mucilages, in terms of building-up viscosity, with the di- and tri-valent cations producing more drastic loss in efficacy than monovalent cations (Charman et al, Drug. Dev. Ind. Pharm., 17(2) :271–280 (1991)).

The objective behind the extrusion-spheronization of carbomer EX214 powder was to formulate carbomer in a readily dispersible form capable of instantaneously generating viscosity with minimal dispersion defects in various matrices using a hydroalcoholic granulating solution to reduce the tackiness.

The percentage of carbomer EX214 released from a 20–30 mesh sieve-cut can be found in Table 7, below

TABLE 7

| | 100:0 MCC/Mannitol | | | | | 50:50 MCC/Mannitol | | | | |
|---|---|---|---|---|---|---|---|---|---|---|
| | 0% | 8.0% CCS* | 16.0% CCS* | 8.0% CP** | 16.0% CP** | 0% | 8.0% CCS* | 16.0% CCS* | 8.0% CP** | 16.0% CP** |
| Code | Y3 | Y4 | Y6 | Y5A | Y7A | Y8A | Y10 | Y11 | Y9 | Y12 |
| Time (min) | | | | | | | | | | |
| 0.5 | 35.4 | 35.8 | 24.4 | 39.6 | 49.0 | 42.5 | 26.9 | 33.0 | 48.8 | 48.5 |
| | (8.7)+ | (0.9) | (6.1) | (2.0) | (1.7) | (7.4) | (0.5) | (1.3) | (1.3) | (1.3) |
| 1.0 | 69.3 | 66.3 | 45.4 | 67.1 | 75.2 | 61.7 | 56.1 | 56.9 | 80.4 | 71.7 |
| | (2.5) | (9.9) | (2.0) | (7.2) | (1.2) | (3.4) | (6.6) | (8.8) | (2.6) | (5.8) |
| 1.5 | 86.5 | 86.3 | 67.3 | 91.0 | 89.9 | 74.5 | 73.1 | 72.7 | 93.1 | 86.6 |
| | (4.4) | (11.9) | (3.7) | (2.9) | (1.0) | (8.1) | (3.0) | (6.1) | (5.9) | (3.3) |
| 3.0 | 98.5 | 94.7 | 98.0 | 97.1 | 95.9 | 100.9 | 95.3 | 98.3 | 98.6 | 94.7 |
| | (3.0) | (5.9) | (0.5) | (5.0) | (0.2) | (2.1) | (5.9) | (1.8) | (3.7) | (2.3) |
| 5.0 | 99.8 | 96.5 | 99.2 | 98.7 | 99.3 | 100.1 | 95.4 | 96.2 | 96.3 | 98.1 |
| | (0.4) | (3.8) | (2.1) | (0.8) | (1.5) | (4.3) | (3.2) | (2.6) | (2.4) | (2.9) |

*Croscarmellose sodium
**Crospovidone
+Relative standard deviation

Figure 11:
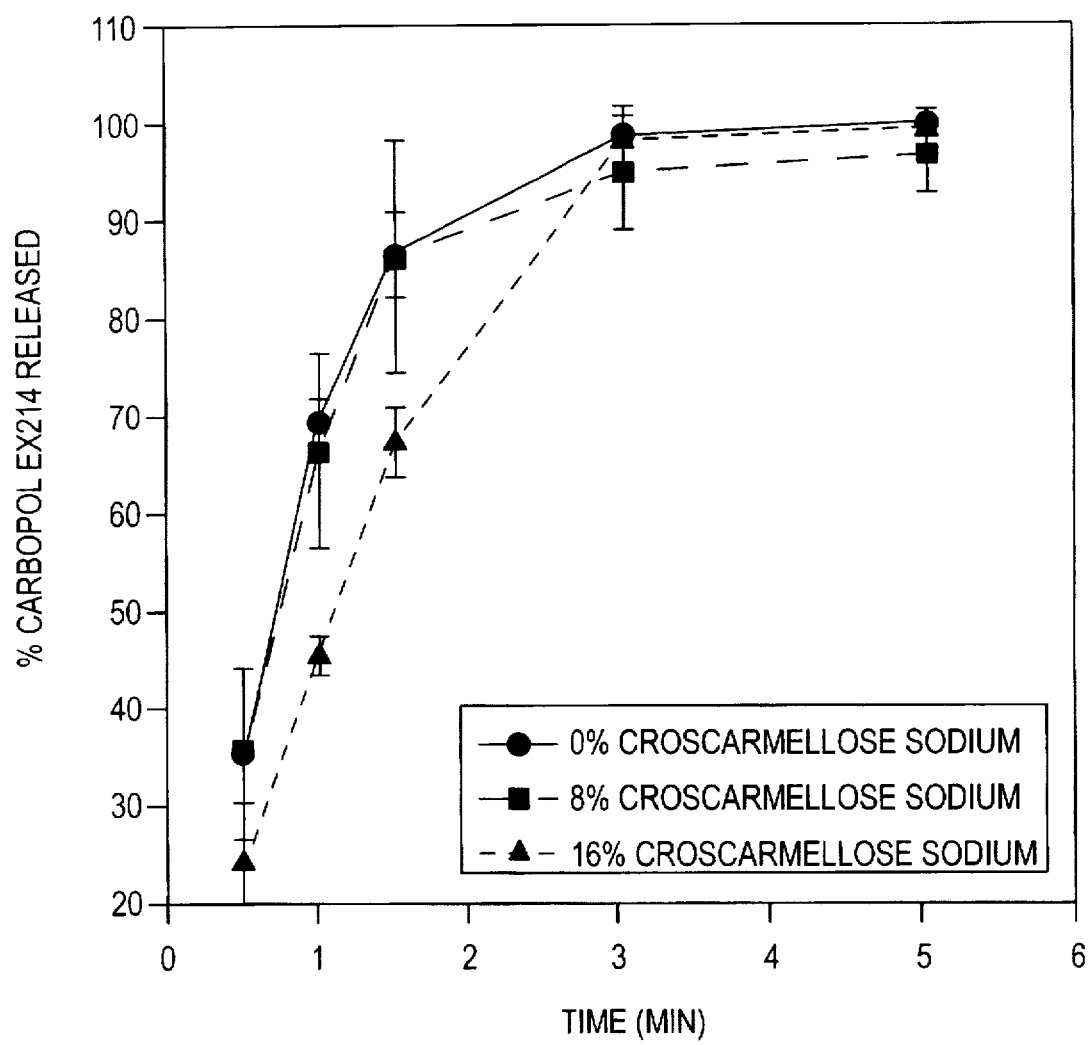
FIG. 11 shows the effect of croscarmellose sodium incorporation on the release of carbomer EX214 as a function of time from beads produced by extrusion-spheronization.
Figure 12:
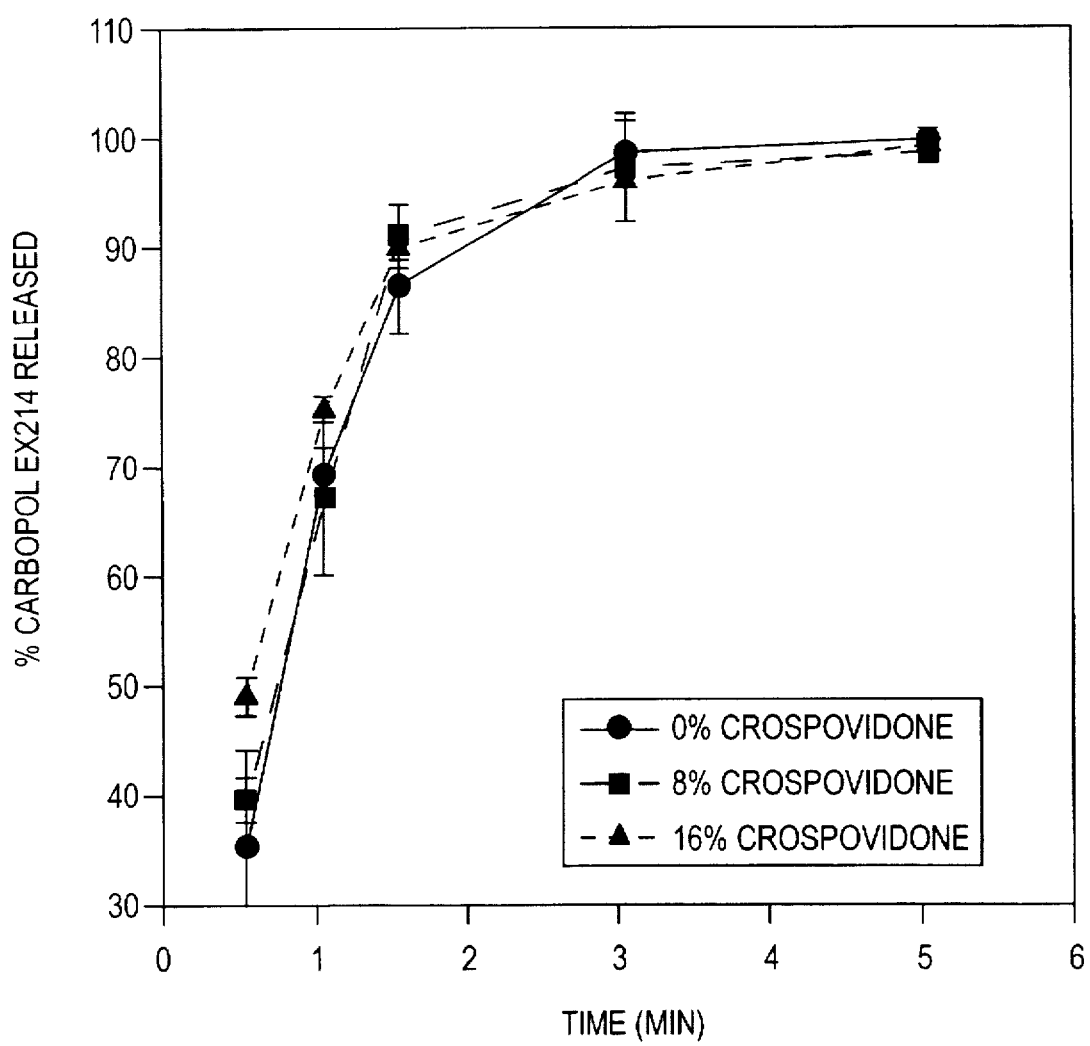
FIG. 12 shows the effect of crospovidone incorporation on the release of carbomer EX214 as a function of time from beads produced by extrusion-spheronization.
Figure 13:
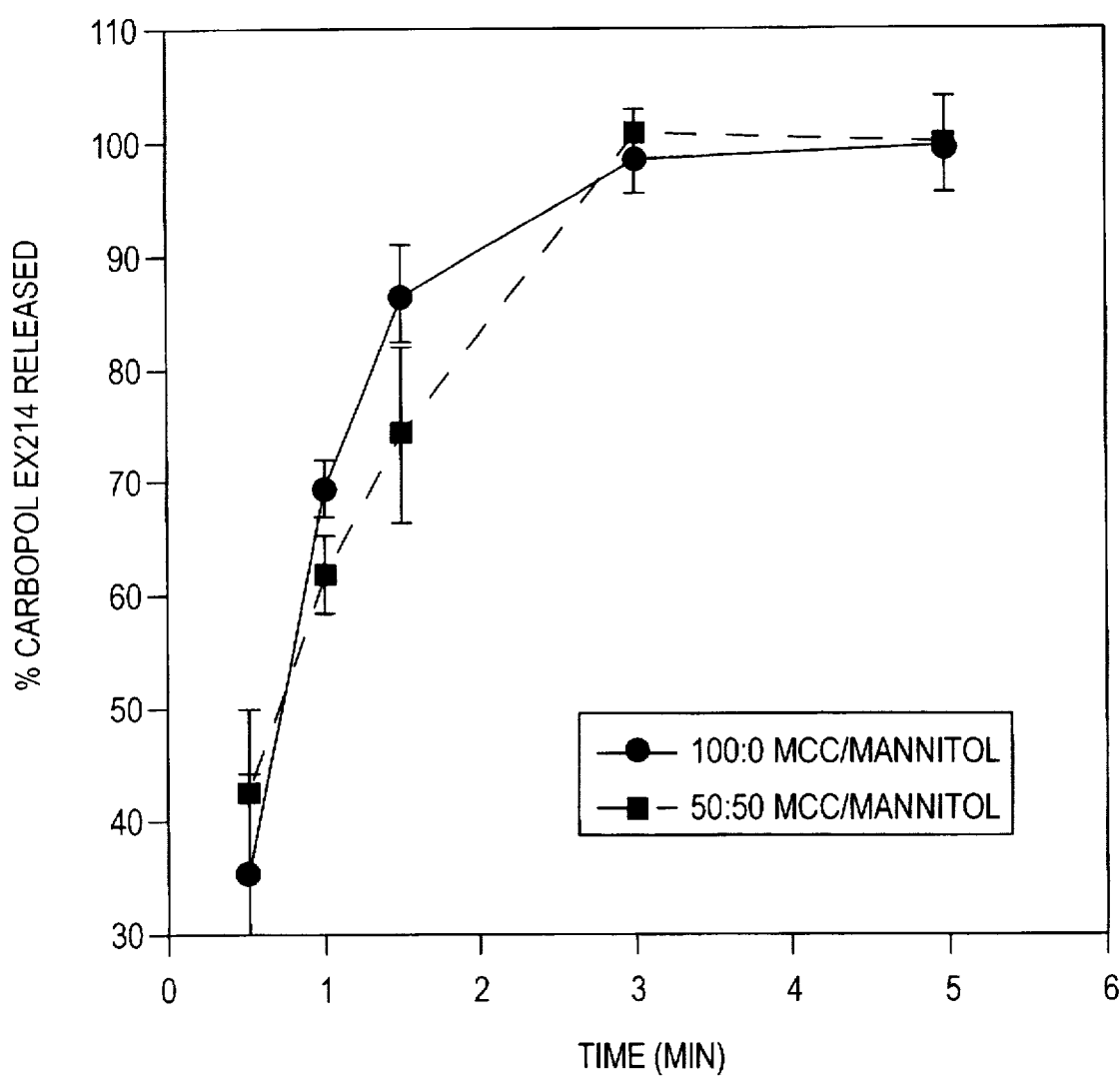
FIG. 13 shows the effect of MCC/mannitol ratio on the release of carbomer EX214 as a function of time from beads produced by extrusion-spheronization.
Figure 14:
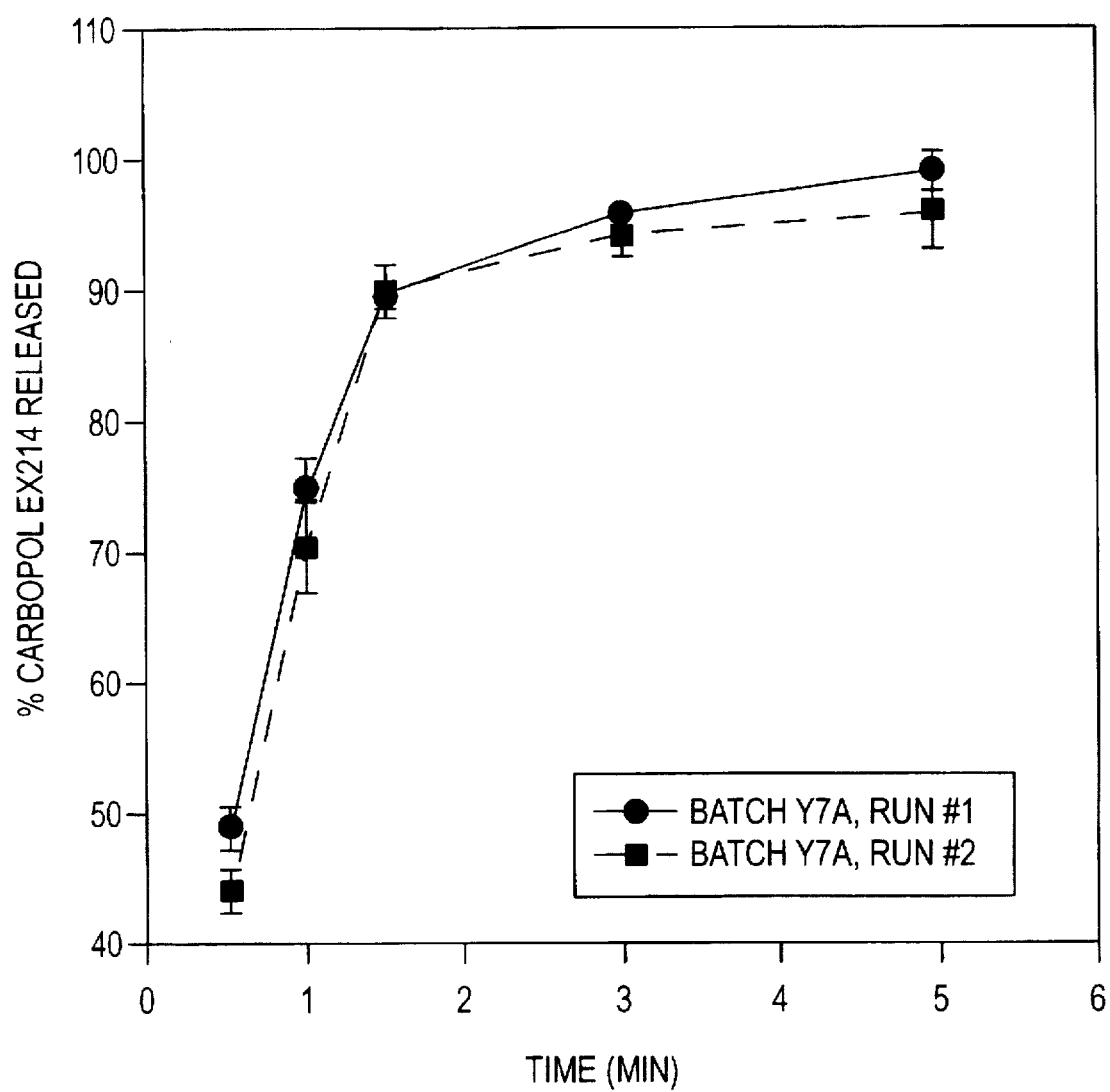
FIG. 14 shows the release of carbomer EX214 as a function of time from duplicate batches of beads produced by extrusion-spheronization.
Figure 15:
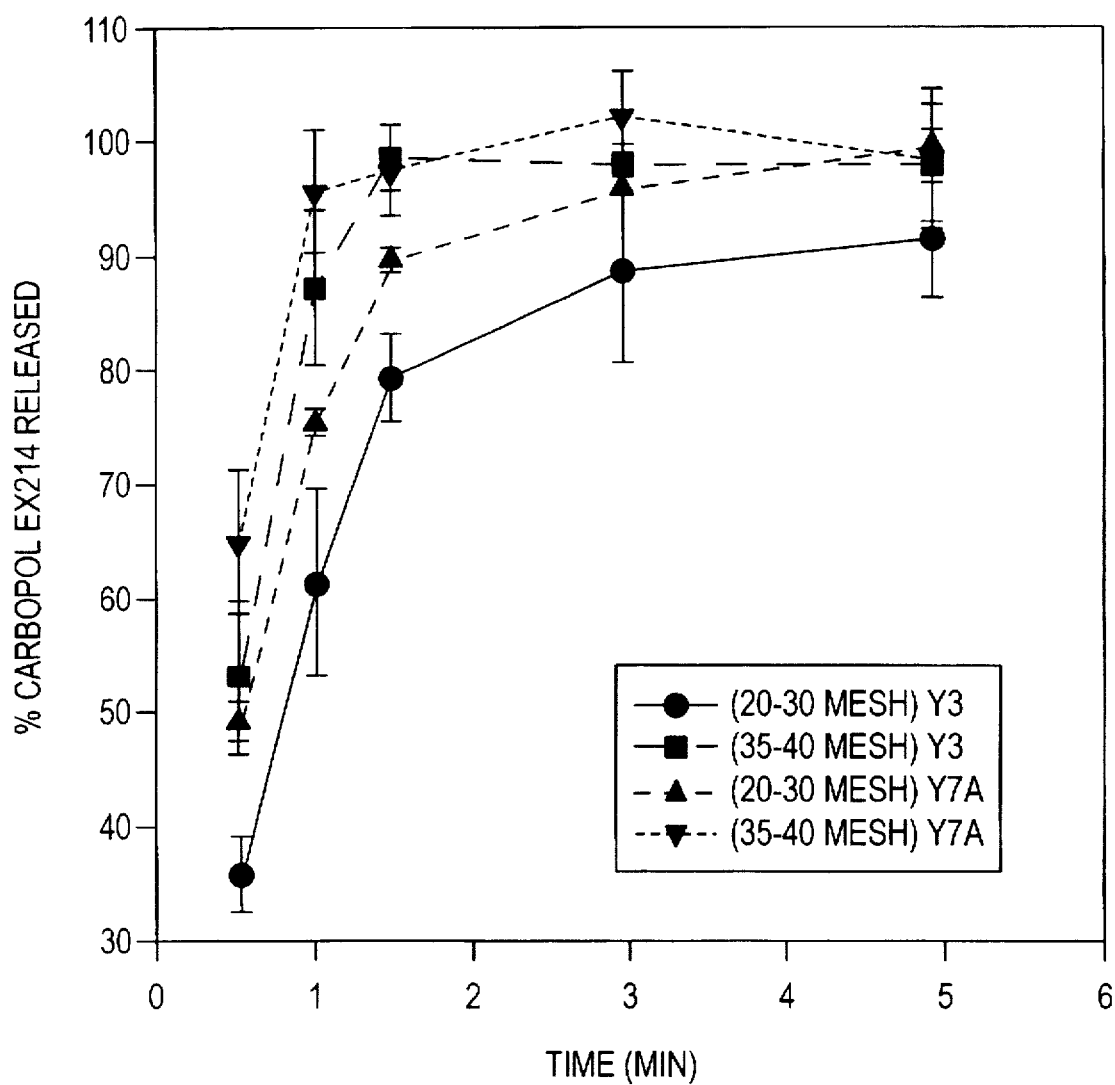
FIG. 15 shows the effect of sphere size on the release of carbomer EX214 as a function of time from beads produced by extrusion-spheronization.
Figure 16:
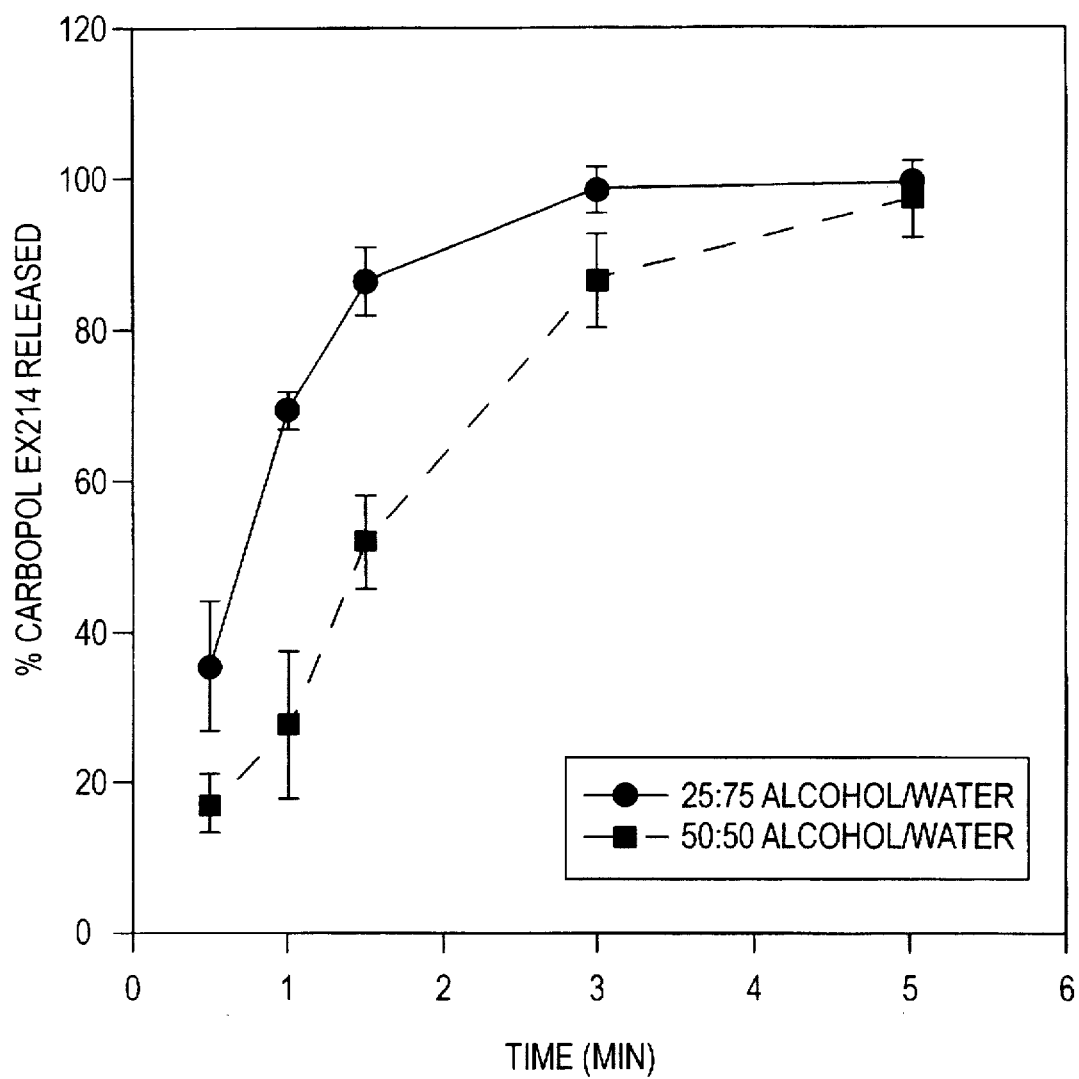
FIG. 16 shows the effect of alcohol/water ratio on the release of carbomer EX214 as a function of time from beads produced by extrusion-spheronization.

The effect of croscarmellose sodium and crospovidone incorporation on the release of carbomer EX214 from beads containing 100% MCC (using 50% hydroalcoholic granulating solution) are depicted in FIGS. 11 and 12, respectively. FIG. 13 represents the effect of MCC/mannitol ratio on the release of carbomer EX214 from beads containing no disintegrants. FIG. 14 represents the release profiles for the two batches of Y7A prepared to check for reproducibility. FIG. 15 depicts the release of carbomer EX214 from different sieve-cuts of spheres; namely: 20–30 mesh and 35–40 mesh cuts, for formulations Y3 and Y7A. Moreover, the percentage released as a function of time for formulation Y3 and X4A, whose granulating fluid alcohol/water ratio was varied from 50/50 to 25/75, respectively, is shown in FIG. 16.

ANOVA analysis for the 20–30 mesh cut of the formulations prepared using a 50% hydroalcoholic solution as the granulating fluid at 0.5, 1.0, 1.5, and 3.0 min intervals revealed that a significant difference in percentage released existed only at 0.5, 1.0, and 1.5 min (p-value less than 0.00001). Regression analysis revealed that crospovidone had no significant effect on carbomer EX214 release (FIG. 12), whereas croscarmellose sodium significantly decreased the release until the 3.0 min interval (FIG. 11). Mannitol significantly decreased the release only at 1 min.

It seems that the carbomer-containing beads produced by extrusion-spheronization do not disintegrate but, rather, dissolve/erode as a function of time. This conclusion is supported by the fact that different sieve cuts for each of the two formulations tested revealed a significant difference in the release profile with the smaller sieve-cut (35–40 mesh fraction) releasing faster than the 20–30 mesh (FIG. 15). The inability of the superdisintegrant incorporated to enhance the release of carbomer by breaking apart the beads supports the fact that disintegration is not contributing significantly to the release of carbomer EX214. This inability can be attributed to the fact that when the beads are hydrated, carbomer EX214 forms a very viscous environment, thereby preventing the disintegrants from exerting their action. The effect of croscarmellose sodium in decreasing the release of carbomer can be attributed to the additional viscosity and gelling action imparted by the wetted croscarmellose sodium, especially when present at high levels. This is seen in FIG. 11 where at the 8.0% croscarmellose sodium level, release was not affected, whereas at the 16% level, croscarmellose sodium significantly decreased the release. Crospovidone tends to be less viscous than croscarmellose sodium, therefore the release was not decreased when crospovidone was present (FIG. 12). Mannitol significantly decreased the release of carbomer EX214 at 1.5 min (FIG. 13). The difference among the various formulations was insignificant at 3.0 min, as detected by ANOVA testing. This is so because at that time, the majority of carbomer EX214 has been released.

The insignificant differences in the release profiles of the two batches of the Y7A (FIG. 14) supports the reproducibility of the process of producing carbomer beads by extrusion-spheronization.

As the ratio of water in the granulating vehicle increases (FIG. 16), the release of carbomer EX214 decreases significantly (p<0.05). This can be due to the fact that as the ratio of water increases, more bonding occurs between the MCC molecules within the spheres, thereby stronger beads are produced which would dissolve slower, resulting in a slower release of carbomer EX214. This is in accordance to previous researchers findings (Millili et al, Drug Dev. Ind. Pharm., 18(5):501–517 (1992)) that water granulated MCC pellets are stronger and harder than those produced using hydroalcoholic solution.

Figure 17:
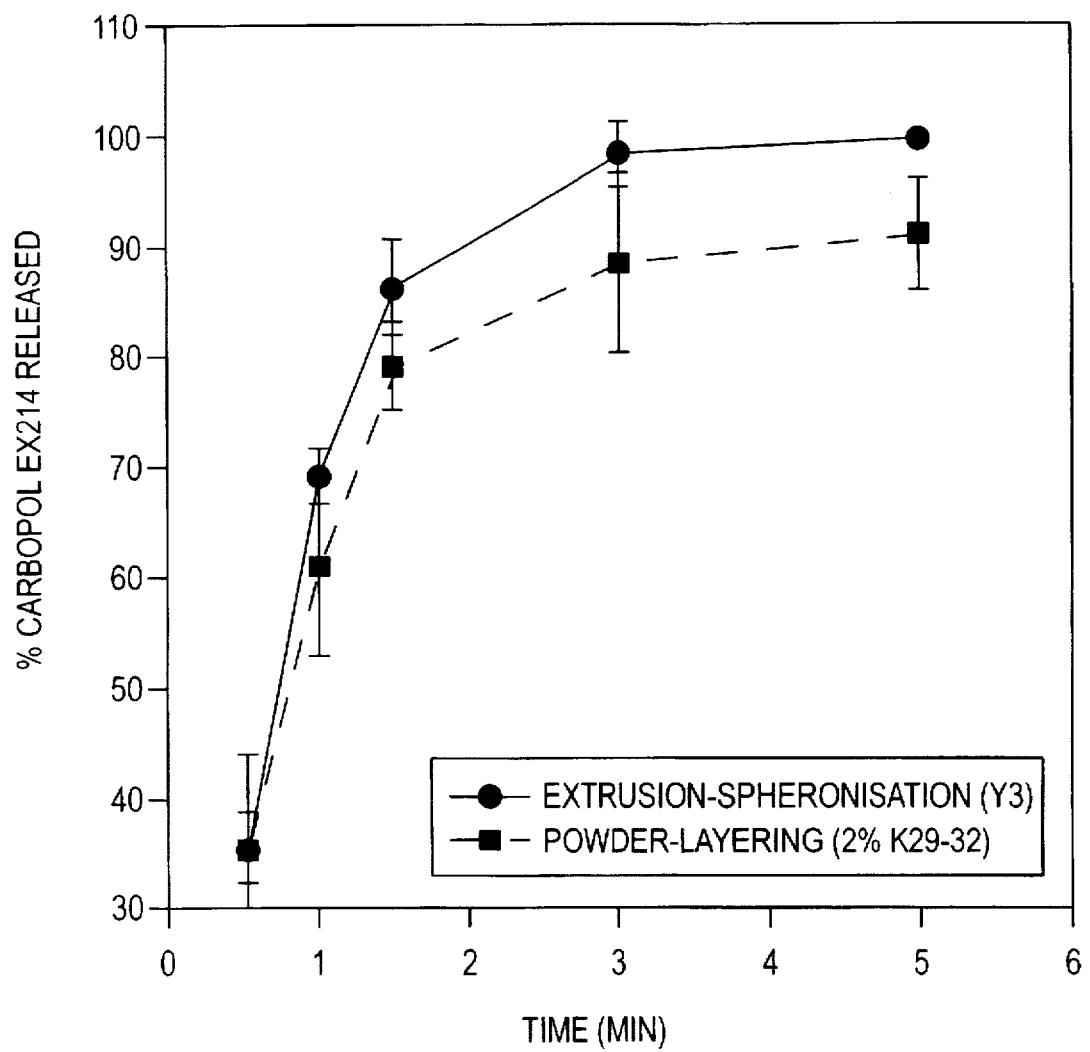
FIG. 17 shows the release of carbomer EX214 as a function of time from beads produced by extrusion-spheronization and powder-layering.

F. Selection of the Processed Carbomer EX214 Formulation to be Incorporated in the Tablet System The choice between the carbomer EX214 beads produced by powder-layering or by extrusion-spheronization was based on the release property as a function of time. A faster release rate is desired in order to ensure a quicker build-up of viscosity. FIG. 17 depicts the release profile of carbomer EX214 from beads produced by extrusion-spheronization (formulation Y3 containing 30% carbomer EX214 in MCC (Table 7 above)), and that produced by powder-layering using the 2.0% K29-32 as the binder solution (Table 6 above). The beads produced by extrusion-spheronization released carbomer EX214 at a faster rate than the powder-layered beads. In powder-layered beads, the hydration of the outer layer of carbomer EX214 impeded the penetration of water to deeper layers, whereas in beads produced by extrusion-spheronization, the presence of MCC seemed to enhance the uptake of water into the inner core of the beads, thereby producing faster hydration and faster release of the carbomer.

Apart from the slower release rate encountered with the powder-layered beads, powder-layering of carbomer EX214 is a more difficult process than extrusion-spheronization. This is so because powder-layering requires a great deal of operator experience. Moreover, the powder to be layered must exhibit good flowability. Carbomer EX214 has a poor flowability due to its fluffy and hygroscopic nature. Atmospheric moisture is quickly absorbed by carbomer EX214, making it more cohesive, and thereby impairing flow.

IV. Conclusions

Among the various polymers evaluated for their rheological properties, carbomer EX214 proved to be an ideal candidate in terms of speed of hydration, presence of yield value and lowest concentration needed to achieve an optimal viscosity required to minimize the sedimentation rate of suspended particles.

Layering of carbomer was achieved by using the EX214 grade, which does not hydrate in alcohol, together with an alcoholic PVP solution. Similar concentrations of the different grades of alcoholic PVP solutions (K29-32 and K90) produced beads with almost equivalent yield, percentage loading, and similar release profiles of carbomer EX214. Increasing the concentration of PVP in the alcoholic binder solution increased the yield, the percentage loading, but decreased the amount of carbomer EX214 released at the early time points.

Extrusion-spheronization of carbomer EX214 was achieved by using a hydroalcoholic granulating liquid to reduce the tackiness. This approach avoided the detrimental effects of ionic salts or pH modifiers on the ability of the polymer to build-up viscosity when hydrated. Increasing the water/alcohol ratio in the granulating solution decreased the amount of carbomer EX214 released as a function of time at the early time points. The size of the carbomer EX214 beads is of significant importance in determining the release profile of carbomer EX214, indicating that dissolution-erosion type of release is involved, rather than disintegration. superdisintegrants were not able to increase the rate of carbomer EX214 released as a function of time.

Processing carbomer EX214 by extrusion-spheronization produced beads with faster release profiles and more carbomer EX214 loading than powder-layering. The beads containing 30% carbomer EX214 in MCC produced by extrusion-spheronization will thus be chosen as the swellable material to be included in the water-dispersible tablets to retard the sedimentation process. These carbomer beads will be mixed with biologically active ingredient-loaded beads which have been coated by a rate controlling membrane to sustain the biologically active ingredient delivery, and a filler system (cushioning beads) capable of preventing the cracking of the membrane controlling the biologically active ingredient release, and will be compressed to form a tablet. This system should disintegrate rapidly in water, thus forming a homogenous suspension which can be swallowed.

EXAMPLE 2

Production of Inert Cushioning Beads

I. Introduction

Beads and coated beads have often been filled into hard gelatin capsules to be used either as conventional or controlled release dosage forms. The concept of tabletting coated biologically active ingredient particles is of interest, especially in the USA, since hard gelatin capsules of Tylenol were manipulated with criminal intent. However, compaction of beads poses difficult problems. If the beads have been coated by a rate controlling membrane to sustain biologically active ingredient delivery, cracking of the membrane will cause the delivery system to change the rate of biologically active ingredient delivery or immediately release the dose. Preventing cracking is therefore of the utmost importance.

Conventional highly compactible fillers such as MCC could be mixed with biologically active ingredient-loaded beads and compressed to form tablets. However, due to particle size differences, segregation would be encountered, resulting in weight variation and content uniformity problems. Granules produced by dry or wet granulation techniques having similar size as the biologically active ingredient-loaded beads have been able to minimize the segregation due to size differences. However, the dry or wet granulation of MCC-containing mixtures decreases its compactibility (Millili et al. supra; and Aulton et al. supra).

MCC is an essential component in the production of beads by extrusion-spheronization. Though MCC is a highly compactible material, studies indicated that beads made from MCC, alone or in combination with brittle materials, such as dicalcium phosphate or lactose, are very hard and not easily deformed or broken (Millili et al. supra; and Aulton et al. supra).

Two approaches can be utilized to produce compacts containing biologically active ingredient-loaded beads coated with a polymeric membrane to sustain the biologically active ingredient action. The first approach involves the production of plastically deforming biologically active ingredient-loaded beads coated with flexible plastically-deforming polymeric membrane which will deform under pressure to form tablets while maintaining the integrity of the coating. Waxes can be incorporated in the biologically active ingredient-loaded beads to impart a plastic component to the deformation process. However, most biologically active ingredient-loaded beads commonly filled in hard gelatin capsules are hard and brittle, and would be expected to crack under the high compression pressures necessary for tablet production. The second approach involves the mixing and compaction of the biologically active ingredient-loaded beads with softer inert cushioning beads which deform at lower pressures during tabletting to prevent the fracture of the membrane-coated biologically active ingredient-loaded beads. The production of softer inert cushioning beads containing MCC was not successful when water was used as the granulating agent. Replacement of part or all of the granulating solution with alcohol to produce softer beads which fragment at lower pressure during tabletting improved the compactibility of those beads to some extent (Millili et al. supra; and Aulton et al. supra), but was not adequate to prevent the fracture of biologically active ingredient-loaded membrane-coated beads (Aulton et al. supra).

Ideal placebo "cushioning" beads intended to be used as diluent to be mixed with biologically active ingredient-loaded beads to prevent segregation, whether due to size or density, should possess the following properties:

(1) Fragment initially into progeny primary powder particles followed by plastic deformation. This is so because during the compaction of the cushioning beads with the biologically active ingredient-loaded membrane-coated millispheres, it is important not only to fill the voids between the biologically active ingredient-loaded millispheres, but also to surround them so that the tablet is held together by excipient-excipient contact;

(2) Minimize segregation propensity by means of similar size and density;

(3) Deform much more readily than the biologically active ingredient-loaded beads;

(4) Produce rapidly disintegrating tablets for releasing biologically active ingredient-loaded beads; and (5) Have no effect on the biologically active ingredient release kinetics.

A significant difference in the physical and mechanical properties of beads produced by extrusion-spheronization is observed as a result of the drying technique used. Freeze-drying (Kleinebudde (1994a), supra) and microwave drying (Bataille et al. supra) of beads containing MCC, alone or in combination with lactose, suppress the shrinking and densification process, resulting in pellets with higher porosities than those dried using oven or fluid-bed drying techniques.

Disintegrants, such as starch, superdisintegrants, such as croscarmellose sodium, crospovidone, and sodium starch glycolate, and hydrophilic materials, such as hydroxypropyl cellulose can be incorporated to increase the water content of the extruded-spheronized beads. Superdisintegrants can be incorporated at much lower levels than regular disintegrants to increase the water content. Materials included in the granulating mixture to increase the water level should be efficient at low concentrations, and should not cause the extrudate to be sticky (which results in balling during spheronization).

The following describes the use of freeze-drying to produce cushioning beads prepared by extrusion-spheronization. The effect of different formulation variables (type and level of disintegrating agents and MCC/lactose ratio) on the water requirement, moisture content of the fresh undried beads, porosity, compactibility, compressibility, and disintegration of tablets produced from freeze-dried beads is investigated.

II. Experiments

The materials used in the production of cushioning beads, including MCC N.F. (Avicel PH101), and anhydrous lactose N.F. (Sheffield D.T.), together with three different superdisintegrants, are depicted in Table 8 below.

TABLE 8

| Material | Trade Name/Grade | Supplier | Lot # |
| --- | --- | --- | --- |
| MCC N.F. | Avicel ® PH101 | FMC Corp., Phil., PA | 1135 |
| Anhydrous lactose N.F. | Sheffield D.T. | Quest Inter'l, Norwich, NY | MRP 534301 |
| Croscarmellose sodium N.F. | Ac-Di-Sol ® | FMC Corp., Phil., PA | T320 |
| Crospovidone N.F. | Polyplasdone ®-XL | ISP Tech., Inc. Wayne, NJ | S50427 |
| Sodium starch glycolate N.F. | Explotab ® CLV | Mendell, Patterson, NY | E50774 |

A. Experimental Design

A full-factorial design investigating the effect of croscarmellose concentration at three levels (0%, 4.0% and 8.0%) and the MCC/lactose ratio at three levels (100/0, 62.5/37.5 and 25/75) with a triplicate run of the center point was implemented. Moreover, two additional formulations containing 4.0% and 8.0% of the crospovidone and sodium starch glycolate in MCC were prepared as shown in Table 9 below.

TABLE 9

| MCC/lactose | 0% | 4.0% | 8.0% |
|---|---|---|---|
| | % Croscarmellose Sodium | | |
| 100/0 | ✓ | ✓ | ✓ |
| 62.5/37.5 | ✓ | ✓✓✓ | ✓ |
| 25/75 | ✓ | ✓ | ✓ |
| | % Polyplasdone | | |
| 100% | ✓ | ✓ | ✓ |
| | % Sodium starch glycolate | | |
| 100/0 | ✓ | ✓ | ✓ |

✓ = Number of batches made

B. Determination of the Optimal Granulating Fluid by Image Analysis

Particle size measurement of the fresh undried beads was performed using an optical microscope (Leitz Wetzlar, Germany) fitted with a camera (MTI 65, Dage-MTI Inc., Michigan City, Ind.) which was cabled directly into a microcomputer (Apple IIe, Apple computer, Cupertino, Calif.). The microscopic field was displayed on the computer monitor, and particle size measurements were made using a microcomputer image analysis system (Bioquant II Microcomputer System, R&M Biometrics, Nashville, Tenn.) with a digital pad and an electronic mouse (Hipad Digitizer, Houston Instruments, Austin, Tex.) to demarcate the microscopic image on the monitor. A micrometer with 10 μm graduations was placed on the microscope stage, and a dimensional calibration was performed. The fresh beads were placed onto a 25×50 mm glass slide as soon as they were discharged from the spheronizer, and the perimeter and area of 100 different spheres were determined. From the perimeter and area, the roundness (4ΠArea/Perimeter$^2$) was calculated, together with the diameter calculated from the area of the projected beads.

C. Extrusion-Spheronization

In a preliminary work, each formulation listed in Table 9 above was granulated using a series of water levels. The roundness and average diameter were calculated. The optimum level was identified as that level which produced nearly round particles whose average size is similar to the aperture of the extrusion screen.

The different formulations were prepared by dry blending the powder mass of each formulation (500 g) in an Erweka® planetary mixer (Model PRS, Erweka Instruments Inc., Milford, Conn.) for 5 min. This was followed by the addition of the optimal amount of the granulating liquid, as determined by image analysis, over a short period of 20 sec. Wet mixing was continued for an additional 10 min with occasional interruptions to scrape the sides of the mixing bowl. Extrusion was carried out using a LUWA® single-screw extruder through a 1.0 mm screen (Model EXKS-1, LCI Corporation, Charlotte, N.C.) at a speed equivalent to 48 RPM. The extrudate was immediately spheronized using a G.B. Caleva® spheronizer (G.B. Caleva Ltd., Ascot, England) for 5 min at a dial reading of 12.

The initial moisture content (IMC) of the beads was determined immediately after spheronization by means of a Computrac® system (Model Max 50, CT Instruments, Inc., Tempe, Ariz.), which measures the moisture content by heating a known weight of a sample until no further change in weight is produced. The upper limit of the heating temperature was set at 105° C. Spheres produced were freeze-dried. The moisture content of the freeze-dried beads was determined after the drying cycle was complete (final moisture content), and the dried product was stored in double plastic bags for later evaluation. Two additional batches containing MCC and 8.0% croscarmellose sodium in MCC were tray-dried.

D. Drying of the Beads Produced by Extrusion-Spheronization

Beads were freeze-dried using a Dura-Top® FTS system (FTS Systems, Inc. Stone Ridge, N.Y.). The freeze-drying conditions are listed in Table 10 below. Two additional batches (the first containing MCC with no disintegrant, and the second containing 8.0% croscarmellose sodium in MCC) were tray-dried in a drying oven (Golton Drying Oven, Arthur Golton Co., Detroit, Mich.) at 60° C. for 20 hrs in order to serve as controls in the compaction and compression experiments.

TABLE 10

| Freezing stage | | Freezing at −20° C. for 2 hrs |
|---|---|---|
| Primary Drying | Stage I | Temperature = −20° C. Vacuum = 10 mT Time = 700 min |
| | Stage II | Temperature = 0° C. Vacuum = 10 mT Time = 600 min |
| Secondary Drying | Stage III | Temperature = 25° C. Vacuum = 10 mT Time = 500 min |
| | Stage IV | Temperature = 25° C. Vacuum = Atm. Pres. Until the end of run |

E. Porosity Determination of the Freeze-dried Beads

The porosity (ε) of the dried beads (18–20 mesh cut) was calculated using the following equation:

$$\epsilon = 100 \left( 1 - \frac{P_a}{P_t} \right)$$

where ($P_t$) is the true density and ($P_a$) is the granular density.

1. True Density Measurement

True densities ($P_t$) of the dried beads were determined by helium displacement using a helium densitometer (Multivolume Pycnometer 1305, Micromeretics Instrument Corp., Norcross, Pittsgurgh, Ga.). The true volume of the sample (an average of five runs) was calculated by determining the volume of helium displaced by the sample during the test. The true density was then calculated by dividing the weight of the sample by the average true volume. For some formulations, true density was measured in duplicate or triplicate to check reproducibility.

2. Granular Density

Determination of the granular density ($P_a$) of the dried beads was made using a mercury intrusion porosimeter at a low pressure of 20 psi (Pore Sizer Model 9305, Micromeretics Instrument Corp., Norcross, Pittsgurgh, GA). A 3.0 cm$^3$ solid sample penetrometer having an internal stem diameter of 0.384 cm$^3$ was used. A high pressure vacuum pump (model A20, Marvac Scientific Manufacturing Co., Concord, Calif.) was used to evacuate the system to a pressure less than 50 μm prior to testing. Once that pressure was reached, mercury was allowed to fill the empty space of the penetrometer that was not occupied by the sample. The penetrometer was weighed after loading the sample prior to beginning the experiment, and after the mercury was allowed to penetrate the sample. The difference in weight was attributed to the weight of the mercury. The volume occupied by the mercury was calculated by dividing the gain in weight by the density of mercury at the temperature at which the experiment was run. The difference between the volume of the empty penetrometer and that of mercury is the granular volume of the beads. The granular density was calculated by dividing the weight of the beads added to the penetrometer by its measured granular volume. For some formulations, granular density was measured in duplicate or triplicate to check reproducibility.

F. Compaction of Inert Cushioning Beads

The freeze-dried beads and the two tray-dried batches were compressed on a single station of an instrumented (Speciality Measurement Inc., Pittstown, N.J.) Manesty D3B tablet press (Thomson Engineering Inc., Hoffman Estates, Ill.) instrumented for the upper compression pressure. The tablet press was run at 25 RPM with one functional die (½" flat-faced beveled edged) at different compression pressures to produce tablets with target weights of 430 mg. The angular separation between filling and compression was 180°. Compression pressures used to produce the tablets ranged from 10–40 MPa. Approximately twenty tablets were collected at 10, 15, 20, 25, 30, 35, and 40 MPa. After 24 hrs of storage, the thickness of 5 individual tablets at each compression pressure was determined using a digital micrometer (Digimatic Caliper, Mitutoyo Ltd., Andover, England). The crushing strength (P) of the tablets was determined by diametral loading in a standard motorized tester (Key Tablet Hardness Tester, Model NT-300 Key International Inc., Englishtown, N.J.). The value used for P was the mean of five crushing strength determinations of tablets at each compression pressure. Tablet tensile strength ($\sigma$) in $Kg/cm^2$ was calculated using Equation (1) set forth above.

G. Disintegration Testing

The disintegration times for three tablets produced at compression pressures of 15 and 20 MPa were evaluated for each formulation according to a modified USP disintegration test in which distilled water at room temperature was used as the medium.

H. Studies to Monitor Changes in Bed Density

Compression studies to monitor changes in bed density were carried out using the compaction simulator located at Smith Kline Beecham (King of flat-faced punches. The compaction simulator system consisted of an upgraded Mand (Mand Nicolet Digital Oscilloscope (Model 440)) and an IBM PS/2 containing an Excel® based software). A sawtooth displacement profile was used to control the upper punch while the lower punch, was kept stationary. Tablet weight for each material (18–20 mesh cut), determined based on the true density of the beads as determined previously via the helium pycnometer, was adjusted to obtain a tablet thickness of 3.0 mm at zero porosity. Three tablets were produced for each formulation at a compression speed of 100 mm/s. From the upper and lower punch pressure and displacement values, it was possible to calculate the thickness of the compact during a single compression event as a function of the punch pressure. From the compact weight and true density data, the relative density of the tablet during compression was calculated.

The Athy-Heckel equation (see Equation (2) set forth above) was used to analyze the relationship between relative density during compression and the applied pressure. Regression analyses were carried out on the Athy-Heckel plots over the range of 50–200 MPa. These results were then used for the determination of the yield pressure for the (18–20 mesh cut) of the different freeze-dried formulations.

The hardness of the compacts was determined using a Vanderkamp VK2000 Tablet Hardness Analyzer (VanKel Industries Inc., Edison, N.J.).

In order to study the mechanism of compaction of the freeze-dried beads two approaches were undertaken:

(1) For selected batches, the yield pressure values were determined at two different punch speeds to estimate the strain-rate sensitivity index (SRS) strain-rate sensitivity index (SRS) according to Equation (3) set forth above. The two punch speeds tested were 100 mm/sec and 20 mm/sec; and (2) For selected batches, the yield pressure values were determined for different sieve cuts at an upper punch speed rate of 100 mm/s. The sieve cuts studied were: 14–18, 18–20, and 20–25 mesh cuts.

I. Scanning Electron Microscopy

The freeze-dried beads, tray-dried beads, cross-sections of some selected freeze-dried beads, together with the tablets, as well as cross-sections of the tablets produced by compacting the freeze-dried beads were photographed under a scanning electron microscope (Model: JSM-T200, Jeol Ltd., Tokyo, Japan). The samples were placed on aluminum mounts. Double-sided Scotch® tape was previously applied to the top of the mounts. Sufficient beads to cover the surface of the mounts were added, and the mounts were tapped after turning them sideways in order to remove any excess beads. For tablet compacts, slight pressure was applied to stick the sample on top of the mounts. The samples were stored overnight at 0% relative humidity in a tightly sealed plastic container, and then sputter coated (Hummer VI Sputtering System, Technics East Inc., Annandale, Va.) with a gold-palladium mixture. Settings used on the sputtering system were as follows: vacuum: 75 milliTorr, voltage: 9 Volts, sputtering time: 5.0 min. The samples were observed at a working distance of 20 mm and an excitation voltage of 25 kV. Photomicrographs of representative fields were taken using a 35 mm camera (Model FT-1, Konica, Japan) and Kodak® film (TMAX 100, Eastman Kodak Co., Rochester, N.Y.).

III. Results and Discussion

In this Example, cushioning beads which deform at lower pressures during tabletting were produced by freeze-drying to prevent the fracture of the membrane-coated biologically active ingredient-loaded beads, and to minimize the segregation propensity due to the size differences. The effect of different formulation variables (type and level of disintegrating agents and MCC/lactose ratio) on the water requirement, moisture content of the fresh undried beads, porosity, compactibility, compressibility, and disintegration of tablets produced from freeze-dried beads were investigated.

A. Effect of Formulation Variables on the Granulating Fluid Requirement and Initial Moisture Content of the Cushioning Beads Produced by Extrusion-Spheronization Changing the moisture content of the wet granulated mass prior to extrusion-spheronization has a major impact on the size and size distribution of beads together with other physico-mechanical properties (Hasznos et al. supra). Thus, in order to investigate the effect of different formulation variables on the properties of beads produced by extrusion-spheronization, it is essential to identify the optimal fluid level required by each formulation. The initial moisture content (IMC) of the fresh undried beads is a function of the amount of granulating liquid required for each formulation. The higher the granulating fluid level used, the higher the IMC is expected to be. The optimal fluid level requirement and the IMC of the fresh undried beads after being discharged from the spheronizer can be found in Table 11 below.

TABLE 11

| Formulation | Optimal Water Level (ml/500 g) | IMC % |
|---|---|---|
| MCC | 625 | 55.7 |
| 4.0% Croscarmellose/MCC | 725 | 59.5 |
| 8.0% Croscarmellose/MCC | 825 | 62.1 |
| MCC:lactose (62.5:37.5) | 300 | 36.8 |
| 4.0% Croscarmellose/MCC:lactose (62.5:37.5) (Run #1) | 410 | 44.8 |
| 4.0% Croscarmellose/MCC:lactose (62.5:37.5) (Run #2) | 410 | 44.8 |
| 4.0% Croscarmellose/MCC:lactose (62.5:37.5) (Run #3) | 410 | 44.6 |
| 8.0% Croscarmellose/MCC/lactose (62.5:37.5) | 500 | 50 |
| MCC:lactose (25:75) | 194 | 26.4 |
| 4.0% Croscarmellose/MCC:lactose (25:75) | 277 | 34.1 |
| 8.0% Croscarmellose/MCC: lactose (25:75) | 360 | 40.2 |
| 4.0% Crospovidone/MCC | 650 | 56.8 |
| 8.0% Crospovidone/MCC | 675 | 57.6 |
| 4.0% Sodium starch glycolate/MCC | 670 | 56.5 |
| 8.0% Sodium starch glycolate/MCC | 750 | 59.7 |

Regression analysis revealed a significant effect of the MCC/lactose ratio, croscarmellose sodium level, and crospovidone level on the IMC. No significant difference was associated with the presence of sodium starch glycolate. An increase in the MCC/lactose ratio, croscarmellose sodium level, and crospovidone level resulted in an increase in the IMC. The coefficients of regression and their corresponding p-values can be found in Table 12 below.

TABLE 12

| Formulation Variable | Coefficient | P-Value |
|---|---|---|
| Croscarmellose Sodium Experiment | | |
| MCC/lactose Ratio | 0.340 | 2.39E-08 |
| % Croscarmellose Sodium | 1.392 | 4.72E-05 |
| Crospovidone Experiment | | |
| % Crospovidone | 0.238 | 0.0082 |
| Sodium Starch Glycolate Experiment | | |
| % Sodium starch glycolate | 0.500 | 0.1000 |

The regression coefficients of the % croscarmellose sodium and the % crospovidone were 1.392 and 0.2375, respectively. Thus, an increase in the IMC due to the presence of croscarmellose sodium is approximately 6 times that of crospovidone, which can be attributed to the fact that croscarmellose sodium can take up more water than crospovidone without causing gross agglomeration and size enlargement of the beads during spheronization. When higher granulation fluid levels were used, formulations containing sodium starch glycolate agglomerated during spheronization resulting in massive balling. This is due to the much higher viscosity encountered with sodium starch glycolate when used at such levels (4.0% and 8.0%) despite the fact that a low viscosity grade was used. Although superdisintegrants tend to increase the fluid level requirement and IMC, they should ideally do this without causing massive agglomeration of the beads during spheronization.

An increase in the MCC/lactose ratio was associated with an increase in the fluid level requirement and IMC. This is in accordance with the findings of others that more granulating liquid is required as the level of MCC is increased (Elber et al. supra; Pinto et al. supra; and Bains et al. supra).

B. Effect of Drying Technique on the Size of Cushioning Beads Produced by Extrusion-Spheronization The average area diameters ($d_a$) of the fresh undried beads and the freeze-dried for all of the formulations, together with the area diameters for the two batches which were tray-dried, can be found in Table 13 below.

TABLE 13

| Formulation | $d_a$ (mm) Undried Beads | $d_a$ (mm) Freeze-Dried Beads | $d_a$ (mm) Tray-Dried Beads |
|---|---|---|---|
| MCC | 0.99 | 0.93 | 0.79 |
| | (0.16)* | (0.13) | (0.12) |
| 4.0% Croscarmellose/MCC | 0.85 | 0.93 | |
| | (0.15) | (0.13) | |
| 8.0% Croscarmellose/MCC | 0.89 | 0.88 | 0.68 |
| | (0.14) | (0.14) | (0.12) |
| MCC:lactose (62.5:37.5) | 1.03 | 1.00 | |
| | (0.14) | (0.11) | |
| 4.0% Croscarmel-lose/MCC:lactose (62.5:37.5) (Run #1) | 0.98 (0.13) | 0.97 (0.12) | |
| 4.0% Croscarmel-lose/MCC:lactose (62.5:37.5) (Run #2) | 1.04 (0.14) | 0.99 (0.12) | |
| 4.0% Croscarmel-lose/MCC:lactose (62.5:37.5) (Run #3) | 0.98 (0.12) | 0.97 (0.13) | |
| 8.0% Croscarmel-lose/MCC/lactose (62.5:37.5) | 0.92 (0.14) | 0.92 (0.16) | |
| MCC:lactose (25:75) | 0.99 | 1.04 | |
| | (0.17) | (0.15) | |
| 4.0% Croscarmel-lose/MCC:lactose (25:75) | 0.98 (0.14) | 1.01 (0.14) | |
| 8.0% Croscarmel-lose/MCC:lactose (25:75) | 1.01 (0.13) | 1.03 (0.13) | |
| 4.0% Crospovidone/MCC | 0.99 | 0.93 | |
| | (0.16) | (0.13) | |
| 8.0% Crospovidone/MCC | 0.99 | 0.91 | |
| | (0.11) | (0.14) | |
| 4.0% Sodium starch glycolate/MCC | 0.99 (0.11) | 0.93 (0.13) | |
| 8.0% Sodium starch glycolate/MCC | 1.00 (0.18) | 0.93 (0.16) | |

*Relative standard deviation

As can be seen from Table 13 above, shrinking occurring during freeze-drying is minimal when compared to that seen with tray-drying. For example, freeze-drying reduced the average size of the fresh undried beads of the plain MCC formulation from 0.99 mm to only 0.93 mm, whereas tray-drying reduced it to 0.79 mm. The same applies to the other tray-dried batch, the 8.0% croscarmellose in MCC formulation, where the average diameter was reduced from 0.89 mm to only 0.88 mm in freeze-drying, and to 0.68 mm in tray-drying. This is in accordance to the finding of Kleinebudde (1994a). supra. that there is a remarkable difference in the physico-mechanical properties of pellets as a result of the drying technique, with only a minor shrinking tendency during freeze-drying. Kleinebudde suggested that removing the water in the frozen state leaves a skeleton of solid materials with resultant freeze-dried pellets having a similar size to the wet pellets, as well as high porosities. Evaporation of water in an oven or fluid-bed is accompanied by a shrinking process. The resultant pellets are smaller than the wet ones and are considerably more dense.

C. Effect of Different Formulation Variables on the Porosity of Cushioning Beads Produced by Extrusion-Spheronization The granular density, true density, and the calculated porosity for the various formulations can be found in Table 14 below.

TABLE 14

| Formulation | Granular Density (g/ml) | True Density | Porosity |
|---|---|---|---|
| MCC (Freeze-dried) | 1.02 | 1.59 | 35.62 |
| 4.0% Croscarmellose/MCC (Fried-dried) | 0.70 | 1.61 | 56.35 |
| 8.0% Croscarmellose/MCC (Freeze-dried) | 0.65 | 1.62 | 60.25 |
| MCC:lactose (62.5:37.5) (Freeze-dried) | 0.95 | 1.58 | 39.89 |
| 4.0% Croscarmellose/ MCC:lactose (62.5:37.5) (Freeze-dried) (Run #1) | 0.80 | 1.59 | 49.87 |
| 4.0% Croscarmellose/ MCC:lactose (62.5:37.5) (Freeze-dried) (Run #2) | 0.81 | 1.59 | 48.75 |
| 4.0% Croscarmellose/ MCC:lactose (62.5:37.5) (Freeze-dried) (Run #3) | 0.81 | 1.58 | 48.93 |
| 8.0% Croscarmellose/ MCC/lactose (62.5:37.5) (Freeze-dried) | 0.69 | 1.60 | 56.54 |
| MCC:lactose (25:75) (Freeze-dried) | 1.05 | 1.61 | 43.08 |
| 4.0% Croscarmellose/ MCC:lactose (25:75) (Freeze-dried) | 0.91 | 1.60 | 43.08 |
| 8.0% Croscarmellose/ MCC:lactose (25:75) (Freeze-dried) | 0.83 | 1.60 | 48.11 |
| 4.0% Crospovidone/MCC (Freeze-dried) | 0.94 | 1.55 | 39.38 |
| 8.0% Crospovidone/MCC (Freeze-dried) | 0.90 | 1.56 | 41.90 |
| 4.0% Sodium starch glycolate/MCC (Freeze-dried) | 0.85 | 1.59 | 46.45 |
| 8.0% Sodium starch glycolate/MCC (Freeze-dried) | 0.65 | 1.64 | 60.65 |
| MCC (Tray-dried) | 1.35 | 1.49 | 3.84 |
| 8.0% Croscarmellose/MCC (Tray-dried) | 1.17 | 1.63 | 28.4 |

Measurement of the true densities were performed in triplicate for two formulations to check for reproducibility and variability associated with the helium pycnometer measurements. The relative standard deviation for the MCC/lactose (25:75) formulation and the 8.0% crospovidone in MCC formulation were 0.47% and 0.49%, respectively. The relative standard deviations for the plain MCC formulation, the 8.0% croscarmellose sodium in MCC formulation, and the 8.0% crospovidone in MCC formulation were 1.99%, 0.5%, and 4.59%, respectively.

Regression analysis revealed a statistical significance ($p<0.05$) of the effect of MCC/lactose ratio, as well as the presence of different superdisintegrants on the porosities of the freeze-dried beads. Increasing the MCC/lactose ratio and the different superdisintegrant levels increased the porosity of the freeze-dried beads. For tray-dried beads, the coefficients of regression and their corresponding p-values can be found in Table 15 below.

TABLE 15

| Formulation Variable | Coefficient | P-Value |
|---|---|---|
| Croscarmellose Sodium Experiment | | |
| MCC/lactose Ratio | 0.083 | 0.0291 |
| % Croscarmellose Sodium | 2.607 | 2.76E-06 |
| Crospovidone Experiment | | |
| % Crospovidone | 0.785 | 0.0127 |
| Sodium Starch Glycolate Experiment | | |
| % Sodium starch glycolate | 3.128 | 0.0060 |

The effect of drying technique on the porosities of plain MCC beads and 8.0% croscarmellose sodium in MCC is seen in Table 14 above. For the MCC beads produced by extrusion-spheronization, tray-drying reduced the porosity to 3.84%, as compared to 35.62% for the freeze-dried formulation. A similar effect is observed with the 8.0% croscarmellose sodium in MCC beads, where the porosity associated with the tray-dried beads was 28.4%, as opposed to 60.25% for the freeze-dried batch. This can be attributed to the shrinking phenomenon associated with tray-drying. Croscarmellose sodium increased the porosities of both dried beads formulation to a similar degree, regardless of the drying technique utilized.

Sodium starch glycolate and croscarmellose sodium increased the porosity to a greater extent than crospovidone, as reflected in their corresponding regression coefficients. Moreover, an increase in the porosity of the freeze-dried beads was observed with increasing the MCC/lactose ratio. The increase in porosity can be attributed to the higher water content of the freshly spheronized beads (IMC). Thus, beads with higher IMC's exhibited higher porosities. Regression analysis revealed that increasing the IMC of the freeze-dried beads by 0.478% tends to increase the porosity of the corresponding compacts by one unit (close to significance relationship, $p=0.05$).

D. Effect of Formulation Variables on the Compactibility of Dried Beads Produced by Extrusion-Spheronization The compaction of the two tray-dried formulations containing plain MCC and 8.0% croscarmellose sodium in MCC was not possible even at a compression pressure of 40 MPa. At this high compression pressure, the compacts ejected from the die, and did not have sufficient hardness to be transferred to the hardness tester so that their crushing strengths could not be measured. This was expected based on previous researchers findings (Millili et al. supra; Aulton et al. supra; Celik et al. supra; and Maganti et al. supra) that tray or fluid-bed drying of beads rich in MCC, were strong, hard and exhibit low compactibility especially when water is the granulating fluid. This can be attributed to the high bond strength of the beads, which were hard and less deformable, thus allowing less surface to surface contacts for bonding to occur, thereby producing weaker tablets. Moreover, tray-dried beads containing MCC have a high elastic modulus so that upon the removal of the compression force, the compressed beads would spring back, causing a weak tablet structure (Aulton et al. supra).

Figure 18:
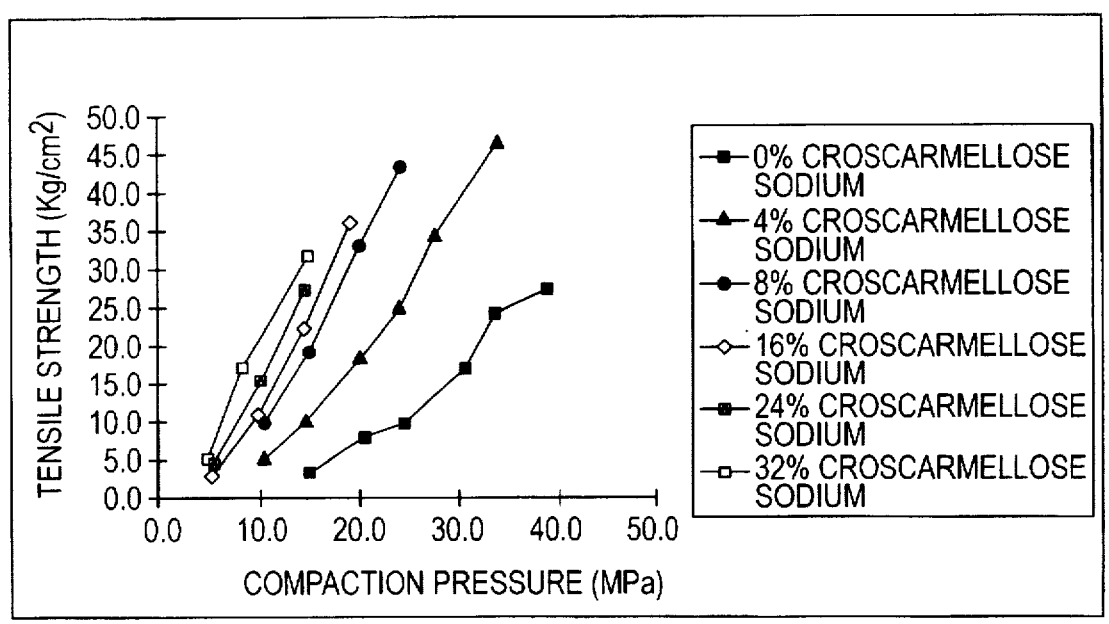
FIG. 18 shows the effect of croscarmellose sodium on the compactibility of freeze-dried MCC beads.
Figure 19:
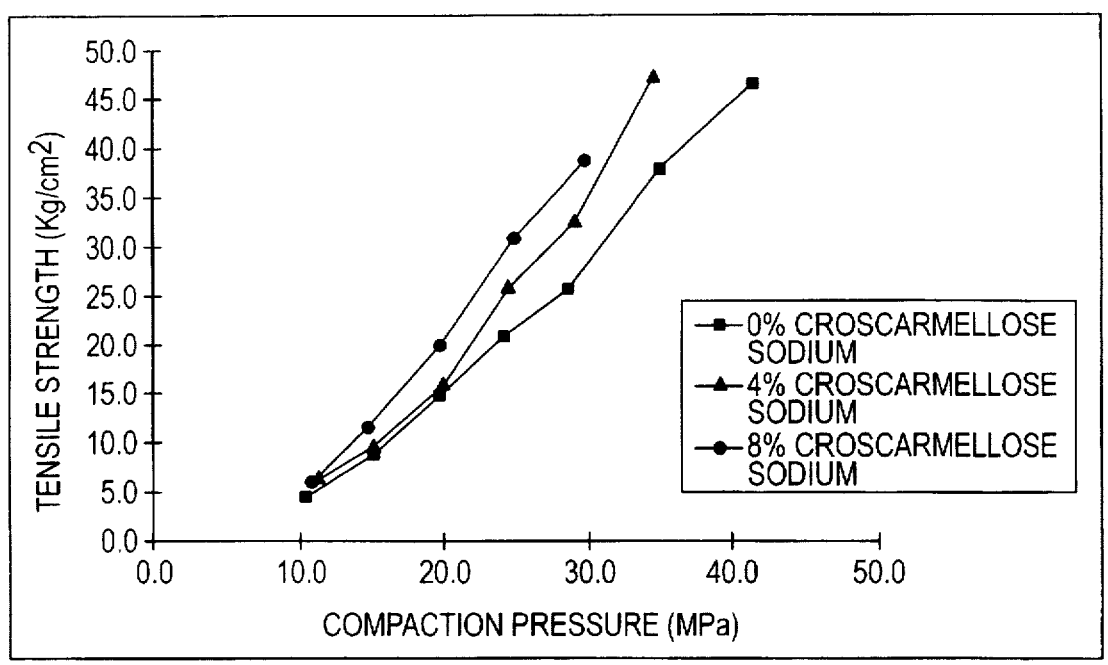
FIG. 19 shows the effect of croscarmellose sodium on the compactibility of freeze-dried MCC:lactose (25:75) beads.
Figure 21:
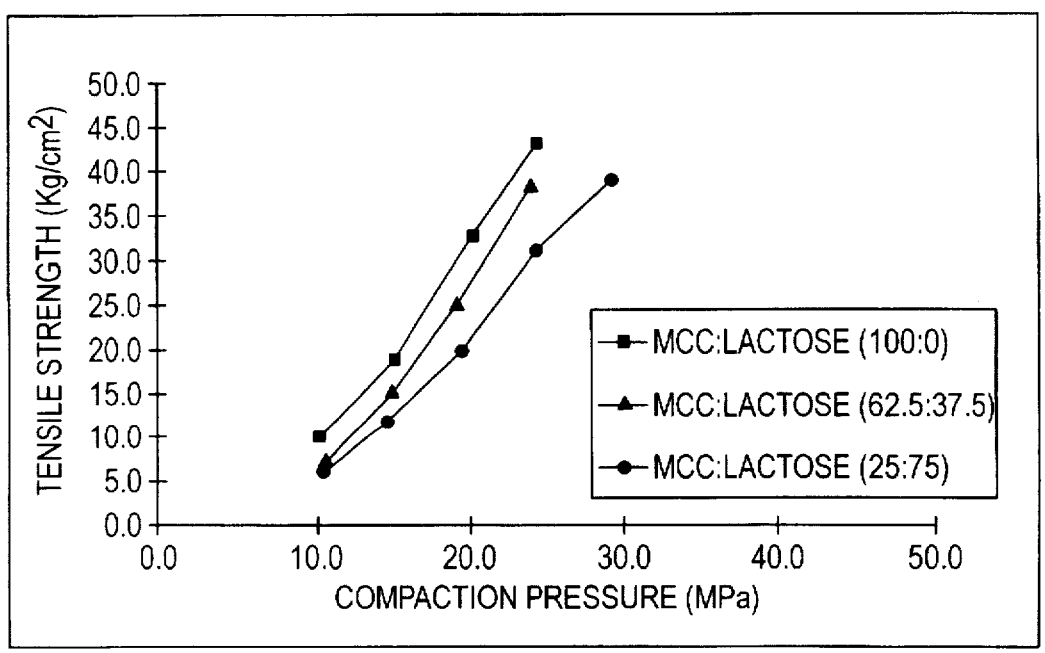
FIG. 21 shows the effect of MCC:lactose ratio on the compactibility of freeze-dried beads containing 8.0% croscarmellose sodium.
Figure 22:
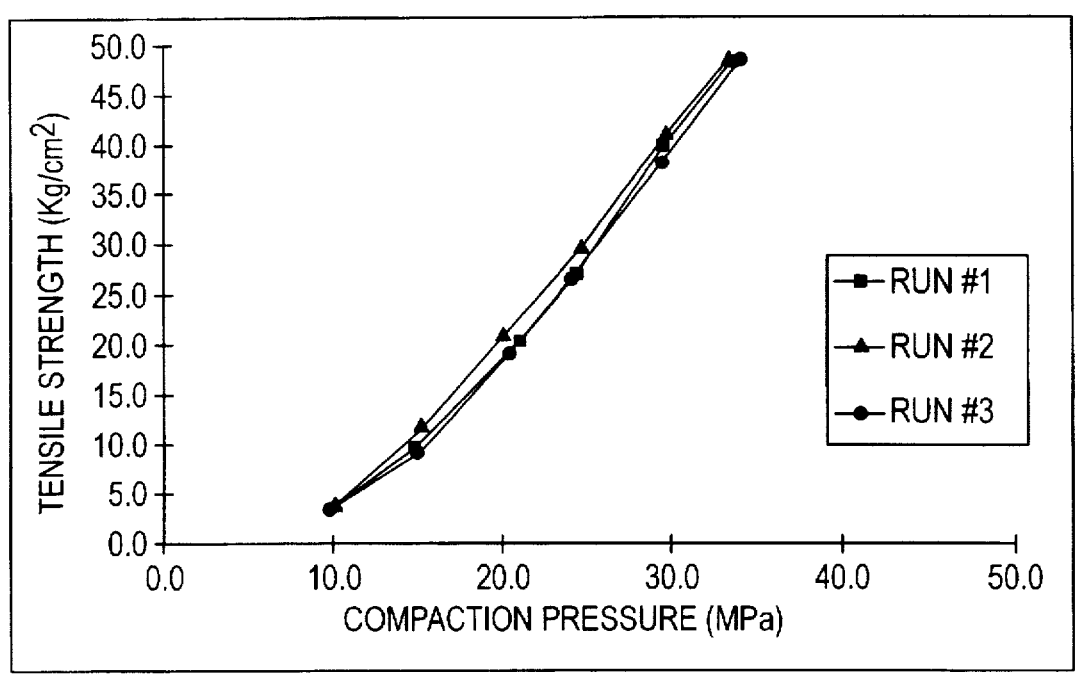
FIG. 22 shows the compactibility of freeze-dried replicate formulation containing 4.0% croscarmellose sodium in MCC:lactose (62.5:37.5).
Figure 23:
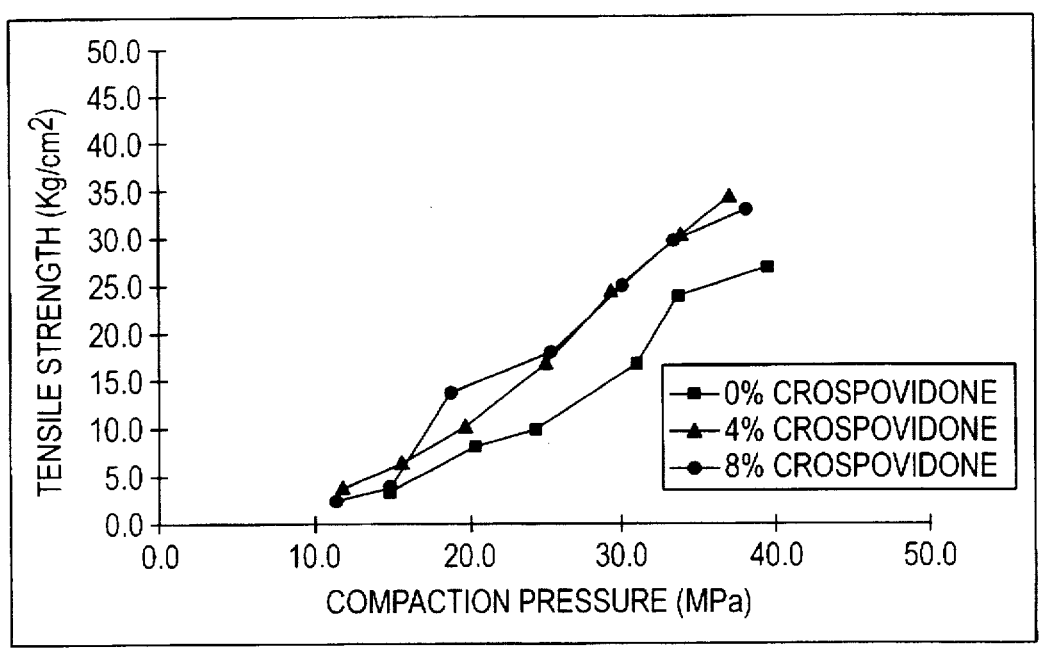
FIG. 23 shows the effect of crospovidone on the compactibility of freeze-dried MCC beads.
Figure 24:
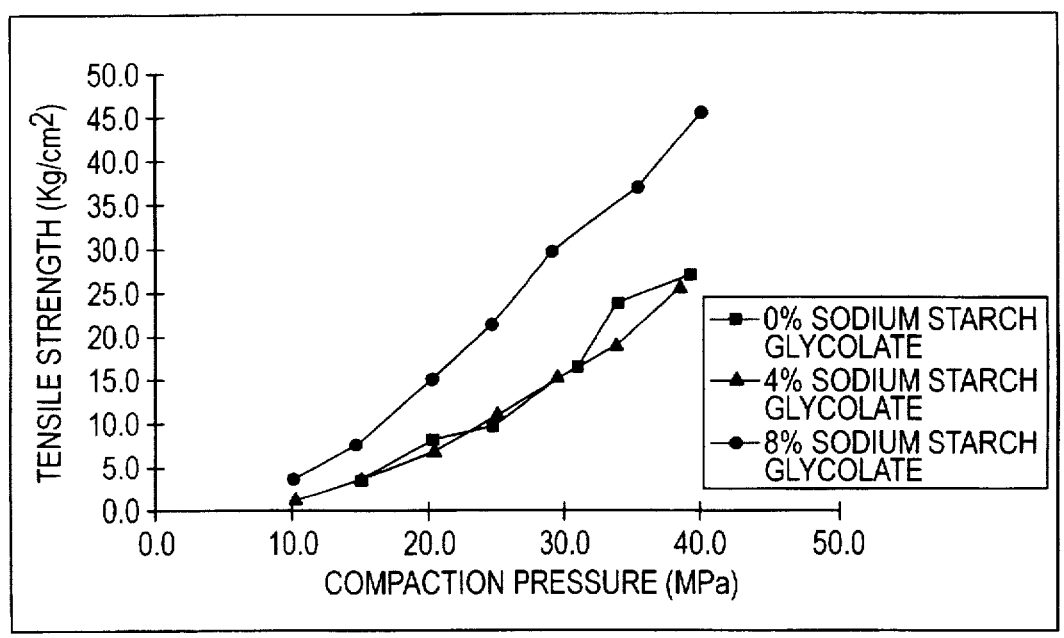
FIG. 24 shows the effect of sodium starch glycolate on the compactibility of freeze-dried MCC beads.
Figure 25:
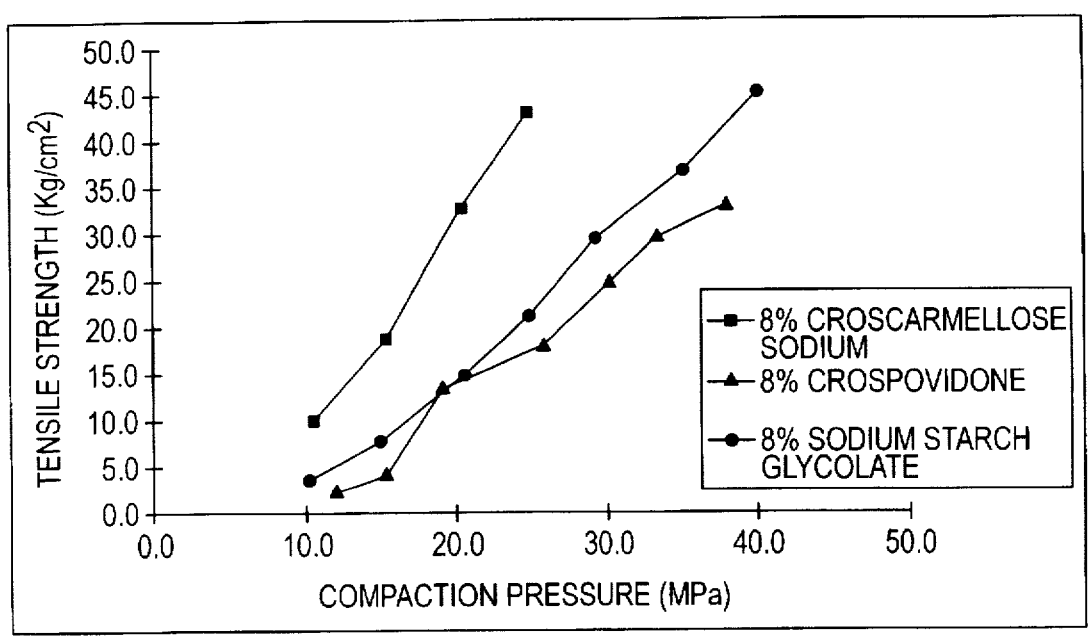
FIG. 25 shows the effect of incorporation of different superdisintegrants at a 8.0% level on the compactibility of freeze-dried MCC beads.
Figure 26:
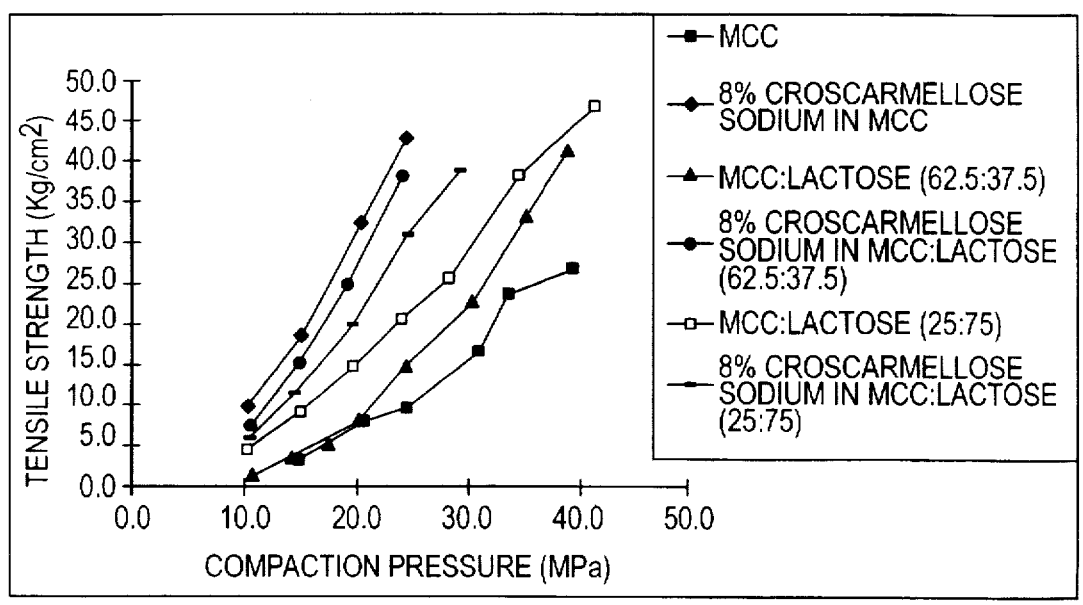
FIG. 26 shows the effect of different croscarmellose and MCC:lactose ratios on the compactibiity of freeze-dried beads.
Figure 27:
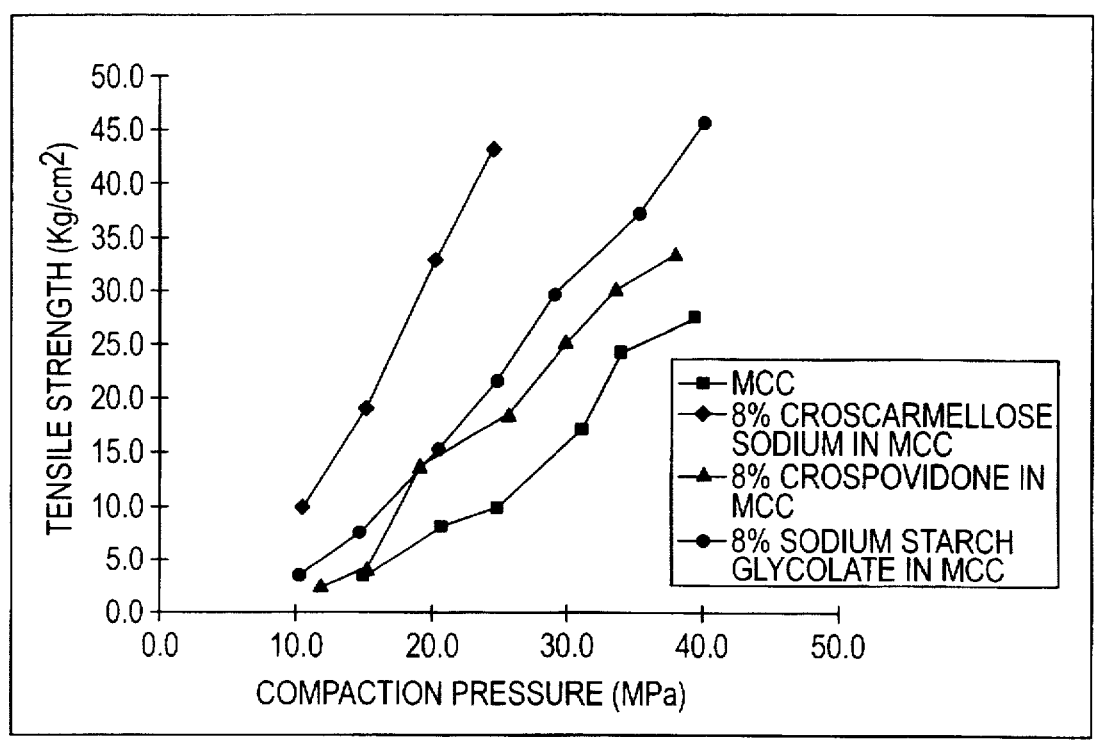
FIG. 27 shows the effect of different superdisintegrants on the compactibility of freeze-dried MCC beads.

The effect of the incorporation of different levels of croscarmellose sodium on the compaction of the freeze-dried MCC beads and MCC/lactose (25:75) beads can be found in FIGS. 18 and 19, respectively. The effect of the MCC/lactose ratio at 0% and 8.0% croscarmellose sodium levels can be found in FIGS. 20 and 21, respectively. FIG. 22 represents the compaction profiles of the center point (4.0% croscarmellose sodium in MCC/lactose (62.5:37.5))

which was run in triplicate to check for reproducibility. FIGS. 23 and 24 represent the effect of crospovidone and sodium starch glycolate incorporation on the compaction of freeze-dried MCC beads. The effect of incorporation of different superdisintegrants at a 8.0% level on the compaction profiles of freeze-dried MCC beads can be seen in FIGS. 25. FIG. 26 represents a summary of the different experiments performed to study the effect of different variables on the compaction of freeze-dried beads containing croscarmellose sodium at 0% and 8.0% levels. Finally, FIG. 27 represents the effect of different superdisintegrants at 0% and 8.0% levels on the compaction of freeze-dried beads containing MCC.

E. Effect of Formulation Variables on the Compactibility of Dried Beads Produced By Extrusion-Spheronization The effect of the different variables on the tensile strength of the compacted tablets cannot be studied unless identical compression pressures are used in the generation of the different compaction profiles. Though tablets were collected at 10, 15, 20, 25, 30, 35 and 40 MPa, these compression pressures were approximate. For accuracy reasons, the compaction pressure/tensile strength data for each formulation was fitted to a straight-line model from which the tensile strengths of each compact at different compaction pressures can be predicted from the regression coefficient of each fitted line. To allow fair comparisons, the predicted tensile strengths of the different formulations at a compression pressure of 15 MPa (750 Kg) studied were calculated, and are listed in Table 16 below. Compression pressure of 15 MPa was chosen because such pressures are commonly encountered in tablet production.

TABLE 16

| Formulation | Predicted Tensile Strength (Kg/cm$^2$) at a Compaction Pressure of 15 Mpa |
|---|---|
| MCC | 1.97 |
| 4.0% Croscarmellose/MCC | 10.56 |
| 8.0% Croscarmellose/MCC | 19.17 |
| MCC:lactose (62.5:37.5) | 3.61 |
| 4.0% Croscarmellose/MCC:lactose (62.5:37.5) (Run #1) | 10.18 |
| 4.0% Croscarmellose/MCC:lactose (62.5:37.5) (Run #2) | 11.20 |
| 4.0% Croscarmellose/MCC:lactose (62.5:37.5) (Run #3) | 9.91 |
| 8.0% Croscarmellose/MCC/lactose (62.5:37.5) | 15.65 |
| MCC:lactose (25:75) | 8.86 |
| 4.0% Croscarmellose/MCC:lactose (25:75) | 9.86 |
| 8.0% Croscarmellose/MCC:lactose (25:75) | 12.37 |
| 4.0% Crospovidone/MCC | 5.16 |
| 8.0% Crospovidone/MCC | 5.89 |
| 4.0% Sodium starch glycolate/MCC | 3.48 |
| 8.0% Sodium starch glycolate/MCC | 8.29 |

Table 16 reveals that the strongest tablets (tensile strength of 19.17 Kg/cm$^2$) were produced by using the formulation composed of 8.0% croscarmellose sodium in MCC. Statistical analysis of the different variables affecting the predicted tensile strength of the tablets compressed at 15 MPa can be seen in Table 17 below.

TABLE 17

| Formulation Variable | Coefficient | P-Value |
|---|---|---|
| Croscarmellose Sodium Experiment | | |
| MCC/lactose Ratio | −0.089 | 2.343E-05 |
| % Croscarmellose Sodium | −0.060 | 0.7000 |
| Interaction (MCC:lactose × % Croscarmellose Sodium) | 0.023 | 1.852E-06 |
| Crospovidone Experiment | | |
| % Crospovidone | 0.4892 | 0.1108 |
| Sodium Starch Glycolate Experiment | | |
| % Sodium starch glycolate | 0.7898 | 0.0807 |

Figure 20:
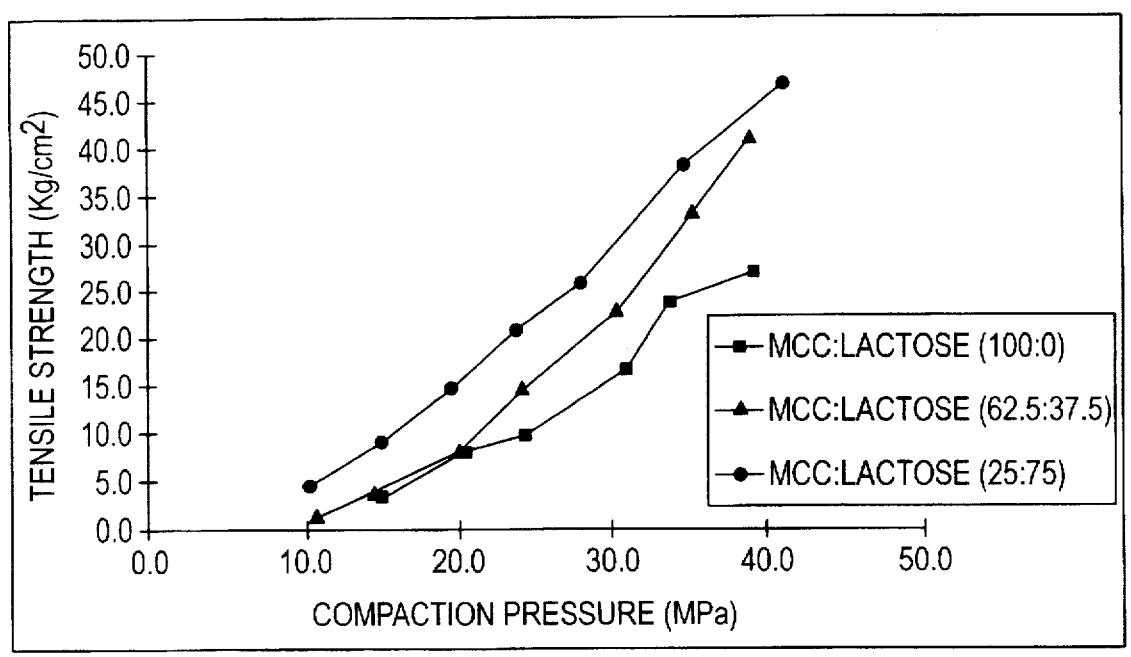
FIG. 20 shows the effect of MCC:lactose ratio on the compactibility of freeze-dried beads containing 0% croscarmellose sodium.

The MCC/lactose ratio is of significant importance in predicting the tablet tensile strength. Decreasing the level of MCC produced tablets with higher tensile strengths (FIG. 20). This is seen numerically in Table 16 above when comparing the plain MCC formulation, MCC/lactose (62.5:37.5) formulation, and the MCC/lactose (25:75) formulation with their corresponding tensile strengths of 1.97, 3.61, and 8.86, respectively. This can be attributed to the fact that increasing the level of MCC in the spheres increases their hardness and strength by the formation of strong adhesive hydrogen bonding (Millili et al. supra; and Aulton et al, supra). Hard beads containing MCC exhibit sufficient deformation to produce tablets. Crospovidone (FIG. 23) and sodium starch glycolate (FIG. 24) had no statistically significant effect on the tensile strength of the compressed tablets (sodium starch glycolate was only significant at p-value of 0.1).

A statistically significant interaction between croscarmellose sodium and MCC/lactose ratio on the tensile strength of the compacts was found (Table 17). Increasing the percentage of croscarmellose sodium in the formulation predominantly containing MCC produced compacts with higher tensile strength than if such an increase occurred in a lactose-predominant formulation. This is seen in FIGS. 20 and 21 where in the absence croscarmellose sodium, higher MCC/lactose ratio produced tablets with lower tensile strengths (FIG. 20). As the concentration of croscarmellose sodium increased to 8.0%, an increase in the MCC/lactose ratio produced tablets with higher tensile strengths (FIG. 21). For beads containing water-soluble materials, such as lactose, it is not unreasonable to anticipate the presence of solute molecules of this component which have dissolved in the aqueous granulating fluid during the wet massing stage. Water removal from those beads during drying following spheronization could lead to the formation of solid bridges within the spheres by fusion at the points of contact of the primary powder particles. This will result in a greater degree of bonding, and hence the formation of relatively strong beads. However, the type of bonds formed in plain MCC beads is different from the solid bridges encountered with lactose (Dyer et al, supra; and Aulton et al, supra). Hydrogen bonding seems to produce stronger beads than those of lactose. Thus, MCC beads are stronger and less easily deformable, resulting in compacts with lower tensile strength (FIG. 20). In the presence of 8.0% croscarmellose sodium in MCC, the high porosity associated with the high granulation fluid requirement decreased the hydrogen bonding between adjacent MCC molecules, resulting in softer beads which will deform readily upon the application of pressure to give hard tablets. In formulations dominated by lactose, the presence of 8.0% croscarmellose sodium increased the water requirement and porosity to a lesser extent, but those beads were still hard due to solid bridge formation.

FIG. 22 demonstrates the reproducibility of the compaction profiles observed with three different batches of a similar formulation. FIGS. 25, 26 and 27 show the superiority of croscarmellose sodium over both crospovidone and sodium starch glycolate in improving the compactibility of the freeze-dried beads.

Thus, combining both MCC and croscarmellose sodium in the production of freeze-dried cushioning beads by extrusion-spheronization produced the most highly compactible beads, which upon compaction, produced tablets with the strongest tensile strengths.

Moreover, regression analysis revealed that increasing the porosity of the freeze-dried beads by 0.467% tends to increase the tensile strength of their corresponding compacts by one unit (p=0.00127).

F. Disintegration Study

The disintegration times of the tablets produced by compressing the freeze-dried beads of different formulations at compaction pressures of 15 and 20 MPa can be found in Table 18 below. It was observed that at higher compression pressures, longer disintegration times were encountered. Moreover, as the MCC/lactose ratio is decreased, the disintegration time is prolonged because lactose tends to dissolve, rather than disintegrate.

TABLE 18

| Formulation | Disintegration time (sec) following compression at 15 Mpa | Disintegration time (sec) following compression at 20 MPa |
| --- | --- | --- |
| MCC | <5 | >5 |
| 4.0% Croscarmellose/MCC | <5 | 14 |
| 8.0% Croscarmellose/MCC | 31 | 110 |
| MCC:lactose (62.5:37.5) | <5 | 68 |
| 4.0% Croscarmellose/MCC:lactose (62.5:37.5) (Run #1) | 367 | 968 |
| 4.0% Croscarmellose/MCC:lactose (62.5:37.5) (Run #2) | 462 | 890 |
| 4.0% Croscarmellose/MCC:lactose (62.5:37.5) (Run #3) | 331 | 669 |
| 8.0% Croscarmellose/MCC/lactose (62.5:37.5) | 667 | 848 |
| MCC:lactose (25:75) | 65 | 164 |
| 4.0% Croscarmellose/MCC:lactose (25:75) | 550 | 1334 |
| 8.0% Croscarmellose/MCC:lactose (25:75) | 659 | 673 |
| 4.0% Crospovidone/MCC | <5 | <5 |
| 8.0% Crospovidone/MCC | <5 | <5 |
| 4.0% Sodium starch glycolate/MCC | <5 | <5 |
| 8.0% Sodium starch glycolate/MCC | 7 | 29 |

The effect of different formulation variables on the disintegration time cannot be statistically analyzed because in order to do so, tablets of similar tensile strengths should be compared. Unfortunately, the compaction study necessitated that compression pressure was varied, resulting in variable tensile strengths.

G. Studies to Monitor Changes in Bed Density

An increase in bulk density of the compacts formed by compressing the cushioning beads of the different formulations was observed with an increase in the applied pressure. The relationship between the applied pressure and density or porosity (Athy-Heckel equation, see Equation (2) above), measured inside of the die, appeared to be linear over almost the entire range of applied pressure studied for the freeze-dried beads, with minimal initial curvilinear region attributed to particle rearrangement. This is so because beads, by virtue of their spherical shape and size, tend to exhibit minimal surface contact, thereby the particle rearrangement tends to be rapid.

Figure 28:
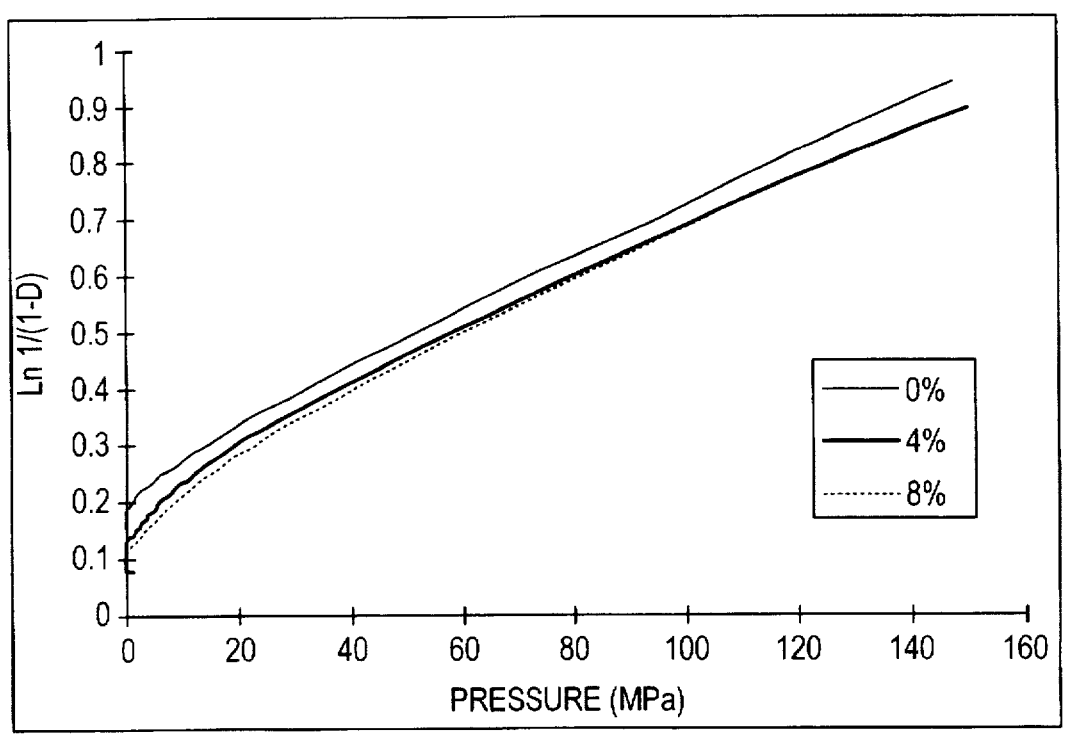
FIG. 28 shows Athy-Heckel plots of freeze-dried beads containing different levels of croscarmellose sodium in MCC.
Figure 29:
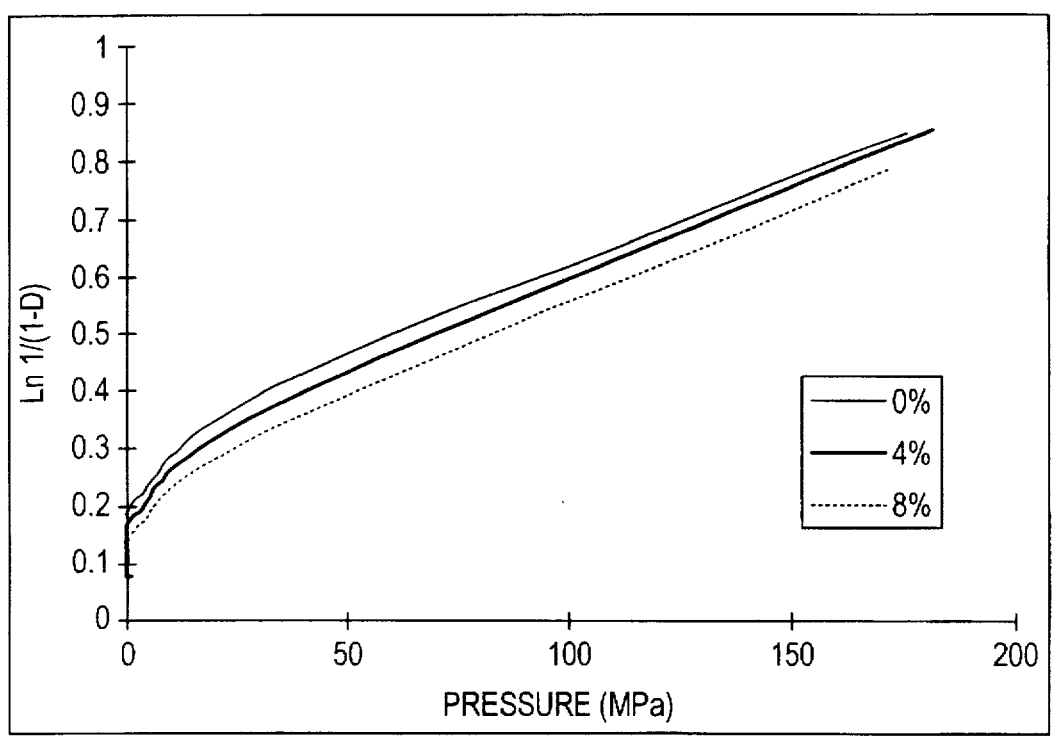
FIG. 29 shows Athy-Heckel plots of freeze-dried beads containing different levels of croscarmellose sodium in MCC:lactose (25:75).
Figure 30:
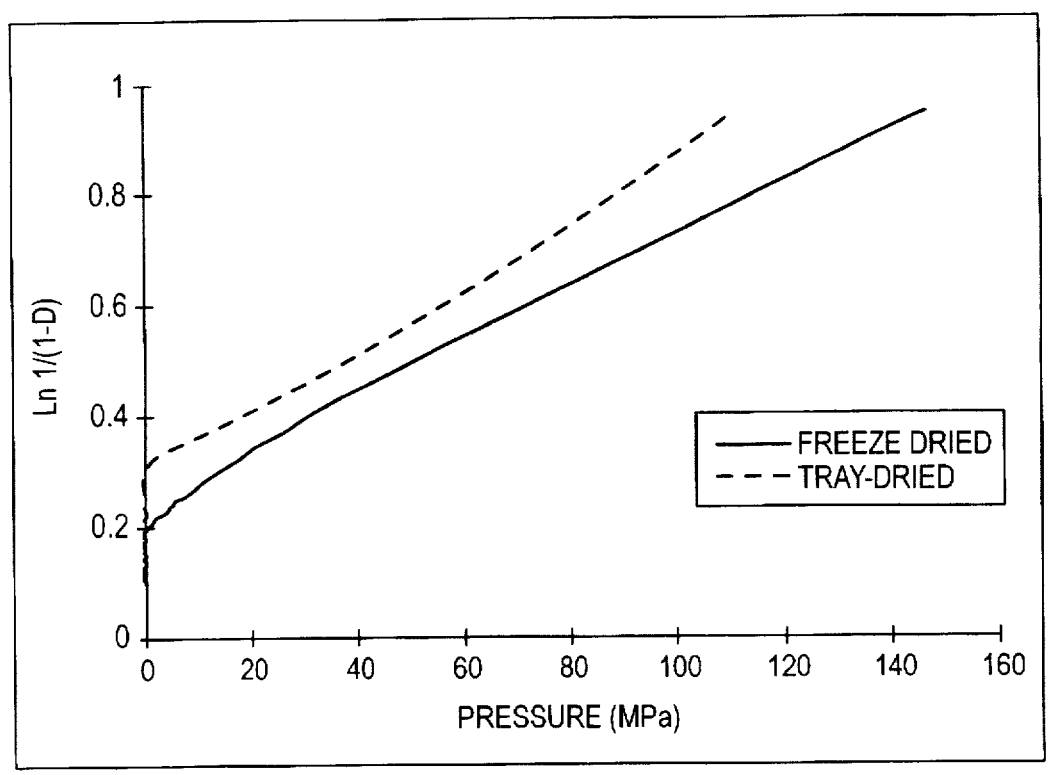
FIG. 30 shows Athy-Heckel plots of tray-dried and freeze-dried beads containing plain MCC.
Figure 31:
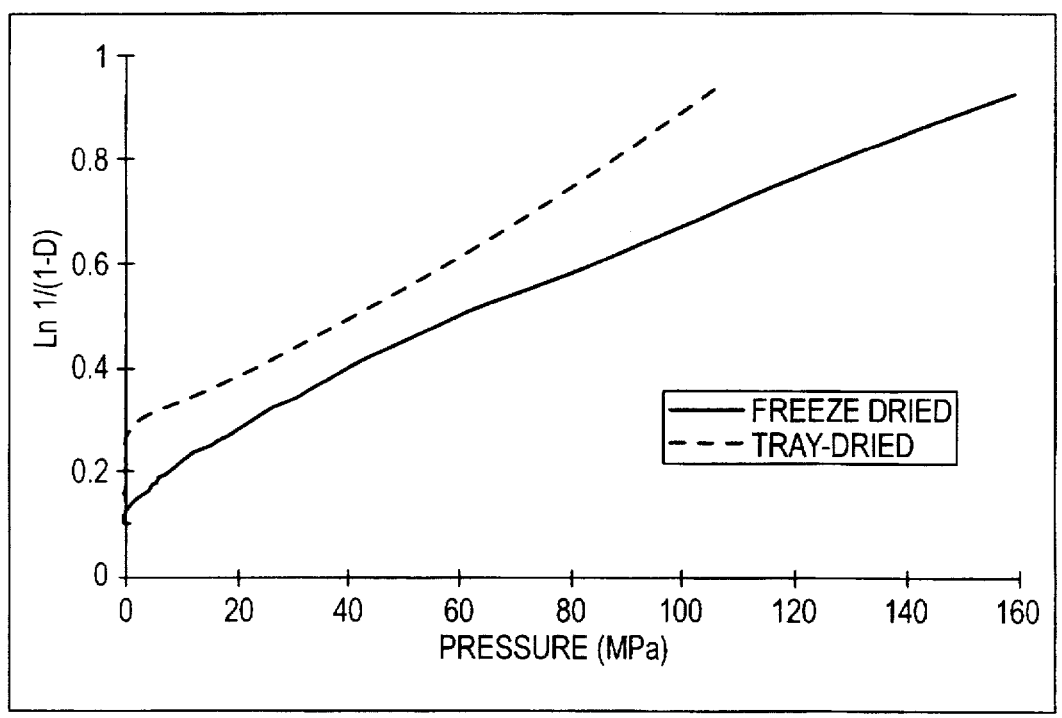
FIG. 31 shows Athy-Heckel plots of tray-dried and freeze-dried beads containing 8.0% croscarmellose sodium in MCC.

Representative Athy-Heckel plots for the freeze-dried MCC formulations and MCC/lactose (25:75) formulations at different croscarmellose sodium levels can be found in FIGS. 28 and 29, respectively. FIGS. 30 and 31 represent the Athy-Heckel plots for the tray-dried and freeze-dried formulations containing MCC and 8.0% croscarmellose sodium in MCC, respectively. The yield values for all of the freeze-dried formulations, measured in triplicate over a compression range of 40–150 MPa at an upper punch speed rate of 100 mm/sec, and those for the two tray-dried batches measured over a compression range of 40–100 MPa at an upper punch speed rate of 100 mm/sec can be found in Table 19 below.

TABLE 19

| Formulation | Yield Value (MPa) | Relative Standard Deviation |
| --- | --- | --- |
| MCC (Freeze-dried) | 216.8 | 1.20 |
| 4.0% Croscarmellose/MCC (Freeze-dried) | 220.6 | 2.30 |
| 8.0% Croscarmellose/MCC (Freeze-dried) | 222.7 | 2.28 |
| MCC:lactose (62.5:37.5) (Freeze-dried) | 262.1 | 1.17 |
| 4.0% Croscarmellose/MCC:lactose (62.5:37.5) (Freeze-dried) (Run #1) | 281.8 | 1.20 |
| 4.0% Croscarmellose/MCC:lactose (62.5:37.5) (Freeze-dried) (Run #2) | 275.2 | 2.36 |
| 4.0% Croscarmellose/MCC:lactose (62.5:37.5) (Freeze-dried) (Run #3) | 274.4 | 0.22 |
| 8.0% Croscarmellose/MCC/lactose (62.5:37.5) (Freeze-dried) | 273.3 | 1.27 |
| MCC:lactose (25:75) (Freeze-dried) | 325.6 | 1.63 |
| 4.0% Croscarmellose/MCC:lactose (25:75) (Freeze-dried) | 310.8 | 0.84 |
| 8.0% Croscarmellose/MCC:lactose (25:75) (Freeze-dried) | 314.7 | 1.08 |
| 4.0% Crospovidone/MCC (Freeze-dried) | 199.0 | 0.70 |
| 8.0% Crospovidone/MCC (Freeze-dried) | 219.0 | 1.22 |
| 4.0% Sodium starch glycolate/MCC (Freeze-dried) | 229.5 | 1.45 |
| 8.0% Sodium starch glycolate/MCC (Freeze-dried) | 264.2 | 1.38 |
| MCC (Tray-Dried) | 174.4 | 1.99 |
| 8.0% Croscarmellose/MCC (Tray-dried) | 166.9 | 0.61 |

Figure 32:
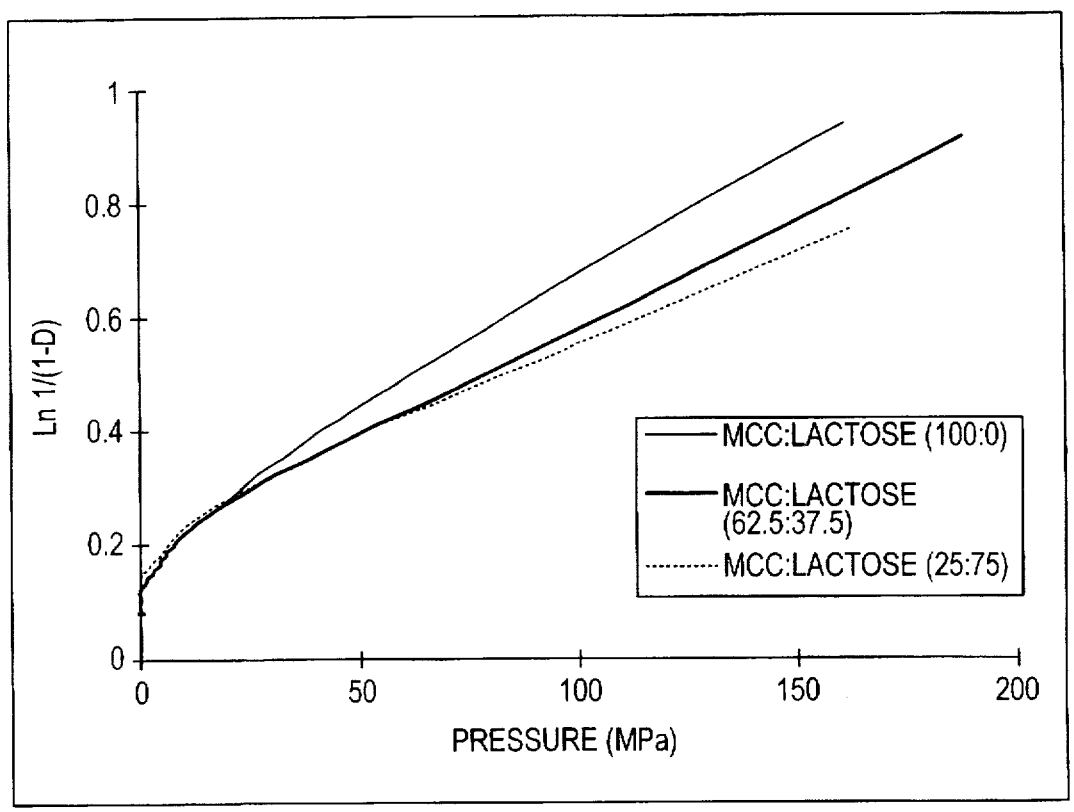
FIG. 32 shows Athy-Heckel plots of freeze-dried beads containing 8.0% croscarmellose sodium in formulations having different MCC:lactose ratio.

Results of the regression analysis to investigate the effect of formulation variables on the compressibility (yield value) of freeze-dried beads as determined by the reciprocal of the Athy-Heckel plots can be found in Table 20 below. The only significant factor was the MCC/lactose ratio. As the MCC/lactose ratio is increased, beads with lower yield values and better compressibility are produced (FIG. 32). In MCC-predominant formulations, steeper slopes (thus lower yield values) than those of the lactose predominant formulations are observed. This can be explained by the fact that lactose has a higher yield value than MCC, thus formulations which are predominant in lactose tend to have higher yield values.

TABLE 20

| Formulation Variable | Coefficient | P-Value |
|---|---|---|
| Croscarmellose Sodium Experiment | | |
| MCC/lactose Ratio | −1.2935 | 1.1E-08 |
| % Croscarmellose Sodium | 0.2517 | 0.7327 |
| Crospovidone Experiment | | |
| % Crospovidone | 0.2750 | 0.929 |
| Sodium Starch Glycolate Experiment | | |
| % Sodium starch glycolate | 5.2925 | 0.065 |

Superdisintegrants had no effect on the yield value. This is depicted in FIGS. 28 and 29 where parallel slopes of the Athy-Heckel plots were observed. The differences in the y-intercept reflect the differences in initial density or porosity of the beads. For example, the formulations containing 8.0% croscarmellose have lower y-intercept values than those which are croscarmellose-free (FIGS. 28 and 29). Since the y-intercept represents the natural logarithm of the reciprocal of porosity, then lower y-intercept values indicate higher porosities. This is in agreement with the porosity measurements determined for the different beads where higher croscarmellose sodium levels produced beads with higher porosities.

Beads produced by tray-drying exhibited statistically significant ($p<0.0001$) lower yield values than those which were freeze-dried. This can be seen in Table 19 above where the yield value for tray-dried MCC formulation was 174.4 MPa, as opposed to 216.8 MPa for the freeze-dried batch. Similarly, the yield value for tray-dried 8.0% croscarmellose sodium in MCC formulation was lower (166.9 MPa) than that which was freeze-dried (222.7 MPa).

Despite the fact that tray-drying produced beads with lower yield values (thus, higher compressibility) than those produced by freeze-drying, tablets of no appreciable hardness were produced when tray-dried beads were compressed. This can be explained by the fact that Athy-Heckel analysis is only a measure of compressibility (reduction in volume), and cannot predict the compactibility of the tablets. compactibility is a term that encompasses both compressibility and bonding of particles. Bonding of particles is the net result of constructive formation of bonds by plastic deformation and/or brittle fracture, and destructive components due to post-compression elastic recovery. Thus, although tray-dried beads were more compressible than their freeze-dried counterparts, tray-dried beads did not establish strong bonds post-compression resulting in weaker tablets. This can be attributed to a high post-compression elastic recovery, together with poor bonding associated with the hard tray-dried beads relative to those which were freeze-dried (Kleinebudde (1993), supra; Kleinebudde (1994a), supra; Kleinebudde (1994b), supra). Moreover, yield values were determined at a compression pressure range of 40–150 MPa (linear region), which is much higher than the compression pressure used to produce the compacts. Therefore, the compressibility of tray-dried and freeze-dried beads cannot be used to account for the compactibility of the tablets of the different beads at lower compaction pressures.

1. Determination of the Deformation Mechanism of Freeze-Dried Beads

Two studies were conducted to elucidate the deformation mechanism of the freeze-dried beads. In the first study, the yield values for selected formulations were evaluated at two punch speeds; a slow speed of 20 mm/sec and a fast speed of 100 mm/sec. Strain rate sensitivity index was then calculated according to Equation (3) above. In the second study, the yield values were evaluated for different sieve cuts of the same formulation, namely: 14–18, 18–20, and 20–25 mesh cuts.

The change in the compressibility (yield value) as a function of the compression speed rate can be found in Table 21 below, together with the strain rate sensitivity index for the different formulations studied.

TABLE 21

| Formulation | Yield Pressure at an Upper Punch Speed Rate of 20 mm/sec (MPa) | Yield Pressure at an Upper Punch Speed Rate of 100 mm/sec (MPa) | Strain-Rate Sensitivity Index |
|---|---|---|---|
| MCC | 174.98 (0.84)* | 216.80 (1.20) | 19.29 |
| 8.0% Croscarmellose/MCC | 181.15 (1.01) | 222.70 (2.28) | 18.66 |
| MCC:lactose (25:75) | 213.18 (6.01) | 325.60 (1.63) | 34.53 |
| 8.0% Croscarmellose/MCC:lactose (25:75) | 222.52 (0.94) | 314.70 (1.08) | 29.29 |
| 8.0% Crospovidone/MCC | 178.92 (1.66) | 219.00 (1.22) | 18.30 |
| 8.0% Sodium starch glycolate/MCC | 117.61 (0.69) | 264.00 (1.38) | 55.45 |

*Relative standard deviation

A difference in the yield pressure values with changing punch speed indicates the existence of a plastic component to the deformation process (Roberts et al, supra) of the freeze-dried beads. This can be attributed either to a change from plastic to brittle behavior, or a reduction in the amount of plastic deformation due to the time-dependent nature of plastic deformation (Rees et al, supra). Thus, at slower punch speeds of 20 mm/sec the compacted beads exhibited more plastic flow than at 100 mm/sec, resulting in a statistically significant lower yield values ($p<0.0001$). Moreover, the change in strain-rate sensitivity index (Table 21) indicates a plastic component to the deformation process, with the formulation containing 8.0% sodium starch glycolate showing the most sensitivity.

Materials that deform by brittle fracture tend to exhibit relatively high yield pressure values, irrespective of the punch speed rate utilized to produce the compacts (Hersey et al, (1971) supra; Hersey et al. (1981) supra; McKenna et al, supra; Rees et al, supra; Sheikh-Salem et al, supra; Fell et al, supra; York et al, (1973) supra; de Boer et al, supra; Rue et al, supra; York. (1979) supra; Chowhan et al, supra; Paronen et al, supra; Duberg et al, supra; Marchall et al, supra; and Hussain et al, supra). Thus, the relatively high values of the yield pressures observed during the compression of the freeze-dried beads, at both punch speeds studied, indicate the coexistence of a brittle fracture component.

Figure 3A:
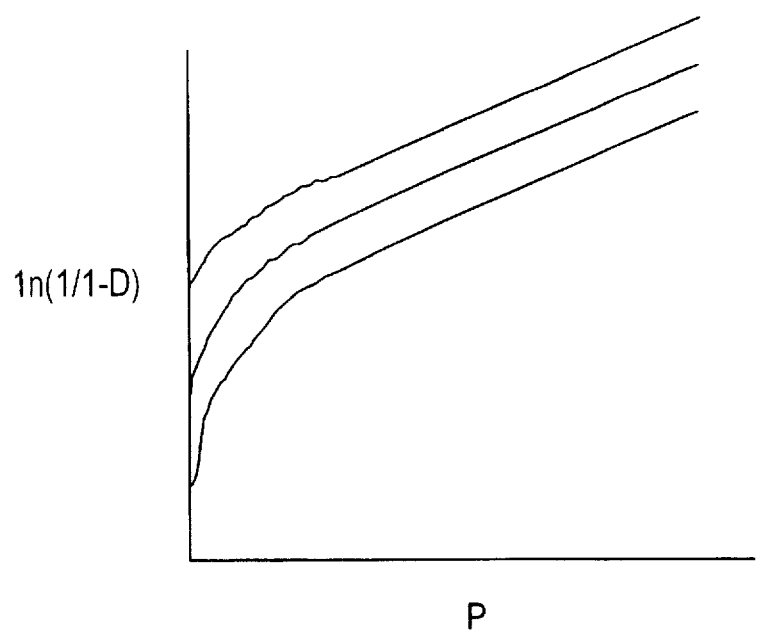
FIGS. 3A and 3B show Athy-Heckel plots for different deformation mechanisms type 1 (FIG. 3A) and type 2 (FIG. 3B).
Figure 3B:
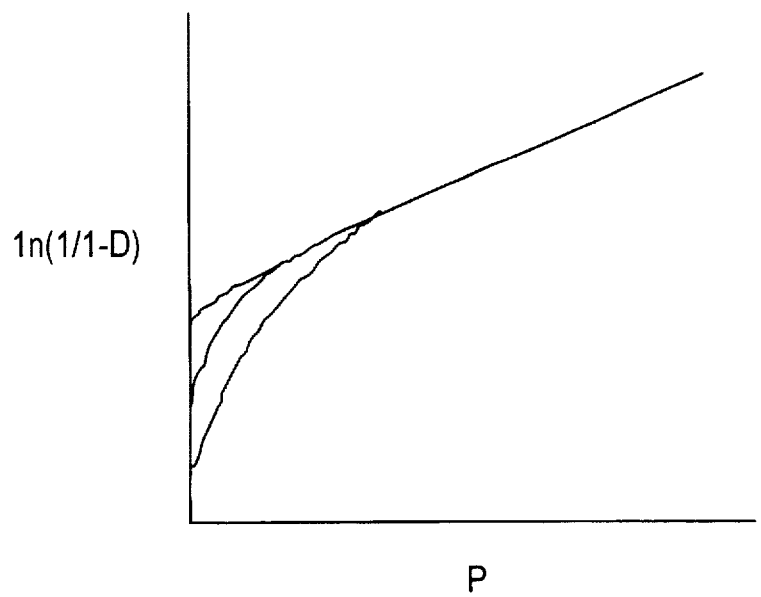
Figure 4:
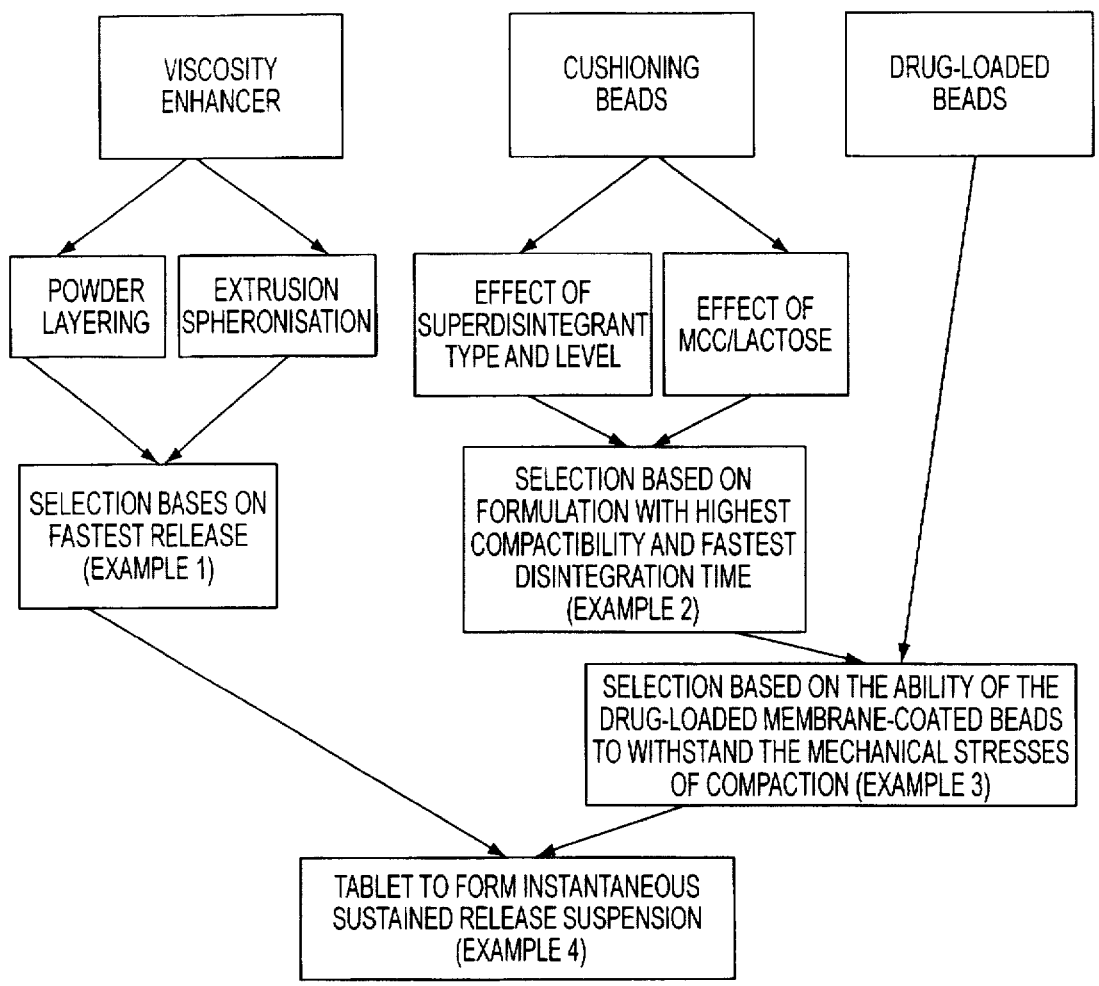
FIG. 4 is a flow chart depicting the formulation and manufacturing of tablets for instantaneous sustained release suspension.
Figure 5:
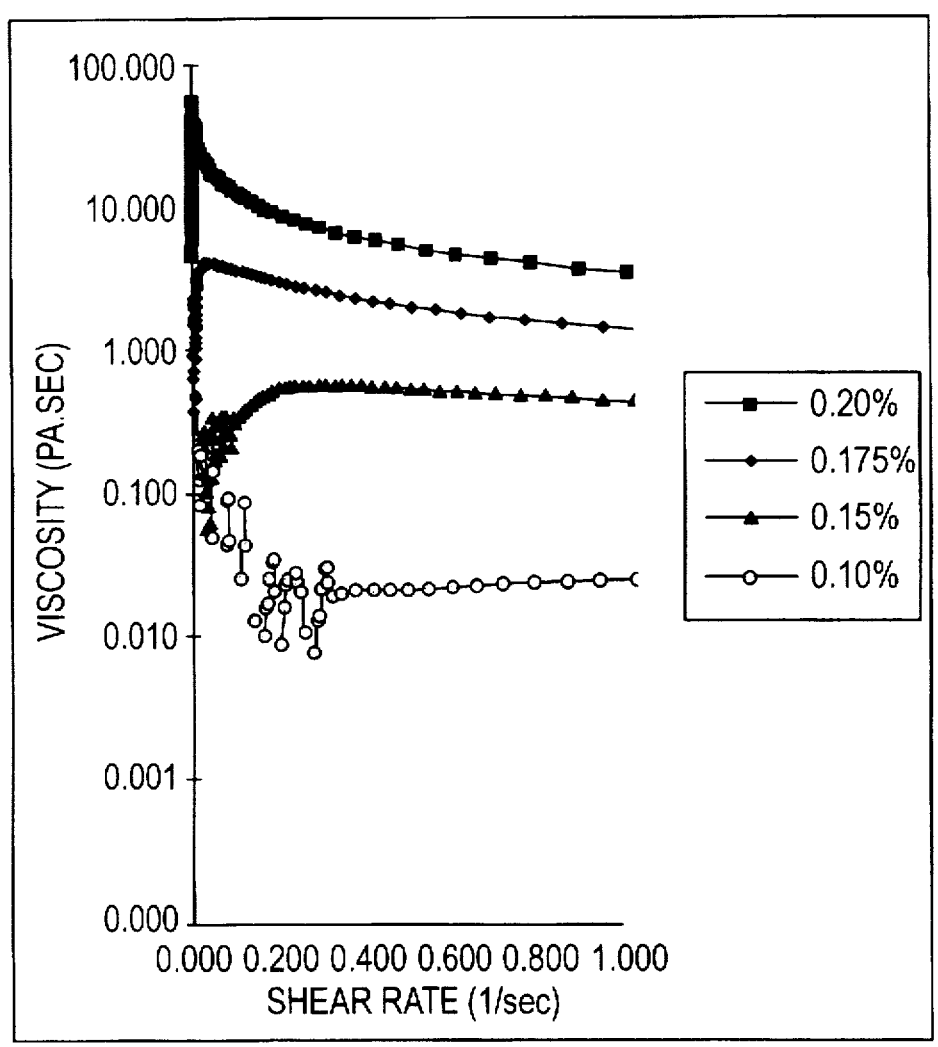
FIG. 5 shows viscosity of different concentrations of carbomer EX214 solutions as a function of shear rate.
Figure 6:
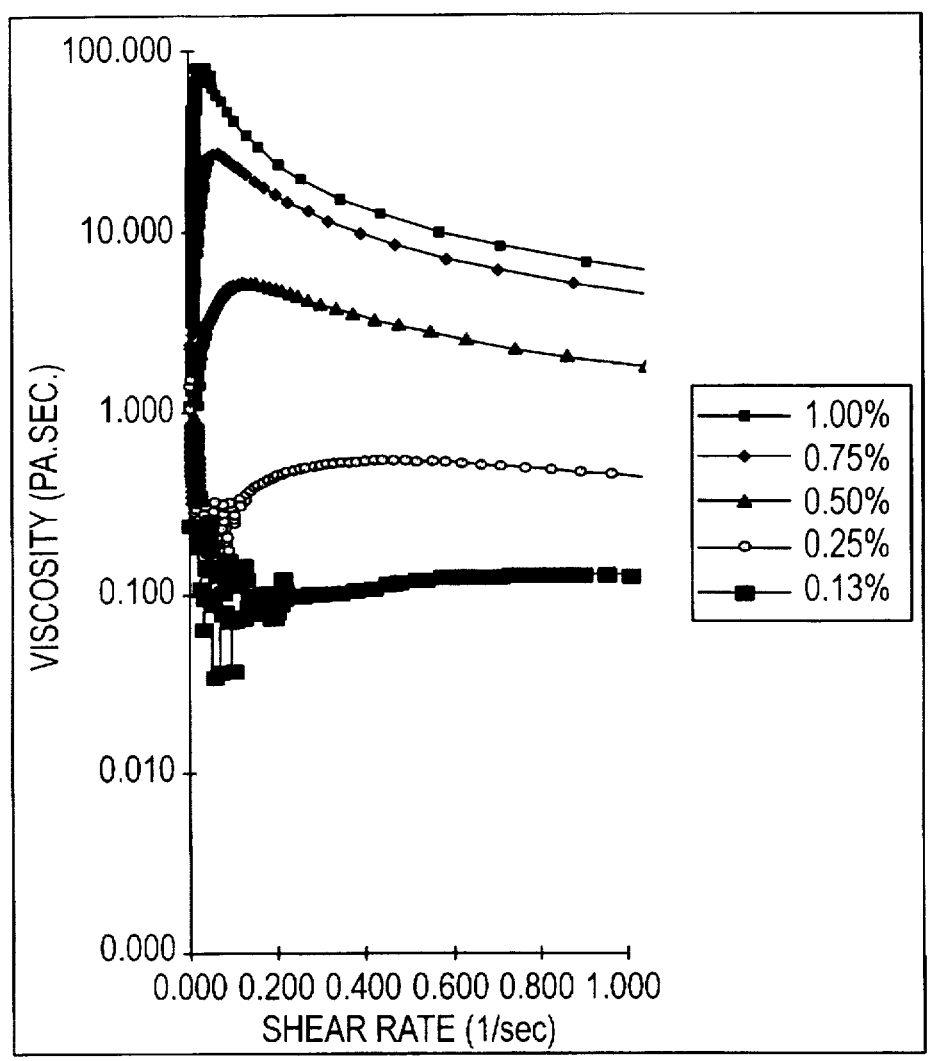
FIG. 6 shows viscosity of different concentration of Visquick® 11 solutions as a function of shear rate.
Figure 7:
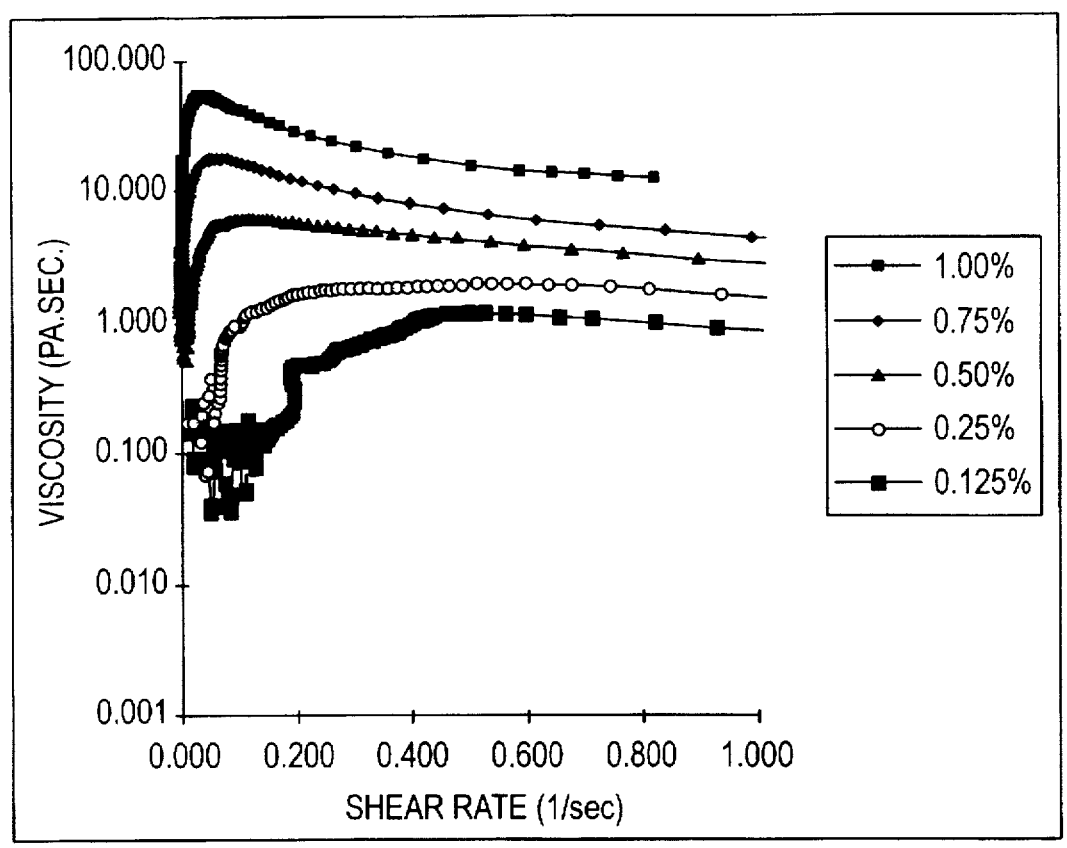
FIG. 7 shows viscosity of different concentrations of Visquick® 21 solutions as function of shear rate.
Figure 8:
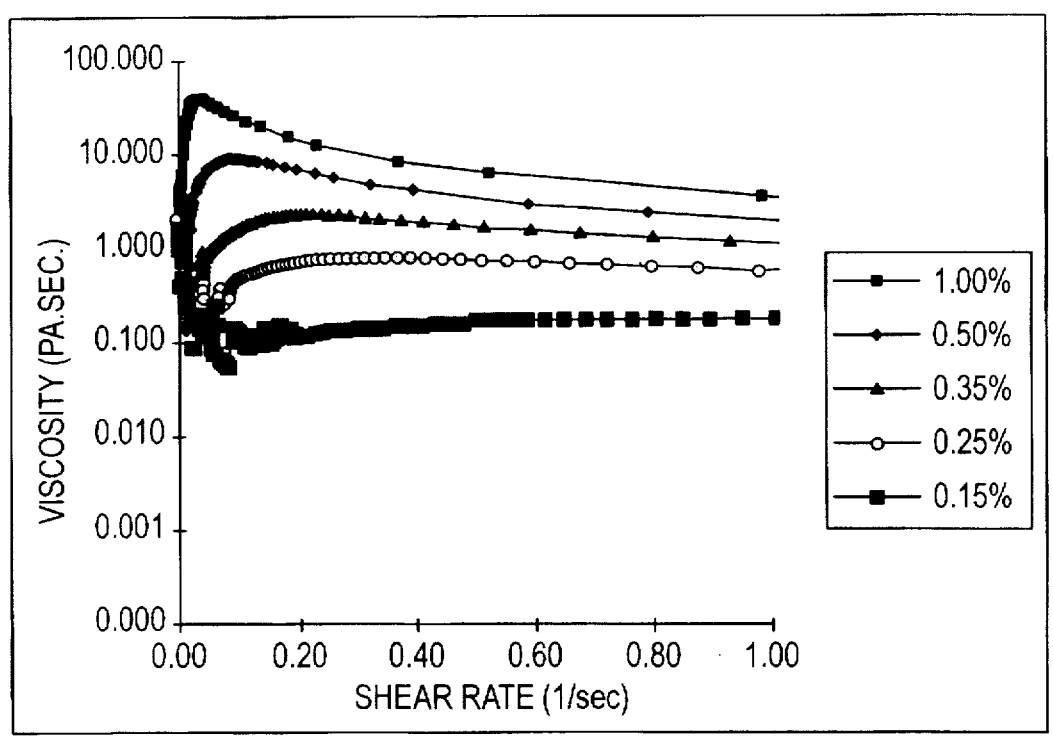
FIG. 8 shows viscosity of different concentrations of Insta*Thick Xanthan® solutions as a function of shear rate.

In the second study to explore the deformation mechanism of the freeze-dried beads, the compression profiles (Athy-Heckel plots) were evaluated for different sieve cuts (14–18, 18–20, and 20–25 mesh cuts) at an upper punch speed rate of 100 mm/sec. If the beads were to exhibit plastic deformation, type 1 behavior (FIG. 3A) would be observed in which the Athy-Heckel plots for different particle size fractions of the beads would be parallel. If brittle fracture is the predominant mechanism of deformation, type 2 behavior (FIG. 3B) would be seen in which the initial structure of the material is progressively destroyed so that above a certain pressure, coincident linear relations would be obtained for all size fractions. The use of different size fractions to detect the predominant mechanism of deformation in freeze-dried beads produced by extrusion-spheronization was not sensitive to detect any difference in the Athy-Heckel compression profiles, which were completely superimpossible. This is due to the narrow size distribution of the beads, which is an inherent advantage of the extrusion-spheronization process. If the size distribution, was wider, sieve-cuts that differ significantly in size might have given different compression profiles from which the mechanism of deformation could have been elucidated.

H. Scanning Electron Microscopy

Scanning electron micrographs (SEM's) were taken of freeze-dried beads containing plain MCC (50X), a cross-section of a freeze-dried bead containing plain MCC(100X), 8.0% croscarmellose sodium in MCC beads (50X), a cross-section of a 8.0% croscarmellose sodium in MCC bead (100X), a cross-section of a MCC:lactose (25:75) bead (100X), and a cross-section of a 8.0% croscarmellose sodium in MCC:lactose (25:75) bead (100X). An SEM of tray-dried beads containing plain MCC (50X) was also taken.

SEM's were also taken of the surface of tablet compacts at a compression pressure of 20 MPa containing freeze-dried plain MCC beads and 8.0% croscarmellose sodium in MCC (35X).

Comparing the SEM's depicting the freeze-dried beads containing plain MCC and 8.0% croscarmellose sodium in MCC reveals that the surface of the latter is more porous. Cross-sections of these two bead formulations clearly show that the freeze-dried beads containing 8.0% croscarmellose sodium in MCC are more porous than those containing plain MCC, which is due to the higher granulation fluid requirement associated with the presence of croscarmellose sodium. A similar trend is observed in the cross-sections of the beads containing MCC:lactose (25:75) and 8.0% croscarmellose sodium in MCC:lactose (25:75) for the same reason.

Tray-drying of beads containing plain MCC resulted in beads with less surface porosity than those which were freeze-dried. This is due to the shrinking phenomenon associated with tray-drying.

The surface of tablets compressed at a similar compression force containing plain MCC and 8.0% croscarmellose sodium in MCC differ significantly. Those tablets made of 8.0% croscarmellose sodium in MCC have a smoother surface than those containing plain MCC beads, where the boundaries of the component beads are still visible. This is because of the difference in porosities of the two bead systems, which resulted in a difference in compactibility.

IV. Conclusions

Inert cushioning beads of different compressibilities, compactibilities and disintegration properties were produced by freeze-drying. The optimal granulating fluid level for the different formulations studied, as determined by image analysis based on the size and roundness of the fresh undried beads, was essential to investigate the effect of different formulation variables on the properties of the dried product.

The presence of high levels of MCC and different superdisintegrants, especially croscarmellose, generally increased the granulating fluid levels requirement, thus producing freeze-dried beads with higher porosities. Compactibility studies indicate that in the absence of croscarmellose, lactose-predominant formulations were more compactible than those predominant in MCC. A major interaction was observed between MCC and croscarmellose. In the presence of high levels of MCC, croscarmellose-containing freeze-dried beads were the most compactible, producing the hardest tablets at the compression pressure ranges studied. These tablets disintegrated very quickly.

Compressibility studies revealed that formulations containing high levels of MCC exhibited lower yield values, and thus were more compressible than those formulations containing high levels of lactose. Superdisintegrants had no effect on the compressibility of beads, which could be attributed to the fact that compressibility measurements (yield values) were determined at compression forces which were higher than the ranges used in the compactibility studies. Thus, the effect of the initial porosities of the beads was diminished.

The yield values were helpful in determining the compaction mechanism of the freeze-dried beads. Freeze-dried beads exhibited both plastic deformation and brittle fracture. The presence of plastic deformation was detected by the presence of strain-rate sensitivity to the compaction process when the upper punch speed rate was varied. Brittle fracture component was detected in the relatively high yield values associated with the freeze-dried beads. The existence of both plastic deformation and brittle fracture is desired in an ideal cushioning bead system. This is so because as the cushioning beads, mixed with biologically active ingredient-loaded beads, are compacted, initial fragmentation into progeny primary powder particles would not only fill the voids between the biologically active ingredient-loaded beads, but surround them. Plastic deformation of the fine particles would then enhance the excipient-excipient interaction producing stronger compacts.

Yield value measurements for different bead-fractions were not able to explain the mechanism of deformation due to the narrow size-range of the beads produced by extrusion-spheronization process.

Tray-drying of selected batches produced beads with smaller average diameters than those which were freeze-dried. This is due to the shrinking associated with the tray-drying process, which reduced the porosity, thereby producing hard and dense beads. The tray-dried beads were not able to form tablets of any appreciable hardness when compacted.

The success of the placebo cushioning beads produced by freeze-drying must be practically evaluated by mixing and compacting them with biologically active ingredient-loaded membrane-coated sustained release beads. The cushioning beads should minimize the segregation propensity due to size and density differences, which will affect the content uniformity and weight variation of the tablets, and should deform more readily than the biologically active ingredient-loaded beads so that fracture of the membrane is minimized. Moreover, the cushioning beads should disintegrate rapidly to release the intact biologically active ingredient-loaded beads and should not affect the release kinetics of the biologically active ingredient. This challenge will be addressed in Example 3 below.

EXAMPLE 3

Formulation of Fast Disintegrating Controlled Release Tablets from Coated Particles I. Introduction Solid oral dosage forms with controlled release properties which disintegrate after administration into a large number of subunits, so-called multi-unit dosage forms, show several highly important advantages as compared to monolithic preparations. The small particles are mixed with the contents of the stomach and intestine and are distributed over a large area. Thus, high local concentration of the biologically active ingredient is avoided and the risk of undesirable side-effects reduced. The particles should be smaller than approximately 2.0 mm to be transported continuously together with the food contents through the digestive tract so that the quality, amount and timing of food uptake, as well as movement and relaxation time of the body is of minor influence on the biologically active ingredient release (Bogentoft et al. Eur. J. Clin. Pharmacol., 14:351 (1987)).

Multi-unit controlled-release dosage forms have been formulated for many years, but in most cases have involved encapsulation in hard gelatin capsules. Such preparations present a number of disadvantages: The capsules themselves are relatively expensive, the bulk density inside the capsule is low so that a larger volume is needed for high doses, and doses cannot be divided by splitting the capsules. On the contrary, tablets can be produced less expensively and can be divided without remarkable influence on the biologically active ingredient release, which is controlled after disintegration of the tablet by the totality, and make up of the still intact coated particles. Moreover, interest in the concept of tabletting coated biologically active ingredient particles increased significantly when hard gelatin capsules were tampered with criminal intent.

Some success with the compression of coated granules or crystals have been reported in the literature (Ventouras, supra; Ventouras et al. supra, Aulton et al. supra; Lehmann et al. supra; Juslin et al. Pharm. Ind., 42:829–832 (1980); and Haubitz et al. Drugs Made In Germany, 38(4) (1995)). Most of these papers dealt with compacting the biologically active ingredient-loaded entities or plastically-deforming coated potassium chloride crystals with fine highly-compressible powders, such as MCC or soft highly deformable granules made up of starch. However, due to size differences, segregation would be encountered, resulting in weight variation and content uniformity problems to varying degrees.

The desirable mechanical properties of coated millispheres to be compacted into a tablet together with excipients or placebo cushioning beads should be that they are strong, not brittle and have low elastic resilience. It is important in this dosage form that the millispheres and their coatings remain undamaged and intact so that the release profile of the biologically active ingredient is not changed. Thus, the mechanical properties of both uncoated biologically active ingredient-containing millispheres and the polymeric coat responsible for sustaining the biologically active ingredient action are of crucial importance in determining the biologically active ingredient release profile when those coated beads are compressed. The presence of a film coat applied by means of an aqueous polymeric dispersion of polymethacrylates or ethylcellulose also influences the mechanical properties of coated millispheres. Ethylcellulose is a very brittle material, and its films are reported to exhibit massive fracture under compression, regardless of the plasticizer or other additives used (Bechard et al. Drug Dev. Ind. Pharm., 18:1927–1944 (1992)). Polymethacrylates film coatings especially Eudragit® NE 30 D, RL 30 D and RS 30D are more flexible and can withstand mechanical stresses of compression so that the release patterns are very similar or nearly the same as the uncompressed particles (Lehmann et al. supra; Juslin et al. supra; and Haubitz et al. supra). Despite the fact that Eudragit® NE 30 D exhibits the most flexible films, only a variation of the thickness of the coating can be used to modify the release profile. The addition of more hydrophilic or hydrophobic additives to the film are not effective, and will influence the technical behavior of the film. Eudragit® NE 30 D is commonly used with the L 30 D-55 grade for enteric coating purposes. Flexible coatings can be generated by using a mixture of Eudragit® RL and RS. By the different permeability but unlimited miscibility of both types, a wide range of permeability can be established, so that the system can be adapted to the diffusion properties of many biologically active ingredients in a narrow range of film thickness (Lehmann et al. supra). Increasing the polymer loading has the effect of increasing the crushing strength of millispheres, whilst simultaneously enhancing millisphere resilience (characterized by a reduction in the elastic modulus) (Aulton et al. supra).

In this Example, different biologically active ingredient-loaded beads coated with (1) ethylcellulose from organic solvent, (2) an aqueous dispersion of ethylcellulose, (3) an aqueous dispersion of polymethacrylates, and (4) a mixture of an aqueous dispersion of ethylcellulose and aqueous dispersion of polymethacrylates were evaluated. These four different biologically active ingredient-loaded membrane coated beads were blended at different percentages with the freeze-dried cushioning beads (described in Example 2 above) containing 8.0% croscarmellose sodium in MCC, and compressed into tablets at various compression forces. The release profiles of each system at different bead loads and selected compression forces were evaluated to detect changes in biologically active ingredient release profiles, and photomicrographs were taken to detect the presence of cracks associated with tablet compression.

II. Experiments

A. Materials

Four different biologically active ingredient-loaded beads coated with different polymeric membranes to sustain biologically active ingredient action were studied. All biologically active ingredient-loaded beads were produced by extrusion-spheronization utilizing MCC as the primary filler binder. The following biologically active ingredient-loaded beads were evaluated:

1. Propranolol hydrochloride beads supplied by Wyeth-Ayerst (Rouses Points, N.Y.). These beads of 60% (w/w) potency were produced by extrusion-spheronization. The sustained action was imparted by coating with ethylcellulose applied from an organic-solvent system.

2. Phenylpropanolamine hydrochloride beads (PPA-HCl) supplied by FMC Corporation (Princeton, N.J.). The uncoated beads of 38% (w/w) potency were produced by extrusion-spheronization. The sustained action was imparted by coating with 10% (w/w) ethylcellulose aqueous polymeric dispersion (Aquacoat®) plasticized with 24% (w/w) dibutyl sebacate. The coated beads were oven-dried for 2 hours at 60° C.

3. Theophylline beads (RD010) supplied by Niro-Aeromatic (Columbia, Md.). These beads, of 60% (w/w) potency, were produced by extrusion-spheronization. The sustained action was imparted by coating with 6.0% (w/w) polymethacrylic acid aqueous polymeric dispersion. The coating was composed of 48% amminomethacrylate copolymer and 9.5% methacrylic acid copolymer plasticized with 9.5% (w/w) triethyl citrate. A 2.0% (w/w) overcoat was also applied.

4. Theophylline beads (RD011) supplied by Niro-Aeromatic (Columbia, Md.). These beads of 60%

(w/w) potency were produced by extrusion-spheronization. The sustained action was imparted by coating with 7.0% (w/w) mixture of polymethacrylic acid and Aquacoat® aqueous polymeric dispersions. The coating was composed of 63% (w/w) Aquacoat®, 16% (w/w) methacrylic acid copolymer and was plasticized with 20% (w/w) triethyl citrate. A 2.0% (w/w) overcoat was also applied.

MCC (Avicel® PH200, FMC Corp., Philadelphia, Pa.) or freeze-dried cushioning beads containing 8.0% (w/w) cros-carmellose sodium in MCC (Avicel® PH101), were prepared as described in Example 2 above, except that a 1.2 mm extrusion screen was used to produce larger beads. These cushioning beads were mixed and compressed with the biologically active ingredient-loaded sustained action beads.

B. Methods

1. Production of Tablets

Blends of various bead loads (Table 22) were prepared by mixing the biologically active ingredient-loaded membrane-coated beads (14–20 mesh cut) with either the (14–20 mesh cut) freeze-dried cushioning beads or MCC. The two filler systems were used to study the effect of filler particle size on the content uniformity and weight variation expected to be encountered due to size segregation. The batch size for each blend was 500 g and blending was performed for 10 min in a 2.0 quart twin-shell blender (Patterson Kelly Twin Shell V-Blender, Model #LB-5695, The Patterson-Kelly Co. Inc. East Stroudsburg, Pa.). Tablets were compressed on a single station of an instrumented rotary tablet press (Stokes RB-2, Stokes Engineering, Philadelphia, Pa.) utilizing a 1.58 mm flat-faced punches. The instrumentation for the measurement of compression force has been previously described by Salpekar et al. *J. Pharm . Sci.*, 63:289–293 (1974)). The angular separation between filling and compression was 180°. Approximately twenty tablets were collected at each compression pressure (Table 22). After 24 hrs of storage, the thickness of 5 individual tablets at each compression force was determined using a digital micrometer (Digimatic Caliper, Mitutoyo Ltd., Andover, England). The crushing strength (P) of the tablets was determined by diametral loading in a standard motorized tester (Key Tablet Hardness Tester, Model NT-300 Key International Inc., Englishtown, N.J.). The value used for P was the mean of five crushing strength determinations of tablets at each compression pressure. Tablet tensile strength ($\sigma$) in $Kg/cm^2$ was calculated using Equation (1) above. Compaction profiles consisting of the different tablets tensile strengths for each of the tablets were generated by plotting tensile strength versus compression pressure.

TABLE 22

| Formulation | Compression Pressure (Kg/cm²) |
|---|---|
| Propranolol Hydrochloride | |
| 25% Propranolol Hydrochloride/ | 187.2, 223.3 |
| 75% Cuhioning Beads | and 264.0 |
| 50% Propranolol Hydrochloride/ | 196.2, 236.9 |
| 50% Cushioning Beads | and 277.6 |
| 25% Propranolol Hydrochloride/ | 155.5, 223.3 |
| 75% Avicel ® PH200 | and 304.7 |
| 50% Propranolol Hydrochloride/ | 169.1, 209.8 |
| 50% Avicel ® PH200 | and 291.1 |
| Phenylpropanolamine Hydrochloride | |
| 12.5% Phenylpropranolamine Hydrochloride/ | 169.1, 223.3 |

TABLE 22-continued

| Formulation | Compression Pressure (Kg/cm²) |
|---|---|
| 87.5% Cushioning Beads | and 331.8 |
| 12.5% Phenylpropanolamine Hydrochloride/ | 94.5, 162.3 |
| 87.5% Avicel ® PH200 | and 250.5 |
| 25% Phenylpropranolamine Hydrochloride/ | 169.1, 223.3 |
| 75% Cushioning Beads | and 331.8 |
| Theophylline RD010 | |
| 12.5% Theophylline RD010/ | 223.3, 331.8 |
| 87.5% Cushioning Beads | and 467.5 |
| 25% Theophylline RD010/ | 223.3, 331.8, |
| 75% Cushioning Beads | 467.5 and 603.1 |
| 25% Theophylline RD010/ | 223.3, 331.8, |
| 75% Avicel ® PH200 | 467.5 and 603.1 |
| Theophylline RD011 | |
| 12.5% Theophylline RD011/ | 223.3, 331.8, |
| 87.5% Cushioning Beads | 467.5 and 603.1 |

2. Determination of the Biologically Active Ingredient Content of Propranolol Hydrochloride Beads and the Content Uniformity of Their Compacts The biologically active ingredient content of beads and the content uniformity of compacted tablets for propranolol hydrochloride were determined according to the USP XXIII with slight modifications. A standard curve was prepared by transferring approximately 100 mg of the propranolol hydrochloride (Gyma Labs, Lot #24642), accurately weighed, to a 50 ml volumetric flask. The contents were dissolved in a solvent mixture composed of a solution of 50:50 methanol:0.012N HCl. Five milliliters of this solution was transferred to a 100 ml volumetric flask, and was diluted to volume with distilled water and mixed. Serial dilutions were made to construct the standard curve. The biologically active ingredient content was measured spectrophotometrically by a UV spectrophotometer (Model UV-106A, Shimadzu Scientific Instruments, Inc., Columbia, Md.) at a wavelength of 290 nm using a quartz cuvette (1.0 cm path length). A 98:2 water:methanol mixture was used as the blank.

The biologically active ingredient content for the propranolol hydrochloride beads was analyzed in triplicate. Moreover, three samples of the tablets produced at each compression pressure of each formulation listed in Table 22 above were randomly selected and analyzed for propranolol hydrochloride content. Each tablet, or a fixed weight of beads, were weighed and transferred separately to a 100 ml volumetric flask containing about 70 ml of a solvent mixture composed of a solution of 50:50 methanol:0.012N HCl. Each flask was placed in a mechanical shaker for 24 hrs to allow the biologically active ingredient to be released. A 24 hr period was adequate for complete release of the biologically active ingredient, as determined from the dissolution profile of uncompacted beads, where the asymptote was reached at 12 hrs. An additional solvent mixture was added to achieve a 100 ml volume, followed by shaking each flask to ensure uniform mixing. A portion of the solution was centrifuged at 1000 RPM for about 10 min to obtain a clear solution. Five milliliters of the clear supernatant was transferred to a 100 ml volumetric flask, and diluted to volume with distilled water and mixed. The content was determined spectrophotometrically at a wavelength of 290 nm using the previously constructed standard curve.

3. Determination of the Biologically Active Ingredient Content of Phenylpropanolamine Hydrochloride Beads and the Content Uniformity of Their Compacts The biologically active ingredient content of beads and the content uniformity of compacted tablets for phenylpropanolamine hydrochloride was determined according to the USP XXIII with slight modifications. A standard curve was prepared by transferring about 250 mg of the phenylpropanolamine hydrochloride USP (Lot# 40560, National Pharm Manufacturing Co.), accurately weighed, to a 1000 ml volumetric flask. The content was dissolved in distilled water. Serial dilutions were made to construct the standard curve. The biologically active ingredient content was determined by HPLC-UV spectrophotometer (Waters 486 Turnable Absorbance Detector, Water Millipore Corporation, Milford, Mass.) at a wavelength of 254 nm. Solvent A was prepared by dissolving 1.9 g of sodium 1-hexanesulfonate in 700 ml of distilled water, followed by the addition of 50 ml of 1.0M monobasic sodium phosphate and 20 ml of 0.25N triethylammonium phosphate (prepared by mixing 500 ml of a solution containing 25.3 g of triethylamine and 500 ml of a solution containing 9.6 g phosphoric acid). Solvent A was diluted with distilled water to 1.0 liter and mixed. The mobile phase was composed of a 100:82 mixture of solvent A and methanol after being degassed. The chromatographic column was a 4.6 mm×25 cm column containing C-18 packing (Type 1B-Sil 5 μ C18, Phenomenex, Torrance, Calif.). The flow rate was 1.5 ml per min. An accurately measured volume of 100 μl was injected into the column, and the peak areas were recorded and compared to those of the standard curve in order to determine the biologically active ingredient concentration in the samples.

The biologically active ingredient content for the phenylpropanolamine hydrochloride beads was analyzed in triplicate. Three samples of the tablets produced at each compression pressure of each formulation listed in Table 22 above were randomly selected and analyzed for phenylpropanolamine hydrochloride content. Each tablet or bead sample was weighed and transferred separately to a 100 ml volumetric flask containing about 70 ml a distilled water. Each flask was placed in a mechanical shaker for 24 hrs to allow the biologically active ingredient to be released, and was then diluted to volume with distilled water. A 24 hr period was adequate for complete release of the biologically active ingredient, as determined from the dissolution profile of uncompacted beads, where the asymptote was reached at 12 hrs. A portion of the solution was centrifuged at 1000 RPM for about 10 min to obtain a clear solution. Five milliliters of the clear supernatant was transferred to a 100 ml volumetric flask and diluted to volume with distilled water and mixed. The content was determined spectrophotometrically at a wavelength of 254 nm using the previously constructed standard curve.

4. Determination of the Biologically Active Ingredient Content of Theophylline RD010 and RD011 Beads and the Content Uniformity of Their Compacts A standard curve was prepared by transferring about 125 mg of the theophylline (Lot# 12F-0630, Sigma Chemical Co.), accurately weighed, to a 1000 ml volumetric flask. The content was dissolved in distilled water. Serial dilutions were made to construct the standard curve. The absorbance was measured spectrophotometrically (Model UV-106A, Shimadzu Scientific Instruments, Inc., Columbia, Md.) at a wavelength of 271 nm using a quartz cuvette (1.0 cm path length), and was used to calculate concentration. Distilled water was used as the blank.

The biologically active ingredient contents for the theophylline RD010 and RD011 beads were analyzed in triplicate. Moreover, three samples of the tablets produced at each compression pressure of each formulation listed in Table 22 above were randomly selected and analyzed for the theophylline content. Each tablet, or a certain amount of beads were weighed and transferred separately to a 100 ml volumetric flask containing about 70 ml distilled water. Each flask was placed in a mechanical shaker for 24 hrs to allow the biologically active ingredient to be released. A 24 hr period was adequate for complete release of the biologically active ingredient, as determined from the dissolution profile of uncompacted beads, where the asymptote was reached at 10 and 6 hrs for the RD010 and RD011 theophylline beads, respectively. An additional distilled water was added to achieve a 100 ml volume, followed by shaking each flask to ensure uniform mixing. A portion of the solution was centrifuged at 1000 RPM for about 10 min to obtain a clear solution. Five milliliters of the clear supernatant was transferred to a 100 ml volumetric flask, and was diluted to volume with distilled water and mixed. The content was determined spectrophotometrically at a wavelength of 271 nm using the previously constructed standard curve.

5. Dissolution of Propranolol Hydrochloride Beads and Their Compacts

Dissolution studies were performed using the USP XXIII apparatus 2 (paddle method, Vanderkamp 600, Van-Kel. Industries Inc., Edison, N.J.) at a paddle speed of 50 RPM. The release profiles of propranolol hydrochloride from uncompacted beads and from tablets at selected compression pressures were evaluated in triplicate to study the effect of compression on the release kinetics of the biologically active ingredient. The dissolution medium consisted of 900 ml of degassed distilled water maintained at 37° C. The dissolution apparatus was calibrated using USP prednisone and salicylic acid calibrator tablets (USP Convention Inc., Rockville, Md.). Direct ultraviolet detection at 290 nm was used to assess the biologically active ingredient concentration in the dissolution medium. The dissolution medium was continuously pumped through 0.1 cm flow cells cuvettes by a peristaltic pump (Rainin Instrument Co., Inc., Woburn, Mass.).

6. Dissolution of Phenylpropanolamine Hydrochloride Beads and Their Compacts

Dissolution studies were performed using the same apparatus and procedure described above except that manual samples of the supernatant were taken manually at 0.5, 1.0, 1.5, 2.0, 3.0, 6.0 and 24 hrs. HPLC analysis as outlined in the content uniformity of phenylpropanolamine section above was performed to determine the amount released as a function of time at a wavelength of 254 nm.

7. Dissolution of Theophylline from RD010 and RD011 Beads and Their Compacts

Dissolution studies were performed using the same apparatus and procedure followed to determine the release profile of propranolol, except that a wavelength of 271 nm was used.

8. Photomicroscopy of Tablet Compacts

Magnified photographs for fractured tablets composed of 25% propranolol hydrochloride, phenylpropanolamine hydrochloride or theophylline RD010 and 12.5% theophylline RD011 in freeze-dried cushioning beads, compacted at a compression pressure of 264.0, 331.8, 331.8 and 331.8 Kg/cm$^2$, respectively, were taken at a magnification of 23× to check for any fracturing of the biologically active ingredient-loaded beads occurring inside the tablet matrix as a result of the compaction process.

Moreover, surface pictures of intact tablets composed of 25% theophylline RD010 or theophylline RD011 and freeze-dried cushioning beads were taken at a similar magnification to examine for any fracturing of the beads exposed to the surface. A Wild Leipz microscope (Wild Leipz USA Inc., Rockleigh, N.J.) connected to a Sony Video Printer (Model UP5000, Sony Corp., Tokyo, Japan) was used.

9. Scanning Electron Microscopy of Biologically Active Ingredient-Loaded Membrane-Coated Beads Scanning electron micrographs for representative fields of the biologically active ingredient-loaded beads, obtained from the internal matrix of tablets composed of 25% propranolol hydrochloride, phenylpropanolamine or theophylline RD010 and 12.5% theophylline RD011 in freeze-dried cushioning beads, compacted at a compression pressure of 264.0, 331.8, 331.8 and 331.8 Kg/cm$^2$, respectively, were taken at a magnification of 75×, 150× and 500× using a scanning electron microscope (Model: JSM-T200, Jeol Ltd., Tokyo, Japan). After removing the excipients adhering to the biologically active ingredient loaded-beads with a brush, the beads were placed on aluminum mounts. Double-sided Scotch® tape was previously applied to the top of the mounts. Beads added to the surface of the mounts were sputter coated (Hummer VI Sputtering System, Technics East Inc., Annandale, Va.) with a gold-palladium mixture. Settings used on the sputtering system were as follows: vacuum: 75 milliTorr, voltage: 9 Volts, sputtering time: 5.0 min. The samples were observed at working distance of 20 mm and an excitation voltage of 25 kV. Photomicrographs were taken using a 35 mm camera (Model FT-1, Konica, Japan) and Kodak film (TMAX 100, Eastman Kodak Co., Rochester, N.Y.).

C. Results and Discussion

The applicability of the placebo cushioning beads produced by freeze-drying (Example 2 above) was practically evaluated in this example by mixing and compacting them with different biologically active ingredient-loaded beads whose action was sustained by different polymeric membranes. The tablets contained propranolol beads coated with ethylcellulose from organic solvent, phenylpropanolamine hydrochloride beads coated with an aqueous dispersion of ethylcellulose, theophylline beads coated with an aqueous dispersion of polymethacrylates, and theophylline beads coated with a mixture of an aqueous dispersion of ethylcellulose and polymethacrylates were prepared using Avicel® PH200 (MCC) or freeze-dried cushioning beads as filler-binder.

The two different filler systems, namely MCC with a mean particle size of 200 μm and the freeze-dried cushioning beads (14–20 mesh cut, 850–1400 μm), were used to study the effect of the filler particle size on the segregation propensity of the biologically active ingredient-loaded beads (14–20 mesh cut). The cushioning beads were expected to minimize the segregation propensity due to size differences, which is reflected in the content uniformity and weight variation of the tablets. Moreover, the cushioning beads should deform more readily than the biologically active ingredient-loaded beads, so that fracture of the membrane is minimized.

Figure 33:
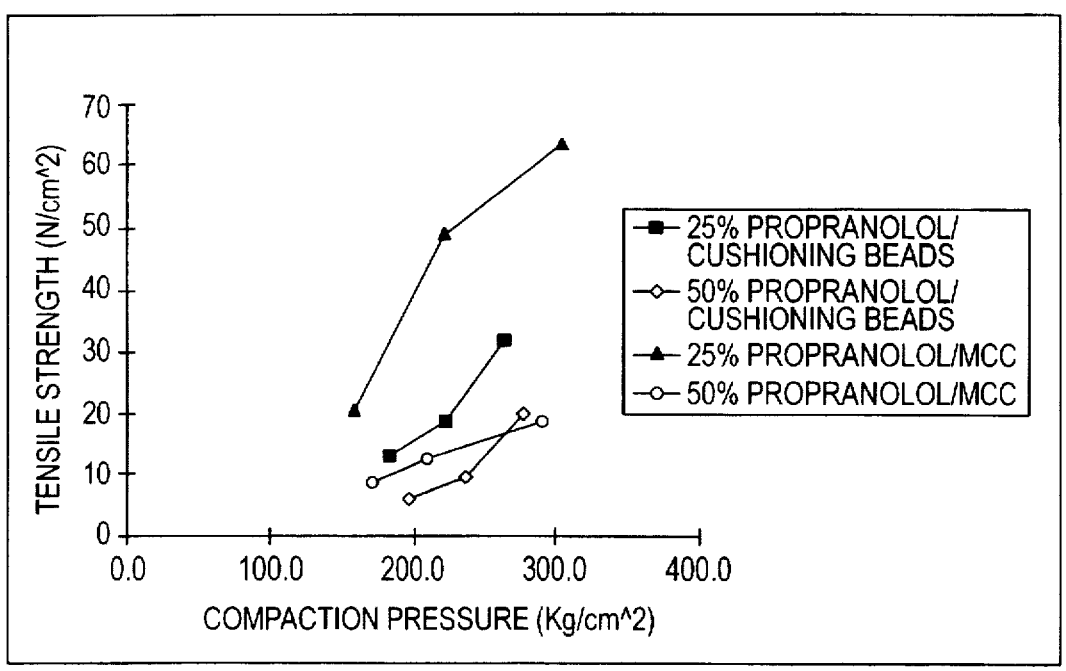
FIG. 33 shows compaction profiles of propranolol hydrochloride beads in different filler systems.
Figure 34:
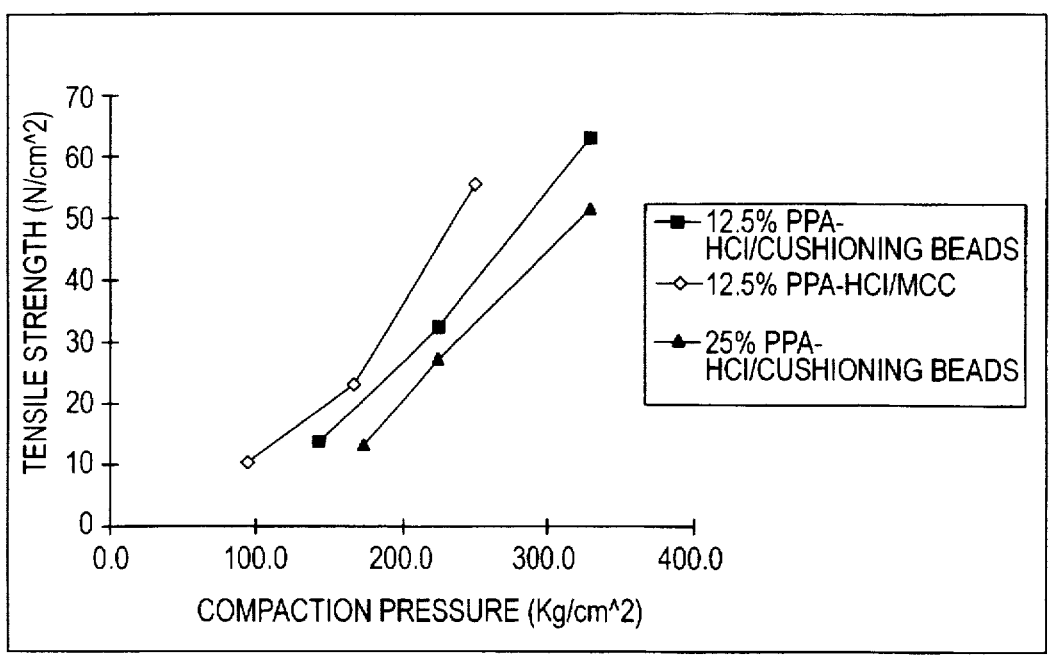
FIG. 34 shows compaction profiles of phenylpropanolamine hydrochloride beads in different filler systems.

1. Compaction of Biologically Active Ingredient-loaded Beads in Different Different Filler Systems The compaction profiles of the 25% and 50% propranolol hydrochloride beads (coated with ethylcellulose from an organic solvent) in MCC and freeze-dried cushioning beads can be found in FIG. 33. Profiles for 12.5% and 25% phenylpropanolamine (PPA-HCl) combined with cushioning beads or MCC can be seen in FIG. 34. Compaction profiles for beads containing 12.5% or 25% theophylline RD010 (coated with methacrylate copolymers) combined with cushioning beads or MCC can be seen in FIG. 35. A single compaction profile for 12.5% theophylline RD011 (coated with a mixture of Aquacoat® and methacrylate copolymers) in cushioning beads was generated and is presented in FIG. 36.

Increasing compaction pressure increased the tensile strengths of tablets, on the other hand, increasing the percentage of biologically active ingredient-loaded beads produced compacts of lower tensile strengths, due to a reduction in the amount of compactible filler-matrix.

Figure 35:
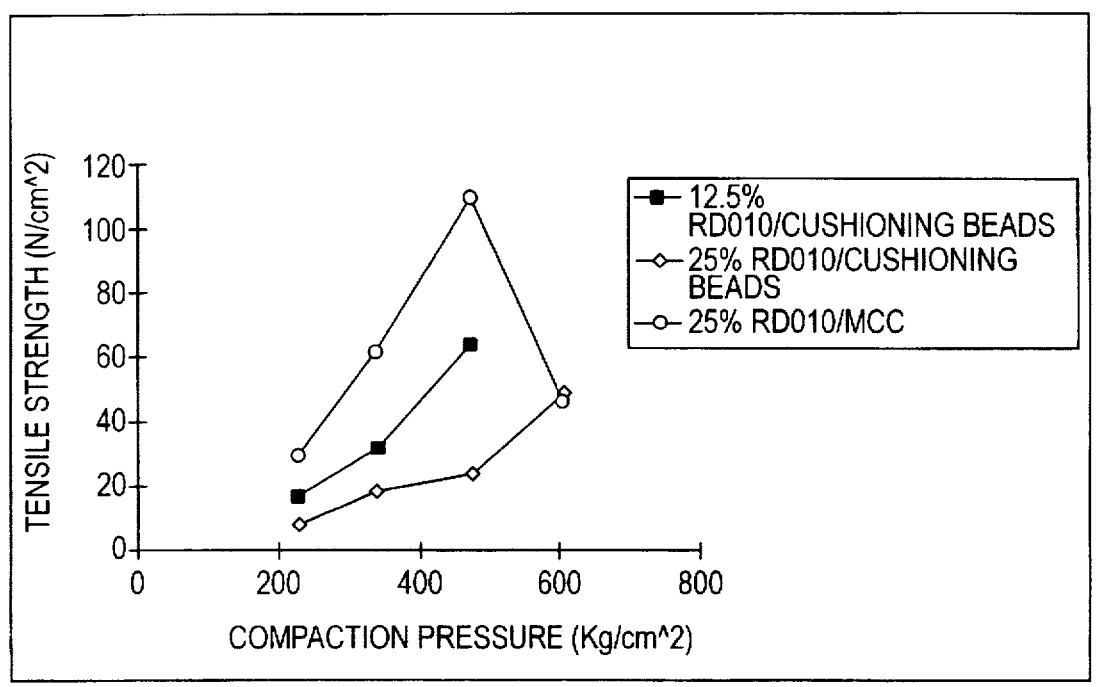
FIG. 35 shows compaction profiles of theophylline RD010 beads in different filler systems.
Figure 36:
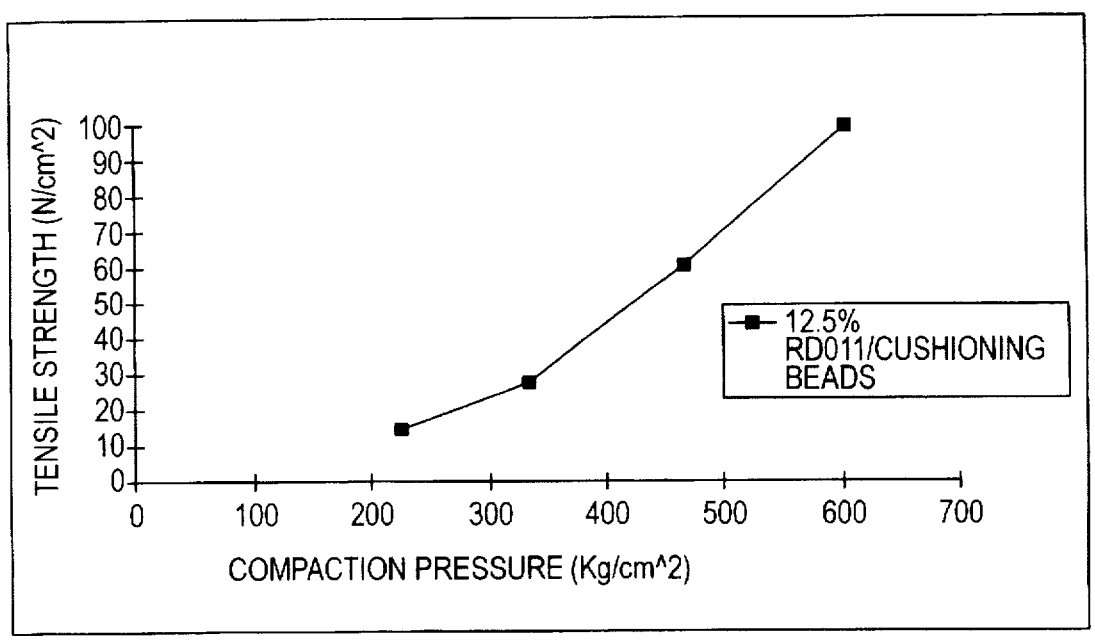
FIG. 36 shows compaction profile of 12.5% theophylline RD011 beads in cushioning beads.
Figure 37:
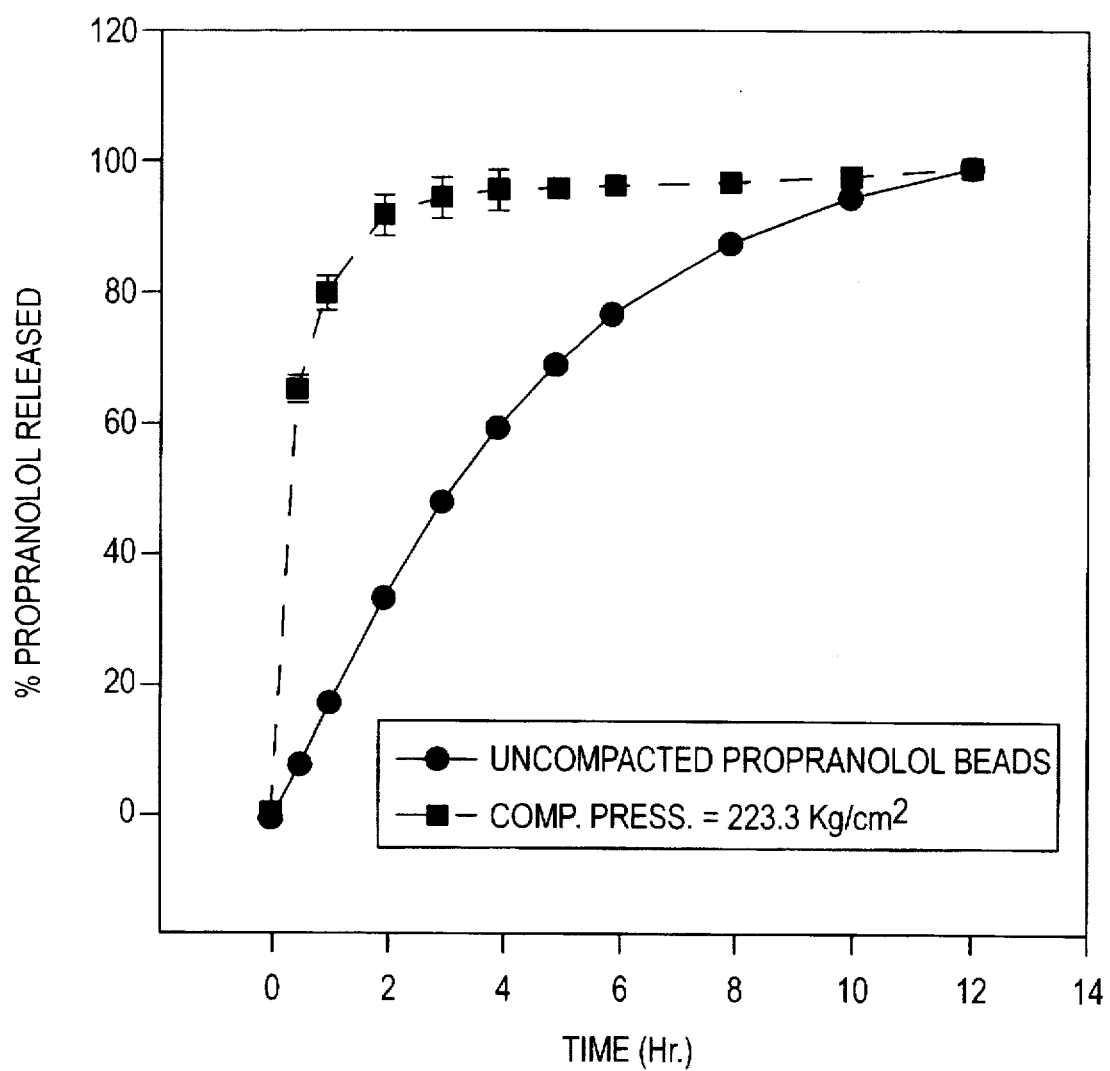
FIG. 37 shows the dissolution of propranolol hydrochloride from uncompacted and compacted beads (25% propranolol beads/75% cushioning beads).
Figure 38:
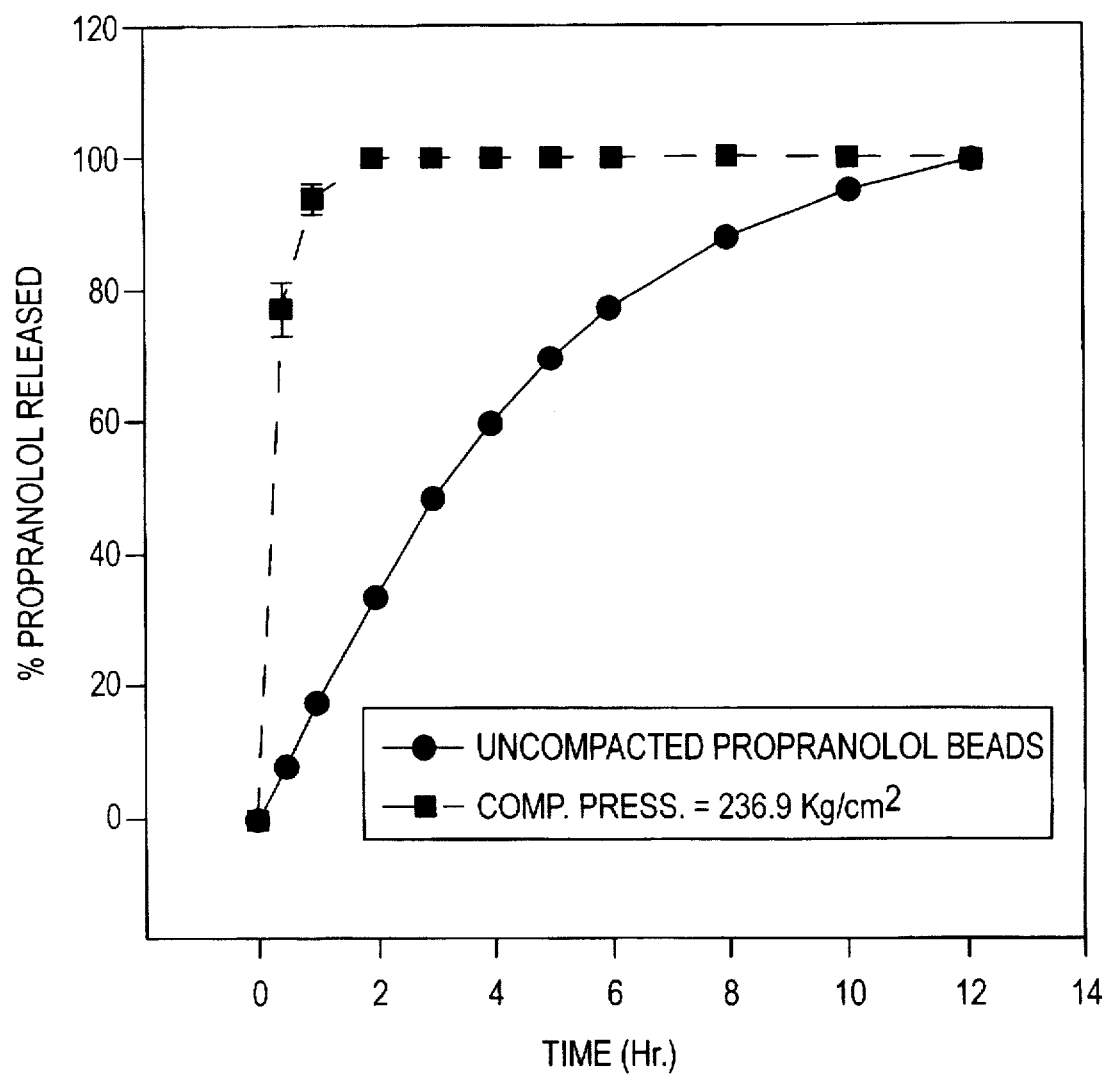
FIG. 38 shows the dissolution of propranolol hydrochloride from uncompacted and compacted beads (50% propranolol beads/50% cushioning beads).
Figure 39:
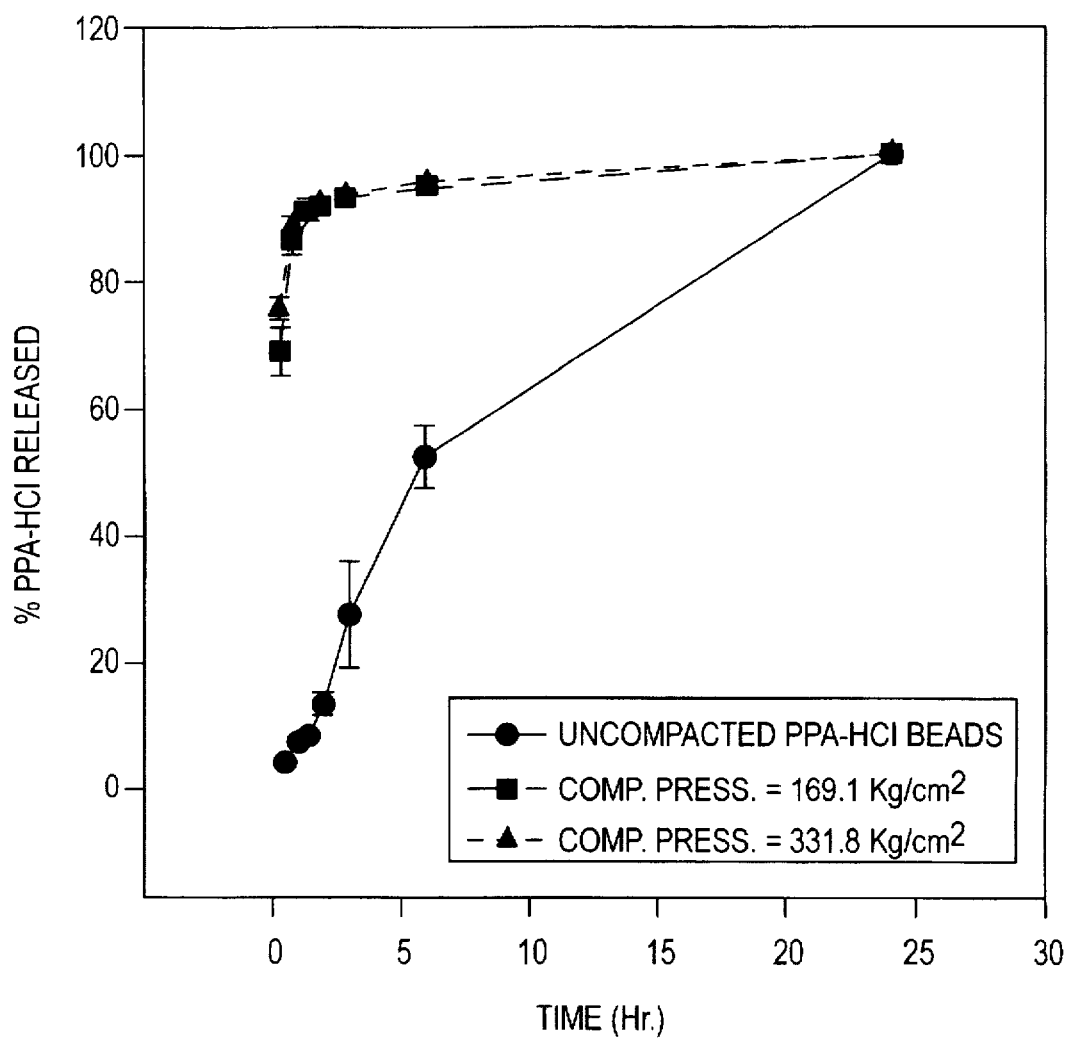
FIG. 39 shows the dissolution of phenylpropanololamine hydrochloride from uncompacted and compacted beads (12.5% PPA-HCl beads/87.5% cushioning beads).
Figure 40:
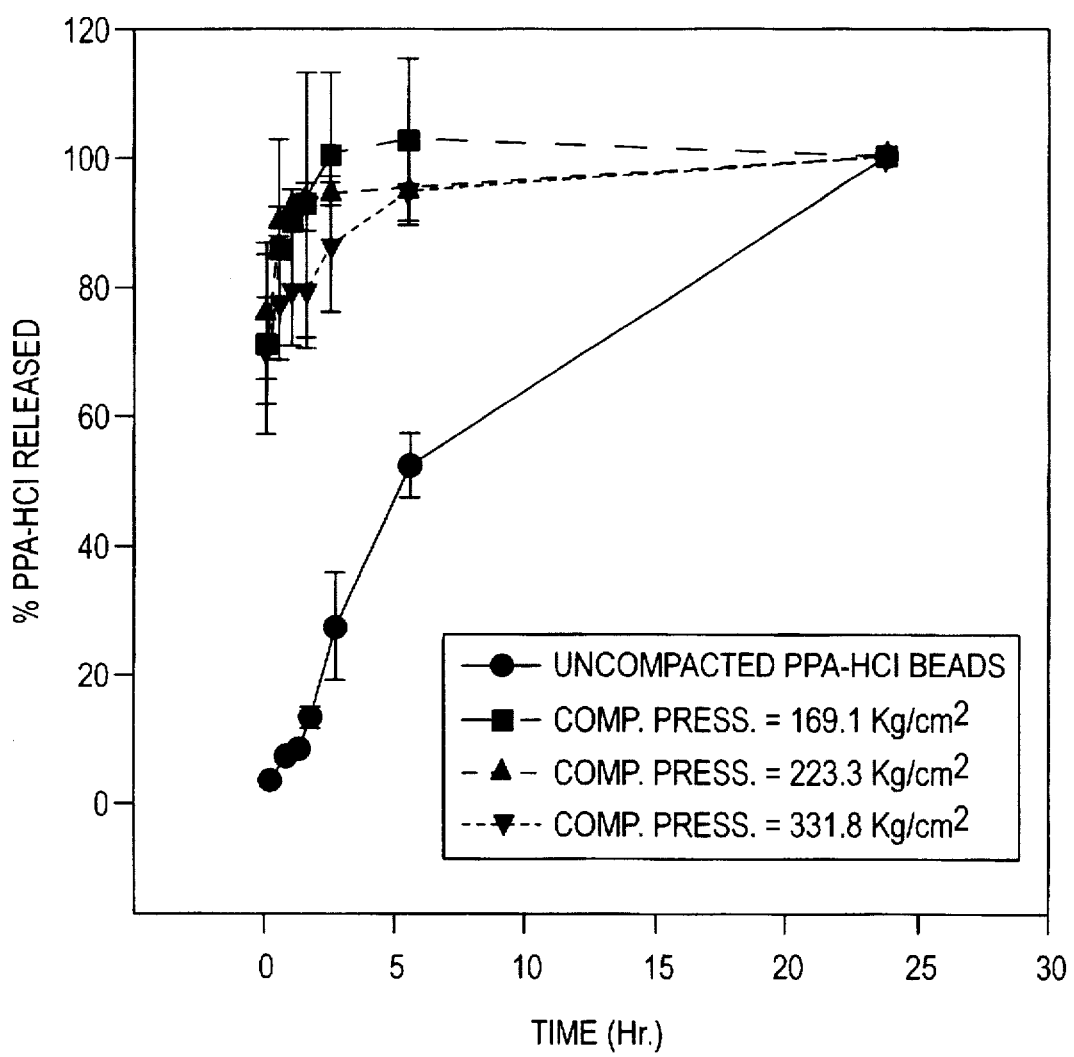
FIG. 40 shows the dissolution of phenylpropanolamine hydrochloride from uncompacted and compacted beads (25% PPA-HCl beads/75% cushioning beads).

When MCC was used as the filler-binder, segregation was visually observed in the tablet feed frame where the biologically active ingredient-loaded beads appeared to be separating from the powder mix as a function of time. Since in the design of the compaction study, tablets at lower compression pressures were collected first, the sifting of MCC throughout the inter-beads void spaces produced tablets which were initially more rich in MCC, while tablets collected towards the end of the compaction study (at high compression pressures) contained higher levels of biologically active ingredient-loaded beads. This segregation confounded the tensile strength/compression pressure measurements, as can be seen in FIG. 35, where the tablets compressed at a pressure of 603.1 Kg/cm$^2$ exhibited lower tensile strengths than those compressed at 467.5 Kg/cm$^2$. However, when cushioning beads were used as the filler-binder, the content uniformity was consistent throughout the run and no segregation was observed.

2. Content Uniformity and Weight Variation Study

The actual amount of the biologically active ingredient analyzed in the different coated-bead systems studied were 66.0% (1.0) for the propranolol hydrochloride beads, 31.0% (7.7) for the PPA-HCl beads, 66.8% (2.8) for the theophylline RD010 beads, and 59.8% (1.9) for the theophylline RD011 beads.

The content uniformity and weight variation of the compacts produced as a function of compression pressures for propranolol hydrochloride, phenylpropanolamine hydrochloride, theophylline RD010 and theophylline RD011 can be seen Tables 23–26 below, respectively.

In general, weight variation was greater when MCC was used as the filler binder in the formulations containing PPA-HCl and theophylline. As seen in Table 24 below, tablets produced from the formulations containing 12.5% and 25% PPA-HCl in cushioning beads (8.0% croscarmellose sodium in MCC) had a smaller C.V. % (0.8% and 0.4%, respectively) than those produced from the formulation containing 12.5% PPA-HCl in MCC (C.V. %=1.8). This difference was even more pronounced in the compacts containing theophylline RD010 beads (Table 25), where the C.V. was 1.4% for the 12.5% RD010 in cushioning beads and 11.1% for MCC. This variation in weight encountered when MCC was used as the filler, can be attributed to the segregation occurring due to particle size differences. Whereas MCC has an average particle size of 200 μm, this is significantly smaller than the biologically active ingredient-loaded beads (850–1400 μm).

TABLE 23

| Compression Force (Kg/cm$^2$) | Tablet Weight (mg) (n = 3) | Actual Amount of Propranolol Present (mg) | Theoretical Amount of Propranolol Present (mg) |
|---|---|---|---|
| 25% Propranolol Hydrochloride Beads/75% Cushioning Beads | | | |
| 182.7 | 830.3 | 133.5 | 137.0 |
|  | (1.8)* | (2.8) | (1.8) |
| 223.3 | 846.7 | 139.3 | 139.7 |

TABLE 23-continued

| Compression Force (Kg/cm²) | Tablet Weight (mg) (n = 3) | Actual Amount of Propranolol Present (mg) | Theoretical Amount of Propranolol Present (mg) |
|---|---|---|---|
|  | (0.7) | (1.2) | (0.7) |
| 264.0 | 820.3 | 135.4 | 135.4 |
|  | (1.9) | (3.9) | (1.9) |
| Average | 832.4 | 136.1 | 137.4 |
| (C.V. %) | (1.9) | (3.1) | (1.9) |

50% Propranolol Hydrochloride Beads/50% Cushioning Beads

| | | | |
|---|---|---|---|
| 196.2 | 826.0 | 274.5 | 272.6 |
|  | (0.7) | (4.3) | (0.7) |
| 236.9 | 817.0 | 270.3 | 269.9 |
|  | (2.6) | (6.2) | (2.6) |
| 277.6 | 770.7 | 268.9 | 254.3 |
| Average | 804.6 | 274.5 | 265.5 |
| (C.V. %) | (3.6) | (4.3) | (3.6) |

25% Propranolol Hydrochloride Beads/75% Avicel ® PH200

| | | | |
|---|---|---|---|
| 155.5 | 770.7 | 90.3 | 127.2 |
|  | (0.8) | (6.9) | (0.8) |
| 223.3 | 771.3 | 107.1 | 127.3 |
|  | (2.0) | (13.6) | (2.0) |
| 304.7 | 798.7 | 138.7 | 131.8 |
|  | (1.6) | (9.4) | (1.6) |
| Average | 780.2 | 112.0 | 128.7 |
| (C.V. %) | (2.2) | (21.0) | (2.2) |

50% Propranolol Hydrochloride Beads/50% Avicel ® PH200

| | | | |
|---|---|---|---|
| 169.1 | 840.3 | 275.9 | 277.3 |
|  | (1.8) | (6.0) | (1.8) |
| 209.8 | 849.7 | 294.0 | 280.4 |
|  | (1.6) | (8.1) | (1.6) |
| 291.1 | 871.7 | 333.0 | 287.7 |
| Average | 853.9 | 301.0 | 281.8 |
| (C.V. %) | (2.1) | (10.2) | (2.1) |

*Relative standard deviation

TABLE 24

25% Propranolol Hydrochloride Beads/87.5% Cushioning Beads

| Compression Force (Kg/cm²) | Tablet Weight (mg) (n = 3) | Actual Amount of PPA-HCl Present (mg) | Theoretical Amount of PPA-HC Present (mg) |
|---|---|---|---|
| 169.1 | 1295.3 | 45.48 | 50.2 |
|  | (0.4)* | (4.1) | (0.4) |
| 223.3 | 1293.0 | 49.4 | 50.1 |
|  | (0.4) | (1.5) | (0.4) |
| 331.8 | 1291.0 | 50.2 | 50.0 |
|  | (0.4) | (7.8) | (0.4) |
| Average | 1293.1 | 48.3 | 50.1 |
| (C.V. %) | (0.4) | (5.0) | (0.4) |

12.5% Phenylpropranolol Hydrochloride Beads/87.5% Avicel ® PH200

| Compression Force (Kg/cm²) | Tablet Weight (mg) (n = 3) | Actual Amount of PPA-HCl Present (mg) | Theoretical Amount of PPA-HCl Present (mg) |
|---|---|---|---|
| 94.5 | 1465.7 | 59.3 | 56.8 |
|  | (1.0) | (7.3) | (1.0) |
| 162.3 | 1426.7 | 61.8 | 55.3 |
|  | (2.4) | (8.5) | (2.4) |
| 250.5 | 1459.0 | 49.6 | 56.5 |
|  | (0.8) | (18.4) | (0.8) |
| Average | 1450.4 | 56.9 | 56.2 |
| (C.V. %) | (1.8) | (14.0) | (1.8) |

TABLE 24-continued

25% Phenylpropranolol Hydrochloride Beads/75% Cushioning Beads

| Compression Force (Kg/cm²) | Tablet Weight (mg) (n = 3) | Actual Amount of Propranolol Present (mg) | Theoretical Amount of Propranolol Present (mg) |
|---|---|---|---|
| 169.1 | 791.3 | 64.1 | 61.3 |
|  | (0.4) | (9.3) | (0.4) |
| 223.3 | 778.3 | 61.4 | 60.3 |
|  | (1.0) | (5.4) | (1.0) |
| 331.8 | 775.0 | 64.8 | 60.1 |
|  | (0.7) | (7.7) | (0.7) |
| Average | 776.7 | 63.4 | 60.2 |
| (C.V. %) | (0.8) | (7.1) | (0.8) |

*Relative standard deviation

TABLE 25

12.5% Theophylline RD010 Beads/87.5% Cushioning Beads

| Compression Force (Kg/cm²) | Tablet Weight (mg) (n = 3) | Actual Amount of PPA-HCl Present (mg) | Theoretical Amount of PPA-HC Present (mg) |
|---|---|---|---|
| 223.3 | 1212.0 | 101.1 | 101.2 |
|  | (0.6)* | (3.6) | (0.6) |
| 331.8 | 1208.7 | 102.1 | 100.9 |
|  | (0.2) | (2.3) | (0.2) |
| 467.5 | 1237.0 | 98.1 | 103.3 |
|  | (1.3) | (6.6) | (1.3) |
| Average | 1219.2 | 100.4 | 101.8 |
| (C.V. %) | (1.4) | (4.3) | (1.4) |

25% Theophylline RD010 Beads/75% Cushioning Beads

| Compression Force (Kg/cm²) | Tablet Weight (mg) (n = 3) | Actual Amount of PPA-HCl Present (mg) | Theoretical Amount of PPA-HCl Present (mg) |
|---|---|---|---|
| 223.3 | 1177.3 | 208.3 | 196.6 |
|  | (0.2) | (0.4) | (0.2) |
| 331.8 | 1164.0 | 204.9 | 194.4 |
|  | (0.4) | (2.2) | (0.4) |
| 467.5 | 1149.0 | 189.8 | 191.9 |
|  | (0.3) | (2.1) | (0.3) |
| 603.1 | 1158.0 | 201.8 | 193.4 |
|  | (0.7) | (4.6) | (0.7) |
| Average | 1162.1 | 201.2 | 194.1 |
| (C.V. %) | (1.0) | (4.3) | (1.0) |

25% Theophylline RD010 Beads/75% Avicel ® PH200

| Compression Force (Kg/cm²) | Tablet Weight (mg) (n = 3) | Actual Amount of Propranolol Present (mg) | Theoretical Amount of Propranolol Present (mg) |
|---|---|---|---|
| 223.3 | 1124.0 | 169.8 | 187.7 |
|  | (1.3) | (9.3) | (1.3) |
| 331.8 | 1128.3 | 170.9 | 188.4 |
|  | (1.4) | (5.0) | (0.3) |
| 467.5 | 1108.3 | 175.1 | 185.1 |
|  | (1.4) | (9.3) | (1.4) |
| 603.1 | 1108.3 | 333.8 | 235.7 |
|  | (1.4) | (1.3) | (1.4) |
| Average | 1192.9 | 212.4 | 199.2 |
| (C.V. %) | (11.1) | (34.8) | (11.1) |

*Relative standard deviation

TABLE 26

12.5% Theophylline RD010 Beads/87.5% Cushioning Beads

| Compression Force (Kg/cm²) | Tablet Weight (mg) (n = 3) | Actual Amount of PPA-HCl Present (mg) | Theoretical Amount of PPA-HC Present (mg) |
|---|---|---|---|
| 223.3 | 1320.0 | 95.9 | 98.7 |
|  | (0.8)* | (1.5) | (0.8) |
| 331.8 | 1302.7 | 96.7 | 97.4 |
|  | (0.1) | (5.2) | (0.1) |
| 467.5 | 1285.0 | 100.1 | 96.1 |
|  | (0.9) | (5.4) | (0.9) |
| 603.1 | 1234.3 | 94.3 | 92.3 |
|  | (0.3) | (4.0) | (0.3) |
| Average | 1219.2 | 100.4 | 96.1 |
| (C.V. %) | (1.4) | (4.3) | (2.7) |

*Relative standard deviation

The content uniformity of the different biologically active ingredients was much better when the freeze-dried cushioning beads were used as the filler system. For the compacts containing propranolol hydrochloride beads in cushioning beads, the C.V. % in the biologically active ingredient content was less than 5.0%, whereas those in MCC, the C.V. % in the biologically active ingredient content was 21.0% and 10.2% for the 25% and 50% propranolol loads, respectively (Table 23). Moreover, it is quite evident that as the compression pressure is increased in formulations containing MCC (tablets produced at later time points), the compacts became richer in propranolol.

The same trend was observed in the content uniformity measurements of PPA-HCl and theophylline RD010. For compacts produced using PPA-HCl in MCC, the C.V. % in the biologically active ingredient content was 14.0% for the formulation containing 12.5% PPA-HCl. This was much lower for the formulations containing 12.5% and 25% PPA-HCl in cushioning beads, where the C.V. % was only 5.0% and 7.1%, respectively (Table 24). For the formulation containing 25% theophylline RD010 in MCC, the C.V. % in the biologically active ingredient content was extremely high (34.8%), with the compacts produced at higher compression pressures (at later time points) exhibiting an increasing amount of the biologically active ingredient content (Table 25). The content uniformity for their cushioning beads counterparts was only 4.3% for both of the 12.5% and 25% theophylline in cushioning beads. Moreover, for the theophylline RD010 in cushioning beads, the C.V. % are acceptable 4.3% (Table 26).

Figure 41:
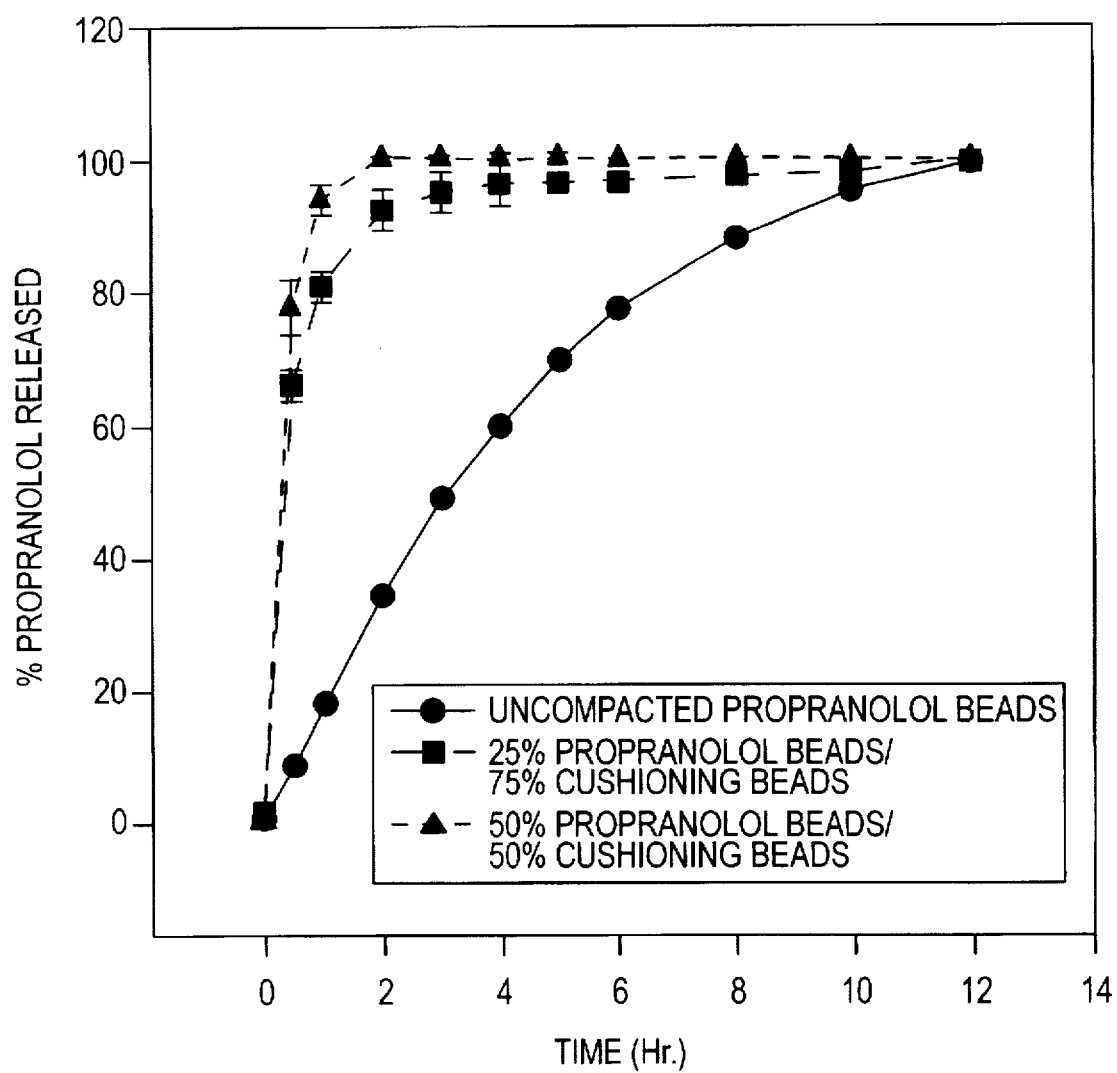
FIG. 41 shows the dissolution of propranolol hydrochloride from uncompacted and compacted beads (Effect of bead load at a compression pressure of approximately 240 Kg/cm$^2$).
Figure 42:
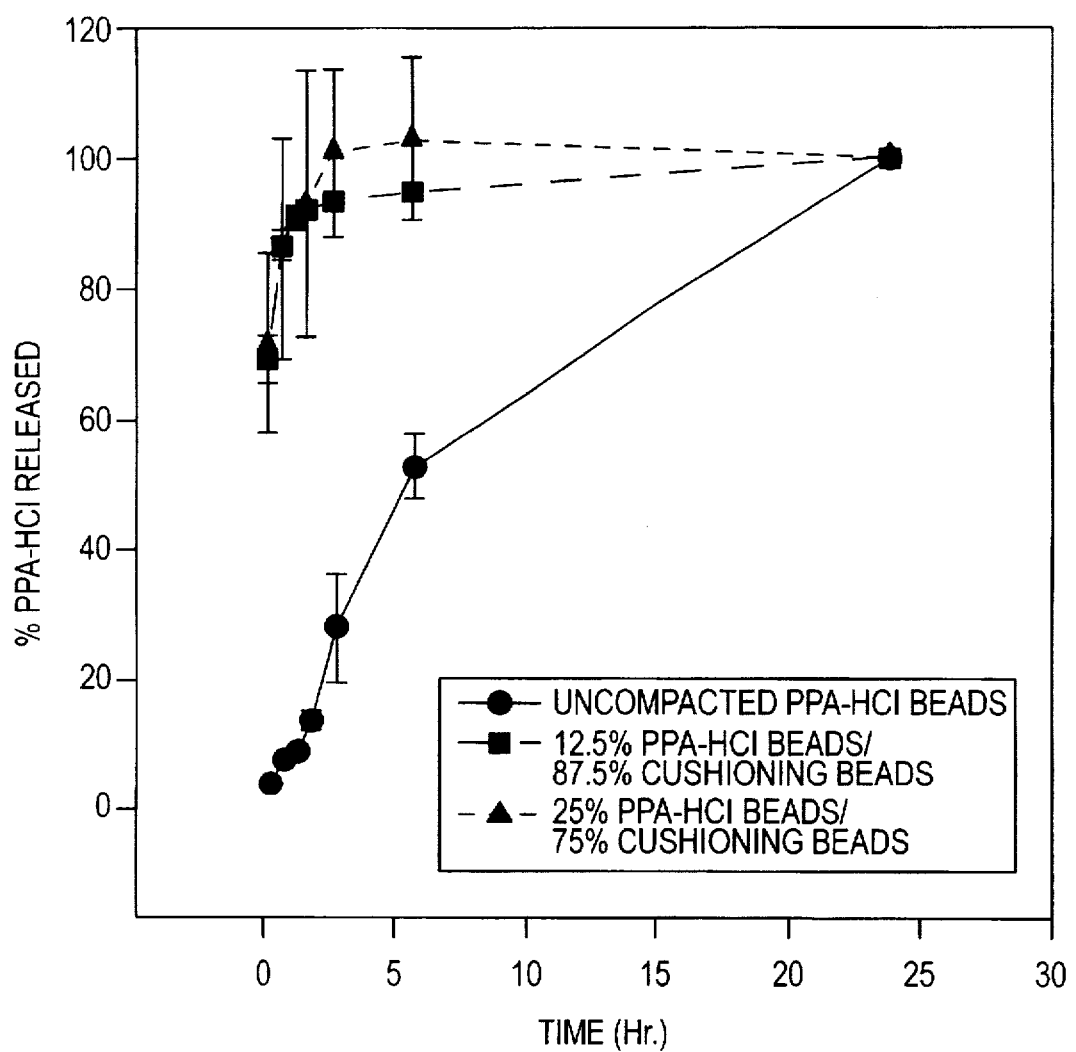
FIG. 42 shows the dissolution of phenylpropanolamine hydrochloride from uncompacted and compacted beads (Effect of bead load at a compression pressure of 168.9 Kg/cm$^2$).
Figure 43:
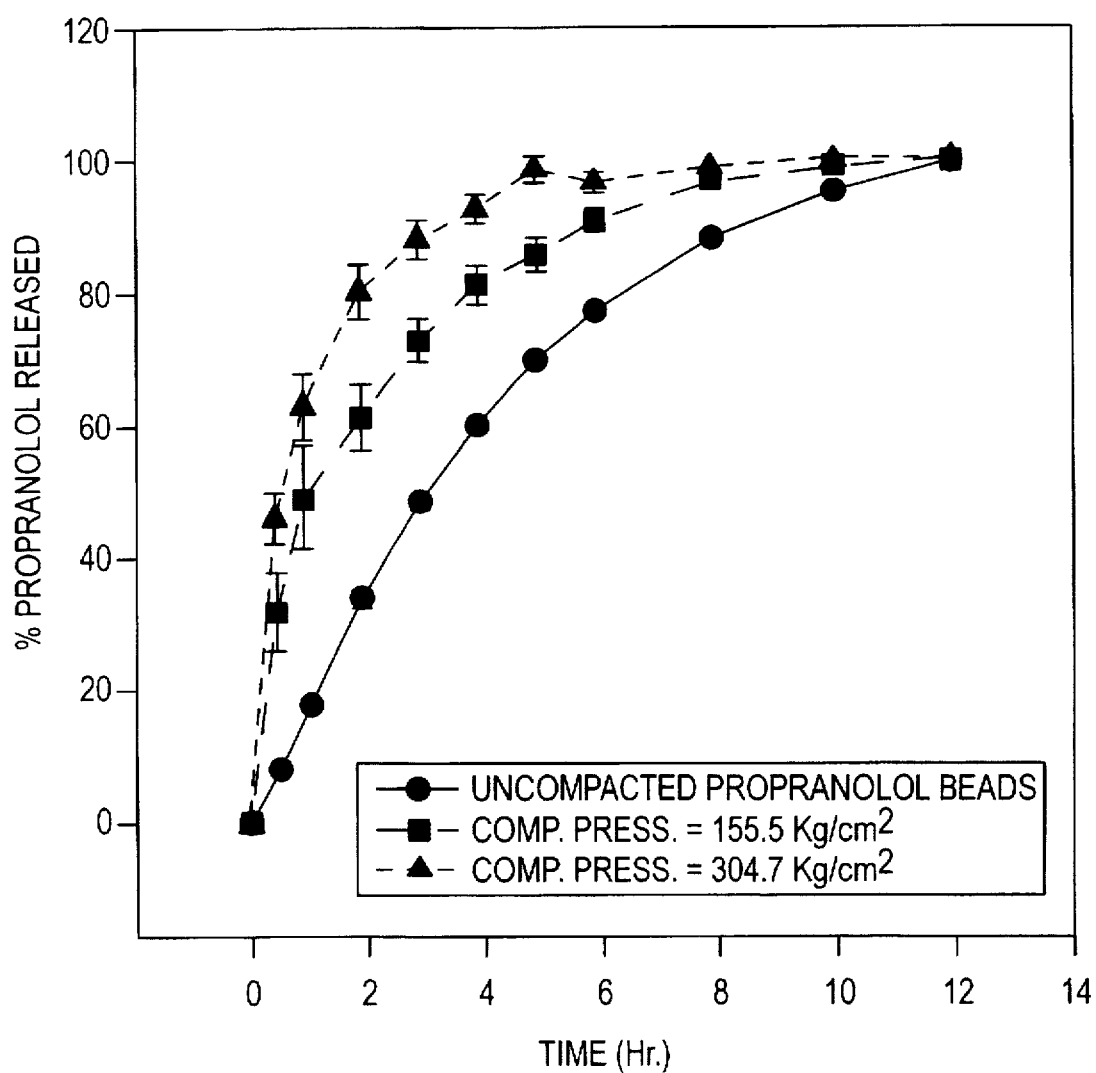
FIG. 43 shows the dissolution of propranolol hydrochloride from uncompacted and compacted beads (25% propranolol beads/75% MCC).
Figure 44:
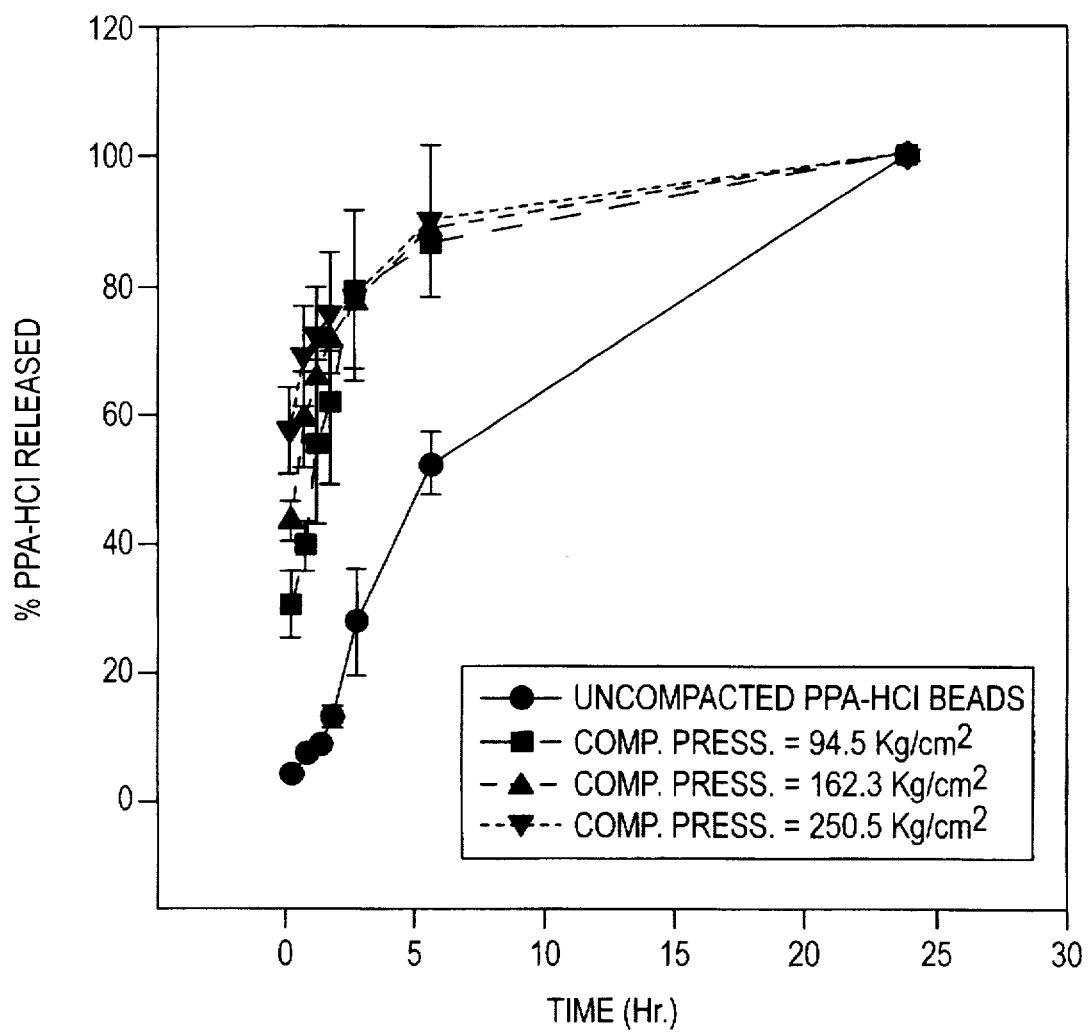
FIG. 44 shows the dissolution of phenylpropanolamine hydrochloride from uncompacted and compacted beads (12.5% PPA-HCl beads/87.5% MCC).
Figure 45:
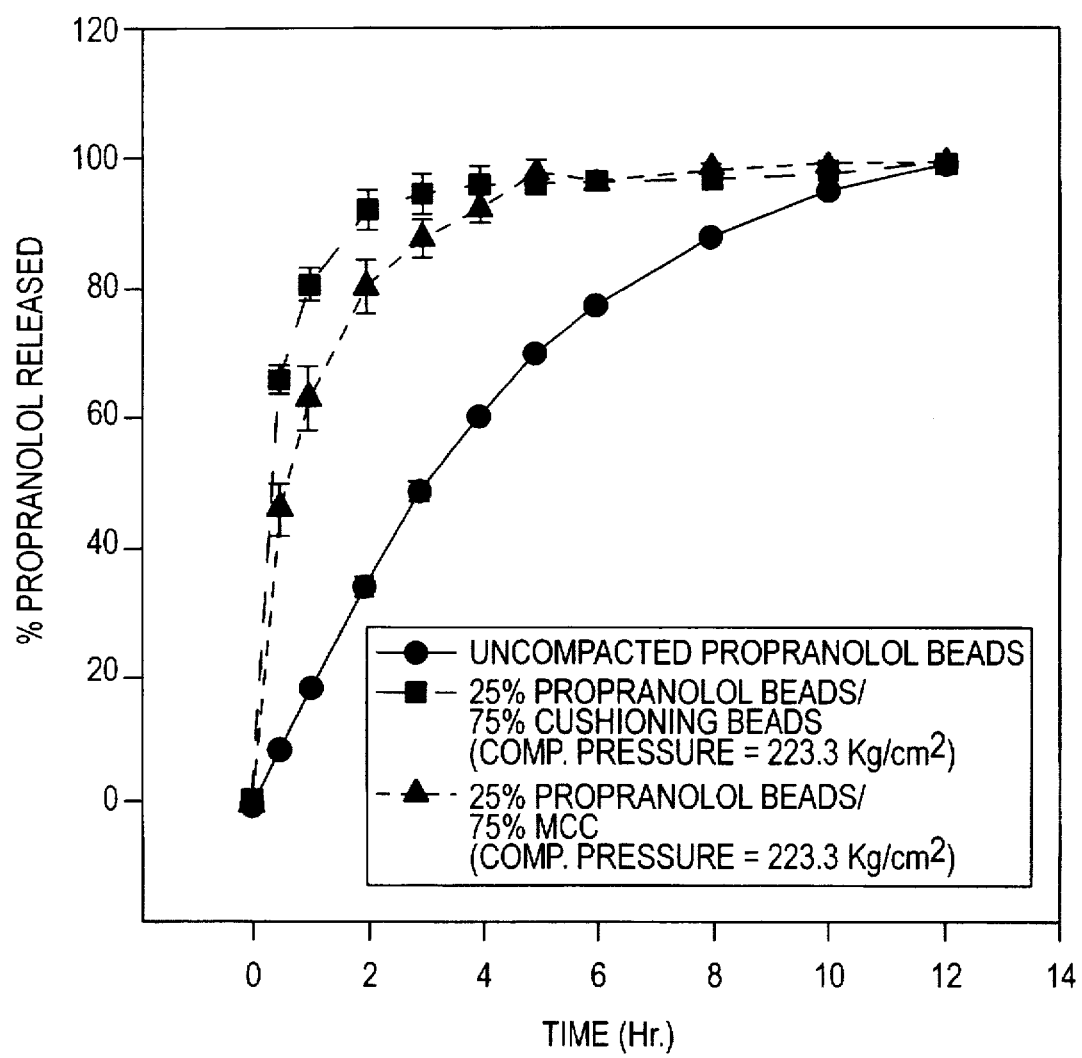
FIG. 45 shows the dissolution of propranolol hydrochloride from uncompacted and compacted beads (Effect of cushioning beads versus MCC).
Figure 46:
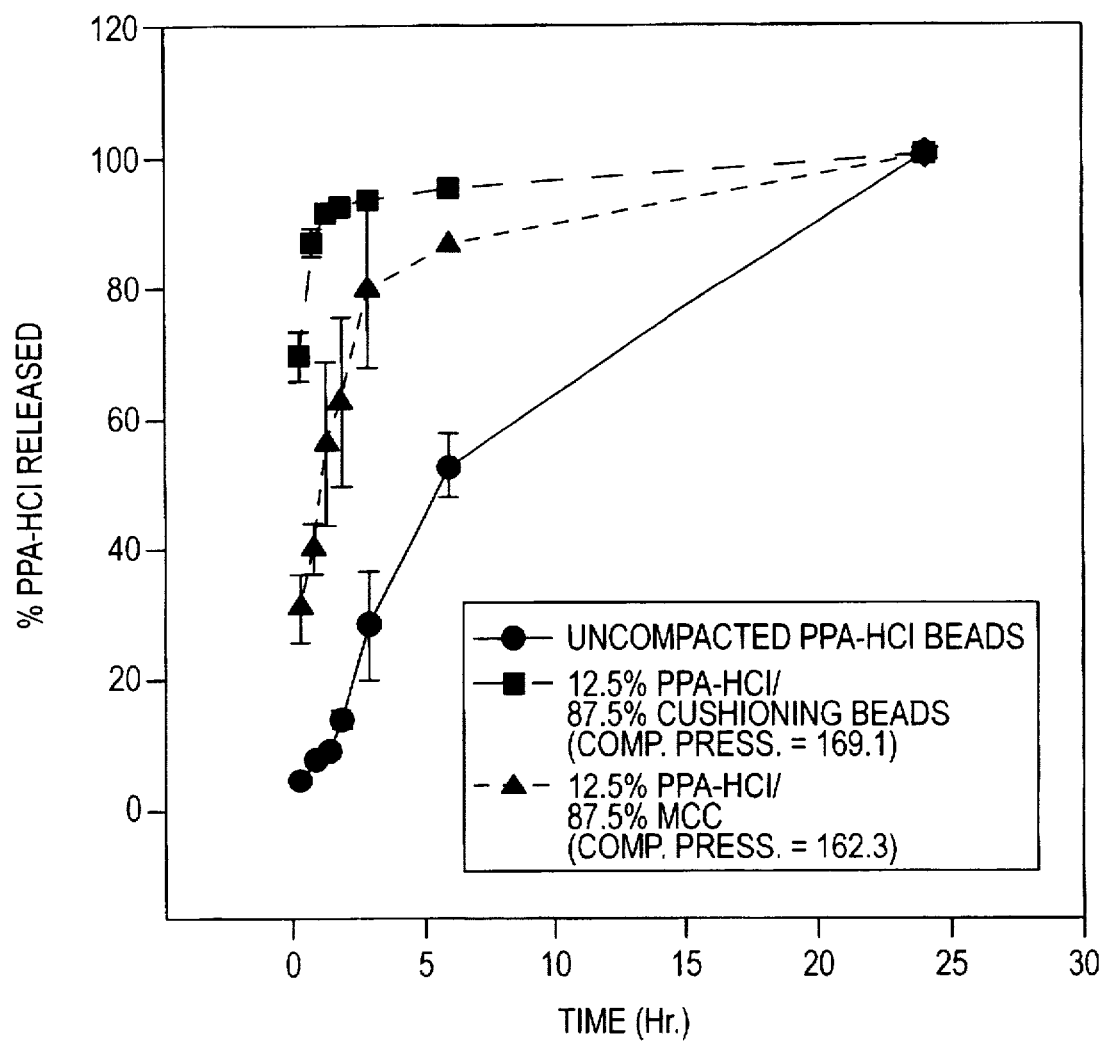
FIG. 46 shows the dissolution of phenylpropanolamine hydrochloride from uncompacted and compacted beads (Effect of cushioning beads versus MCC).

3. Effect of Compression Pressure on the Release of Biologically Active Ingredient from Tablets The effect of compression pressure on the release of biologically active ingredient from formulations composed of 25% and 50% propranolol in cushioning beads and 12.5% and 25% phenylpropanolamine in cushioning beads is depicted in FIGS. 37–40, respectively. Dose dumping even at low compression pressure is obvious when comparing the dissolution profiles of the uncompacted and compacted beads. Increasing the load of the propranolol beads from 25% to 50% (FIG. 41) and PPA-HCl beads from 12.5% to 25% (FIG. 42) was associated with an increase in the release profiles. This increase can be attributed to the fact that as the percentage of the biologically active ingredient-loaded beads is increased, fewer cushioning beads were available to protect the membrane around the biologically active ingredient-loaded beads from fracturing. FIGS. 43 and 44 depict the effect of increasing compression pressure on the release of propranolol and PPA-HCl from the formulations containing 25% propranolol hydrochloride and 12.5% PPA-HCl in MCC, respectively. Higher compression pressures were associated with faster release profiles and more dose dumping, due to increased fracturing of the coated beads. The ability of the different filler systems utilized to protect the propranolol beads and PPA-HCl beads from fracturing at approximately similar compression pressures can be seen in FIGS. 45 and 46, respectively. MCC seems to provide a slightly better cushioning effect for the biologically active ingredient-loaded beads than the freeze-dried cushioning beads. However, in all of the compressed propranolol bead and PPA-HCl formulations, severe dose dumping occurred regardless of the pressure used to form the compacts. Examining the photomicrograph of the fractured tablet containing 25% propranolol in 75% cushioning beads produced at a compression pressure of 264.0 Kg/cm², and that of the fractured tablet containing 12.5% PPA-HCl in 87.5% cushioning beads produced at a compression pressure of 331.8 Kg/cm² revealed that the beads present in the interior part of the tablet matrix do not appear to deform, which suggests that the dose dumping is due to the cracking of the ethylcellulose coating, rather than the fracturing of the beads themselves. The scanning electron micrographs (55X) of representative propranolol hydrochloride beads and PPA-HCl beads obtained from the interior part of the tablet matrix revealed severe cracking of the ethylcellulose membrane coating. Ethylcellulose is a very brittle material, and its films were reported to exhibit massive fracture under compression regardless of the plasticizer or other additives used (Béchard et al. supra).

Figure 47:
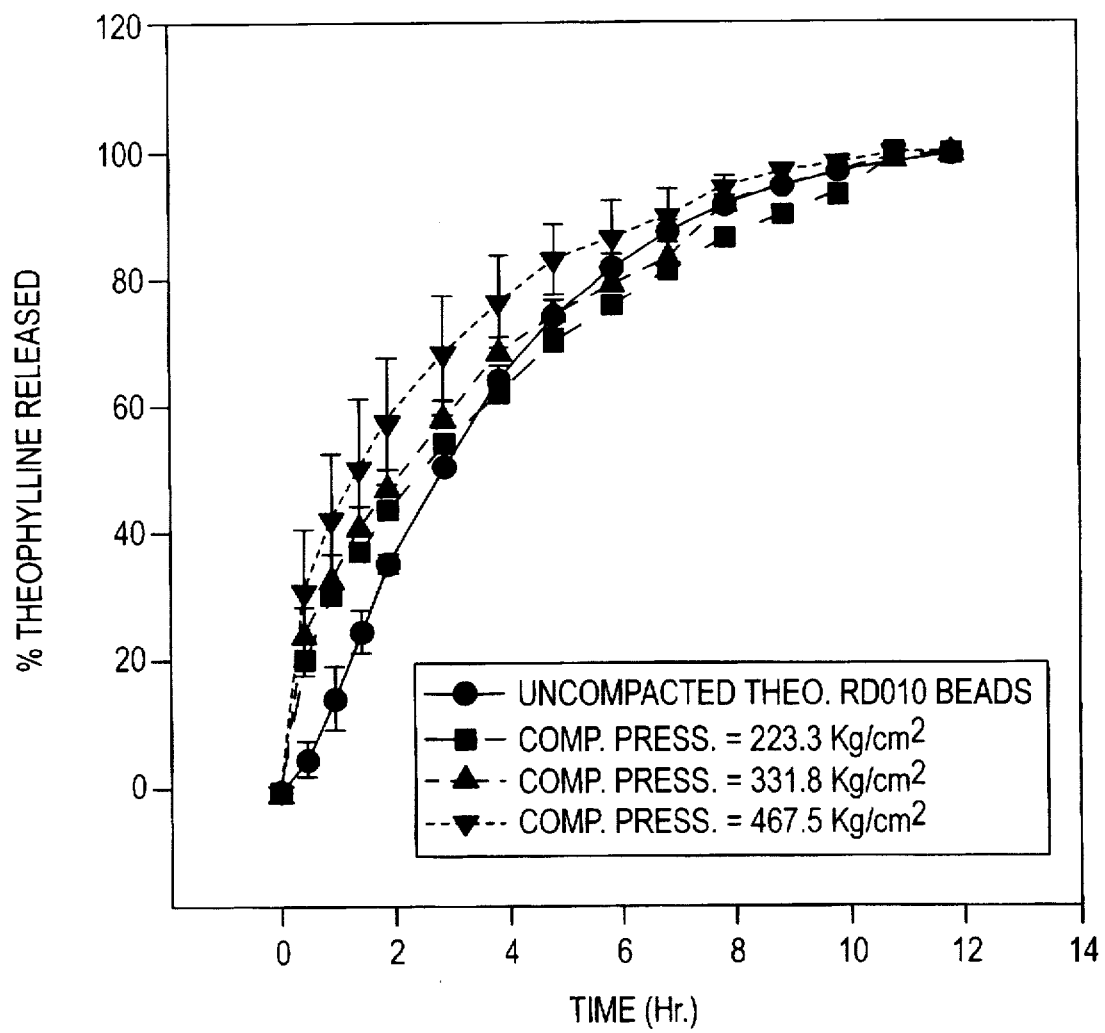
FIG. 47 shows the dissolution of theophylline from uncompacted and compacted theophylline RD010 beads (12.5% theophylline RD010 beads/87.5% cushioning beads).
Figure 48:
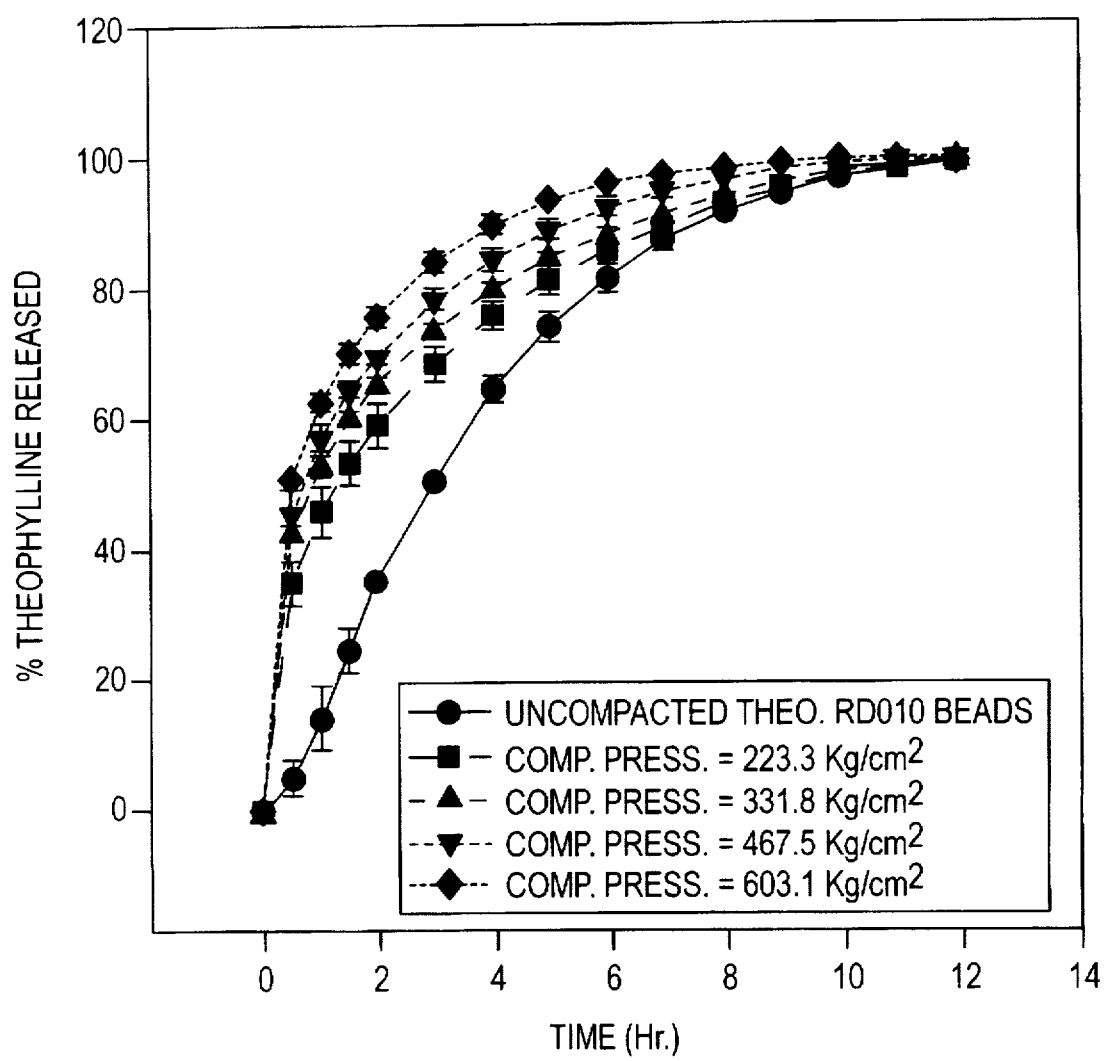
FIG. 48 shows the dissolution of theophylline from uncompacted and compacted theophylline RD010 beads (25% theophylline RD010 beads/75% cushioning beads).
Figure 49:
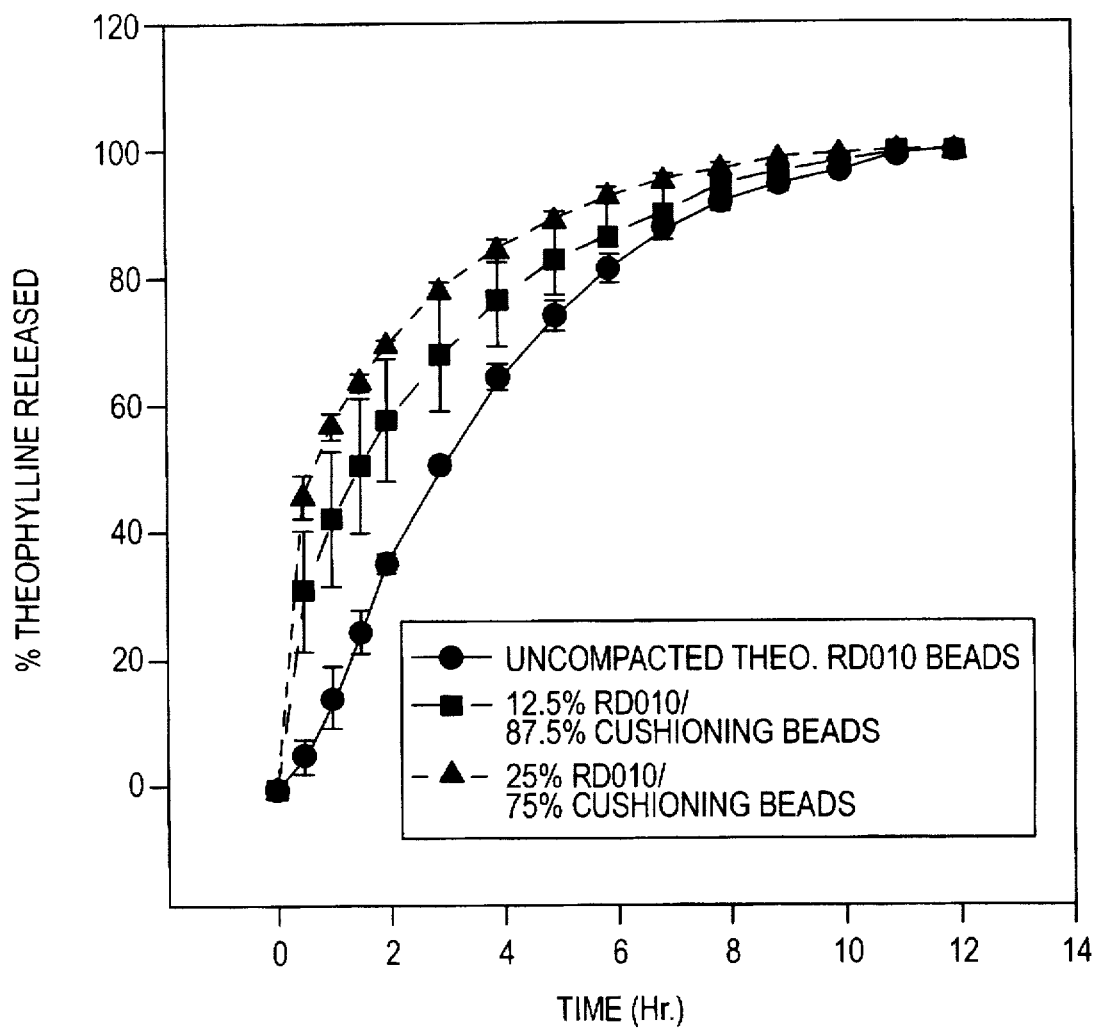
FIG. 49 shows the dissolution of theophylline from uncompacted and compacted theophylline RD010 beads (Effect of bead load at a compression pressure of 331.8 Kg/cm$^2$).
Figure 50:
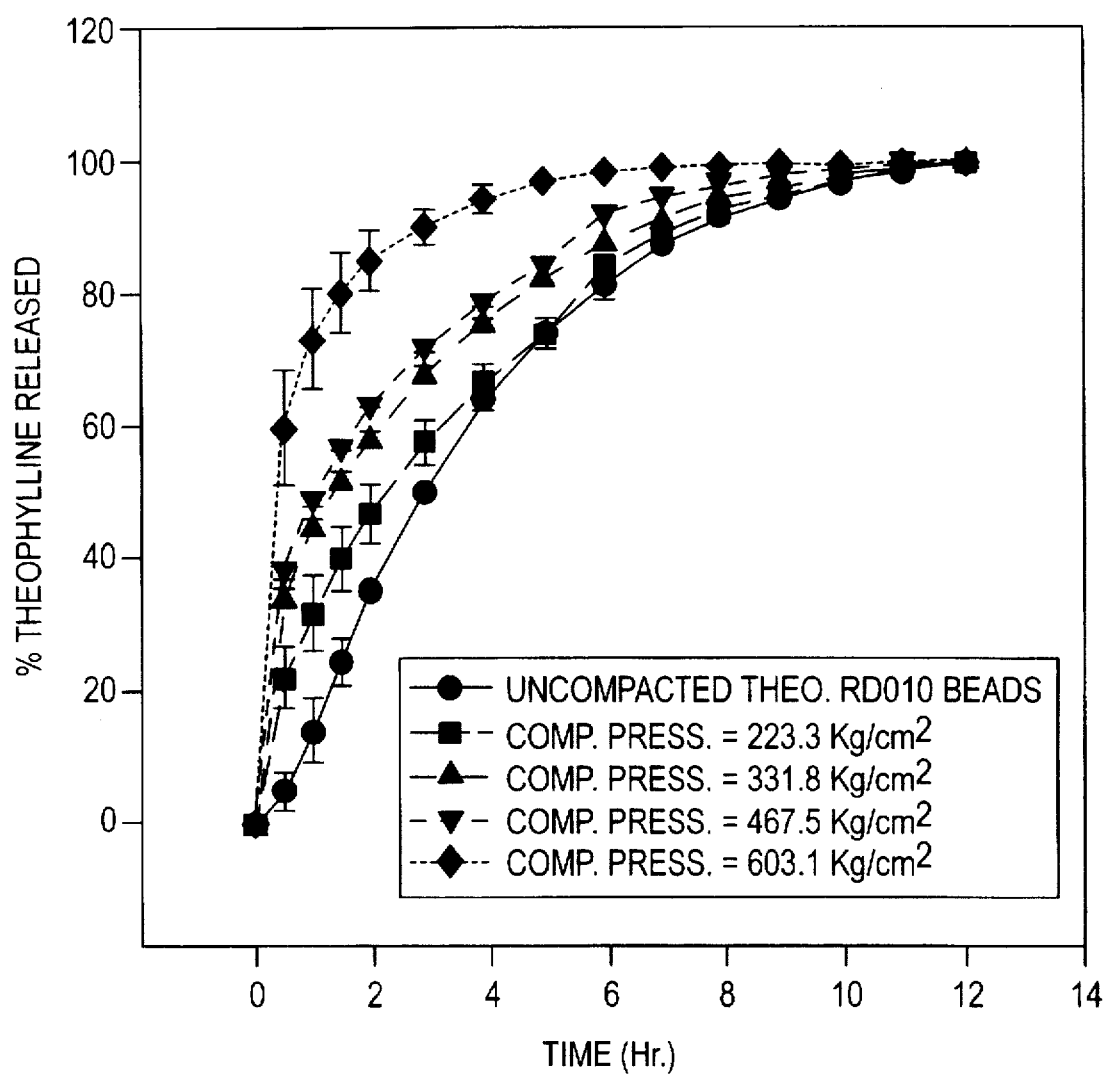
FIG. 50 shows the dissolution of theophylline from uncompacted and compacted theophylline RD010 beads (25% theophylline RD010 beads/75% MCC).
Figure 51:
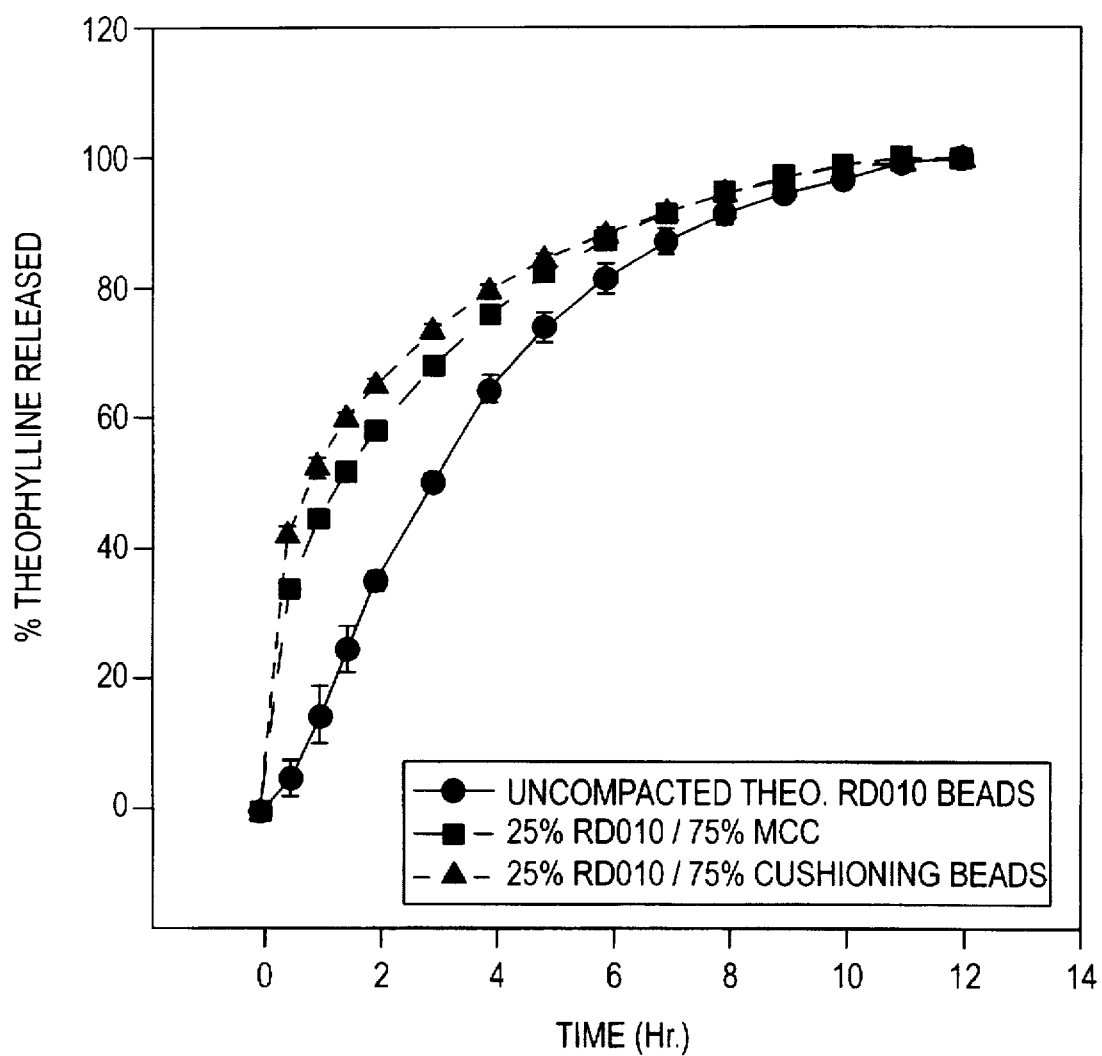
FIG. 51 shows the dissolution of theophylline from uncompacted and compacted theophylline RD010 beads (Effect of cushioning beads versus MCC at a compression pressure of 331.8 Kg/cm$^2$).
Figure 52:
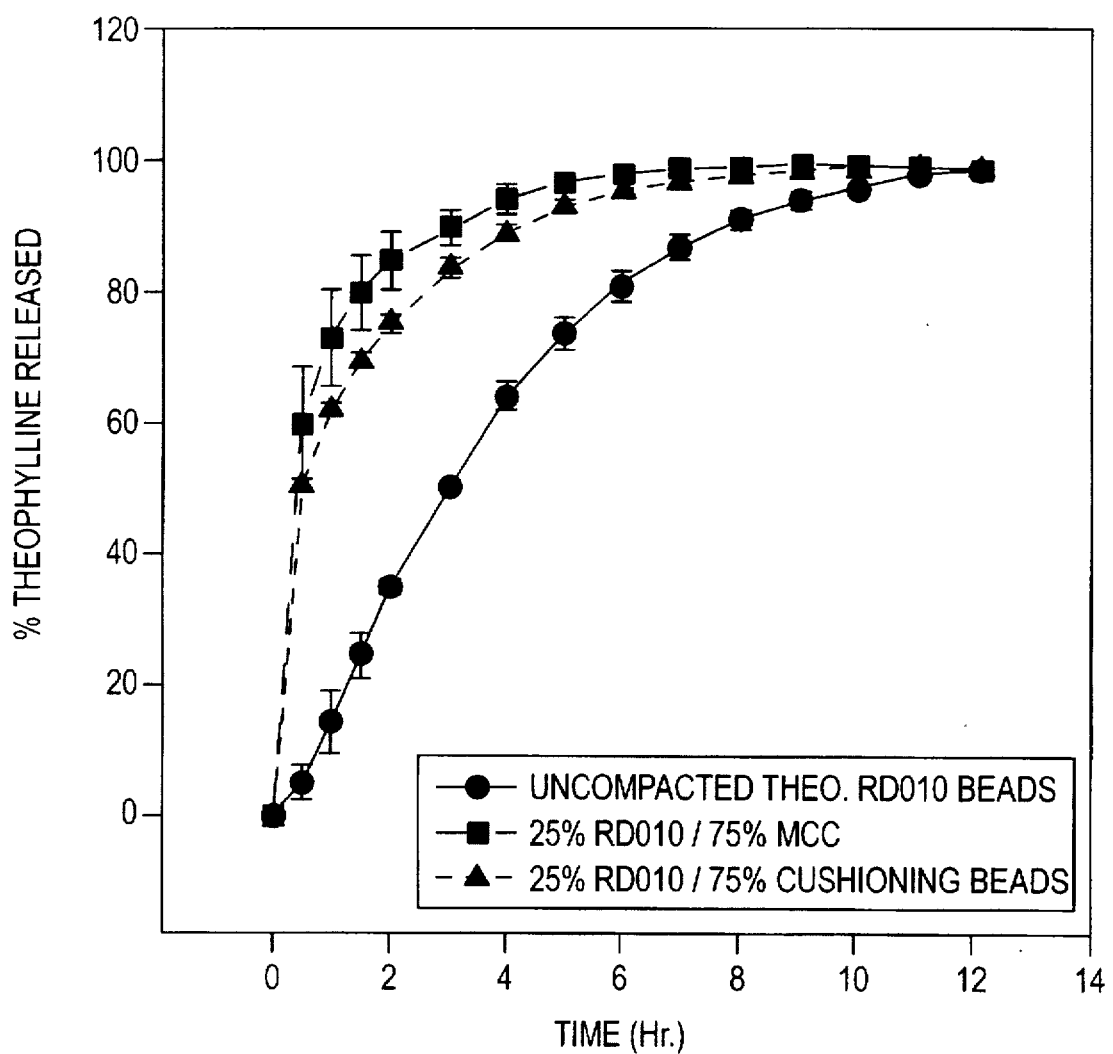
FIG. 52 shows the dissolution of theophylline from uncompacted and compacted theophylline RD010 beads (Effect of cushioning beads versus MCC at a compression pressure of 603.1 Kg/cm$^2$).

The effect of compression pressure on the release of theophylline from formulations composed of 12.5% and 25% theophylline RD010 beads in cushioning beads is depicted in FIGS. 47 and 48, respectively. At both bead load levels, increasing the compression pressure resulted in an increase in the release of the biologically active ingredient as a function of time, due to more cracking of the membrane-coated beads. When comparing the dissolution profiles of the compacted tablets to that of the uncompacted theophylline RD010 beads, dose dumping is not as significant as that encountered with ethylcellulose-coated beads containing propranolol and PPA-HCl. However, more change in the release profiles is encountered with the 25% theophylline RD010/cushioning beads profiles than the 12.5% counterparts. Increasing the theophylline RD010 beads load from 12.5% to 25% (FIG. 49) was associated with an increase in the release profiles of tablets compacted at similar compression pressure of 331.8 Kg/cm², due to less cushioning beads available to protect the biologically active ingredient-loaded beads from fracturing. FIG. 50 depicts the effect of increasing the compression pressure on the release of theophylline from the formulation containing 25% theophylline RD010 in MCC. Higher compression pressures are associated with a slightly faster release profiles and more dose dumping. The most severe dose dumping associated with that formulation compressed at a 603.1 Kg/cm² can be explained by the fact that due to segregation encountered with the use of MCC as the filler-binder, the tablets compacted at high compression pressures (at later time points of the compaction study) showed poor content uniformity (higher amount of biologically active ingredient-loaded beads and less amount of MCC). Thus, the amount of MCC available to protect the biologically active ingredient-loaded beads was reduced. The ability of the different filler systems utilized to protect the theophylline RD010 beads from fracturing at similar compression pressures is seen in FIGS. 51 and 52. At a compression pressure of 331.8 Kg/cm² (FIG. 51), MCC provided a slightly better cushioning effect for the theophylline RD010 beads than the freeze-dried cushioning beads. This is reflected in the slower release profiles from the formulation containing MCC when compared to the formulation containing cushioning beads as the filler system. However, at a compression pressure of 603.1 Kg/cm² (FIG.

52), the cushioning beads protected the theophylline RD010 beads better than MCC. This is because at higher compression pressure, the theophylline RD010/MCC had a content uniformity problem with a lower amount of MCC present. Thus, the effect of both filler systems studied on protecting the integrity of the theophylline RD010 beads is not conclusive, since it is confounded by segregation problems. In all of the theophylline RD010/cushioning beads release profiles, regardless of the compression pressure used to form the compacts, dose dumping was not significant. The amount of theophylline released from the tablets containing 12.5% and 25% theophylline RD010 loads in cushioning beads relative to the uncompacted theophylline RD010 is presented in Tables 27 and 28 below, respectively. Examining the photomicrograph of the fractured tablet containing 25% theophylline RD010 in 75% cushioning beads produced at a compression pressure of 467.5 Kg/cm$^2$ reveals that the theophylline RD010 beads present in the interior part of the tablet matrix remained intact. However, the beads present at the surface were damaged severely. The increase in the biologically active ingredient release with higher compression pressure can be attributed to the fact that at higher pressures, the tablet thickness is reduced, resulting in higher surface area/volume ratio. Thus, chances of the beads getting exposed to the surface where the damage is occurring is greater. These results suggest that the films formed using the methacrylate copolymers can withstand the stresses of compaction with minimal change in the release profile, which is mainly attributed to the cracking of the beads exposed to the surface. Polymethacrylates film coatings are flexible enough and can withstand the mechanical stresses of compression so that the release patterns from compressed or uncompressed beads are similar (Lehmann et al supra, Juslin et al, supra; and Haubitz et al, supra).

TABLE 27

| Time (Hr) | Uncompacted RD010 Beads (% Released) | Comp. Press, 223.3 Kg/cm$^2$ (% Released) | Comp. Press, 331.8 Kg/cm$^2$ (% Released) | Comp. Press, 467.5 Kg/cm$^2$ (% Released) |
|---|---|---|---|---|
| 0 | 0.0 | 0.0 | 0.0 | 0.0 |
| 0.5 | 5.1 | 10.7 | 24.2 | 31.2 |
| 1 | 14.4 | 19.8 | 32.8 | 42.4 |
| 1.5 | 24.8 | 28.8 | 40.7 | 50.6 |
| 2 | 35.3 | 37.2 | 47.0 | 57.8 |
| 3 | 50.5 | 50.6 | 58.0 | 68.2 |
| 4 | 64.7 | 63.3 | 68.3 | 76.5 |
| 5 | 74.2 | 72.4 | 74.9 | 82.9 |
| 6 | 1.6 | 79.6 | 78.9 | 86.2 |
| 7 | 87.4 | 85.6 | 83.5 | 89.8 |
| 8 | 91.7 | 90.1 | 91.7 | 94.4 |
| 9 | 94.6 | 93.5 | 95.0 | 96.6 |
| 10 | 96.8 | 96.1 | 97.2 | 98.1 |
| 11 | 99.4 | 99.1 | 98.6 | 99.7 |
| 12 | 100.0 | 100.0 | 100.0 | 100.0 |

TABLE 28

| Time (Hr) | Uncompacted RD010 Beads (% Released) | Comp. Press, 223.3 Kg/cm$^2$ (% Released) | Comp. Press, 331.8 Kg/cm$^2$ (% Released) | Comp. Press, 467.5 Kg/cm$^2$ (% Released) | Comp. Press, 603.1 Kg/cm$^2$ (% Released) |
|---|---|---|---|---|---|
| 0 | 0.0 | 0.0 | 0.0 | 0.0 | 0.0 |
| 0.5 | 8.3 | 34.8 | 42.4 | 45.6 | 50.8 |
| 1 | 19.1 | 45.9 | 52.9 | 57.0 | 62.4 |
| 1.5 | 28.6 | 53.2 | 60.0 | 64.0 | 69.9 |
| 2 | 37.4 | 59.0 | 65.2 | 69.4 | 75.6 |
| 3 | 52.7 | 68.4 | 73.5 | 78.1 | 84.1 |
| 4 | 65.1 | 75.7 | 79.8 | 84.3 | 89.5 |
| 5 | 75.3 | 81.3 | 84.7 | 88.9 | 93.5 |
| 6 | 83.5 | 85.9 | 88.5 | 92.4 | 95.9 |
| 7 | 90.3 | 89.7 | 91.6 | 94.8 | 97.2 |
| 8 | 95.6 | 92.8 | 94.4 | 96.5 | 98.2 |
| 9 | 99.8 | 95.5 | 96.6 | 98.3 | 99.2 |
| 10 | 98.9 | 97.4 | 98.2 | 99.1 | 99.7 |
| 11 | 98.8 | 98.7 | 99.2 | 100.0 | 100.0 |
| 12 | 100.0 | 100.0 | 100.0 | 100.0 | 100.0 |

Figure 53:
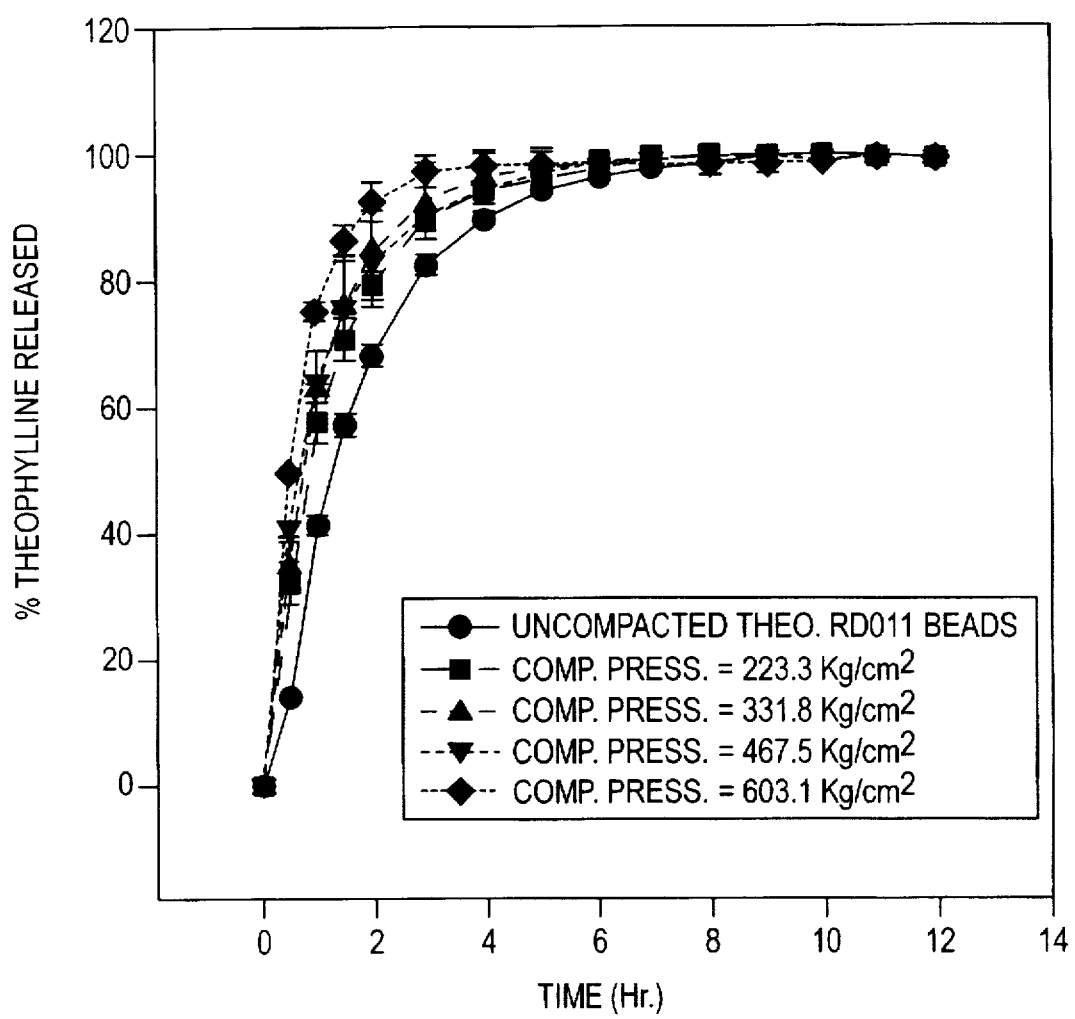
FIG. 53 shows the dissolution of theophylline from uncompacted and compacted theophylline RD011 beads (12.5% theophylline RD011 beads/87.5% cushioning beads).

Similar results were obtained with the theophylline RD011 beads coated with a mixture of polymethacrylates and ethylcellulose aqueous dispersions. Increasing the compression pressure for the formulation containing 12.5% theophylline RD011 in cushioning beads resulted in a minor increase in the percent of the biologically active ingredient releases as a function of time (FIG. 53). The amount of theophylline released from those tablets relative to the uncompacted theophylline RD011 beads is present in Table 29 below. Examining the photomicrograph of the fractured tablet containing 12.5% theophylline RD010 in 87.5% cushioning beads produced at a compression pressure of 467.5 Kg/cm$^2$ reveals that the theophylline RD011 beads present in the interior part of the tablet matrix remained intact. However, the beads present at the surface were damaged severely.

TABLE 29

| Time (Hr) | Uncompacted RD011 Beads (% Released) | Comp. Press, 223.3 Kg/cm$^2$ (% Released) | Comp. Press, 331.8 Kg/cm$^2$ (% Released) | Comp. Press, 467.5 Kg/cm$^2$ (% Released) | Comp. Press, 603.1 Kg/cm$^2$ (% Released) |
|---|---|---|---|---|---|
| 0 | 0.0 | 0.0 | 0.0 | 0.0 | 0.0 |
| 0.5 | 14.2 | 32.1 | 35.0 | 40.9 | 49.7 |
| 1 | 41.4 | 57.6 | 62.9 | 64.2 | 75.3 |
| 1.5 | 57.3 | 70.8 | 76.0 | 75.8 | 86.4 |
| 2 | 68.3 | 79.5 | 84.3 | 82.9 | 92.6 |
| 3 | 82.6 | 89.9 | 93.0 | 90.7 | 97.4 |
| 4 | 90.1 | 94.5 | 96.7 | 94.1 | 98.3 |
| 5 | 94.4 | 97.1 | 97.9 | 96.4 | 98.4 |
| 6 | 96.5 | 98.8 | 98.5 | 97.9 | 98.4 |
| 7 | 97.8 | 99.5 | 98.9 | 98.7 | 98.4 |
| 8 | 98.8 | 99.8 | 99.2 | 99.2 | 98.5 |
| 9 | 99.3 | 99.8 | 99.3 | 99.6 | 98.6 |
| 10 | 100.0 | 100.0 | 99.3 | 99.9 | 98.9 |
| 11 | 100.0 | 100.0 | 100.0 | 99.9 | 100.0 |
| 12 | 100.0 | 100.0 | 100.0 | 100.0 | 100.0 |

III. Conclusions

The mixing and compaction of the different biologically active ingredient-loaded beads with Avicel® PH200 (MCC) was associated with more significant weight variation and content uniformity problems than when the freeze-dried cushioning beads were used as the filler binder. This is attributed to the segregation due to size differences between the biologically active ingredient-loaded beads (850–1400 μm) and MCC (200 μm). When the freeze-dried cushioning beads of 14–20 mesh cut was used, segregation was minimal.

The freeze-dried cushioning beads, when mixed and compacted with the theophylline biologically active ingredient-loaded beads coated with polymethacrylate copolymer (RD010) and a mixture of polymethacrylate copolymer and ethylcellulose from aqueous dispersions (RD011), were able to cushion the biologically active ingredient-loaded beads, and minimize dose dumping. The change in the release profiles of the uncompacted and compacted theophylline beads can be attributed to the inevitable fracturing of the beads occurring at the surface. However, dose dumping from tablets compressed with propranolol beads coated with ethylcellulose from organic solvent and phenylpropanolamine hydrochloride beads coated with an aqueous dispersion of ethylcellulose was pronounced at all loading levels and compression forces. This is because ethylcellulose films are very brittle, regardless of the plasticizers added. Polymethacrylate copolymers are much more flexible, and can withstand the mechanical stresses of the compaction process.

Increasing the compression pressure resulted in a slight increase in the dissolution profile of theophylline beads (both RD010 and RD011) compressed with the freeze-dried beads. This increase is due to the fact that with an increase in compression pressure, tablet thickness decreases, resulting in greater chance of exposing the theophylline beads to the surface where beads damage is prone to occur. Whereas the photomicrographs of the compacted beads revealed severe damage of the theophylline beads present at the surface, beads present in the interior tablet matrix remained intact.

Increasing the thickness of the compacts is expected to reduce the percentage of the theophylline beads (RD010 or RD011) experiencing damage at the surface. Thick compacts should not impose any problem if the tablet is to be dispersed in water prior to dose administration.

A biologically active ingredient load of 25% of theophylline in cushioning beads appears to be a reasonable figure to be used in later studies to manufacture the self-disintegrating tablets intended to provide a sustained release aqueous suspension. This self-disintegrating tablet will contain 25% of both carbomer EX214 beads described in Example 1 above and the theophylline beads coated with polymethacrylate copolymer (RD010) and 75% of the freeze-dried cushioning beads described in Example 2 above.

EXAMPLE 4

Formulation and Manufacture of Tablets for Instantaneous Preparation of Sustained Release Suspensions

I. Introduction

A water-dispersible tablet containing biologically active ingredient-loaded beads, a disintegrant, and a swellable material capable of generating a high viscosity when coming in contact with water is described in this Example. Biologically active ingredient-loaded membrane-coated beads, consisting of theophylline produced by extrusion-spheronization and coated with polymethacrylate copolymer as described in Example 3, and capable of withstanding the mechanical stresses of compression, were mixed with the carbomer/MCC beads, described in Example 1, and the freeze-dried cushioning beads containing 8.0% croscarmellose in MCC described in Example 2 above. These three components were compressed to form a tablet, which when dispersed in water, is expected to disintegrate rapidly to release the theophylline beads together with the carbomer beads, resulting in a homogenous suspension.

II. Experiments

A. Materials

Theophylline beads (RD010) were supplied by Niro-Aeromatic (Columbia, Md.). The theophylline beads (60% biologically active ingredient content) were produced by extrusion-spheronization. The sustained action was imparted by coating with a 6.0% (w/w) polymethacrylic acid aqueous polymeric dispersion. The coating was composed of 48% amminomethacrylate copolymer and 9.5% methacrylic acid copolymer plasticized with 9.5% (w/w) triethyl citrate. A 2.0% (w/w) overcoat was also applied.

The carbomer beads consisted of 30% (w/w) neutralized carbomer (Carbopol® EX214) in MCC were produced, as described in Example 1 above, by extrusion-spheronization using a 50% hydroalcoholic solution as the wet massing agent.

The cushioning beads, composed of 8.0% croscarmellose sodium in MCC, were produced by extrusion-spheronization as described in Example 2 above, using water as the wet massing agent, followed by freeze-drying.

III. Methods

A. Production of Tablets

A 500 g batch containing 8.3% Theophylline (RD010) biologically active ingredient-loaded membrane-coated beads (14–20 mesh cut), 16.7% carbomer beads (20–30 mesh cut) and 75% freeze-dried cushioning beads (14–20 mesh cut) was blended for 10 min in a 2.0 quart twin-shell blender. Tablets were compressed on a single station of an instrumented rotary tablet press (Stokes RB-2) utilizing a 1.58 mm flat-faced beveled-edge punches. The instrumentation for the measurement of compression force has been previously described by Salpekar et al, supra. The angular separation between filling and compression was 180° C. Approximately twenty tablets were collected at compression pressures of 223.3, 331.8, 603.1 and 467.5 Kg/cm$^2$. After 24 hrs of storage, the thickness of 5 individual tablets at each compression force was determined using a digital micrometer. The crushing strength (P) of the tablets was determined by diametral loading in a standard motorized tester. The value used for P was the mean of five crushing strength determinations of tablets at each compression pressure. Tablet tensile strength (σ) in Kg/cm$^2$ was calculated using Equation (1) above. Compaction profiles were generated consisting of the different tablets tensile strengths as a function of compression pressures utilized in their production.

B. Determination of the Content Uniformity of the Compacts

Three samples of the tablets produced at each compression pressure were randomly selected and analyzed for the theophylline content. Each tablet was weighed and transferred separately to a 100 ml volumetric flask containing about 70 ml of distilled water. Each flask was placed in a mechanical shaker for 24 hrs to allow the biologically active ingredient to be released. A 24 hr period was adequate for complete release of the biologically active ingredient, as determined from the dissolution profile of uncompacted beads as described in Example 3, where the asymptote was reached at 10 hrs. Dilution to volume was followed by shaking each flask to ensure uniform mixing. A portion of the solution was centrifuged at 1000 RPM for about 10 min to obtain a clear solution. 5.0 ml of the clear supernatant was transferred to a 100 ml volumetric flask, and was diluted to volume with distilled water and mixed. The content was determined spectrophotometrically at a wavelength of 271 nm using the previously constructed standard curve.

C. Dissolution of the Bead Mixture and its Compacts

Dissolution studies were performed using the USP XXIII apparatus 2 at a paddle speed of 50 RPM. The release profiles of theophylline from the uncompacted bead blend and for tablets at the different compression pressures were evaluated in triplicate to study the effect of compression on the release kinetics of the biologically active ingredient. The dissolution medium consisted of 900 ml of degassed distilled water maintained at 37° C. The dissolution apparatus was calibrated using USP prednisone and salicylic acid calibrator tablets. Direct ultraviolet detection at 271 nm was used to assess the biologically active ingredient concentration in the dissolution medium. Dissolution medium was continuously pumped through 0.1 cm flow cells cuvettes by a peristaltic pump.

D. Photomicroscopy of Tablet Compacts

Magnified photographs for the fractured tablets produced at a compression pressure of 467.5 Kg/cm$^2$ were taken at a magnification of 19× to check for any fracturing of the biologically active ingredient-loaded beads and carbomer beads occurring inside the tablet matrix as a result of the compaction process. Moreover, surface pictures of intact tablets were taken at a similar magnification to examine for any fracturing of the beads exposed to the surface. A Wild Leipz microscope (Wild Leipz USA Inc., Rockleigh, N.J.) connected to Sony Video Printer (Model UP5000, Sony Corp., Tokyo, Japan) was used.

E. Evaluation of the Suspension

The ability of the tablet containing the biologically active ingredient-loaded beads, carbomer beads and cushioning beads to form a suspension was evaluated by dispersing 3 tablets (average weight of each 1375.5 g) in a beaker containing 100 ml of distilled water. The beaker was stirred for 0.5, 1.0 or 1.5 min at a fixed speed (level 7) on a Nuova II Stir Plate. The experiment was repeated at three different stirring times, after which the dispersion was transferred to a 100 ml graduated cylinder and after 5.0 sec were allowed for settling to occur, photographs of the settling suspension were taken. The three tablets provided a 687.5 mg of the carbomer beads (30% (w/w) carbomer) which when dispersed in 100 ml of water provide a final concentration of carbomer of 0.2%. A concentration of 0.175–0.2% is shown in Example 3 to provide a good suspending ability.

IV. Results and Discussion

Water-dispersible tablets containing beads which have been coated by a rate controlling membrane to sustain biologically active ingredient delivery, a swellable material able to rapidly generate viscosity when coming in contact with water, and a filler system capable of protecting the membrane controlling the biologically active ingredient release, as well as improving content uniformity, were manufactured. Compaction properties of the mixture, content uniformity and weight variation of the tablets, and the effect of compression pressure on the release of the biologically active ingredient from the tablets were evaluated.

A. Compaction Study

Figure 54:
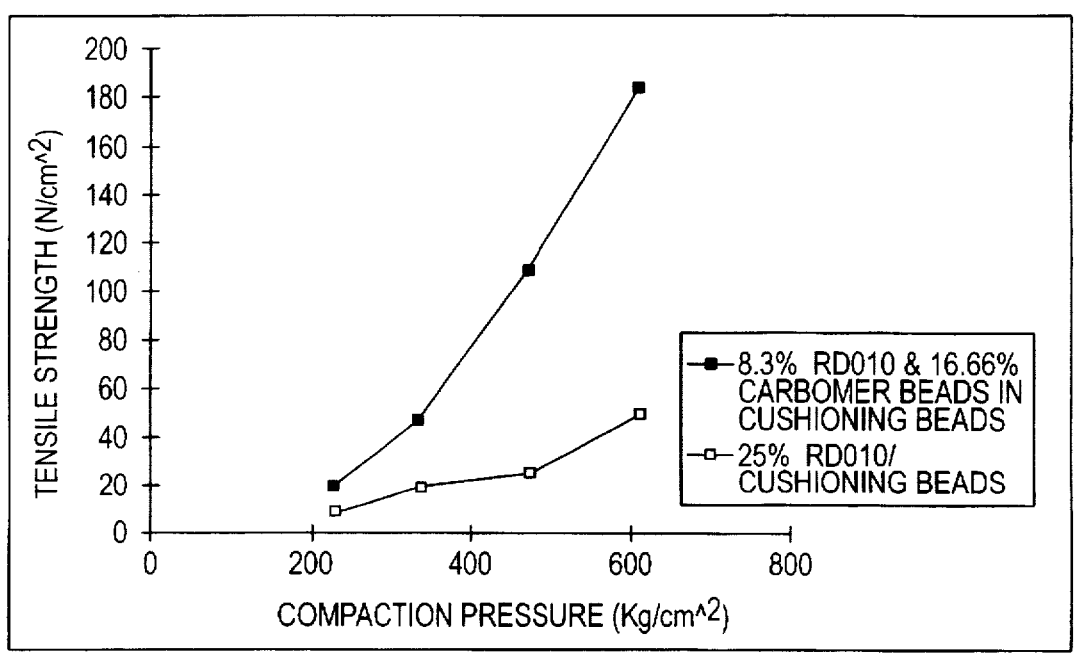
FIG. 54 shows the compaction profile of theophylline RD010 beads in cushioning beads and carbomer beads.

The compaction profiles of the blend containing theophylline RD010 beads, carbomer beads and cushioning beads and that containing 25% RD010 in cushioning beads (see Example 2) is depicted in FIG. 54. Increasing the compression pressure increased the tensile strengths of tablets. Although the level of the cushioning beads in both formulations was 75%, the increase in the tensile strength was much more pronounced with the formulation containing the carbomer beads. This could be attributed to the hygroscopic nature of carbomer, which might have absorbed some moisture from the atmosphere during blending and tabletting, resulting in an additional adhesive power enhancing the tablet tensile strength.

B. Content Uniformity and Weight Variation Study

The actual amount of the biologically active ingredient detected in the theophylline RD010 coated-beads was 66.8% (±2.8). The content uniformity and weight variation of the compacts produced as a function of compression pressures are seen Table 30 below. Weight variation was 4.3% and the content uniformity was 4.9%. No segregation was evident, as reflected in the tight content uniformity achieved.

TABLE 30

8.3% Theophylline RD010 Beads and 16.7% Carbomer Beads in 75% cushioning Beads

| Compression Force (Kg/cm$^2$) | Tablet Weight (mg) (n = 3) | Actual Amount of Theophylline Present (mg) | Theoretical Amount of Theophylline Present (mg) |
|---|---|---|---|
| 223.3 | 1463.7 (1.5)* | 78.4 (6.4) | 80.7 (1.5) |
| 331.8 | 1381.0 (0.7) | 74.5 (1.2) | 76.1 (0.7) |
| 467.5 | 1335.3 (0.4) | 75.4 (6.2) | 73.6 (0.4) |
| 603.1 | 1322.0 (0.6) | 74.6 (5.0) | 72.9 (0.6) |
| Average (C.V. %) | 1375.5 (4.3) | 75.7 (4.9) | 75.8 (4.3) |

*Relative standard deviation

Figure 55:
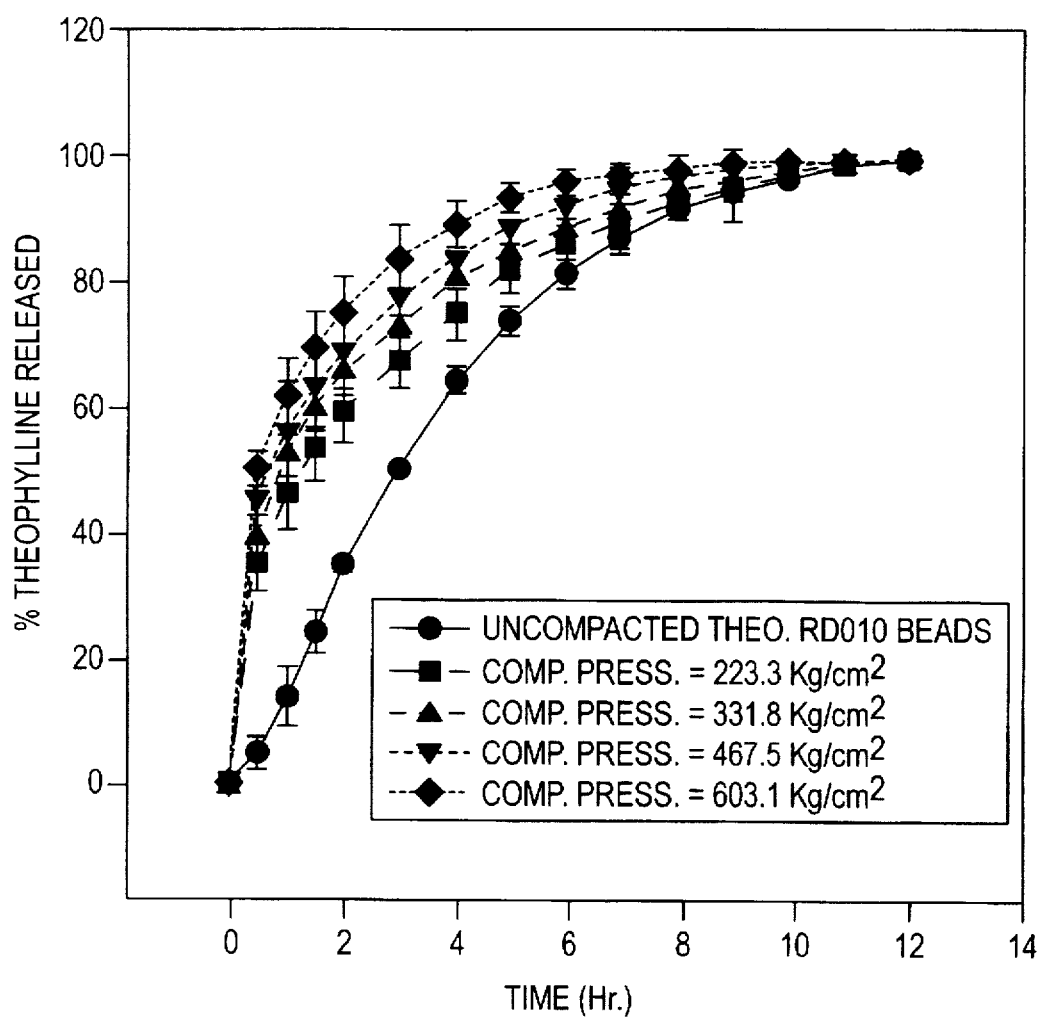
FIG. 55 shows the dissolution of theophylline from uncompacted and compacted theophylline RD010 beads (8.3% theophylline RD010 beads, 16.7% carbomer beads and 75% cushioning beads).

C. Effect of Compression Pressure on the Release of Biologically Active Ingredient from Tablets The effect of compression pressure on the release of theophylline from the uncompacted blend and the compressed tablets is depicted in FIG. 55. Higher compression pressures were associated with slightly faster release profiles. This is because at higher compression pressures, more cracking of the membrane-coated beads occurred, which can be attributed to the fact that at higher pressures, the tablet thickness is reduced, resulting in higher surface area/volume ratio. Thus, chances of the beads getting exposed to the surface where the damage is occurring is greater. Examining the photomicrograph of the fractured tablet reveals that the theophylline RD010 beads and carbomer beads present in the interior part of the tablet matrix remained intact, whereas the cushioning beads deformed and surrounded the other beads so that the tablet is held together by excipient-excipient contact. The surface photomicrograph of the intact tablet reveals a severe damage of the theophylline RD010 beads. The freeze-dried cushioning beads, when mixed and compacted with the theophylline biologically active ingredient-loaded beads coated with polymethacrylate copolymer (RD010) and carbomer beads, were able to cushion the biologically active ingredient-loaded beads and minimize dose dumping.

D. Evaluation of the Suspension

A stirring time of 0.5 min was associated with a relatively quick sedimentation rate of the beads in the formed suspension. However, a stirring time of 1.0 min resulted in a uniform suspension where the settling of the beads was relatively slow, a time sufficient to allow the patient to swallow the dose before appreciable sedimentation takes place. Stirring for 1.5 min produced a very stable suspension where the beads did not show any sign of settling at all. The decrease in settling of beads as a function of stirring time is attributed to the increase in the release of viscosity enhancer from the carbomer beads with time.

IV. Conclusions

A novel approach for the oral administration of multi-particulates is to suspend them in a liquid vehicle which spontaneously forms a suspension, when a tablet is reconstituted with water by the patient just prior to administration.

The tablets produced in this Example had a good tensile strength, which can be attributed to the excipient-excipient contact formed by the initial fragmentation, and plastic deformation of the freeze-dried cushioning beads, together with the adhesive action of the carbomer beads. The carbomer beads, being hygroscopic in nature, tend to absorb moisture from the atmosphere, resulting in an additional binding power. The disintegration of the tablets was not impeded due to this additional adhesive power of the carbomer beads.

The content uniformity and weight variation were less than 5.0% because of the absence of segregation, due to similar sizes of the beads and the filler system.

The freeze-dried cushioning beads and carbomer beads, when mixed and compacted with the theophylline biologically active ingredient-loaded beads coated with polymethacrylate copolymer (RD010) were able to cushion the biologically active ingredient-loaded beads and minimize dose dumping. Increasing the compression pressure resulted in a slight increase in the dissolution profile of theophylline beads. This increase is due to the fact that with an increase in compression pressure, tablet thickness decreases, resulting in a greater chance of exposing the theophylline beads to the surface where beads damage is prone to occur. Whereas the photomicrographs of the compacted beads revealed severe damage of the theophylline beads present at the surface, beads present in the interior tablet matrix appear to remain intact.

The tablets were able to generate a homogenous suspension and to minimize the settling of the biologically active ingredient-loaded beads for a time sufficient for the dispersed dose to be administered.

SUMMARY AND CONCLUSIONS

Multi-unit dosage forms of controlled release have been formulated with coated particles for many years, but in most cases have been filled into hard gelatin capsules. Such preparations present numerous disadvantages: The capsules themselves are relatively expensive, the bulk density inside the capsule is low so that a larger volume is needed for high doses, and the dose cannot be divided. Tablets can be produced less expensively and can be divided without significant influence on the biologically active ingredient release, which is controlled after disintegration of the tablet by the intact coated particles. Moreover, the concept of tabletting coated biologically active ingredient particles prevents criminal tampering with the product.

Compaction of beads posed problems for pharmaceutical formulators. If the beads have been coated by a rate controlling membrane to sustain biologically active ingredient delivery, cracking of the membrane will cause the delivery system to change the rate of biologically active ingredient delivery or completely dose dump. Thus, it is of great interest to investigate methods by which cracking can be prevented.

Conventional highly compactible fillers, such as MCC, can be mixed with biologically active ingredient-loaded beads and compressed to form tablets. However, due to particle size differences, segregation is encountered, resulting in weight variation and content uniformity problems. Granules produced by dry or wet granulation techniques having similar size to biologically active ingredient-loaded beads minimized segregation. However, dry or wet granulations of MCC-containing mixtures decreases compactibility. Moreover, the use of large amounts of filler-binders or cushioning agents to prevent the cracking of the membrane-coated beads can result in large tablets which are difficult to swallow.

An alternative approach for the oral administration of multi-particulates is to suspend them in a liquid vehicle to form a suspension or into a dry powder system or a tablet, which is to be reconstituted with water by the patient just prior to administration. These types of dosage forms overcome the above-mentioned problems, and are often preferred for infants, children, and elderly patients.

An aim of the present invention was to produce a water-dispersible tablet containing biologically active ingredient-loaded microparticles, a filler, and a swellable material capable of generating a high viscosity when dispersed in water. When coming in contact with water, the tablet disintegrated rapidly to surpass the opposite swelling effect caused by the viscosity enhancer. After the tablet has disintegrated in water, the viscosity enhancer swells, resulting in a homogenous suspension consisting of biologically active ingredient-loaded beads and other excipients. The distribution of the viscosity enhancer particles within the tablet is important because complete disintegration of the tablet has to take place before the swelling of the viscosity enhancer prevents the disintegration.

A systematic approach was used in the design of the self-disintegrating tablet for the formation of extemporaneous sustained release suspension. The first step was to screen different viscosity enhancers which exhibit quick hydration, and find one that increase the viscosity of the dispersion medium at a low concentration. Carbomer (Carbopol® EX214) was chosen as the viscosity enhancer. This was followed by processing the fine powder of the viscosity enhancer into separate entities (beads) to allow the tablet to disintegrate first, followed by the build-up of viscosity. If powdered the viscosity enhancers were used instead, the disintegration process would be impeded, resulting in a voluminous tablet mass, which is difficult to disintegrate.

The second step was to formulate cushioning beads to act as a filler. The filler should have minimal segregation propensity (similar size, density, and shape), and should cushion the sustained-release biologically active ingredient-loaded beads to prevent dose dumping. It should preferably exhibit initial fragmentation into primary powder particles, followed by plastic deformation during the compaction with the biologically active ingredient-loaded membrane-coated millispheres. This is so because the filler should not only fill the voids between the biologically active ingredient-loaded beads, but also should surround them so that the tablet is held together by excipient-excipient contact. The filler should disintegrate rapidly to release the intact biologically active ingredient-loaded beads, and should have a minimal effect on biologically active ingredient release kinetics. Freeze-drying of beads provided a successful approach for cushioning beads production.

The third step was to test the ability of the cushioning beads to protect the coated biologically active ingredient-loaded beads so that the release profile of the biologically active ingredient is not changed. Polymethacrylate copolymer coatings were able withstand the mechanical stresses of compression with minimal dose dumping.

The final step was to produce tablets intended to be used for the instantaneous preparation of a sustained release suspension. Biologically active ingredient-loaded membrane-coated beads, consisting of theophylline produced by extrusion-spheronization and coated with polymethacrylate copolymer, carbomer/MCC beads and freeze-dried cushioning beads were compressed to form a tablet. When dispersed in water, the tablet disintegrated quickly to release the intact biologically active ingredient-loaded beads together with the carbomer beads, resulting in a homogenous suspension.

I. Screening of Viscosity Enhancers and its Processing

Standard viscosity enhancers could be incorporated into such a tablet system to reduce sedimentation or floating of the particles. Two factors played a role in the choice of a viscosity enhancer. The first was the concentration needed in the final dispersed form to impart enough structure. The second was the rate of viscosity build-up which should be fast enough to provide adequate suspension properties, yet should not interfere with the disintegration of the tablet.

The presence of the viscosity enhancer as fine powder particles in a tablet matrix prevents the rapid disintegration and subsequent dispersion of the contents of the tablet. This is because the fine powder of the viscosity enhancer tends to network with each other, so that upon contact with water, the networked polymer particles at the surface would hydrate, preventing the further penetration of water to the interior of the tablet and the disintegration process is inhibited. The layering of the viscosity enhancers onto placebo sugar spheres or extrusion-spheronization of the viscosity enhancer to form beads are among the various approaches attempted in the present invention to solve the problems of tablet disintegration and powder dispersion.

Among the various polymers evaluated for their rheological properties, carbomer (Carbopol® EX214) proved to be an ideal candidate, in terms of speed of hydration, presence of yield value and lowest concentration needed to achieve an optimal viscosity required to minimize the sedimentation rate of suspended particles.

The powder-layering of carbomer on the surface of sugar spheres was achieved by using the EX214 grade, which does not hydrate in alcohol together with an alcoholic PVP solution. Similar concentrations of the different grades of alcoholic PVP solutions (K29-32 and K90) produced beads with almost equivalent yield, percentage loading, and similar release profiles of carbomer. Increasing the concentration of PVP in the alcoholic binder solution increased the yield, and the percentage loading, but decreased the amount of carbomer released at the early time points.

Extrusion-spheronization of carbomer was achieved by using a hydroalcoholic granulating liquid to reduce the tackiness. This approach avoided the detrimental effects of ionic salts or pH modifiers on the ability of the polymer to build-up viscosity when hydrated. Increasing the water/alcohol ratio in the granulating solution decreased the amount of carbomer released as a function of time at the early time points. The size of the carbomer beads is of significant importance in determining the release profile of carbomer, indicating that dissolution-erosion type of release is involved, rather than disintegration. Superdisintegrants were not able to increase the rate of carbomer released as a function of time.

Processing carbomer by extrusion-spheronization produced beads with faster release profiles and more carbomer loading than powder-layering. The beads containing 30% carbomer in MCC (Avicel® PH101) produced by extrusion-spheronization was selected as the swellable material to be included in the water-dispersible tablets to retard the sedimentation process.

II. Formulation of Cushioning Beads

Ideal inert "cushioning" beads intended to be used as diluent to be mixed with biologically active ingredient-loaded beads to prevent segregation, whether due to size or density, should have minimal segregation propensity (similar size, density, and shape) and should cushion the sustained-release biologically active ingredient-loaded pellets to prevent dose dumping. Freeze-drying of beads of different composition provided a successful approach for cushioning beads production.

Different materials, including disintegrants such as starch, superdisintegrants, such as croscarmellose sodium, crospovidone, and sodium starch glycolate, and hydrophilic materials, such as hydroxypropyl cellulose, can be incorporated to increase the water content of the extruded-spheronized beads. Superdisintegrants can be incorporated at much lower levels than regular disintegrants to increase the water content. Materials included in the granulating mixture to increase the water level should be efficient at low concentrations and should not cause the extrudate to be sticky, so that during spheronization, balling of the beads should not occur. Hydroxypropyl cellulose, starch and sodium starch glycolate form viscous and sticky extrudates, which are difficult to spheronize.

Inert cushioning beads of different compressibilities, compactibilities and disintegration ability were produced by freeze-drying. The optimal granulating fluid level for the different formulations studied, as determined by image analysis based on the size and roundness of the fresh undried beads, was essential to investigate the effect of different formulation variables on the properties of the dried product.

The presence of high levels of MCC and different superdisintegrants, especially croscarmellose, generally increased the granulating fluid levels requirement, thus producing freeze-dried beads with higher porosities. Compactibility studies indicated that in the absence of croscarmellose, lactose-predominant formulations were more compactible than those predominant in MCC. A major interaction was observed between MCC and croscarmellose. In the presence of high levels of MCC in the formulation, croscarmellose-containing freeze-dried beads were the most compactible, producing the hardest tablets at the compression pressure ranges studied.

Compressibility studies revealed that formulations containing high levels of MCC exhibited lower yield values, thus were more compressible, than those formulations containing high levels of lactose. Superdisintegrants had no effect on the compressibility of beads, which could be attributed to the fact that compressibility measurements (yield values) were determined at compression forces which were higher than the ranges used in the compactibility studies. Thus, the effect of the initial porosities of the beads was diminished.

The yield values were very helpful in determining the compaction mechanism of the freeze-dried beads. Freeze-dried beads exhibited both plastic deformation and brittle fracture. The presence of plastic deformation was detected by the presence of strain-rate sensitivity to the compaction process when the upper punch speed rate was varied. Brittle fracture component was detected in the relatively high yield values associated with the freeze-dried beads. The existence of both plastic deformation and brittle fracture is desired in an ideal cushioning bead system. This is so because when the cushioning beads, mixed with biologically active ingredient-loaded beads, are compacted, initial fragmentation into progeny primary powder particles would not only fill the voids between the biologically active ingredient-loaded beads, but surround them. Plastic deformation of the fine particles would then enhance the excipient-excipient interaction, producing stronger compacts.

Yield value measurements for different bead-fractions were not able to depict the mechanism of deformation, due to the narrow size-range of the beads produced by extrusion-spheronization process.

Tray-drying of some batches produced beads with smaller average diameters than those which were freeze-dried. This is due to the shrinking associated with tray-drying, which produced hard and dense beads. The tray-dried beads were not able to form tablets of any appreciable hardness when compacted.

III. Formulation of Fast Disintegrating Controlled Release Tablets from Coated Particles The performance of the inert cushioning beads produced by freeze-drying in minimizing the segregation propensity and cushioning the biologically active ingredient-loaded beads was practically evaluated by mixing and compacting them with different biologically active ingredient-loaded beads whose action was sustained by different polymeric membranes. Tablets containing propranolol beads coated with ethylcellulose from organic solvent, phenylpropanolamine hydrochloride beads coated with an aqueous dispersion of ethylcellulose, theophylline beads coated with an aqueous dispersion of polymethacrylates, and theophylline beads coated with a mixture of an aqueous dispersion of ethylcellulose and polymethacrylates were prepared using MCC (Avicel® PH200), or freeze-dried cushioning beads as filler-binder.

The two different filler systems, namely Avicel® PH200 with a mean particle size of 200 μm and the freeze-dried cushioning beads (14–20 mesh cut, 850–1400 μm), were used to study the effect of the filler particle size on the segregation propensity of the biologically active ingredient-loaded beads (14–20 mesh cut, 850–1400 μm). The cushioning beads minimized the segregation propensity due to size differences, as reflected in the content uniformity and weight variation of the tablets. Moreover, the cushioning beads deformed more readily than the biologically active ingredient-loaded beads, so that fracture of the membrane was minimized.

The mixing and compaction of the different biologically active ingredient-loaded beads with MCC (Avicel® PH200) was associated with more significant weight variation and content uniformity problems than when the freeze-dried cushioning beads containing 8.0% croscarmellose sodium in MCC was used as the filler binder. This is attributed to the segregation due to size differences between the biologically active ingredient-loaded beads (14–20 mesh cut, 850–1400 μm) and MCC (200 μm). When the freeze-dried cushioning beads of 14–20 mesh cut (850–1400 μm) were used, segregation was minimal.

The freeze-dried cushioning beads, when mixed and compacted with the theophylline biologically active ingredient-loaded beads coated with polymethacrylate copolymer (RD010) and a mixture of polymethacrylate copolymer and ethylcellulose from aqueous dispersions (RD011), were able to cushion the biologically active ingredient-loaded beads and minimize dose dumping. However, dose dumping with propranolol beads coated with ethylcellulose from organic solvent and phenylpropanolamine hydrochloride beads coated with an aqueous dispersion of ethylcellulose was inevitable. This is because ethylcellulose films are very brittle, regardless of the plasticizers added. Polymethacrylate copolymers are much flexible, and can withstand the mechanical stresses of the compaction process.

Increasing the compression pressure resulted in a slight increase in the dissolution profile of theophylline beads (both RD010 and RD011) compressed with the freeze-dried beads. This increase is due to the fact that with an increase in compression pressure, tablet thickness decreases with a corresponding increase in surface area/volume ratio, resulting in a greater chance of exposing the theophylline beads to the surface where beads damage is prone to occur. Whereas the photomicrographs of the compacted beads revealed severe damage of the theophylline beads present at the surface, beads present in the interior tablet matrix remained intact.

A biologically active ingredient load of 25% of theophylline in cushioning beads appeared to be a reasonable figure to be used to manufacture the self-disintegrating tablets intended to deliver sustained release aqueous suspension.

IV. Formulation and Manufacture of Tablets for Extemporaneous Preparation of Sustained Release Suspension Biologically active ingredient-loaded membrane-coated beads, consisting of theophylline produced by extrusion-spheronization and coated with polymethacrylate copolymer, capable of withstanding the mechanical stresses of compression, were mixed with the carbomer/MCC beads and freeze-dried cushioning beads containing 8.0% croscarmellose in MCC. These three components were compressed to form a tablet which, when dispersed in water, disintegrated quickly to release the theophylline beads together with the carbomer beads, resulting in a homogenous suspension.

The tablets produced had a good tensile strength, which can be attributed to the excipient-excipient contact formed by the initial fragmentation and plastic deformation of the freeze-dried cushioning beads, together with the adhesive action of the carbomer beads. The carbomer beads, being hygroscopic in nature, absorbed moisture from the atmosphere, resulting in an additional binding power. The disintegration of the tablets was not impeded, due to this additional adhesive power of the carbomer beads.

The content uniformity and weight variation were less than 5.0% because of the absence of segregation, due to similar sizes of the beads and the filler system.

The freeze-dried cushioning beads and carbomer beads when mixed and compacted with the theophylline biologically active ingredient-loaded beads coated with polymethacrylate copolymer (RD010) were able to cushion the biologically active ingredient-loaded beads, and minimize dose dumping. Increasing the compression pressure resulted in a slight increase in the dissolution profile of theophylline beads. This increase is due to the fact that with an increase in compression pressure, tablet thickness decreases, resulting in greater chance of exposing the theophylline beads to the surface where beads damage is prone to occur. Whereas the photomicrographs of the compacted beads revealed severe damage of the theophylline beads present at the surface, beads present in the interior tablet matrix remained intact.

The tablets were able to generate a homogenous suspension and to minimize the settling of the biologically active ingredient-loaded beads for a time sufficient for the dispersed dose to be administered.

The production of viscosity enhancers in the form of beads without incorporating additional materials which having detrimental effects on the functionality of the viscosity enhancer, together with the production of freeze-dried cushioning beads of microcrystalline cellulose are some of the unique features of the present invention.

While the invention has been described in detail, and with reference to specific embodiments thereof, it will be apparent to one of ordinary skill in the art that various changes and modifications can be made therein without departing from the spirit and scope thereof.

What is claimed:

1. A cushioning bead comprising microcrystalline cellulose, wherein said cushioning bead is prepared by extrusion-spheronization, followed by freeze-drying, wherein said cushioning bead has a diameter of about 0.2–2.0 mm.

2. The cushioning bead as claimed in claim 1, wherein said microcrystalline cellulose is present in the cushioning bead in an amount of from about 20–100%.

3. The cushioning bead as claimed in claim 2, wherein said microcrystalline cellulose is present in the cushioning bead in an amount of from about 60–95%.

4. The cushioning bead as claimed in claim 1, wherein said cushioning bead additionally comprises a disintegrant.

5. The cushioning bead as claimed in claim 4, wherein said disintegrant is selected from the group consisting of croscarmellose sodium, sodium starch glycolate, crospovidone, starch, and pregelatinized starch.

6. The cushioning bead as claimed in claim 5, wherein said disintegrant is croscarmellose sodium.

7. The cushioning bead as claimed in claim 4, wherein said disintegrant is present in the cushioning bead in an amount of from greater than 0–50%.

8. The cushioning bead as claimed in claim 7, wherein said disintegrant is present in the cushioning bead in an amount of from about 5.0–40%.

9. The cushioning bead as claimed in claim 4, wherein the ratio of microcrystalline cellulose to disintegrant is about 1:0–0.2:0.8.

10. The cushioning bead as claimed in claim 9, wherein the ratio of microcrystalline cellulose to disintegrant is about 0.95:0.05–0.6:0.4.

11. The cushioning bead as claimed in claim 4, wherein said cushioning bead additionally comprises a filler.

12. The cushioning bead as claimed in claim 11, wherein said filler is a water-soluble filler selected from the group consisting of lactose and sorbitol.

13. The cushioning bead as claimed in claim 11, wherein said filler is dibasic calcium phosphate.

14. The cushioning bead as claimed in claim 11, wherein said filler is present in the cushioning bead in an amount of from greater than 0–80%.

15. The cushioning bead as claimed in claim 14, wherein said filler is present in the cushioning bead in an amount of from greater than 0–50%.

16. A tablet comprising:
  (i) biologically active ingredient-loaded beads; and
  (ii) cushioning beads comprising microcrystalline cellulose, wherein said cushioning beads are prepared by extrusion-spheronization, followed by freeze-drying, wherein said cushioning beads have an average diameter of about 0.2–2.0 mm.

17. The tablet as claimed in claim 16, wherein said microcrystalline cellulose is present in the cushioning beads in an amount of from about 20–100%.

18. The tablet as claimed in claim 17, wherein said microcrystalline cellulose is present in the cushioning beads in an amount of from about 60–95%.

19. The tablet as claimed in claim 16, wherein said cushioning beads additionally comprise a disintegrant.

20. The tablet as claimed in claim 19, wherein said disintegrant is selected from the group consisting of croscarmellose sodium, sodium starch glycolate, crospovidone, starch, and pregelatinized starch.

21. The tablet as claimed in claim 20, wherein said disintegrant is croscarmellose sodium.

22. The tablet as claimed in claim 19, wherein said disintegrant is present in the cushioning beads in an amount of from greater than 0–50%.

23. The tablet as claimed in claim 22, wherein said disintegrant is present in the cushioning beads in an amount of from about 5.0–40%.

24. The tablet as claimed in claim 19, wherein the ratio of microcrystalline cellulose to disintegrant is about 1:0–0.2:0.8.

25. The tablet as claimed in claim 24, wherein the ratio of microcrystalline cellulose to disintegrant is about 0.95:0.05–0.6:0.4.

26. The tablet as claimed in claim 19, wherein said cushioning beads additionally comprise a filler.

27. The tablet as claimed in claim 26, wherein said filler is a water-soluble filler selected from the group consisting of lactose and sorbitol.

28. The tablet as claimed in claim 26, wherein said filler is dibasic calcium phosphate.

29. The tablet as claimed in claim 26, wherein said filler is present in the cushioning beads in an amount of from greater than 0–80%.

30. The tablet as claimed in claim 29, wherein said filler is present in the cushioning beads in an amount of from greater than 0–50%.

31. The tablet as claimed in claim 16, wherein said biologically active ingredient is selected from the group consisting of a pharmaceutical, a pesticide and a herbicide.

32. The tablet as claimed in claim 31, wherein said pharmaceutical is selected from the group consisting of potassium chloride, a lithium salt, a nonsteroidal anti-inflammatory drug, a calcium salt, sodium fluoride, pridinol or a salt thereof, dimethindine or a salt thereof, a methylxanthine, O-β-hydroxymethyl-rutoside, butamirate or a salt thereof, codeine or a derivative thereof, noscapine, acetaminophen, a vitamin, a β-blocker, pyrisuccideanol, ticlopidine, dipyridamole, diazepam, erythromycin or a salt thereof, and doxycycline or a salt thereof.

33. The tablet as claimed in claim 31, wherein said pesticide is selected from the group consisting of clomazone, sulfentrazone and clomazone/trifluralin.

34. The tablet as claimed in claim 31, wherein said herbicide is selected from the group consisting of zeta cypermephrin, cadusafos and bifenthrin.

35. The tablet as claimed in claim 16, said biologically active ingredient-loaded beads are coated with a coating material for controlling or sustaining the release properties of the biologically active ingredient, for taste masking, or for imparting resistance to gastric fluid, or said biologically active ingredient-loaded beads contain said material in the matrix thereof.

36. The tablet as claimed in claim 35, said coating material for controlling or sustaining the release properties of the biologically active ingredient and for taste masking is selected from the group consisting of methylcellulose, hydroxypropyl cellulose, ethylcellulose or a latex derivative thereof, and a methylacrylate ester copolymer.

37. The tablet as claimed in claim 35, said coating material for imparting resistance to gastric fluid is selected from the group consisting of shellac, cellulose acetate phthalate, cellulose acetate trimelliate, hydroxypropyl methylcellulose phthalate, polyvinyl acetate phthalate, hydroxypropyl methylcellulose acetate succinate, and a methacrylic acid copolymer.

38. The tablet of claim 19, wherein said tablet additionally comprises:

(iii) a viscosity enhancer.

39. The tablet of claim 38, wherein said viscosity enhancer is in the form of individual viscosity enhancer beads.

40. The tablet of claim 38, wherein said viscosity enhancer is present in the biologically active ingredient-loaded beads.

41. The tablet of claim 38, wherein said viscosity enhancer is selected from the group consisting of a carbomer, xanthan gum, guar gum, alginate, dextran, pectin, pregelatinized starch, polysaccharide and a cellulose derivative.

42. The tablet of claim 41, wherein said cellulose derivative is selected from the group consisting of sodium or calcium carboxymethlycellulose, hydroxypropyl cellulose and hydroxypropylmethyl cellulose.

43. The tablet of claim 41, wherein said viscosity enhancer is a carbomer.

44. The tablet of claim 39, wherein said viscosity enhancer beads are produced by extrusion-spheronization using a hydroalcoholic solution.

45. The tablet of claim 16, wherein said cushioning beads and biologically active ingredient-loaded beads each have an average diameter of about 0.2–2.0 mm.

46. The tablet of claim 45, wherein said cushioning beads and biologically active ingredient-loaded beads each have an average diameter of about 0.5–1.5 mm.

47. The tablet of claim 39, wherein said cushioning beads and biologically active ingredient-loaded beads and viscosity enhancer beads each have an average diameter of about 0.2–2.0 mm.

48. The tablet of claim 47, wherein said cushioning beads and biologically active ingredient-loaded beads and viscosity enhancer beads each have an average diameter of about 0.5–1.5 mm.

49. The tablet of claim 16, wherein the weight ratio of cushioning beads to biologically active ingredient-loaded beads is about 20:80–90:10.

50. The tablet of claim 49, wherein the weight ratio of cushioning beads to biologically active ingredient-loaded beads is about 50:50–75:25.

51. The tablet of claim 38, wherein the viscosity enhancer is present in an amount to achieve an apparent viscosity, at 20° C., of 30–3000 mPa.s.

52. The tablet of claim 51, wherein the viscosity enhancer is present in an amount to achieve an apparent viscosity, at 20° C., of 500–1000 mPa.s.

53. An in situ suspension formed by dispersing the tablet of claim 38 in an aqueous solution.

* * * * *